US011020429B2

(12) United States Patent
Thompson

(10) Patent No.: US 11,020,429 B2
(45) Date of Patent: Jun. 1, 2021

(54) VECTORS AND GENETICALLY ENGINEERED IMMUNE CELLS EXPRESSING METABOLIC PATHWAY MODULATORS AND USES IN ADOPTIVE CELL THERAPY

(71) Applicant: Juno Therapeutics, Inc., Seattle, WA (US)

(72) Inventor: Lucas James Thompson, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 233 days.

(21) Appl. No.: 15/773,153

(22) PCT Filed: Nov. 4, 2016

(86) PCT No.: PCT/US2016/060734
§ 371 (c)(1),
(2) Date: May 2, 2018

(87) PCT Pub. No.: WO2017/079703
PCT Pub. Date: May 11, 2017

(65) Prior Publication Data

US 2018/0318349 A1 Nov. 8, 2018

Related U.S. Application Data

(60) Provisional application No. 62/251,615, filed on Nov. 5, 2015.

(51) Int. Cl.
*A61K 35/17* (2015.01)
*A61K 39/00* (2006.01)
*C12N 5/0783* (2010.01)

(52) U.S. Cl.
CPC .......... *A61K 35/17* (2013.01); *A61K 39/0011* (2013.01); *C12N 5/0636* (2013.01); *A61K 2039/5156* (2013.01); *A61K 2039/5158* (2013.01); *C12N 2500/02* (2013.01); *C12N 2501/998* (2013.01)

(58) Field of Classification Search
CPC ...................................................... A61K 35/17
See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |
| 4,795,698 | A | 1/1989 | Owen |
| 5,087,616 | A | 2/1992 | Myers |
| 5,200,084 | A | 4/1993 | Liberti |
| 5,219,740 | A | 6/1993 | Miller |
| 6,040,177 | A | 3/2000 | Riddell |
| 6,207,453 | B1 | 3/2001 | Maass |
| 6,410,319 | B1 | 6/2002 | Raubitschek |
| 6,451,995 | B1 | 9/2002 | Cheung |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 8,324,353 | B2 | 12/2012 | Jensen |
| 8,389,282 | B2 | 3/2013 | Sadelain |
| 8,399,645 | B2 | 3/2013 | Campana |
| 8,497,118 | B2 | 7/2013 | Jensen |
| 8,822,647 | B2 | 9/2014 | Jensen |
| 8,911,993 | B2 | 12/2014 | June |
| 2002/0131960 | A1 | 9/2002 | Sadelain |
| 2002/0150914 | A1 | 10/2002 | Andersen |
| 2003/0170238 | A1 | 9/2003 | Gruenberg |
| 2007/0116690 | A1 | 5/2007 | Yang |
| 2007/0249550 | A1 | 10/2007 | Sitkovsky |

(Continued)

FOREIGN PATENT DOCUMENTS

| | | |
|---|---|---|
| EP | 0 452 342 | 10/1991 |
| EP | 2 537 416 | 11/2014 |

(Continued)

OTHER PUBLICATIONS

US 8,252,592 B2, 08/2012, Sadelain (withdrawn)
Okoye et al. (Science. Apr. 16, 2015. 348 (6238), 995-1001) (Year: 2015).*
Abken et al., "Costimulation Engages the Gear in Driving CARs," Immunity. Feb. 16, 2016;44(2):214-6.
Ackerman et al., "Abstract B33: Assessing the role of DGAT activity on lipid homeostasis and cancer cell survival," Mol Cancer Res (2016) 14(1 Supplement): Abstract B33.
Alcantara-Hernandez et al., "Overexpression of hypoxia-inducible factor 1 alpha impacts FoxP3 levels in mycosis fungoides—Cutaneous T-cell lymphoma: Clinical implications," Int J Cancer (2014) 134:2136-2145.

(Continued)

*Primary Examiner* — Scott Long
(74) *Attorney, Agent, or Firm* — Morrison & Foerster LLP

(57) ABSTRACT

Provided are cells, e.g., engineered immune cells, expressing recombinant or engineered molecules involved in metabolic pathways, such as those that promote or inhibit one or more metabolic steps, reactions, or pathways, for example, in T cells. Such molecules include those that induce or repress a particular functional outcome or metabolic event, for example, one that promotes differentiation or reprogramming into a particular phenotypic state, such as memory, long-lived, activated or activatable, non-exhausted, phenotype or stem-like phenotype. The cells generally further express an immune receptor, such as an antigen receptor, which may be an engineered receptor, such as a CAR or recombinant TCR, or may be a natural immune receptor. Also provided are cells, such as T cells, expressing such molecules and combinations thereof, compositions comprising such cells, nucleic acids such as vectors encoding the same, and methods of administration to subjects in adoptive cell therapy.

49 Claims, No Drawings

Specification includes a Sequence Listing.

(56) References Cited

U.S. PATENT DOCUMENTS

| | | | | |
|---|---|---|---|---|
| 2011/0003380 | A1 | 1/2011 | Miltenyi | |
| 2013/0149337 | A1 | 6/2013 | Cooper | |
| 2013/0287748 | A1 | 10/2013 | June | |
| 2014/0271635 | A1 | 9/2014 | Brogdon | |
| 2014/0294841 | A1 | 10/2014 | Scheinberg | |
| 2017/0137783 | A1* | 5/2017 | Bedoya | C07K 14/7051 |
| 2017/0204372 | A1 | 7/2017 | Mohler | |
| 2018/0142035 | A1* | 5/2018 | Lobb | C07K 16/2803 |
| 2018/0161368 | A1 | 6/2018 | Odegard | |

FOREIGN PATENT DOCUMENTS

| | | |
|---|---|---|
| WO | WO 1992/008796 | 5/1992 |
| WO | WO 1994/028143 | 12/1994 |
| WO | WO 1999/067268 | 12/1999 |
| WO | WO 2000/014257 | 3/2000 |
| WO | WO 2005/030946 | 4/2005 |
| WO | WO 2009/072003 | 6/2009 |
| WO | WO 2010/033140 | 3/2010 |
| WO | WO 2012/129514 | 9/2012 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2014/188220 | 11/2014 |
| WO | WO 2015/157399 | 10/2015 |
| WO | WO 2016/083811 | 6/2016 |
| WO | WO 2016/102272 | 6/2016 |

OTHER PUBLICATIONS

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Baba et al., "HIF1A Overexpression Is Associated with Poor Prognosis in a Cohort of 731 Colorectal Cancers," Am J Pathol (2010) 176(5):2292-2301.

Bagnato et al., "Overexpression of Diacylglycerol Acyltransferase-1 Reduces Phospholipid Synthesis, Proliferation, and Invasiveness in Simian Virus 40-transformed Human Lung Fibroblasts," Journal of Biological Chemistry (2003) 278:52203-52211.

Balaban et al., "Obesity and Cancer Progression: Is There a Role of Fatty Acid Metabolism?," BioMed Research International (2015) vol. 2015: Article ID 274585, 17 pages.

Barrett et al., "Chimeric antigen receptor therapy for cancer," Annu Rev Med (2014); 65:333-347.

Baum et al., "Retrovirus vectors: toward the plentivirus?," Molecular Therapy: The Journal of the American Society of Gene Therapy (2006) 13:1050-1063.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Buck et al., "T cell metabolism drives immunity," J Exp Med. Aug. 24, 2015;212(9):1345-1360.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Cao et al., "Hypoxia-inducible transgene expression in differentiated human NT2N neurons—a cell culture model for gene therapy of postichemic neuronal loss," Gene Ther Sep. 2001;8(17):1357-1362.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Cavalieri et al., "Human T lymphocytes transduced by lentiviral vectors in the absence of TCR activation maintain an intact immune competence," Blood (2003) 102(2): 497-505.

Chaika et al., "Differential Expression of Metabolic Genes in Tumor and Stromal Components of Primary and Metastatic Loci in Pancreatic Adenocarcinoma," PLOS One (2012) 7(3):e32996.

Cheadle et al., "Chimeric antigen receptors for T-cell based therapy," Methods Mol Biol (2012); 907:645-666.

Chen et al., "T Cell Receptor Signaling Co-regulates Multiple Golgi Genes to Enhance N-Glycan Branching," J Biol Chem (2009) 284(47):32454-32461.

Chicaybam et al., "An efficient low cost method for gene transfer to T lymphocytes," PLoS One (2013) 8(3): e60298.

Cho et al., "Human mammalian cell sorting using a highly integrated micro-fabricated fluorescence-activated cell sorter (microFACS)," Lab Chip (2010) 10: 1567-1573.

Chothia et al., "The outline structure of the T-cell alpha beta receptor," EMBO J. (1988) 7(12):3745-3755.

Clackson et al., "Making antibody fragments using phage display libraries," Nature (1991) 352:624-628.

Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.

Cohen et al., "Recognition of fresh human tumor by human peripheral blood lymphocytes transduced with a bicistronic retroviral vector encoding a murine anti-p53 TCR," J Immunol. (2005) 175:5799-5808.

Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.

Cooper et al., "T-cell clones can be rendered specific for CD19: toward the selective augmentation of the graft-versus-B-lineage leukemia effect," Blood. (2003) 101:1637-1644.

Cui et al., "IL-7-Induced Glycerol Transport and TAG Synthesis Promotes Memory CD8+ T Cell Longevity," Cell. May 7, 2015;161(4):750-61.

Currie et al., "Cellular Fatty Acid Metabolism and Cancer," Cell Metab. Aug. 6, 2013; 18(2): 153-161.

Dachs et al., "Hypoxia modulated gene expression: angiogenesis, netastasis and therapeutic exploitation," Eur J Cancer Aug. 2000;36(13 Spec No):1649-1660.

Davila et al., "CD19 CAR-targeted T cells induce long-term remission and B Cell Aplasia in an immunocompetent mouse model of B cell acute lymphoblastic leukemia," PLoS ONE (2013) 8(4): e61338.

De Felipe et al., "Targeting of proteins derived from self-processing polyproteins containing multiple signal sequences," Traffic Aug. 2004; 5(8):616-626.

De Felipe, "Skipping the co-expression problem: the new 2A "CHYSEL" technology," Genet Vaccines Ther Sep. 13, 2004;2(1):13.

Depra, D., "Scientists Accidentally Discover Protein That Can Boost Immune System Against Cancer," Retrieved on Oct. 17, 2018. Retrieved at https://www.techtimes.com/articles/46931/20150417/scientists-accidentally-discover-protein-that-can-boost-immune-system-against-cancer.htm.

Doedens et al., "Hypoxia-inducible factors enhance the effector responses of $CD8^+$ T cells to persistent antigen," Nat Immunol Nov. 2013; 14(11):1173-1182.

Faris et al., "Mitochondrial glycerol-3-phosphate acyltransferase-1 is essential for murine CD4+ T cell metabolic activation," BioChim Biophys Acta (2014) 1842(10):1475-1482.

Faris et al., "Mitochondrial Glycerol-3-Phosphate Acyltransferase-Dependent Phospholipid Synthesis Modulates Phospholipid Mass and IL-2 Production in Jurkat T Cells," Lipids (2016) 51(3):291-301.

Faris, "Glycerol-3-Phosphate Acyltransferase Regulates T Cell Effector Function and Metabolism," Dissertation for the University of Texas (2013) 110 pages.

Fedorov et al., "PD-1- and CTLA-4-based inhibitory chimeric antigen receptors (iCARs) divert off-target immunotherapy responses," Sci Transl Med. (2013) 5(215):215ra172.

(56) References Cited

OTHER PUBLICATIONS

Frecha et al., "Advances in the field of lentivector-based transduction of T and B lymphocytes for gene therapy," Molecular Therapy: The Journal of the American Society of Gene Therapy (2010) 18:1748-1757.
Godin et al., "Microfluidics and photonics for Bio-System-on-a-Chip: a review of advancements in technology towards a microfluidic flow cytometry chip," J Biophoton. (2008) 1(5):355-376.
Greco et al., "Novel chimeric gene promoters responsive to hypoxia and ionizing radiation," Gene Ther Oct. 2002; 9(20):1403-1411.
Grigorian et al., "Control of T Cell-mediated Autoimmunity by Metabolite Flux to N-Glycan Biosynthesis," Journal of Biological Chemistry (2007) 282:20027-20035.
Hackett et al., "A transposon and transposase system for human application," Molecular Therapy: The Journal of the American Society of Gene Therapy (2010) 18:674-683.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Ho et al., "Phosphoenolpyruvate Is a Metabolic Checkpoint of Anti-tumor T Cell Responses," Cell. Sep. 10, 2015;162(6):1217-28.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res Jun. 15, 2013;19(12):3153-1364.
Janeway et al., Immunobiology: The Immune System in Health and Disease, 3rd Ed., Current Biology Publications (1997), p. 4:33.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity," Proc Natl Acad Sci U S A. (1990) 87(23):9138-9142.
Kindt et al., Kuby Immunology 6th ed., W.H. Freeman and Co. (2007) p. 91.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Koste et al., "T-cell receptor transfer into human T cells with ecotropic retroviral vectors," Gene Therapy (2014) 21: 533-538.
Kruse, R., "LEM-onade for the CAR ride," Retrieved on Oct. 17, 2018. Retrieved at http://www.biotechr.com/2015/04/lem-onade-for-car-ride.html.
Lau et al., "N-Glycans in cancer progression," Glycobiology (2008) 18(10):750-760.
Lefranc et al., "IMGT unique numbering for immunoglobulin and T cell receptor variable domains and Ig superfamily V-like domains," Dev Comp Immunol (2003) 27(1):55-77.
Leibovici et al., "Targeting the tumor microenvironment by immunotherapy: part 2." Immunotherapy. Nov. 2011;3(11):1385-408.
Li et al., "Directed evolution of human T-cell receptors with picomolar affinities by phage display," Nat Biotechnol. (2005) 23:349-354.
Ligtenberg et al., "Coexpressed Catalase Protects Chimeric Antigen Receptor-Redirected T Cells as well as Bystander Cells from Oxidative Stress-Induced Loss of Antitumor Activity," J Immunol. Jan. 15, 2016;196(2):759-66.
Lukashev et al., "Cutting Edge: Hypoxia-Inducible Factor 1α and Its Activation-Inducible Short Isoform I.1 Negatively Regulate Functions of CD4+ and CD8+ T Lymphocytes," J Immunol (2006) 177(8):4962-4965.
Lupton S. D. et al., "Dominant positive and negative selection using a hygromycin phosphotransferase-thymidine kinase fusion gene," Mol. and Cell Biol. (1991) 11(6):3374-3378.
Manuri et al., "piggyBac transposon/transposase system to generate CD19-specific T cells for the treatment of B-lineage malignancies," Hum Gene Ther (2010) 21(4): 427-437.
Mcnamee et al., "Hypoxia and hypoxia-inducible factors as regulators of T cell development, differentiation, and function," Immunol Res (2013) 55(0):58-70.
Mendelsohn et al., "Complex N-Glycan and Metabolic Control in Tumor Cells," Cancer Research (2007) 67(20):9771-9780.
Miller et al., "Improved retroviral vectors for gene transfer and expression," BioTechniques (1989) 7:980-990.
Miller et al., "Retrovirus packaging cells," Human Gene Therapy (1990) 1:5-14.
Mockler et al., "Targeting T cell immunometabolism for cancer immunotherapy; understanding the impact of the tumor microenvironment," Front. Oncol May 16, 2014;4:107.
Mullen et al., "Transfer of the bacterial gene for cytosine deaminase to mammalian cells confers lethal sensitivity to 5-fluorocytosine: a negative selection system," Proc. Natl. Acad. Sci. USA (1992)89(1):33-37.
Okoye et al., "T cell metabolism. The protein LEM promotes $CD8^+$ T cell immunity through effects on mitochondrial respiration," Science. May 29, 2015;348(6238):995-1001.
O'Sullivan et al., "Targeting T cell metabolism for therapy," Trends Immunol. Feb. 2015;36(2):71-80.
Park et al., "Expression of phosphoenolpyruvate carboxykinase linked to chemoradiation susceptibility of human colon cancer cells," BMC Cancer (2014) 14:160.
Park et al., "Treating cancer with genetically engineered T cells," Trends Biotechnol. (2011) 29(11): 550-557.
Parkhurst et al., "Characterization of genetically modified T-cell receptors that recognize the CEA:691-699 peptide in the context of HLA-A2.1 on human colorectal cancer cells," Clin Cancer Res. (2009) 15:169-180.
Parmley, S., "LEM-on aid for cancer," Retrieved on Oct. 17, 2018. Retrieved at https://www.biocentury.com/bc-innovations/targets-mechanisms/2015-04-23/how-new-protein-lem-could-displace-anti-pd-1-and-car-t.
Patsoukis et al., "PD-1 alters T-cell metabolic reprogramming by inhibiting glycolysis and promoting lipolysis and fatty acid oxidation," Nature Communications (2015) 6:6692.
Portolano et al., "Lack of promiscuity in autoantigen-specific H and L chain combinations as revealed by human H and L chain "roulette"," J. Immunol. (1993) 150:880-887.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rosenberg, "Cell transfer immunotherapy for metastatic solid cancer—what clinicians need to know," Nat Rev Clin Oncol. (2011) 8(10):577-585.
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Sharma et al., "Efficient sleeping beauty DNA transposition from DNA minicircles," Molec Ther Nucl Acids (2013) 2:e74.
Staron et al., "The transcription factor FoxO1 sustains expression of the inhibitory receptor PD-1 and survival of antiviral CD8(+) T cells during chronic infection," Immunity. Nov. 20, 2014;41(5):802-14.
Sukumar et al., "Inhibiting glycolytic metabolism enhances CD8+ T cell memory and antitumor function," J Clin Invest. Oct. 2013;123(10):4479-88.
Takeuchi et al., "Biochemistry, physiology, and genetics of GPAT, AGPAT, and lipin enzymes in triglyceride synthesis," Am J Physiol Endocrinol Metab Jun. 2009;296(6):E1195-E1209.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.

(56) References Cited

OTHER PUBLICATIONS

Tsukahara et al., "CD19 target-engineered T-cells accumulate at tumor lesions in human B-cell lymphoma xenograft mouse models," Biochem Biophys Res Commun (2013) 438(1): 84-9.

Turtle et al., "Engineered T cells for anti-cancer therapy," Curr. Opin. Immunol. (2012) 24(5): 633-639.

Van Tendeloo et al., "High-level transgene expression in primary human T lymphocytes and adult bone marrow CD34+ cells via electroporation-mediated gene delivery," Gene Therapy (2000) 7(16): 1431-1437.

Varela-Rohena et al., "Control of HIV-1 immune escape by CD8 T cells expressing enhanced T-cell receptor," Nat Med. (2008) 14:1390-1395.

Verhoeyen et al., "Lentiviral vector gene transfer into human T cells," Methods Mol Biol. (2009) 506: 97-114.

Wadhwa et al., "Receptor mediated glycotargeting," J. Drug Targeting (1995) 3(2):111-127.

Wang et al., "Metabolic checkpoints in activated T cells," Nature Immunol. Oct. 2012; 13(10): 907-915.

Wang et al., "Negative regulation of Hif1a expression and TH17 differentiation by the hypoxia-regulated microRNA miR-210," Nat Immunol (2014) 15(4):393-401.

Wang et al., "Phenotypic and functional attributes of lentivirus-modified CD19-specific human CD8+ central memory T cells manufactured at clinical scale," J Immunother (2012) 35(9):689-701.

Wong, S., "Scientists discover protein that boosts immunity to viruses and cancer," Retrieved on Oct. 17, 2018. Retrieved at http://www.imperial.ac.uk/news/165032/scientists-discover-protein-that-boosts-immunity/.

Wu et al., "Adoptive T-cell therapy using autologous tumor-infiltrating lymphocytes for metastatic melanoma: current status and future outlook," Cancer (2012) 18(2): 160-175.

Wu et al., "Effect of HIF1α on Foxp3 expression in $CD4^+CD25^-$ T lymphocytes," Microbiol Immunol (2014) 58:409-415.

Zhao et al., "Structural Design of Engineered Costimulation Determines Tumor Rejection Kinetics and Persistence of CAR T Cells," Cancer Cell. Oct. 12, 2015;28(4):415-428.

Zhao-Emonet et al., "T cell-specific expression from Mo-MLV retroviral vectors containing a CD4 mini-promoter/enhancer," J Gene Med Nov.-Dec. 2000;2(6):416-425.

* cited by examiner

SEQUENCE LISTING

<160> NUMBER OF SEQ ID NOS: 97

<210> SEQ ID NO 1
<211> LENGTH: 414
<212> TYPE: PRT
<213> ORGANISM: Homo sapiens
<220> FEATURE:
<223> OTHER INFORMATION: C1ORF177 isoform 1(huLEM)
<300> PUBLICATION INFORMATION:
<308> DATABASE ACCESSION NUMBER: NCBI NP_689820.2
<309> DATABASE ENTRY DATE: 2007-11-16

<400> SEQUENCE: 1

```
Met Arg Glu Ser Gln Asp Ala Ala Gly Ala His Gly Trp Asn Arg Val
1               5                   10                  15

Gly Ser Thr Ala Thr Lys Trp Phe Thr Gly Ala Pro Phe Gly Val Gln
            20                  25                  30

Ser His Arg Phe Asp Ile Ser Ala Val Tyr Pro Asn Trp Lys Lys Phe
        35                  40                  45

Ser Thr Phe Thr Glu Ala Pro Tyr Ser Thr Arg Tyr Ser Thr Gln Val
    50                  55                  60

Ser His Ile Gly Pro Gly Thr Tyr Ser Ser Lys Glu Thr Cys Phe Ser
65                  70                  75                  80

Lys Lys Lys Leu Met Lys Glu Val Asp Thr Gly Trp Ala Lys Ala Gln
                85                  90                  95

Glu Ala Thr Arg Leu Thr Gln Leu Pro His Phe Gln Tyr Gln Ala Ile
            100                 105                 110
```

-continued

```
Met Lys Glu Lys Arg Leu Lys Glu Gln Lys Leu Gly Pro Gly Ser Tyr
        115                 120                 125

Asn Leu Lys Asp Phe Leu Glu Gln Leu Arg Glu Lys Pro Cys Ser Thr
    130                 135                 140

Arg Gly Leu Leu Ser Ser Gly Glu Val Arg Phe Arg Gly Leu Thr Gly
145                 150                 155                 160

Asn Tyr Tyr Pro Gly Pro Gly Asn Tyr Gly Glu Lys Gly Asn Pro Tyr
                165                 170                 175

Thr Lys Leu Glu Glu Asn Ala Trp Asn Arg Ser His Ser Glu Gly Leu
            180                 185                 190

Met Cys Arg Met Ser Asn Lys Pro His Pro Arg Pro His Gln Gly Ser
        195                 200                 205

Gly Leu Gly Pro Gly Thr Tyr Phe Phe Lys Ser Asp Leu Glu Thr Tyr
    210                 215                 220

Val Ala Arg Ser Val Gly Thr Arg Gly Pro Tyr Asp Thr Phe Ser Gly
225                 230                 235                 240

Asp Arg Ser Lys Pro Leu Pro Tyr Gly His Tyr Ser Met Gln Lys Lys
                245                 250                 255

Lys Pro Arg Glu Leu Met Asn Phe Lys Ser Phe Val Glu Glu Leu Asn
            260                 265                 270

Ser His His Asn Lys Lys His Gly Val Phe Ser Lys Leu Pro Arg Asn
        275                 280                 285

Pro Lys Thr Pro Thr Glu Arg Ile Tyr Trp Ala Asn Leu Ser Gln Cys
    290                 295                 300

Pro Arg Thr Leu Ala Thr Ser Gly Pro Ser Phe Trp Leu Pro Gln Glu
305                 310                 315                 320

Lys Lys Cys Lys Pro Val Asn Gln Pro Pro Phe Leu Leu Thr Ser Lys
                325                 330                 335

Gly Ser Gly Ala Lys Ala Cys Gln Met Ile Met Gly Ser Trp Asn Pro
            340                 345                 350

Val Gly Val Gly Arg Tyr Leu Asn Thr Trp Leu Met Glu Thr Lys Asp
        355                 360                 365

Arg Arg Gln Arg Tyr Arg Ser Leu Phe Leu Ser Gly Ser Lys Arg Tyr
    370                 375                 380

Leu Ser Asp Leu Ala Arg Asp Met Leu Met Gln Ile Arg Leu Phe Cys
385                 390                 395                 400

Trp Lys Gly Leu Glu Val Ile Asn Phe Gly Leu Ser Pro Met
                405                 410
```

<210> SEQ ID NO 2
<211> LENGTH: 418
<212> TYPE: PRT
<213> ORGANISM: Homo sapiens
<220> FEATURE:
<223> OTHER INFORMATION: C1ORF177 isoform2 (huLEM)
<300> PUBLICATION INFORMATION:
<308> DATABASE ACCESSION NUMBER: UniProt Q3ZCV2
<309> DATABASE ENTRY DATE: 2007-08-21

<400> SEQUENCE: 2

```
Met Arg Glu Ser Gln Asp Ala Ala Gly Ala His Gly Trp Asn Arg Val
1               5                   10                  15

Gly Ser Thr Ala Thr Lys Trp Phe Thr Gly Ala Pro Phe Gly Val Gln
            20                  25                  30

Ser His Arg Phe Asp Ile Ser Ala Val Tyr Pro Asn Trp Lys Lys Phe
        35                  40                  45
```

-continued

```
Ser Thr Phe Thr Glu Ala Pro Tyr Ser Thr Arg Tyr Ser Thr Gln Val
    50                  55                  60

Ser His Ile Gly Pro Gly Thr Tyr Ser Ser Lys Glu Thr Cys Phe Ser
65                  70                  75                  80

Lys Lys Lys Leu Met Lys Glu Val Asp Thr Gly Trp Ala Lys Ala Gln
                85                  90                  95

Glu Ala Thr Arg Leu Thr Gln Leu Pro His Phe Gln Tyr Gln Ala Ile
            100                 105                 110

Met Lys Glu Lys Arg Leu Lys Glu Gln Lys Leu Gly Pro Gly Ser Tyr
        115                 120                 125

Asn Leu Lys Asp Phe Leu Glu Gln Leu Arg Glu Lys Pro Cys Ser Thr
    130                 135                 140

Arg Gly Leu Leu Ser Ser Gly Glu Val Arg Phe Arg Gly Leu Thr Gly
145                 150                 155                 160

Asn Tyr Tyr Pro Gly Pro Gly Asn Tyr Gly Glu Lys Gly Asn Pro Tyr
                165                 170                 175

Thr Lys Leu Glu Glu Asn Ala Trp Asn Arg Ser His Ser Glu Gly Leu
            180                 185                 190

Met Cys Arg Met Ser Asn Lys Pro His Pro Arg Pro Tyr Gln Gly Ser
        195                 200                 205

Gly Leu Gly Pro Gly Thr Tyr Phe Phe Lys Ser Asp Leu Glu Thr Tyr
    210                 215                 220

Val Ala Arg Ser Val Gly Thr Arg Gly Pro Tyr Asp Thr Phe Ser Gly
225                 230                 235                 240

Asp Arg Ser Lys Pro Leu Pro Tyr Gly His Tyr Ser Met Gln Lys Lys
                245                 250                 255

Lys Pro Arg Glu Leu Met Asn Phe Lys Ser Phe Val Glu Glu Leu Asn
            260                 265                 270

Ser His His Asn Lys Lys His Gly Val Phe Ser Lys Leu Pro Arg Asn
        275                 280                 285

Pro Lys Thr Pro Thr Glu Arg Ile Tyr Trp Ala Asn Leu Ser Gln Cys
    290                 295                 300

Pro Arg Thr Leu Ala Thr Ser Gly Pro Ser Phe Trp Leu Pro Gln Glu
305                 310                 315                 320

Lys Lys Cys Lys Pro Val Asn Gln Pro Pro Phe Leu Leu Thr Ser Lys
                325                 330                 335

Gly Ser Gly Ala Lys Ala Cys Gln Met Ile Met Gly Ser Trp Asn Pro
            340                 345                 350

Val Gly Val Gly Arg Tyr Leu Asn Thr Trp Leu Met Glu Thr Lys Asp
        355                 360                 365

Arg Arg Gln Arg Tyr Arg Ser Leu Phe Leu Ser Gly Ser Lys Arg Tyr
    370                 375                 380

Leu Ser Asp Leu Ala Arg Asp Met Leu Met Gln Glu Arg Ile Thr Pro
385                 390                 395                 400

Phe Thr Lys Gly Lys Cys Pro Pro Thr Val Asp Tyr Asn Ser Asp Pro
                405                 410                 415

Thr Pro


<210> SEQ ID NO 3
<211> LENGTH: 395
<212> TYPE: PRT
<213> ORGANISM: Homo sapiens
<220> FEATURE:
<223> OTHER INFORMATION: C1ORF177 isoform 1(huLEM)
```

<400> SEQUENCE: 3

Met Arg Glu Ser Gln Asp Ala Ala Gly Ala His Gly Trp Asn Arg Val
1 5 10 15

Gly Ser Thr Ala Thr Lys Trp Phe Thr Gly Ala Pro Phe Gly Val Gln
20 25 30

Ser His Arg Phe Asp Ile Ser Ala Val Tyr Pro Asn Trp Lys Lys Phe
35 40 45

Ser Thr Phe Thr Glu Ala Pro Tyr Ser Thr Arg Tyr Ser Thr Gln Val
50 55 60

Ser His Ile Gly Pro Gly Thr Tyr Ser Ser Lys Glu Thr Cys Phe Ser
65 70 75 80

Lys Lys Lys Leu Met Lys Glu Val Asp Thr Gly Trp Ala Lys Ala Gln
85 90 95

Glu Ala Thr Arg Leu Thr Gln Leu Pro His Phe Gln Tyr Gln Ala Ile
100 105 110

Met Lys Glu Lys Arg Leu Lys Glu Gln Lys Leu Gly Pro Gly Ser Tyr
115 120 125

Asn Leu Lys Asp Phe Leu Glu Gln Leu Arg Glu Lys Pro Cys Ser Thr
130 135 140

Arg Gly Leu Leu Ser Ser Gly Glu Val Arg Phe Arg Gly Leu Thr Gly
145 150 155 160

Asn Tyr Tyr Pro Gly Pro Gly Asn Tyr Gly Glu Lys Gly Asn Pro Tyr
165 170 175

Thr Lys Leu Glu Glu Asn Ala Trp Asn Arg Ser His Ser Glu Gly Leu
180 185 190

Met Cys Arg Met Ser Asn Lys Pro His Pro Arg Pro His Gln Gly Ser
195 200 205

Gly Leu Gly Pro Gly Thr Tyr Phe Phe Lys Ser Asp Leu Glu Thr Tyr
210 215 220

Val Ala Arg Ser Val Gly Thr Arg Gly Pro Tyr Asp Thr Phe Ser Gly
225 230 235 240

Asp Arg Ser Lys Pro Leu Pro Tyr Gly His Tyr Ser Met Gln Lys Lys
245 250 255

Lys Pro Arg Glu Leu Met Asn Phe Lys Ser Phe Val Glu Glu Leu Asn
260 265 270

Ser His His Asn Lys Lys His Gly Val Phe Ser Lys Leu Pro Arg Asn
275 280 285

Pro Lys Thr Pro Thr Glu Arg Ile Tyr Trp Ala Asn Leu Ser Gln Cys
290 295 300

Pro Arg Thr Leu Ala Thr Ser Gly Pro Ser Phe Trp Leu Pro Gln Glu
305 310 315 320

Lys Lys Cys Lys Pro Val Asn Gln Pro Pro Phe Leu Leu Thr Ser Lys
325 330 335

Gly Ser Gly Ala Lys Ala Cys Gln Met Ile Met Gly Ser Trp Asn Pro
340 345 350

Val Gly Val Gly Arg Tyr Leu Asn Thr Trp Leu Met Glu Thr Lys Asp
355 360 365

Arg Arg Gln Arg Tyr Arg Ser Leu Phe Leu Ser Gly Ser Lys Arg Tyr
370 375 380

Leu Ser Asp Leu Ala Arg Asp Met Leu Met Gln
385 390 395

<210> SEQ ID NO 4

<211> LENGTH: 559
<212> TYPE: PRT
<213> ORGANISM: Homo sapiens
<220> FEATURE:
<223> OTHER INFORMATION: Glycerol kinase (Gyk)
<300> PUBLICATION INFORMATION:
<308> DATABASE ACCESSION NUMBER: UniProt Q14410
<309> DATABASE ENTRY DATE: 2001-01-11

<400> SEQUENCE: 4

```
Met Ala Ala Ser Lys Lys Ala Val Leu Gly Pro Leu Val Gly Ala Val
1               5                   10                  15

Asp Gln Gly Thr Ser Ser Thr Arg Phe Leu Val Phe Asn Ser Lys Thr
            20                  25                  30

Ala Glu Leu Leu Ser His His Gln Val Glu Ile Lys Gln Glu Phe Pro
        35                  40                  45

Arg Glu Gly Trp Val Glu Gln Asp Pro Lys Glu Ile Leu His Ser Val
    50                  55                  60

Tyr Glu Cys Ile Glu Lys Thr Cys Glu Lys Leu Gly Gln Leu Asn Ile
65                  70                  75                  80

Asp Ile Ser Asn Ile Lys Ala Ile Gly Val Ser Asn Gln Arg Glu Thr
                85                  90                  95

Thr Val Val Trp Asp Lys Ile Thr Gly Glu Pro Leu Tyr Asn Ala Val
            100                 105                 110

Val Trp Leu Asp Leu Arg Thr Gln Ser Thr Val Glu Ser Leu Ser Lys
        115                 120                 125

Arg Ile Pro Gly Asn Asn Asn Phe Val Lys Ser Lys Thr Gly Leu Pro
    130                 135                 140

Leu Ser Thr Tyr Phe Ser Ala Val Lys Leu Arg Trp Leu Leu Asp Asn
145                 150                 155                 160

Val Arg Lys Val Gln Lys Ala Val Glu Glu Lys Arg Ala Leu Phe Gly
                165                 170                 175

Thr Ile Asp Ser Trp Leu Ile Trp Ser Leu Thr Gly Gly Val Asn Gly
            180                 185                 190

Gly Val His Cys Thr Asp Val Thr Asn Ala Ser Arg Thr Met Leu Phe
        195                 200                 205

Asn Ile His Ser Leu Glu Trp Asp Lys Gln Leu Cys Glu Phe Phe Gly
    210                 215                 220

Ile Pro Met Glu Ile Leu Pro Asn Val Arg Ser Ser Ser Glu Ile Tyr
225                 230                 235                 240

Gly Leu Met Lys Ile Ser His Ser Val Lys Ala Gly Ala Leu Glu Gly
                245                 250                 255

Val Pro Ile Ser Gly Cys Leu Gly Asp Gln Ser Ala Ala Leu Val Gly
            260                 265                 270

Gln Met Cys Phe Gln Ile Gly Gln Ala Lys Asn Thr Tyr Gly Thr Gly
        275                 280                 285

Cys Phe Leu Leu Cys Asn Thr Gly His Lys Cys Val Phe Ser Asp His
    290                 295                 300

Gly Leu Leu Thr Thr Val Ala Tyr Lys Leu Gly Arg Asp Lys Pro Val
305                 310                 315                 320

Tyr Tyr Ala Leu Glu Gly Ser Val Ala Ile Ala Gly Ala Val Ile Arg
                325                 330                 335

Trp Leu Arg Asp Asn Leu Gly Ile Ile Lys Thr Ser Glu Glu Ile Glu
            340                 345                 350

Lys Leu Ala Lys Glu Val Gly Thr Ser Tyr Gly Cys Tyr Phe Val Pro
        355                 360                 365
```

```
Ala Phe Ser Gly Leu Tyr Ala Pro Tyr Trp Glu Pro Ser Ala Arg Gly
    370                 375                 380

Ile Ile Cys Gly Leu Thr Gln Phe Thr Asn Lys Cys His Ile Ala Phe
385                 390                 395                 400

Ala Ala Leu Glu Ala Val Cys Phe Gln Thr Arg Glu Ile Leu Asp Ala
                405                 410                 415

Met Asn Arg Asp Cys Gly Ile Pro Leu Ser His Leu Gln Val Asp Gly
            420                 425                 430

Gly Met Thr Ser Asn Lys Ile Leu Met Gln Leu Gln Ala Asp Ile Leu
        435                 440                 445

Tyr Ile Pro Val Val Lys Pro Ser Met Pro Glu Thr Thr Ala Leu Gly
    450                 455                 460

Ala Ala Met Ala Ala Gly Ala Ala Glu Gly Val Gly Val Trp Ser Leu
465                 470                 475                 480

Glu Pro Glu Asp Leu Ser Ala Val Thr Met Glu Arg Phe Glu Pro Gln
                485                 490                 495

Ile Asn Ala Glu Glu Ser Glu Ile Arg Tyr Ser Thr Trp Lys Lys Ala
            500                 505                 510

Val Met Lys Ser Met Gly Trp Val Thr Thr Gln Ser Pro Glu Ser Gly
        515                 520                 525

Asp Pro Ser Ile Phe Cys Ser Leu Pro Leu Gly Phe Phe Ile Val Ser
    530                 535                 540

Ser Met Val Met Leu Ile Gly Ala Arg Tyr Ile Ser Gly Ile Pro
545                 550                 555


<210> SEQ ID NO 5
<211> LENGTH: 553
<212> TYPE: PRT
<213> ORGANISM: Homo sapiens
<220> FEATURE:
<223> OTHER INFORMATION: Glycerol kinase (Gyk)
<300> PUBLICATION INFORMATION:
<308> DATABASE ACCESSION NUMBER: GenBank CAA55365.1
<309> DATABASE ENTRY DATE: 2008-10-07

<400> SEQUENCE: 5

Met Ala Ala Pro Lys Thr Ala Ala Val Gly Pro Leu Val Gly Ala Val
1               5                   10                  15

Val Gln Gly Thr Asn Ser Thr Arg Phe Leu Val Phe Asn Ser Lys Thr
            20                  25                  30

Ala Glu Leu Leu Ser His His Lys Val Glu Leu Thr Gln Glu Phe Pro
        35                  40                  45

Lys Glu Gly Trp Val Glu Gln Asp Pro Lys Glu Ile Leu Gln Ser Val
    50                  55                  60

Tyr Glu Cys Ile Ala Arg Thr Cys Glu Lys Leu Asp Glu Leu Asn Ile
65                  70                  75                  80

Asp Ile Ser Asn Ile Lys Ala Val Gly Val Ser Asn Gln Arg Glu Thr
                85                  90                  95

Thr Val Ile Trp Asp Lys Leu Thr Gly Glu Pro Leu Tyr Asn Ala Val
            100                 105                 110

Val Trp Leu Asp Leu Arg Thr Gln Thr Thr Val Glu Asp Leu Ser Lys
        115                 120                 125

Lys Ile Pro Gly Asn Ser Asn Phe Val Lys Ser Lys Thr Gly Leu Pro
    130                 135                 140

Leu Ser Thr Tyr Phe Ser Ala Val Lys Leu Arg Trp Met Leu Asp Asn
145                 150                 155                 160
```

-continued

```
Val Arg Asn Val Gln Lys Ala Val Glu Glu Gly Arg Ala Leu Phe Gly
                165                 170                 175

Thr Ile Asp Ser Trp Leu Ile Trp Ser Leu Thr Gly Gly Val Asn Gly
            180                 185                 190

Gly Val His Cys Thr Asp Val Thr Asn Ala Ser Arg Thr Met Leu Phe
        195                 200                 205

Asn Ile His Ser Leu Glu Trp Asp Lys Glu Leu Cys Asp Phe Phe Glu
    210                 215                 220

Ile Pro Met Asp Leu Leu Pro Asn Val Phe Ser Ser Ser Glu Ile Tyr
225                 230                 235                 240

Gly Leu Ile Lys Thr Gly Ala Leu Glu Gly Val Pro Ile Ser Gly Cys
                245                 250                 255

Leu Gly Asp Gln Cys Ala Ala Leu Val Gly Gln Met Cys Phe Gln Glu
            260                 265                 270

Gly Gln Ala Lys Asn Thr Tyr Gly Thr Gly Cys Phe Leu Leu Cys Asn
        275                 280                 285

Thr Gly Arg Lys Cys Val Phe Ser Glu His Gly Leu Leu Thr Thr Val
    290                 295                 300

Ala Tyr Lys Leu Gly Arg Glu Lys Pro Ala Tyr Tyr Ala Leu Glu Gly
305                 310                 315                 320

Ser Val Ala Ile Ala Gly Ala Val Ile Arg Trp Leu Arg Asp Asn Leu
                325                 330                 335

Gly Ile Ile Glu Thr Ser Gly Asp Ile Glu Arg Leu Ala Lys Glu Val
            340                 345                 350

Gly Thr Ser Tyr Gly Cys Tyr Phe Val Pro Ala Phe Ser Gly Leu Tyr
        355                 360                 365

Ala Pro Tyr Trp Glu Pro Ser Ala Arg Gly Ile Leu Cys Gly Leu Thr
    370                 375                 380

Gln Phe Thr Asn Lys Cys His Ile Ala Phe Ala Ala Leu Glu Ala Val
385                 390                 395                 400

Cys Phe Gln Thr Arg Glu Ile Leu Glu Ala Met Asn Arg Asp Cys Gly
                405                 410                 415

Ile Pro Leu Arg His Leu Gln Val Asp Gly Gly Met Thr Asn Asn Lys
            420                 425                 430

Val Leu Met Gln Leu Gln Ala Asp Ile Leu His Ile Pro Val Ile Lys
        435                 440                 445

Pro Phe Met Pro Glu Thr Thr Ala Leu Gly Ala Ala Met Ala Ala Gly
    450                 455                 460

Ala Ala Glu Gly Val Ser Val Trp Ser Leu Glu Pro Gln Ala Leu Ser
465                 470                 475                 480

Val Leu Arg Met Glu Arg Phe Glu Pro Gln Ile Gln Ala Thr Glu Ser
                485                 490                 495

Glu Ile Arg Tyr Ala Thr Trp Lys Lys Ala Val Met Lys Ser Met Gly
            500                 505                 510

Trp Val Thr Ser Gln Ser Pro Glu Gly Gly Asp Pro Ser Ile Phe Cys
        515                 520                 525

Ser Leu Pro Leu Gly Phe Phe Ile Val Ser Ser Met Val Met Leu Ile
    530                 535                 540

Gly Ala Arg Tyr Ile Ser Gly Val Pro
545                 550
```

<210> SEQ ID NO 6
<211> LENGTH: 553

<212> TYPE: PRT
<213> ORGANISM: Homo sapiens
<220> FEATURE:
<223> OTHER INFORMATION: Glycerol kinase (Gyk)
<300> PUBLICATION INFORMATION:
<308> DATABASE ACCESSION NUMBER: GenBank CAA55364.1
<309> DATABASE ENTRY DATE: 2005-04-18

<400> SEQUENCE: 6

```
Met Ala Ala Ser Lys Lys Ala Val Leu Gly Pro Leu Val Gly Ala Val
1               5                   10                  15

Asp Gln Gly Thr Ser Ser Thr Arg Phe Leu Val Phe Asn Ser Arg Thr
            20                  25                  30

Ala Glu Leu Leu Ser His His Gln Val Glu Ile Lys Gln Glu Phe Pro
        35                  40                  45

Arg Glu Gly Trp Val Glu Gln Asp Pro Lys Glu Ile Leu His Ser Val
    50                  55                  60

Tyr Glu Cys Ile Glu Lys Thr Cys Glu Lys Leu Gly Gln Leu Asn Ile
65                  70                  75                  80

Gly Ile Ser Asn Ile Lys Ala Ile Gly Val Ser Asn Gln Arg Glu Thr
                85                  90                  95

Thr Val Ala Trp Asp Lys Ile Thr Gly Glu Pro Leu Tyr Asn Ala Val
            100                 105                 110

Val Trp Leu Asp Leu Arg Thr Gln Ser Thr Val Glu Ser Leu Ser Lys
        115                 120                 125

Arg Ile Pro Gly Asn Asn Asn Phe Val Lys Ser Lys Thr Gly Leu Pro
    130                 135                 140

Leu Ser Thr Tyr Phe Ser Ala Val Lys Leu Arg Trp Leu Leu Asp Asn
145                 150                 155                 160

Val Arg Lys Val Gln Lys Ala Val Glu Glu Lys Arg Ala Leu Phe Gly
                165                 170                 175

Thr Ile Asp Ser Trp Leu Ile Trp Ser Leu Thr Gly Gly Val Asn Gly
            180                 185                 190

Gly Val His Cys Thr Asp Val Thr Asn Ala Ser Arg Thr Met Leu Phe
        195                 200                 205

Asn Ile His Ser Leu Glu Trp Asp Lys Gln Leu Cys Glu Phe Phe Gly
    210                 215                 220

Ile Pro Met Glu Ile Leu Pro His Val Arg Ser Ser Ser Glu Ile Tyr
225                 230                 235                 240

Gly Leu Met Lys Ala Gly Ala Leu Glu Gly Val Pro Ile Ser Gly Cys
                245                 250                 255

Leu Gly Asp Gln Ser Ala Ala Leu Val Gly Gln Met Cys Phe Gln Ile
            260                 265                 270

Gly Gln Ala Lys Asn Thr Tyr Gly Thr Gly Cys Phe Leu Leu Cys Asn
        275                 280                 285

Thr Gly His Lys Cys Val Phe Ser Asp His Gly Leu Leu Thr Thr Val
    290                 295                 300

Ala Tyr Lys Leu Gly Arg Asp Lys Pro Val Tyr Tyr Ala Leu Glu Gly
305                 310                 315                 320

Ser Val Ala Ile Ala Gly Ala Val Ile Arg Trp Leu Arg Asp Asn Leu
                325                 330                 335

Gly Ile Ile Lys Thr Ser Glu Glu Ile Glu Lys Leu Ala Lys Glu Val
            340                 345                 350

Gly Thr Ser Tyr Gly Cys Tyr Phe Val Pro Ala Phe Ser Gly Leu Tyr
        355                 360                 365
```

```
Ala Pro Tyr Trp Glu Pro Ser Ala Arg Gly Ile Ile Cys Gly Leu Thr
    370                 375                 380

Gln Phe Thr Asn Lys Cys His Ile Ala Phe Ala Ala Leu Glu Ala Val
385                 390                 395                 400

Cys Phe Gln Thr Arg Glu Ile Leu Asp Ala Met Asn Arg Asp Cys Gly
                405                 410                 415

Ile Pro Leu Ser His Leu Gln Val Asp Gly Gly Met Thr Ser Asn Lys
            420                 425                 430

Ile Leu Met Gln Leu Gln Ala Asp Ile Leu Tyr Ile Pro Val Val Lys
        435                 440                 445

Pro Leu Met Pro Glu Thr Thr Ala Leu Gly Ala Ala Met Ala Ala Gly
    450                 455                 460

Ala Ala Glu Gly Val Asp Val Trp Ser Leu Glu Pro Glu Asp Leu Ser
465                 470                 475                 480

Ala Val Thr Met Glu Arg Phe Glu Pro Gln Ile Asn Ala Glu Glu Ser
                485                 490                 495

Glu Ile Arg Tyr Ser Thr Trp Lys Lys Ala Val Met Lys Ser Met Gly
            500                 505                 510

Trp Val Thr Thr Gln Ser Pro Glu Gly Gly Asp Pro Ser Val Phe Cys
        515                 520                 525

Ser Leu Pro Leu Gly Phe Phe Ile Val Ser Ser Met Ala Met Leu Ile
    530                 535                 540

Gly Ala Arg Tyr Ile Ser Gly Ile Pro
545                 550


<210> SEQ ID NO 7
<211> LENGTH: 488
<212> TYPE: PRT
<213> ORGANISM: Homo sapiens
<220> FEATURE:
<223> OTHER INFORMATION: DAG O-acetyltransferase 1 (DGAT1)
<300> PUBLICATION INFORMATION:
<308> DATABASE ACCESSION NUMBER: UniProt O75907
<309> DATABASE ENTRY DATE: 2001-10-18

<400> SEQUENCE: 7

Met Gly Asp Arg Gly Ser Ser Arg Arg Arg Arg Thr Gly Ser Arg Pro
1               5                   10                  15

Ser Ser His Gly Gly Gly Gly Pro Ala Ala Ala Glu Glu Glu Val Arg
            20                  25                  30

Asp Ala Ala Ala Gly Pro Asp Val Gly Ala Ala Gly Asp Ala Pro Ala
        35                  40                  45

Pro Ala Pro Asn Lys Asp Gly Asp Ala Gly Val Gly Ser Gly His Trp
    50                  55                  60

Glu Leu Arg Cys His Arg Leu Gln Asp Ser Leu Phe Ser Ser Asp Ser
65                  70                  75                  80

Gly Phe Ser Asn Tyr Arg Gly Ile Leu Asn Trp Cys Val Val Met Leu
                85                  90                  95

Ile Leu Ser Asn Ala Arg Leu Phe Leu Glu Asn Leu Ile Lys Tyr Gly
            100                 105                 110

Ile Leu Val Asp Pro Ile Gln Val Val Ser Leu Phe Leu Lys Asp Pro
        115                 120                 125

Tyr Ser Trp Pro Ala Pro Cys Leu Val Ile Ala Ala Asn Val Phe Ala
    130                 135                 140

Val Ala Ala Phe Gln Val Glu Lys Arg Leu Ala Val Gly Ala Leu Thr
145                 150                 155                 160
```

```
Glu Gln Ala Gly Leu Leu Leu His Val Ala Asn Leu Ala Thr Ile Leu
                165                 170                 175

Cys Phe Pro Ala Ala Val Val Leu Leu Val Glu Ser Ile Thr Pro Val
            180                 185                 190

Gly Ser Leu Leu Ala Leu Met Ala His Thr Ile Leu Phe Leu Lys Leu
        195                 200                 205

Phe Ser Tyr Arg Asp Val Asn Ser Trp Cys Arg Arg Ala Arg Ala Lys
    210                 215                 220

Ala Ala Ser Ala Gly Lys Lys Ala Ser Ser Ala Ala Ala Pro His Thr
225                 230                 235                 240

Val Ser Tyr Pro Asp Asn Leu Thr Tyr Arg Asp Leu Tyr Tyr Phe Leu
                245                 250                 255

Phe Ala Pro Thr Leu Cys Tyr Glu Leu Asn Phe Pro Arg Ser Pro Arg
            260                 265                 270

Ile Arg Lys Arg Phe Leu Leu Arg Arg Ile Leu Glu Met Leu Phe Phe
        275                 280                 285

Thr Gln Leu Gln Val Gly Leu Ile Gln Gln Trp Met Val Pro Thr Ile
    290                 295                 300

Gln Asn Ser Met Lys Pro Phe Lys Asp Met Asp Tyr Ser Arg Ile Ile
305                 310                 315                 320

Glu Arg Leu Leu Lys Leu Ala Val Pro Asn His Leu Ile Trp Leu Ile
                325                 330                 335

Phe Phe Tyr Trp Leu Phe His Ser Cys Leu Asn Ala Val Ala Glu Leu
            340                 345                 350

Met Gln Phe Gly Asp Arg Glu Phe Tyr Arg Asp Trp Trp Asn Ser Glu
        355                 360                 365

Ser Val Thr Tyr Phe Trp Gln Asn Trp Asn Ile Pro Val His Lys Trp
    370                 375                 380

Cys Ile Arg His Phe Tyr Lys Pro Met Leu Arg Arg Gly Ser Ser Lys
385                 390                 395                 400

Trp Met Ala Arg Thr Gly Val Phe Leu Ala Ser Ala Phe Phe His Glu
                405                 410                 415

Tyr Leu Val Ser Val Pro Leu Arg Met Phe Arg Leu Trp Ala Phe Thr
            420                 425                 430

Gly Met Met Ala Gln Ile Pro Leu Ala Trp Phe Val Gly Arg Phe Phe
        435                 440                 445

Gln Gly Asn Tyr Gly Asn Ala Ala Val Trp Leu Ser Leu Ile Ile Gly
    450                 455                 460

Gln Pro Ile Ala Val Leu Met Tyr Val His Asp Tyr Tyr Val Leu Asn
465                 470                 475                 480

Tyr Glu Ala Pro Ala Ala Glu Ala
                485
```

<210> SEQ ID NO 8
<211> LENGTH: 828
<212> TYPE: PRT
<213> ORGANISM: Homo sapiens
<220> FEATURE:
<223> OTHER INFORMATION: Glycerol-3-phosphate acetyltransferase mitochondrial (GPAM)
<300> PUBLICATION INFORMATION:
<308> DATABASE ACCESSION NUMBER: UniProt Q9HCL2
<309> DATABASE ENTRY DATE: 2001-06-01

<400> SEQUENCE: 8

```
Met Asp Glu Ser Ala Leu Thr Leu Gly Thr Ile Asp Val Ser Tyr Leu
1               5                   10                  15
```

```
Pro His Ser Ser Glu Tyr Ser Val Gly Arg Cys Lys His Thr Ser Glu
            20                  25                  30

Glu Trp Gly Glu Cys Gly Phe Arg Pro Thr Ile Phe Arg Ser Ala Thr
        35                  40                  45

Leu Lys Trp Lys Glu Ser Leu Met Ser Arg Lys Arg Pro Phe Val Gly
    50                  55                  60

Arg Cys Cys Tyr Ser Cys Thr Pro Gln Ser Trp Asp Lys Phe Phe Asn
65                  70                  75                  80

Pro Ser Ile Pro Ser Leu Gly Leu Arg Asn Val Ile Tyr Ile Asn Glu
                85                  90                  95

Thr His Thr Arg His Arg Gly Trp Leu Ala Arg Arg Leu Ser Tyr Val
            100                 105                 110

Leu Phe Ile Gln Glu Arg Asp Val His Lys Gly Met Phe Ala Thr Asn
        115                 120                 125

Val Thr Glu Asn Val Leu Asn Ser Ser Arg Val Gln Glu Ala Ile Ala
    130                 135                 140

Glu Val Ala Ala Glu Leu Asn Pro Asp Gly Ser Ala Gln Gln Gln Ser
145                 150                 155                 160

Lys Ala Val Asn Lys Val Lys Lys Lys Ala Lys Arg Ile Leu Gln Glu
                165                 170                 175

Met Val Ala Thr Val Ser Pro Ala Met Ile Arg Leu Thr Gly Trp Val
            180                 185                 190

Leu Leu Lys Leu Phe Asn Ser Phe Phe Trp Asn Ile Gln Ile His Lys
        195                 200                 205

Gly Gln Leu Glu Met Val Lys Ala Ala Thr Glu Thr Asn Leu Pro Leu
    210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255

Asn Asn Leu Asn Ile Pro Ile Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285

Asp Val Leu Tyr Arg Ala Leu Leu His Gly His Ile Val Glu Leu Leu
    290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Thr Asn Val Ile Pro Asp Ile Leu Ile Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
    370                 375                 380

Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415

Pro Val Ser Ala Leu Leu Ser Leu Glu Gln Ala Leu Leu Pro Ala Ile
            420                 425                 430
```

```
Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile Asp Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
    530                 535                 540

Thr Ile Thr His Thr Ser Arg Asn Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Leu Tyr Ala
            580                 585                 590

Val Leu Asn Lys Arg Gly Leu Gly Gly Pro Thr Ser Thr Pro Pro Asn
        595                 600                 605

Leu Ile Ser Gln Glu Gln Leu Val Arg Lys Ala Ala Ser Leu Cys Tyr
    610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
                645                 650                 655

Thr Val Ala Glu His Asp Asp Gln Glu Asp Ile Ser Pro Ser Leu Ala
            660                 665                 670

Glu Gln Gln Trp Asp Lys Lys Leu Pro Glu Pro Leu Ser Trp Arg Ser
        675                 680                 685

Asp Glu Glu Asp Glu Asp Ser Asp Phe Gly Glu Glu Gln Arg Asp Cys
    690                 695                 700

Tyr Leu Lys Val Ser Gln Ser Lys Glu His Gln Gln Phe Ile Thr Phe
705                 710                 715                 720

Leu Gln Arg Leu Leu Gly Pro Leu Leu Glu Ala Tyr Ser Ser Ala Ala
                725                 730                 735

Ile Phe Val His Asn Phe Ser Gly Pro Val Pro Glu Pro Glu Tyr Leu
            740                 745                 750

Gln Lys Leu His Lys Tyr Leu Ile Thr Arg Thr Glu Arg Asn Val Ala
        755                 760                 765

Val Tyr Ala Glu Ser Ala Thr Tyr Cys Leu Val Lys Asn Ala Val Lys
    770                 775                 780

Met Phe Lys Asp Ile Gly Val Phe Lys Glu Thr Lys Gln Lys Arg Val
785                 790                 795                 800

Ser Val Leu Glu Leu Ser Ser Thr Phe Leu Pro Gln Cys Asn Arg Gln
                805                 810                 815

Lys Leu Leu Glu Tyr Ile Leu Ser Phe Val Val Leu
            820                 825
```

<210> SEQ ID NO 9
<211> LENGTH: 335
<212> TYPE: PRT

```
<213> ORGANISM: Homo sapiens
<220> FEATURE:
<223> OTHER INFORMATION: Monoacylglycerol O-acetyltransferase (MOGAT1)
<300> PUBLICATION INFORMATION:
<308> DATABASE ACCESSION NUMBER: UniProt Q96PD6
<309> DATABASE ENTRY DATE: 2006-09-05

<400> SEQUENCE: 9

Met Lys Val Glu Phe Ala Pro Leu Asn Ile Gln Leu Ala Arg Arg Leu
1               5                   10                  15

Gln Thr Val Ala Val Leu Gln Trp Val Leu Lys Tyr Leu Leu Leu Gly
            20                  25                  30

Pro Met Ser Ile Gly Ile Thr Val Met Leu Ile Ile His Asn Tyr Leu
        35                  40                  45

Phe Leu Tyr Ile Pro Tyr Leu Met Trp Leu Tyr Phe Asp Trp His Thr
    50                  55                  60

Pro Glu Arg Gly Gly Arg Arg Ser Ser Trp Ile Lys Asn Trp Thr Leu
65                  70                  75                  80

Trp Lys His Phe Lys Asp Tyr Phe Pro Ile His Leu Ile Lys Thr Gln
                85                  90                  95

Asp Leu Asp Pro Ser His Asn Tyr Ile Phe Gly Phe His Pro His Gly
            100                 105                 110

Ile Met Ala Val Gly Ala Phe Gly Asn Phe Ser Val Asn Tyr Ser Asp
        115                 120                 125

Phe Lys Asp Leu Phe Pro Gly Phe Thr Ser Tyr Leu His Val Leu Pro
    130                 135                 140

Leu Trp Phe Trp Cys Pro Val Phe Arg Glu Tyr Val Met Ser Val Gly
145                 150                 155                 160

Leu Val Ser Val Ser Lys Lys Ser Val Ser Tyr Met Val Ser Lys Glu
                165                 170                 175

Gly Gly Gly Asn Ile Ser Val Ile Val Leu Gly Gly Ala Lys Glu Ser
            180                 185                 190

Leu Asp Ala His Pro Gly Lys Phe Thr Leu Phe Ile Arg Gln Arg Lys
        195                 200                 205

Gly Phe Val Lys Ile Ala Leu Thr His Gly Ala Ser Leu Val Pro Val
    210                 215                 220

Val Ser Phe Gly Glu Asn Glu Leu Phe Lys Gln Thr Asp Asn Pro Glu
225                 230                 235                 240

Gly Ser Trp Ile Arg Thr Val Gln Asn Lys Leu Gln Lys Ile Met Gly
                245                 250                 255

Phe Ala Leu Pro Leu Phe His Ala Arg Gly Val Phe Gln Tyr Asn Phe
            260                 265                 270

Gly Leu Met Thr Tyr Arg Lys Ala Ile His Thr Val Val Gly Arg Pro
        275                 280                 285

Ile Pro Val Arg Gln Thr Leu Asn Pro Thr Gln Glu Gln Ile Glu Glu
    290                 295                 300

Leu His Gln Thr Tyr Met Glu Glu Leu Arg Lys Leu Phe Glu Glu His
305                 310                 315                 320

Lys Gly Lys Tyr Gly Ile Pro Glu His Glu Thr Leu Val Leu Lys
                325                 330                 335


<210> SEQ ID NO 10
<211> LENGTH: 826
<212> TYPE: PRT
<213> ORGANISM: Homo sapiens
<220> FEATURE:
<223> OTHER INFORMATION: HIF1alpha
```

-continued

<300> PUBLICATION INFORMATION:
<308> DATABASE ACCESSION NUMBER: UniProt Q16665
<309> DATABASE ENTRY DATE: 1997-11-01

<400> SEQUENCE: 10

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
```

```
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815
```

```
Glu Leu Leu Arg Ala Leu Asp Gln Val Asn
            820                 825


<210> SEQ ID NO 11
<211> LENGTH: 488
<212> TYPE: PRT
<213> ORGANISM: Homo sapiens
<220> FEATURE:
<223> OTHER INFORMATION: DAG O-acetyltransferase 1 (DGAT1)
<300> PUBLICATION INFORMATION:
<308> DATABASE ACCESSION NUMBER: NCBI NP_036211.2
<309> DATABASE ENTRY DATE: 2007-04-27

<400> SEQUENCE: 11

Met Gly Asp Arg Gly Ser Ser Arg Arg Arg Arg Thr Gly Ser Arg Pro
1               5                   10                  15

Ser Ser His Gly Gly Gly Gly Pro Ala Ala Ala Glu Glu Glu Val Arg
            20                  25                  30

Asp Ala Ala Ala Gly Pro Asp Val Gly Ala Ala Gly Asp Ala Pro Ala
        35                  40                  45

Pro Ala Pro Asn Lys Asp Gly Asp Ala Gly Val Gly Ser Gly His Trp
    50                  55                  60

Glu Leu Arg Cys His Arg Leu Gln Asp Ser Leu Phe Ser Ser Asp Ser
65                  70                  75                  80

Gly Phe Ser Asn Tyr Arg Gly Ile Leu Asn Trp Cys Val Val Met Leu
                85                  90                  95

Ile Leu Ser Asn Ala Arg Leu Phe Leu Glu Asn Leu Ile Lys Tyr Gly
            100                 105                 110

Ile Leu Val Asp Pro Ile Gln Val Val Ser Leu Phe Leu Lys Asp Pro
        115                 120                 125

Tyr Ser Trp Pro Ala Pro Cys Leu Val Ile Ala Ala Asn Val Phe Ala
    130                 135                 140

Val Ala Ala Phe Gln Val Glu Lys Arg Leu Ala Val Gly Ala Leu Thr
145                 150                 155                 160

Glu Gln Ala Gly Leu Leu Leu His Val Ala Asn Leu Ala Thr Ile Leu
                165                 170                 175

Cys Phe Pro Ala Ala Val Val Leu Leu Val Glu Ser Ile Thr Pro Val
            180                 185                 190

Gly Ser Leu Leu Ala Leu Met Ala His Thr Ile Leu Phe Leu Lys Leu
        195                 200                 205

Phe Ser Tyr Arg Asp Val Asn Ser Trp Cys Arg Arg Ala Arg Ala Lys
    210                 215                 220

Ala Ala Ser Ala Gly Lys Lys Ala Ser Ser Ala Ala Ala Pro His Thr
225                 230                 235                 240

Val Ser Tyr Pro Asp Asn Leu Thr Tyr Arg Asp Leu Tyr Tyr Phe Leu
                245                 250                 255

Phe Ala Pro Thr Leu Cys Tyr Glu Leu Asn Phe Pro Arg Ser Pro Arg
            260                 265                 270

Ile Arg Lys Arg Phe Leu Leu Arg Arg Ile Leu Glu Met Leu Phe Phe
        275                 280                 285

Thr Gln Leu Gln Val Gly Leu Ile Gln Gln Trp Met Val Pro Thr Ile
    290                 295                 300

Gln Asn Ser Met Lys Pro Phe Lys Asp Met Asp Tyr Ser Arg Ile Ile
305                 310                 315                 320

Glu Arg Leu Leu Lys Leu Ala Val Pro Asn His Leu Ile Trp Leu Ile
                325                 330                 335
```

```
Phe Phe Tyr Trp Leu Phe His Ser Cys Leu Asn Ala Val Ala Glu Leu
            340                 345                 350

Met Gln Phe Gly Asp Arg Glu Phe Tyr Arg Asp Trp Trp Asn Ser Glu
        355                 360                 365

Ser Val Thr Tyr Phe Trp Gln Asn Trp Asn Ile Pro Val His Lys Trp
    370                 375                 380

Cys Ile Arg His Phe Tyr Lys Pro Met Leu Arg Arg Gly Ser Ser Lys
385                 390                 395                 400

Trp Met Ala Arg Thr Gly Val Phe Leu Ala Ser Ala Phe Phe His Glu
                405                 410                 415

Tyr Leu Val Ser Val Pro Leu Arg Met Phe Arg Leu Trp Ala Phe Thr
            420                 425                 430

Gly Met Met Ala Gln Ile Pro Leu Ala Trp Phe Val Gly Arg Phe Phe
        435                 440                 445

Gln Gly Asn Tyr Gly Asn Ala Ala Val Trp Leu Ser Leu Ile Ile Gly
    450                 455                 460

Gln Pro Ile Ala Val Leu Met Tyr Val His Asp Tyr Tyr Val Leu Asn
465                 470                 475                 480

Tyr Glu Ala Pro Ala Ala Glu Ala
                485


<210> SEQ ID NO 12
<211> LENGTH: 622
<212> TYPE: PRT
<213> ORGANISM: Homo sapiens
<220> FEATURE:
<223> OTHER INFORMATION: PCK1
<300> PUBLICATION INFORMATION:
<308> DATABASE ACCESSION NUMBER: UniProt P35558
<309> DATABASE ENTRY DATE: 1994-06-01

<400> SEQUENCE: 12

Met Pro Pro Gln Leu Gln Asn Gly Leu Asn Leu Ser Ala Lys Val Val
1               5                   10                  15

Gln Gly Ser Leu Asp Ser Leu Pro Gln Ala Val Arg Glu Phe Leu Glu
            20                  25                  30

Asn Asn Ala Glu Leu Cys Gln Pro Asp His Ile His Ile Cys Asp Gly
        35                  40                  45

Ser Glu Glu Glu Asn Gly Arg Leu Leu Gly Gln Met Glu Glu Glu Gly
    50                  55                  60

Ile Leu Arg Arg Leu Lys Lys Tyr Asp Asn Cys Trp Leu Ala Leu Thr
65                  70                  75                  80

Asp Pro Arg Asp Val Ala Arg Ile Glu Ser Lys Thr Val Ile Val Thr
                85                  90                  95

Gln Glu Gln Arg Asp Thr Val Pro Ile Pro Lys Thr Gly Leu Ser Gln
            100                 105                 110

Leu Gly Arg Trp Met Ser Glu Glu Asp Phe Glu Lys Ala Phe Asn Ala
        115                 120                 125

Arg Phe Pro Gly Cys Met Lys Gly Arg Thr Met Tyr Val Ile Pro Phe
    130                 135                 140

Ser Met Gly Pro Leu Gly Ser Pro Leu Ser Lys Ile Gly Ile Glu Leu
145                 150                 155                 160

Thr Asp Ser Pro Tyr Val Val Ala Ser Met Arg Ile Met Thr Arg Met
                165                 170                 175

Gly Thr Pro Val Leu Glu Ala Val Gly Asp Gly Glu Phe Val Lys Cys
            180                 185                 190
```

-continued

```
Leu His Ser Val Gly Cys Pro Leu Pro Leu Gln Lys Pro Leu Val Asn
        195                 200                 205

Asn Trp Pro Cys Asn Pro Glu Leu Thr Leu Ile Ala His Leu Pro Asp
    210                 215                 220

Arg Arg Glu Ile Ile Ser Phe Gly Ser Gly Tyr Gly Gly Asn Ser Leu
225                 230                 235                 240

Leu Gly Lys Lys Cys Phe Ala Leu Arg Met Ala Ser Arg Leu Ala Lys
                245                 250                 255

Glu Glu Gly Trp Leu Ala Glu His Met Leu Ile Leu Gly Ile Thr Asn
            260                 265                 270

Pro Glu Gly Glu Lys Lys Tyr Leu Ala Ala Ala Phe Pro Ser Ala Cys
        275                 280                 285

Gly Lys Thr Asn Leu Ala Met Met Asn Pro Ser Leu Pro Gly Trp Lys
    290                 295                 300

Val Glu Cys Val Gly Asp Asp Ile Ala Trp Met Lys Phe Asp Ala Gln
305                 310                 315                 320

Gly His Leu Arg Ala Ile Asn Pro Glu Asn Gly Phe Phe Gly Val Ala
                325                 330                 335

Pro Gly Thr Ser Val Lys Thr Asn Pro Asn Ala Ile Lys Thr Ile Gln
            340                 345                 350

Lys Asn Thr Ile Phe Thr Asn Val Ala Glu Thr Ser Asp Gly Gly Val
        355                 360                 365

Tyr Trp Glu Gly Ile Asp Glu Pro Leu Ala Ser Gly Val Thr Ile Thr
    370                 375                 380

Ser Trp Lys Asn Lys Glu Trp Ser Ser Glu Asp Gly Glu Pro Cys Ala
385                 390                 395                 400

His Pro Asn Ser Arg Phe Cys Thr Pro Ala Ser Gln Cys Pro Ile Ile
                405                 410                 415

Asp Ala Ala Trp Glu Ser Pro Glu Gly Val Pro Ile Glu Gly Ile Ile
            420                 425                 430

Phe Gly Gly Arg Arg Pro Ala Gly Val Pro Leu Val Tyr Glu Ala Leu
        435                 440                 445

Ser Trp Gln His Gly Val Phe Val Gly Ala Ala Met Arg Ser Glu Ala
    450                 455                 460

Thr Ala Ala Ala Glu His Lys Gly Lys Ile Ile Met His Asp Pro Phe
465                 470                 475                 480

Ala Met Arg Pro Phe Phe Gly Tyr Asn Phe Gly Lys Tyr Leu Ala His
                485                 490                 495

Trp Leu Ser Met Ala Gln His Pro Ala Ala Lys Leu Pro Lys Ile Phe
            500                 505                 510

His Val Asn Trp Phe Arg Lys Asp Lys Glu Gly Lys Phe Leu Trp Pro
        515                 520                 525

Gly Phe Gly Glu Asn Ser Arg Val Leu Glu Trp Met Phe Asn Arg Ile
    530                 535                 540

Asp Gly Lys Ala Ser Thr Lys Leu Thr Pro Ile Gly Tyr Ile Pro Lys
545                 550                 555                 560

Glu Asp Ala Leu Asn Leu Lys Gly Leu Gly His Ile Asn Met Met Glu
                565                 570                 575

Leu Phe Ser Ile Ser Lys Glu Phe Trp Glu Lys Glu Val Glu Asp Ile
            580                 585                 590

Glu Lys Tyr Leu Glu Asp Gln Val Asn Ala Asp Leu Pro Cys Glu Ile
        595                 600                 605
```

Glu Arg Glu Ile Leu Ala Leu Lys Gln Arg Ile Ser Gln Met
    610                 615                 620

<210> SEQ ID NO 13
<211> LENGTH: 257
<212> TYPE: PRT
<213> ORGANISM: Homo sapiens
<220> FEATURE:
<223> OTHER INFORMATION: AGPAT1
<300> PUBLICATION INFORMATION:
<308> DATABASE ACCESSION NUMBER: UniProt Q99943
<309> DATABASE ENTRY DATE: 1998-12-15

<400> SEQUENCE: 13

Phe Cys Ser Pro Ser Ala Lys Tyr Phe Phe Lys Met Ala Phe Tyr Asn
1               5                   10                  15

Gly Trp Ile Leu Phe Leu Ala Val Leu Ala Ile Pro Val Cys Ala Val
            20                  25                  30

Arg Gly Arg Asn Val Glu Asn Met Lys Ile Leu Arg Leu Met Leu Leu
        35                  40                  45

His Ile Lys Tyr Leu Tyr Gly Ile Arg Val Glu Val Arg Gly Ala His
    50                  55                  60

His Phe Pro Pro Ser Gln Pro Tyr Val Val Val Ser Asn His Gln Ser
65                  70                  75                  80

Ser Leu Asp Leu Leu Gly Met Met Glu Val Leu Pro Gly Arg Cys Val
                85                  90                  95

Pro Ile Ala Lys Arg Glu Leu Leu Trp Ala Gly Ser Ala Gly Leu Ala
            100                 105                 110

Cys Trp Leu Ala Gly Val Ile Phe Ile Asp Arg Lys Arg Thr Gly Asp
        115                 120                 125

Ala Ile Ser Val Met Ser Glu Val Ala Gln Thr Leu Leu Thr Gln Asp
    130                 135                 140

Val Arg Val Trp Val Phe Pro Glu Gly Thr Arg Asn His Asn Gly Ser
145                 150                 155                 160

Met Leu Pro Phe Lys Arg Gly Ala Phe His Leu Ala Val Gln Ala Gln
                165                 170                 175

Val Pro Ile Val Pro Ile Val Met Ser Ser Tyr Gln Asp Phe Tyr Cys
            180                 185                 190

Lys Lys Glu Arg Arg Phe Thr Ser Gly Gln Cys Gln Val Arg Val Leu
        195                 200                 205

Pro Pro Val Pro Thr Glu Gly Leu Thr Pro Asp Asp Val Pro Ala Leu
    210                 215                 220

Ala Asp Arg Val Arg His Ser Met Leu Thr Val Phe Arg Glu Ile Ser
225                 230                 235                 240

Thr Asp Gly Arg Gly Gly Gly Asp Tyr Leu Lys Lys Pro Gly Gly Gly
                245                 250                 255

Gly

<210> SEQ ID NO 14
<211> LENGTH: 255
<212> TYPE: PRT
<213> ORGANISM: Homo sapiens
<220> FEATURE:
<223> OTHER INFORMATION: AGPAT2 isoform alpha precursor
<300> PUBLICATION INFORMATION:
<308> DATABASE ACCESSION NUMBER: UniProt O15120
<309> DATABASE ENTRY DATE: 1998-12-15

<400> SEQUENCE: 14

-continued

```
Ala Glu Phe Tyr Ala Lys Val Ala Leu Tyr Cys Ala Leu Cys Phe Thr
1               5                   10                  15

Val Ser Ala Val Ala Ser Leu Val Cys Leu Leu Arg His Gly Gly Arg
            20                  25                  30

Thr Val Glu Asn Met Ser Ile Ile Gly Trp Phe Val Arg Ser Phe Lys
        35                  40                  45

Tyr Phe Tyr Gly Leu Arg Phe Glu Val Arg Asp Pro Arg Arg Leu Gln
    50                  55                  60

Glu Ala Arg Pro Cys Val Ile Val Ser Asn His Gln Ser Ile Leu Asp
65                  70                  75                  80

Met Met Gly Leu Met Glu Val Leu Pro Glu Arg Cys Val Gln Ile Ala
                85                  90                  95

Lys Arg Glu Leu Leu Phe Leu Gly Pro Val Gly Leu Ile Met Tyr Leu
            100                 105                 110

Gly Gly Val Phe Phe Ile Asn Arg Gln Arg Ser Ser Thr Ala Met Thr
        115                 120                 125

Val Met Ala Asp Leu Gly Glu Arg Met Val Arg Glu Asn Leu Lys Val
    130                 135                 140

Trp Ile Tyr Pro Glu Gly Thr Arg Asn Asp Asn Gly Asp Leu Leu Pro
145                 150                 155                 160

Phe Lys Lys Gly Ala Phe Tyr Leu Ala Val Gln Ala Gln Val Pro Ile
                165                 170                 175

Val Pro Val Val Tyr Ser Ser Phe Ser Ser Phe Tyr Asn Thr Lys Lys
            180                 185                 190

Lys Phe Phe Thr Ser Gly Thr Val Thr Val Gln Val Leu Glu Ala Ile
        195                 200                 205

Pro Thr Ser Gly Leu Thr Ala Ala Asp Val Pro Ala Leu Val Asp Thr
    210                 215                 220

Cys His Arg Ala Met Arg Thr Thr Phe Leu His Ile Ser Lys Thr Pro
225                 230                 235                 240

Gln Glu Asn Gly Ala Thr Ala Gly Ser Gly Val Gln Pro Ala Gln
                245                 250                 255


<210> SEQ ID NO 15
<211> LENGTH: 223
<212> TYPE: PRT
<213> ORGANISM: Homo sapiens
<220> FEATURE:
<223> OTHER INFORMATION: AGPAT2 isoform beta precursor
<300> PUBLICATION INFORMATION:
<308> DATABASE ACCESSION NUMBER: NCBI NP_001012745.1
<309> DATABASE ENTRY DATE: 2008-07-01

<400> SEQUENCE: 15

Ala Glu Phe Tyr Ala Lys Val Ala Leu Tyr Cys Ala Leu Cys Phe Thr
1               5                   10                  15

Val Ser Ala Val Ala Ser Leu Val Cys Leu Leu Arg His Gly Gly Arg
            20                  25                  30

Thr Val Glu Asn Met Ser Ile Ile Gly Trp Phe Val Arg Ser Phe Lys
        35                  40                  45

Tyr Phe Tyr Gly Leu Arg Phe Glu Val Arg Asp Pro Arg Arg Leu Gln
    50                  55                  60

Glu Ala Arg Pro Cys Val Ile Val Ser Asn His Gln Ser Ile Leu Asp
65                  70                  75                  80

Met Met Gly Leu Met Glu Val Leu Pro Glu Arg Cys Val Gln Ile Ala
                85                  90                  95
```

```
Lys Arg Glu Leu Leu Phe Leu Gly Pro Val Gly Leu Ile Met Tyr Leu
            100                 105                 110

Gly Gly Val Phe Phe Ile Asn Arg Gln Arg Ser Ser Thr Ala Met Thr
        115                 120                 125

Val Met Ala Asp Leu Gly Glu Arg Met Val Arg Glu Asn Val Pro Ile
    130                 135                 140

Val Pro Val Val Tyr Ser Ser Phe Ser Ser Phe Tyr Asn Thr Lys Lys
145                 150                 155                 160

Lys Phe Phe Thr Ser Gly Thr Val Thr Val Gln Val Leu Glu Ala Ile
                165                 170                 175

Pro Thr Ser Gly Leu Thr Ala Ala Asp Val Pro Ala Leu Val Asp Thr
            180                 185                 190

Cys His Arg Ala Met Arg Thr Thr Phe Leu His Ile Ser Lys Thr Pro
        195                 200                 205

Gln Glu Asn Gly Ala Thr Ala Gly Ser Gly Val Gln Pro Ala Gln
    210                 215                 220


<210> SEQ ID NO 16
<211> LENGTH: 376
<212> TYPE: PRT
<213> ORGANISM: Homo sapiens
<220> FEATURE:
<223> OTHER INFORMATION: AGPAT3
<300> PUBLICATION INFORMATION:
<308> DATABASE ACCESSION NUMBER: UniProt Q9NRZ7
<309> DATABASE ENTRY DATE: 2001-01-11

<400> SEQUENCE: 16

Met Gly Leu Leu Ala Phe Leu Lys Thr Gln Phe Val Leu His Leu Leu
1               5                   10                  15

Val Gly Phe Val Phe Val Val Ser Gly Leu Val Ile Asn Phe Val Gln
            20                  25                  30

Leu Cys Thr Leu Ala Leu Trp Pro Val Ser Lys Gln Leu Tyr Arg Arg
        35                  40                  45

Leu Asn Cys Arg Leu Ala Tyr Ser Leu Trp Ser Gln Leu Val Met Leu
    50                  55                  60

Leu Glu Trp Trp Ser Cys Thr Glu Cys Thr Leu Phe Thr Asp Gln Ala
65                  70                  75                  80

Thr Val Glu Arg Phe Gly Lys Glu His Ala Val Ile Ile Leu Asn His
                85                  90                  95

Asn Phe Glu Ile Asp Phe Leu Cys Gly Trp Thr Met Cys Glu Arg Phe
            100                 105                 110

Gly Val Leu Gly Ser Ser Lys Val Leu Ala Lys Lys Glu Leu Leu Tyr
        115                 120                 125

Val Pro Leu Ile Gly Trp Thr Trp Tyr Phe Leu Glu Ile Val Phe Cys
    130                 135                 140

Lys Arg Lys Trp Glu Glu Asp Arg Asp Thr Val Val Glu Gly Leu Arg
145                 150                 155                 160

Arg Leu Ser Asp Tyr Pro Glu Tyr Met Trp Phe Leu Leu Tyr Cys Glu
                165                 170                 175

Gly Thr Arg Phe Thr Glu Thr Lys His Arg Val Ser Met Glu Val Ala
            180                 185                 190

Ala Ala Lys Gly Leu Pro Val Leu Lys Tyr His Leu Leu Pro Arg Thr
        195                 200                 205

Lys Gly Phe Thr Thr Ala Val Lys Cys Leu Arg Gly Thr Val Ala Ala
    210                 215                 220
```

-continued

```
Val Tyr Asp Val Thr Leu Asn Phe Arg Gly Asn Lys Asn Pro Ser Leu
225                 230                 235                 240

Leu Gly Ile Leu Tyr Gly Lys Lys Tyr Glu Ala Asp Met Cys Val Arg
                245                 250                 255

Arg Phe Pro Leu Glu Asp Ile Pro Leu Asp Glu Lys Glu Ala Ala Gln
            260                 265                 270

Trp Leu His Lys Leu Tyr Gln Glu Lys Asp Ala Leu Gln Glu Ile Tyr
        275                 280                 285

Asn Gln Lys Gly Met Phe Pro Gly Glu Gln Phe Lys Pro Ala Arg Arg
    290                 295                 300

Pro Trp Thr Leu Leu Asn Phe Leu Ser Trp Ala Thr Ile Leu Leu Ser
305                 310                 315                 320

Pro Leu Phe Ser Phe Val Leu Gly Val Phe Ala Ser Gly Ser Pro Leu
                325                 330                 335

Leu Ile Leu Thr Phe Leu Gly Phe Val Gly Ala Ala Ser Phe Gly Val
            340                 345                 350

Arg Arg Leu Ile Gly Val Thr Glu Ile Glu Lys Gly Ser Ser Tyr Gly
        355                 360                 365

Asn Gln Glu Phe Lys Lys Lys Glu
    370                 375


<210> SEQ ID NO 17
<211> LENGTH: 368
<212> TYPE: PRT
<213> ORGANISM: Homo sapiens
<220> FEATURE:
<223> OTHER INFORMATION: AGPAT3
<300> PUBLICATION INFORMATION:
<308> DATABASE ACCESSION NUMBER: GenBank AAQ89067.1
<309> DATABASE ENTRY DATE: 2003-10-03

<400> SEQUENCE: 17

Met Gly Leu Leu Ala Phe Leu Lys Thr Gln Phe Val Leu His Leu Leu
1               5                   10                  15

Val Gly Phe Val Phe Val Val Ser Gly Leu Val Ile Asn Phe Val Gln
            20                  25                  30

Leu Cys Thr Leu Ala Leu Trp Pro Val Ser Lys Gln Leu Tyr Arg Arg
        35                  40                  45

Leu Asn Cys Arg Leu Ala Tyr Ser Leu Trp Ser Gln Leu Val Met Leu
    50                  55                  60

Leu Glu Trp Trp Ser Cys Thr Glu Cys Thr Leu Phe Thr Asp Gln Ala
65                  70                  75                  80

Thr Val Glu Arg Phe Gly Lys Glu His Ala Val Ile Ile Leu Asn His
                85                  90                  95

Asn Phe Glu Ile Asp Phe Leu Cys Gly Trp Thr Met Cys Glu Arg Phe
            100                 105                 110

Gly Val Leu Gly Ser Ser Lys Val Leu Ala Lys Lys Glu Leu Leu Tyr
        115                 120                 125

Val Pro Leu Ile Gly Trp Thr Trp Tyr Phe Leu Glu Ile Val Phe Cys
    130                 135                 140

Lys Arg Lys Trp Glu Glu Asp Arg Asp Thr Val Val Glu Gly Leu Arg
145                 150                 155                 160

Arg Leu Ser Asp Tyr Pro Glu Tyr Met Trp Phe Leu Leu Tyr Cys Glu
                165                 170                 175

Gly Thr Arg Phe Thr Glu Thr Lys His Arg Val Ser Met Glu Val Ala
            180                 185                 190
```

-continued

```
Ala Ala Lys Gly Leu Pro Val Leu Lys Tyr His Leu Leu Pro Arg Thr
        195                 200                 205

Lys Gly Phe Thr Thr Ala Val Lys Cys Leu Arg Gly Thr Val Ala Ala
    210                 215                 220

Val Tyr Asp Val Thr Leu Asn Phe Arg Gly Asn Lys Asn Pro Ser Leu
225                 230                 235                 240

Leu Gly Ile Leu Tyr Gly Lys Lys Tyr Glu Ala Asp Met Cys Val Arg
                245                 250                 255

Arg Phe Pro Leu Glu Asp Ile Pro Leu Asp Glu Lys Glu Ala Ala Gln
            260                 265                 270

Trp Leu His Lys Leu Tyr Gln Glu Lys Asp Ala Leu Gln Glu Ile Tyr
        275                 280                 285

Asn Gln Lys Gly Met Phe Pro Gly Glu Gln Phe Lys Pro Ala Arg Arg
    290                 295                 300

Pro Trp Thr Leu Leu Asn Phe Leu Ser Trp Ala Thr Ile Leu Leu Ser
305                 310                 315                 320

Pro Leu Phe Ser Phe Val Leu Gly Val Phe Ala Ser Gly Ser Pro Leu
                325                 330                 335

Leu Ile Leu Thr Phe Leu Gly Phe Val Gly Ala Ala Ser Phe Gly Val
            340                 345                 350

Arg Arg Leu Ile Gly Glu Ser Leu Glu Pro Gly Arg Trp Arg Leu Gln
        355                 360                 365
```

<210> SEQ ID NO 18
<211> LENGTH: 419
<212> TYPE: PRT
<213> ORGANISM: Homo sapiens
<220> FEATURE:
<223> OTHER INFORMATION: AGPAT6 (LPA-MAG PA)
<300> PUBLICATION INFORMATION:
<308> DATABASE ACCESSION NUMBER: UniProt Q86UL3
<309> DATABASE ENTRY DATE: 2005-06-21

<400> SEQUENCE: 18

```
Val Ser Phe Gly Ile Arg Lys Leu Tyr Met Lys Ser Leu Leu Lys Ile
1               5                   10                  15

Phe Ala Trp Ala Thr Leu Arg Met Glu Arg Gly Ala Lys Glu Lys Asn
            20                  25                  30

His Gln Leu Tyr Lys Pro Tyr Thr Asn Gly Ile Ile Ala Lys Asp Pro
        35                  40                  45

Thr Ser Leu Glu Glu Glu Ile Lys Glu Ile Arg Arg Ser Gly Ser Ser
    50                  55                  60

Lys Ala Leu Asp Asn Thr Pro Glu Phe Glu Leu Ser Asp Ile Phe Tyr
65                  70                  75                  80

Phe Cys Arg Lys Gly Met Glu Thr Ile Met Asp Asp Glu Val Thr Lys
                85                  90                  95

Arg Phe Ser Ala Glu Glu Leu Glu Ser Trp Asn Leu Leu Ser Arg Thr
            100                 105                 110

Asn Tyr Asn Phe Gln Tyr Ile Ser Leu Arg Leu Thr Val Leu Trp Gly
        115                 120                 125

Leu Gly Val Leu Ile Arg Tyr Cys Phe Leu Leu Pro Leu Arg Ile Ala
    130                 135                 140

Leu Ala Phe Thr Gly Ile Ser Leu Leu Val Val Gly Thr Thr Val Val
145                 150                 155                 160

Gly Tyr Leu Pro Asn Gly Arg Phe Lys Glu Phe Met Ser Lys His Val
                165                 170                 175
```

His Leu Met Cys Tyr Arg Ile Cys Val Arg Ala Leu Thr Ala Ile Ile
180 185 190

Thr Tyr His Asp Arg Glu Asn Arg Pro Arg Asn Gly Gly Ile Cys Val
195 200 205

Ala Asn His Thr Ser Pro Ile Asp Val Ile Ile Leu Ala Ser Asp Gly
210 215 220

Tyr Tyr Ala Met Val Gly Gln Val His Gly Gly Leu Met Gly Val Ile
225 230 235 240

Gln Arg Ala Met Val Lys Ala Cys Pro His Val Trp Phe Glu Arg Ser
245 250 255

Glu Val Lys Asp Arg His Leu Val Ala Lys Arg Leu Thr Glu His Val
260 265 270

Gln Asp Lys Ser Lys Leu Pro Ile Leu Ile Phe Pro Glu Gly Thr Cys
275 280 285

Ile Asn Asn Thr Ser Val Met Met Phe Lys Lys Gly Ser Phe Glu Ile
290 295 300

Gly Ala Thr Val Tyr Pro Val Ala Ile Lys Tyr Asp Pro Gln Phe Gly
305 310 315 320

Asp Ala Phe Trp Asn Ser Ser Lys Tyr Gly Met Val Thr Tyr Leu Leu
325 330 335

Arg Met Met Thr Ser Trp Ala Ile Val Cys Ser Val Trp Tyr Leu Pro
340 345 350

Pro Met Thr Arg Glu Ala Asp Glu Asp Ala Val Gln Phe Ala Asn Arg
355 360 365

Val Lys Ser Ala Ile Ala Arg Gln Gly Gly Leu Val Asp Leu Leu Trp
370 375 380

Asp Gly Gly Leu Lys Arg Glu Lys Val Lys Asp Thr Phe Lys Glu Glu
385 390 395 400

Gln Gln Lys Leu Tyr Ser Lys Met Ile Val Gly Asn His Lys Asp Arg
405 410 415

Ser Arg Ser

<210> SEQ ID NO 19
<211> LENGTH: 795
<212> TYPE: PRT
<213> ORGANISM: Homo sapiens
<220> FEATURE:
<223> OTHER INFORMATION: GPAT2
<300> PUBLICATION INFORMATION:
<308> DATABASE ACCESSION NUMBER: UniProt Q6NUI2
<309> DATABASE ENTRY DATE: 2008-03-18

<400> SEQUENCE: 19

Met Ala Thr Met Leu Glu Gly Arg Cys Gln Thr Gln Pro Arg Ser Ser
1 5 10 15

Pro Ser Gly Arg Glu Ala Ser Leu Trp Ser Ser Gly Phe Gly Met Lys
20 25 30

Leu Glu Ala Val Thr Pro Phe Leu Gly Lys Tyr Arg Pro Phe Val Gly
35 40 45

Arg Cys Cys Gln Thr Cys Thr Pro Lys Ser Trp Glu Ser Leu Phe His
50 55 60

Arg Ser Ile Thr Asp Leu Gly Phe Cys Asn Val Ile Leu Val Lys Glu
65 70 75 80

Glu Asn Thr Arg Phe Arg Gly Trp Leu Val Arg Arg Leu Cys Tyr Phe
85 90 95

Leu Trp Ser Leu Glu Gln His Ile Pro Pro Cys Gln Asp Val Pro Gln

-continued

```
            100                 105                 110

Lys Ile Met Glu Ser Thr Gly Val Gln Asn Leu Leu Ser Gly Arg Val
        115                 120                 125

Pro Gly Gly Thr Gly Glu Gly Gln Val Pro Asp Leu Val Lys Lys Glu
    130                 135                 140

Val Gln Arg Ile Leu Gly His Ile Gln Ala Pro Pro Arg Pro Phe Leu
145                 150                 155                 160

Val Arg Leu Phe Ser Trp Ala Leu Leu Arg Phe Leu Asn Cys Leu Phe
                165                 170                 175

Leu Asn Val Gln Leu His Lys Gly Gln Met Lys Met Val Gln Lys Ala
            180                 185                 190

Ala Gln Ala Gly Leu Pro Leu Val Leu Leu Ser Thr His Lys Thr Leu
        195                 200                 205

Leu Asp Gly Ile Leu Leu Pro Phe Met Leu Leu Ser Gln Gly Leu Gly
    210                 215                 220

Val Leu Arg Val Ala Trp Asp Ser Arg Ala Cys Ser Pro Ala Leu Arg
225                 230                 235                 240

Ala Leu Leu Arg Lys Leu Gly Gly Leu Phe Leu Pro Pro Glu Ala Ser
                245                 250                 255

Leu Ser Leu Asp Ser Ser Glu Gly Leu Leu Ala Arg Ala Val Val Gln
            260                 265                 270

Ala Val Ile Glu Gln Leu Leu Val Ser Gly Gln Pro Leu Leu Ile Phe
        275                 280                 285

Leu Glu Glu Pro Pro Gly Ala Leu Gly Pro Arg Leu Ser Ala Leu Gly
    290                 295                 300

Gln Ala Trp Val Gly Phe Val Val Gln Ala Val Gln Val Gly Ile Val
305                 310                 315                 320

Pro Asp Ala Leu Leu Val Pro Val Ala Val Thr Tyr Asp Leu Val Pro
                325                 330                 335

Asp Ala Pro Cys Asp Ile Asp His Ala Ser Ala Pro Leu Gly Leu Trp
            340                 345                 350

Thr Gly Ala Leu Ala Val Leu Arg Ser Leu Trp Ser Arg Trp Gly Cys
        355                 360                 365

Ser His Arg Ile Cys Ser Arg Val His Leu Ala Gln Pro Phe Ser Leu
    370                 375                 380

Gln Glu Tyr Ile Val Ser Ala Arg Ser Cys Trp Gly Gly Arg Gln Thr
385                 390                 395                 400

Leu Glu Gln Leu Leu Gln Pro Ile Val Leu Gly Gln Cys Thr Ala Val
                405                 410                 415

Pro Asp Thr Glu Lys Glu Gln Glu Trp Thr Pro Ile Thr Gly Pro Leu
            420                 425                 430

Leu Ala Leu Lys Glu Glu Asp Gln Leu Leu Val Arg Arg Leu Ser Cys
        435                 440                 445

His Val Leu Ser Ala Ser Val Gly Ser Ser Ala Val Met Ser Thr Ala
    450                 455                 460

Ile Met Ala Thr Leu Leu Leu Phe Lys His Gln Lys Leu Leu Gly Glu
465                 470                 475                 480

Phe Ser Trp Leu Thr Glu Glu Ile Leu Leu Arg Gly Phe Asp Val Gly
                485                 490                 495

Phe Ser Gly Gln Leu Arg Ser Leu Leu Gln His Ser Leu Ser Leu Leu
            500                 505                 510

Arg Ala His Val Ala Leu Leu Arg Ile Arg Gln Gly Asp Leu Leu Val
        515                 520                 525
```

```
Val Pro Gln Pro Gly Pro Gly Leu Thr His Leu Ala Gln Leu Ser Ala
    530                 535                 540

Glu Leu Leu Pro Val Phe Leu Ser Glu Ala Val Gly Ala Cys Ala Val
545                 550                 555                 560

Arg Gly Leu Leu Ala Gly Arg Val Pro Pro Gln Gly Pro Trp Glu Leu
                565                 570                 575

Gln Gly Ile Leu Leu Leu Ser Gln Asn Glu Leu Tyr Arg Gln Ile Leu
            580                 585                 590

Leu Leu Met His Leu Leu Pro Gln Asp Leu Leu Leu Leu Lys Pro Cys
        595                 600                 605

Gln Ser Ser Tyr Cys Tyr Cys Gln Glu Val Leu Asp Arg Leu Ile Gln
    610                 615                 620

Cys Gly Leu Leu Val Ala Glu Glu Thr Pro Gly Ser Arg Pro Ala Cys
625                 630                 635                 640

Asp Thr Gly Arg Gln Arg Leu Ser Arg Lys Leu Leu Trp Lys Pro Ser
                645                 650                 655

Gly Asp Phe Thr Asp Ser Asp Ser Asp Asp Phe Gly Glu Ala Asp Gly
            660                 665                 670

Arg Tyr Phe Arg Leu Ser Gln Gln Ser His Cys Pro Asp Phe Phe Leu
        675                 680                 685

Phe Leu Cys Arg Leu Leu Ser Pro Leu Leu Lys Ala Phe Ala Gln Ala
    690                 695                 700

Ala Ala Phe Leu Arg Gln Gly Gln Leu Pro Asp Thr Glu Leu Gly Tyr
705                 710                 715                 720

Thr Glu Gln Leu Phe Gln Phe Leu Gln Ala Thr Ala Gln Glu Glu Gly
                725                 730                 735

Ile Phe Glu Cys Ala Asp Pro Lys Leu Ala Ile Ser Ala Val Trp Thr
            740                 745                 750

Phe Arg Asp Leu Gly Val Leu Gln Gln Thr Pro Ser Pro Ala Gly Pro
        755                 760                 765

Arg Leu His Leu Ser Pro Thr Phe Ala Ser Leu Asp Asn Gln Glu Lys
    770                 775                 780

Leu Glu Gln Phe Ile Arg Gln Phe Ile Cys Ser
785                 790                 795


<210> SEQ ID NO 20
<211> LENGTH: 334
<212> TYPE: PRT
<213> ORGANISM: Homo sapiens
<220> FEATURE:
<223> OTHER INFORMATION: MOGAT2
<300> PUBLICATION INFORMATION:
<308> DATABASE ACCESSION NUMBER: UniProt Q3SYC2
<309> DATABASE ENTRY DATE: 2006-09-05

<400> SEQUENCE: 20

Met Val Glu Phe Ala Pro Leu Phe Met Pro Trp Glu Arg Arg Leu Gln
1               5                   10                  15

Thr Leu Ala Val Leu Gln Phe Val Phe Ser Phe Leu Ala Leu Ala Glu
            20                  25                  30

Ile Cys Thr Val Gly Phe Ile Ala Leu Leu Phe Thr Arg Phe Trp Leu
        35                  40                  45

Leu Thr Val Leu Tyr Ala Ala Trp Trp Tyr Leu Asp Arg Asp Lys Pro
    50                  55                  60

Arg Gln Gly Gly Arg His Ile Gln Ala Ile Arg Cys Trp Thr Ile Trp
65                  70                  75                  80
```

```
Lys Tyr Met Lys Asp Tyr Phe Pro Ile Ser Leu Val Lys Thr Ala Glu
                85                  90                  95

Leu Asp Pro Ser Arg Asn Tyr Ile Ala Gly Phe His Pro His Gly Val
            100                 105                 110

Leu Ala Val Gly Ala Phe Ala Asn Leu Cys Thr Glu Ser Thr Gly Phe
        115                 120                 125

Ser Ser Ile Phe Pro Gly Ile Arg Pro His Leu Met Met Leu Thr Leu
    130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Leu Arg Asn Arg Lys Gly
        195                 200                 205

Phe Val Arg Leu Ala Leu Thr His Gly Ala Pro Leu Val Pro Ile Phe
    210                 215                 220

Ser Phe Gly Glu Asn Asp Leu Phe Asp Gln Ile Pro Asn Ser Ser Gly
225                 230                 235                 240

Ser Trp Leu Arg Tyr Ile Gln Asn Arg Leu Gln Lys Ile Met Gly Ile
                245                 250                 255

Ser Leu Pro Leu Phe His Gly Arg Gly Val Phe Gln Tyr Ser Phe Gly
            260                 265                 270

Leu Ile Pro Tyr Arg Arg Pro Ile Thr Thr Val Val Gly Lys Pro Ile
        275                 280                 285

Glu Val Gln Lys Thr Leu His Pro Ser Glu Glu Glu Val Asn Gln Leu
    290                 295                 300

His Gln Arg Tyr Ile Lys Glu Leu Cys Asn Leu Phe Glu Ala His Lys
305                 310                 315                 320

Leu Lys Phe Asn Ile Pro Ala Asp Gln His Leu Glu Phe Cys
                325                 330
```

<210> SEQ ID NO 21
<211> LENGTH: 284
<212> TYPE: PRT
<213> ORGANISM: Homo sapiens
<220> FEATURE:
<223> OTHER INFORMATION: MOGAT2
<300> PUBLICATION INFORMATION:
<308> DATABASE ACCESSION NUMBER: GenBank AAI03879.1
<309> DATABASE ENTRY DATE: 2006-10-04

<400> SEQUENCE: 21

```
Met Val Glu Phe Ala Pro Leu Phe Met Pro Trp Glu Arg Arg Leu Gln
1               5                   10                  15

Thr Leu Ala Val Leu Gln Phe Val Phe Ser Phe Leu Ala Leu Ala Glu
            20                  25                  30

Ile Cys Thr Val Gly Phe Ile Ala Leu Leu Phe Thr Arg Phe Trp Leu
        35                  40                  45

Leu Thr Val Leu Tyr Ala Ala Trp Trp Tyr Leu Asp Arg Asp Lys Pro
    50                  55                  60

Arg Gln Gly Gly Arg His Ile Gln Ala Ile Arg Cys Trp Thr Ile Trp
65                  70                  75                  80

Lys Tyr Met Lys Asp Tyr Phe Pro Ile Ser Leu Val Lys Thr Ala Glu
                85                  90                  95
```

```
Leu Asp Pro Ser Arg Asn Tyr Ile Ala Gly Phe His Pro His Gly Val
            100                 105                 110

Leu Ala Val Gly Ala Phe Ala Asn Leu Cys Thr Glu Ser Thr Gly Phe
        115                 120                 125

Ser Ser Ile Phe Pro Gly Ile Arg Pro His Leu Met Met Leu Thr Leu
    130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Leu Arg Asn Arg Lys Gly
        195                 200                 205

Phe Val Arg Leu Ala Leu Thr His Gly Tyr Gln Ala Ser Gly Lys Ser
    210                 215                 220

Thr Leu Gly Ser Val Gly Asn Trp Gln Gly Phe Tyr Phe Gly Gly Lys
225                 230                 235                 240

Met Ala Glu Thr Asn Ala Asp Ser Ile Leu Val Glu Ile Phe Ser Pro
                245                 250                 255

Phe Thr Ile Lys Ile Ile Phe Trp Cys Leu Met Pro Lys Tyr Leu Glu
            260                 265                 270

Lys Phe Pro Gln Arg Arg Leu Ser Asp Leu Arg Asn
        275                 280
```

<210> SEQ ID NO 22
<211> LENGTH: 388
<212> TYPE: PRT
<213> ORGANISM: Homo sapiens
<220> FEATURE:
<223> OTHER INFORMATION: DGAT2
<300> PUBLICATION INFORMATION:
<308> DATABASE ACCESSION NUMBER: UniProt Q96PD7
<309> DATABASE ENTRY DATE: 2006-09-05

<400> SEQUENCE: 22

```
Met Lys Thr Leu Ile Ala Ala Tyr Ser Gly Val Leu Arg Gly Glu Arg
1               5                   10                  15

Gln Ala Glu Ala Asp Arg Ser Gln Arg Ser His Gly Gly Pro Ala Leu
            20                  25                  30

Ser Arg Glu Gly Ser Gly Arg Trp Gly Thr Gly Ser Ser Ile Leu Ser
        35                  40                  45

Ala Leu Gln Asp Leu Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Ala Ile Leu Met Tyr Ile Phe Cys
                85                  90                  95

Thr Asp Cys Trp Leu Ile Ala Val Leu Tyr Phe Thr Trp Leu Val Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160
```

His Pro His Gly Ile Met Gly Leu Gly Ala Phe Cys Asn Phe Ser Thr
165 170 175

Glu Ala Thr Glu Val Ser Lys Lys Phe Pro Gly Ile Arg Pro Tyr Leu
180 185 190

Ala Thr Leu Ala Gly Asn Phe Arg Met Pro Val Leu Arg Glu Tyr Leu
195 200 205

Met Ser Gly Gly Ile Cys Pro Val Ser Arg Asp Thr Ile Asp Tyr Leu
210 215 220

Leu Ser Lys Asn Gly Ser Gly Asn Ala Ile Ile Ile Val Val Gly Gly
225 230 235 240

Ala Ala Glu Ser Leu Ser Ser Met Pro Gly Lys Asn Ala Val Thr Leu
245 250 255

Arg Asn Arg Lys Gly Phe Val Lys Leu Ala Leu Arg His Gly Ala Asp
260 265 270

Leu Val Pro Ile Tyr Ser Phe Gly Glu Asn Glu Val Tyr Lys Gln Val
275 280 285

Ile Phe Glu Glu Gly Ser Trp Gly Arg Trp Val Gln Lys Lys Phe Gln
290 295 300

Lys Tyr Ile Gly Phe Ala Pro Cys Ile Phe His Gly Arg Gly Leu Phe
305 310 315 320

Ser Ser Asp Thr Trp Gly Leu Val Pro Tyr Ser Lys Pro Ile Thr Thr
325 330 335

Val Val Gly Glu Pro Ile Thr Ile Pro Lys Leu Glu His Pro Thr Gln
340 345 350

Gln Asp Ile Asp Leu Tyr His Thr Met Tyr Met Glu Ala Leu Val Lys
355 360 365

Leu Phe Asp Lys His Lys Thr Lys Phe Gly Leu Pro Glu Thr Glu Val
370 375 380

Leu Glu Val Asn
385

<210> SEQ ID NO 23
<211> LENGTH: 295
<212> TYPE: PRT
<213> ORGANISM: Homo sapiens
<220> FEATURE:
<223> OTHER INFORMATION: AQP9
<300> PUBLICATION INFORMATION:
<308> DATABASE ACCESSION NUMBER: UniProt O43315
<309> DATABASE ENTRY DATE: 1998-12-15

<400> SEQUENCE: 23

Met Gln Pro Glu Gly Ala Glu Lys Gly Lys Ser Phe Lys Gln Arg Leu
1 5 10 15

Val Leu Lys Ser Ser Leu Ala Lys Glu Thr Leu Ser Glu Phe Leu Gly
20 25 30

Thr Phe Ile Leu Ile Val Leu Gly Cys Gly Cys Val Ala Gln Ala Ile
35 40 45

Leu Ser Arg Gly Arg Phe Gly Gly Val Ile Thr Ile Asn Val Gly Phe
50 55 60

Ser Met Ala Val Ala Met Ala Ile Tyr Val Ala Gly Gly Val Ser Gly
65 70 75 80

Gly His Ile Asn Pro Ala Val Ser Leu Ala Met Cys Leu Phe Gly Arg
85 90 95

Met Lys Trp Phe Lys Leu Pro Phe Tyr Val Gly Ala Gln Phe Leu Gly
100 105 110

```
Ala Phe Val Gly Ala Ala Thr Val Phe Gly Ile Tyr Tyr Asp Gly Leu
        115                 120                 125

Met Ser Phe Ala Gly Gly Lys Leu Leu Ile Val Gly Glu Asn Ala Thr
    130                 135                 140

Ala His Ile Phe Ala Thr Tyr Pro Ala Pro Tyr Leu Ser Leu Ala Asn
145                 150                 155                 160

Ala Phe Ala Asp Gln Val Val Ala Thr Met Ile Leu Leu Ile Ile Val
                165                 170                 175

Phe Ala Ile Phe Asp Ser Arg Asn Leu Gly Ala Pro Arg Gly Leu Glu
            180                 185                 190

Pro Ile Ala Ile Gly Leu Leu Ile Ile Val Ile Ala Ser Ser Leu Gly
        195                 200                 205

Leu Asn Ser Gly Cys Ala Met Asn Pro Ala Arg Asp Leu Ser Pro Arg
    210                 215                 220

Leu Phe Thr Ala Leu Ala Gly Trp Gly Phe Glu Val Phe Arg Ala Gly
225                 230                 235                 240

Asn Asn Phe Trp Trp Ile Pro Val Val Gly Pro Leu Val Gly Ala Val
                245                 250                 255

Ile Gly Gly Leu Ile Tyr Val Leu Val Ile Glu Ile His His Pro Glu
            260                 265                 270

Pro Asp Ser Val Phe Lys Thr Glu Gln Ser Glu Asp Lys Pro Glu Lys
        275                 280                 285

Tyr Glu Leu Ser Val Ile Met
    290                 295


<210> SEQ ID NO 24
<211> LENGTH: 890
<212> TYPE: PRT
<213> ORGANISM: Homo sapiens
<220> FEATURE:
<223> OTHER INFORMATION: LPIN1 (Lipin 1)
<300> PUBLICATION INFORMATION:
<308> DATABASE ACCESSION NUMBER: UniProt Q14693
<309> DATABASE ENTRY DATE: 1997-11-01

<400> SEQUENCE: 24

Met Asn Tyr Val Gly Gln Leu Ala Gly Gln Val Phe Val Thr Val Lys
1               5                   10                  15

Glu Leu Tyr Lys Gly Leu Asn Pro Ala Thr Leu Ser Gly Cys Ile Asp
            20                  25                  30

Ile Ile Val Ile Arg Gln Pro Asn Gly Asn Leu Gln Cys Ser Pro Phe
        35                  40                  45

His Val Arg Phe Gly Lys Met Gly Val Leu Arg Ser Arg Glu Lys Val
    50                  55                  60

Val Asp Ile Glu Ile Asn Gly Glu Ser Val Asp Leu His Met Lys Leu
65                  70                  75                  80

Gly Asp Asn Gly Glu Ala Phe Phe Val Gln Glu Thr Asp Asn Asp Gln
                85                  90                  95

Glu Val Ile Pro Met His Leu Ala Thr Ser Pro Ile Leu Ser Glu Gly
            100                 105                 110

Ala Ser Arg Met Glu Cys Gln Leu Lys Arg Gly Ser Val Asp Arg Met
        115                 120                 125

Arg Gly Leu Asp Pro Ser Thr Pro Ala Gln Val Ile Ala Pro Ser Glu
    130                 135                 140

Thr Pro Ser Ser Ser Ser Val Val Lys Lys Arg Arg Lys Arg Arg Arg
145                 150                 155                 160
```

-continued

```
Lys Ser Gln Leu Asp Ser Leu Lys Arg Asp Asp Asn Met Asn Thr Ser
                165                 170                 175

Glu Asp Glu Asp Met Phe Pro Ile Glu Met Ser Ser Asp Glu Ala Met
            180                 185                 190

Glu Leu Leu Glu Ser Ser Arg Thr Leu Pro Asn Asp Ile Pro Pro Phe
        195                 200                 205

Gln Asp Asp Ile Pro Glu Glu Asn Leu Ser Leu Ala Val Ile Tyr Pro
    210                 215                 220

Gln Ser Ala Ser Tyr Pro Asn Ser Asp Arg Glu Trp Ser Pro Thr Pro
225                 230                 235                 240

Ser Pro Ser Gly Ser Arg Pro Ser Thr Pro Lys Ser Asp Ser Glu Leu
                245                 250                 255

Val Ser Lys Ser Thr Glu Arg Thr Gly Gln Lys Asn Pro Glu Met Leu
            260                 265                 270

Trp Leu Trp Gly Glu Leu Pro Gln Ala Ala Lys Ser Ser Ser Pro His
        275                 280                 285

Lys Met Lys Glu Ser Ser Pro Leu Ser Ser Arg Lys Ile Cys Asp Lys
    290                 295                 300

Ser His Phe Gln Ala Ile His Ser Glu Ser Ser Asp Thr Phe Ser Asp
305                 310                 315                 320

Gln Ser Pro Thr Leu Val Gly Gly Ala Leu Leu Asp Gln Asn Lys Pro
                325                 330                 335

Gln Thr Glu Met Gln Phe Val Asn Glu Glu Asp Leu Glu Thr Leu Gly
            340                 345                 350

Ala Ala Ala Pro Leu Leu Pro Met Ile Glu Glu Leu Lys Pro Pro Ser
        355                 360                 365

Ala Ser Val Val Gln Thr Ala Asn Lys Thr Asp Ser Pro Ser Arg Lys
    370                 375                 380

Arg Asp Lys Arg Ser Arg His Leu Gly Ala Asp Gly Val Tyr Leu Asp
385                 390                 395                 400

Asp Leu Thr Asp Met Asp Pro Glu Val Ala Ala Leu Tyr Phe Pro Lys
                405                 410                 415

Asn Gly Asp Pro Ser Gly Leu Ala Lys His Ala Ser Asp Asn Gly Ala
            420                 425                 430

Arg Ser Ala Asn Gln Ser Pro Gln Ser Val Gly Ser Ser Gly Val Asp
        435                 440                 445

Ser Gly Val Glu Ser Thr Ser Asp Gly Leu Arg Asp Leu Pro Ser Ile
    450                 455                 460

Ala Ile Ser Leu Cys Gly Gly Leu Ser Asp His Arg Glu Ile Thr Lys
465                 470                 475                 480

Asp Ala Phe Leu Glu Gln Ala Val Ser Tyr Gln Gln Phe Val Asp Asn
                485                 490                 495

Pro Ala Ile Ile Asp Asp Pro Asn Leu Val Val Lys Ile Gly Ser Lys
            500                 505                 510

Tyr Tyr Asn Trp Thr Thr Ala Ala Pro Leu Leu Leu Ala Met Gln Ala
        515                 520                 525

Phe Gln Lys Pro Leu Pro Lys Ala Thr Val Glu Ser Ile Met Arg Asp
    530                 535                 540

Lys Met Pro Lys Lys Gly Gly Arg Trp Trp Phe Ser Trp Arg Gly Arg
545                 550                 555                 560

Asn Thr Thr Ile Lys Glu Glu Ser Lys Pro Glu Gln Cys Leu Ala Gly
                565                 570                 575
```

-continued

```
Lys Ala His Ser Thr Gly Glu Gln Pro Pro Gln Leu Ser Leu Ala Thr
            580                 585                 590

Arg Val Lys His Glu Ser Ser Ser Ser Asp Glu Glu Arg Ala Ala Ala
        595                 600                 605

Lys Pro Ser Asn Ala Gly His Leu Pro Leu Leu Pro Asn Val Ser Tyr
    610                 615                 620

Lys Lys Thr Leu Arg Leu Thr Ser Glu Gln Leu Lys Ser Leu Lys Leu
625                 630                 635                 640

Lys Asn Gly Pro Asn Asp Val Val Phe Ser Val Thr Thr Gln Tyr Gln
                645                 650                 655

Gly Thr Cys Arg Cys Glu Gly Thr Ile Tyr Leu Trp Asn Trp Asp Asp
            660                 665                 670

Lys Val Ile Ile Ser Asp Ile Asp Gly Thr Ile Thr Arg Ser Asp Thr
        675                 680                 685

Leu Gly His Ile Leu Pro Thr Leu Gly Lys Asp Trp Thr His Gln Gly
    690                 695                 700

Ile Ala Lys Leu Tyr His Lys Val Ser Gln Asn Gly Tyr Lys Phe Leu
705                 710                 715                 720

Tyr Cys Ser Ala Arg Ala Ile Gly Met Ala Asp Met Thr Arg Gly Tyr
                725                 730                 735

Leu His Trp Val Asn Glu Arg Gly Thr Val Leu Pro Gln Gly Pro Leu
            740                 745                 750

Leu Leu Ser Pro Ser Ser Leu Phe Ser Ala Leu His Arg Glu Val Ile
        755                 760                 765

Glu Lys Lys Pro Glu Lys Phe Lys Val Gln Cys Leu Thr Asp Ile Lys
    770                 775                 780

Asn Leu Phe Phe Pro Asn Thr Glu Pro Phe Tyr Ala Ala Phe Gly Asn
785                 790                 795                 800

Arg Pro Ala Asp Val Tyr Ser Tyr Lys Gln Val Gly Val Ser Leu Asn
                805                 810                 815

Arg Ile Phe Thr Val Asn Pro Lys Gly Glu Leu Val Gln Glu His Ala
            820                 825                 830

Lys Thr Asn Ile Ser Ser Tyr Val Arg Leu Cys Glu Val Val Asp His
        835                 840                 845

Val Phe Pro Leu Leu Lys Arg Ser His Ser Ser Asp Phe Pro Cys Ser
    850                 855                 860

Asp Thr Phe Ser Asn Phe Thr Phe Trp Arg Glu Pro Leu Pro Pro Phe
865                 870                 875                 880

Glu Asn Gln Asp Ile His Ser Ala Ser Ala
                885                 890
```

<210> SEQ ID NO 25
<211> LENGTH: 222
<212> TYPE: PRT
<213> ORGANISM: Homo sapiens
<220> FEATURE:
<223> OTHER INFORMATION: CRIF1
<300> PUBLICATION INFORMATION:
<308> DATABASE ACCESSION NUMBER: UniProt Q8TAE8
<309> DATABASE ENTRY DATE: 2006-03-21

<400> SEQUENCE: 25

```
Met Ala Ala Ser Val Arg Gln Ala Arg Ser Leu Leu Gly Val Ala Ala
1               5                   10                  15

Thr Leu Ala Pro Gly Ser Arg Gly Tyr Arg Ala Arg Pro Pro Pro Arg
            20                  25                  30
```

-continued

```
Arg Arg Pro Gly Pro Arg Trp Pro Asp Pro Glu Asp Leu Leu Thr Pro
        35                  40                  45

Arg Trp Gln Leu Gly Pro Arg Tyr Ala Ala Lys Gln Phe Ala Arg Tyr
    50                  55                  60

Gly Ala Ala Ser Gly Val Val Pro Gly Ser Leu Trp Pro Ser Pro Glu
65                  70                  75                  80

Gln Leu Arg Glu Leu Glu Ala Glu Glu Arg Glu Trp Tyr Pro Ser Leu
                85                  90                  95

Ala Thr Met Gln Glu Ser Leu Arg Val Lys Gln Leu Ala Glu Glu Gln
            100                 105                 110

Lys Arg Arg Glu Arg Glu Gln His Ile Ala Glu Cys Met Ala Lys Met
        115                 120                 125

Pro Gln Met Ile Val Asn Trp Gln Gln Gln Gln Arg Glu Asn Trp Glu
    130                 135                 140

Lys Ala Gln Ala Asp Lys Glu Arg Arg Ala Arg Leu Gln Ala Glu Ala
145                 150                 155                 160

Gln Glu Leu Leu Gly Tyr Gln Val Asp Pro Arg Ser Ala Arg Phe Gln
                165                 170                 175

Glu Leu Leu Gln Asp Leu Glu Lys Lys Glu Arg Lys Arg Leu Lys Glu
            180                 185                 190

Glu Lys Gln Lys Arg Lys Lys Glu Ala Arg Ala Ala Ala Leu Ala Ala
        195                 200                 205

Ala Val Ala Gln Asp Pro Ala Ala Ser Gly Ala Pro Ser Ser
    210                 215                 220


<210> SEQ ID NO 26
<211> LENGTH: 268
<212> TYPE: PRT
<213> ORGANISM: Homo sapiens
<220> FEATURE:
<223> OTHER INFORMATION: PD1
<300> PUBLICATION INFORMATION:
<308> DATABASE ACCESSION NUMBER: UniProt Q15116
<309> DATABASE ENTRY DATE: 1997-11-01

<400> SEQUENCE: 26

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160
```

```
Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265


<210> SEQ ID NO 27
<211> LENGTH: 414
<212> TYPE: PRT
<213> ORGANISM: Mus musculus
<220> FEATURE:
<223> OTHER INFORMATION: Lymphocyte expansion molecule (LEM)
<300> PUBLICATION INFORMATION:
<308> DATABASE ACCESSION NUMBER: GenBank AKD95359.1
<309> DATABASE ENTRY DATE: 2015-04-26

<400> SEQUENCE: 27

Met Arg Pro Arg Thr His Gly Ala Pro Pro Arg Asn Ile Met Ser Thr
1               5                   10                  15

Ile Pro Lys Trp Phe Lys Gly Ala Pro Phe Gly Val Gln Ser His Arg
            20                  25                  30

Phe Asp Val Ser Ala Val Tyr Pro Asn Gln Lys Lys Phe Ser Thr Phe
        35                  40                  45

Thr Glu Ala Pro Tyr Ser Arg His His Ser Val Glu Leu Ser His Ile
    50                  55                  60

Gly Pro Gly Thr Tyr Asn Ser Lys Asp Thr Cys Phe Ser Lys Lys Phe
65                  70                  75                  80

Leu Glu Gln Lys Leu Gly Ser Gly Trp Ser Gln Ala His Glu Ala Thr
                85                  90                  95

Arg Leu Thr Gln Leu Pro His Phe His Tyr Gln Ala Ile Lys Lys Glu
            100                 105                 110

Lys Glu Gln Gln Val His Lys Arg Gly Pro Gly Ser Tyr Asn Ile Lys
        115                 120                 125

Asp Phe Ile Thr Glu Leu Gln Lys Lys Pro Gln Ser Lys Arg Gly Leu
    130                 135                 140

Leu Ser Ser Gly Glu Thr Arg Phe Arg Gly Phe Ile Gly Asn Tyr Tyr
145                 150                 155                 160

Pro Gly Pro Gly Asn Tyr Gly Glu Lys Gly Asn Pro Tyr Thr Gln Leu
                165                 170                 175

Glu Glu Lys Ala Trp Asn Arg Ser His Ser Asp Gly Leu Met Cys Arg
            180                 185                 190

Val Ser Asn Lys Pro Pro Leu Phe His Gln Gly Ser Gly Leu Gly Pro
        195                 200                 205

Gly Thr Tyr Thr Ile Lys Ser Asp Leu Glu Thr Phe Val Lys Lys Ser
    210                 215                 220

Thr Gly Asn Arg Gly Pro Tyr Asp Ile Phe Ser Gly Glu Arg Ser Ser
225                 230                 235                 240
```

```
Pro Leu Pro Tyr Gly His Tyr Ser Val Gln Lys Met Lys Pro Lys Glu
                245                 250                 255

Leu Thr Asp Tyr Lys Ser Phe Leu Asp Glu Met Asn Ser Gln His Lys
            260                 265                 270

Lys Lys Gln Gly Val Phe Ser Lys Tyr Pro Arg Asp Pro Lys His Pro
        275                 280                 285

Thr Glu Arg Ile Phe Trp Thr Thr Leu Ser Gln Cys Pro Lys Asn Met
    290                 295                 300

Asp Ile Ala Gly Pro Gly Ser Trp Leu Pro His Glu Thr Glu Gln Lys
305                 310                 315                 320

His Val Asn Arg Pro Pro Phe Leu Leu Ala Ser Lys Arg Cys Gly Leu
                325                 330                 335

Lys Ala Tyr Gln Met Ile Leu Gly Thr Trp Asn Pro Val Gly Val Gly
            340                 345                 350

Arg Tyr Leu Asn Thr Thr Leu Met Glu Ser Ile Asp Arg Arg Gln Arg
        355                 360                 365

Tyr Arg Ser Leu Tyr Met Ser Glu Pro Lys Arg Tyr Leu Gln Asp Leu
    370                 375                 380

Thr Arg Asp Arg Leu Met Gln Lys Arg Ile Thr Pro Ile Thr Lys Gly
385                 390                 395                 400

Lys Cys Arg Pro Thr Val Asp Tyr Asn Ser Asp Pro Thr Pro
                405                 410


<210> SEQ ID NO 28
<211> LENGTH: 1245
<212> TYPE: DNA
<213> ORGANISM: Homo sapiens
<220> FEATURE:
<223> OTHER INFORMATION: C1ORF177 1 (huLEM)
<300> PUBLICATION INFORMATION:
<308> DATABASE ACCESSION NUMBER: NCBI NM_152607.2
<309> DATABASE ENTRY DATE: 2007-11-16

<400> SEQUENCE: 28

atgagggaaa gccaggatgc cgccggagct catggctgga accgcgtcgg ctccacggcc     60

accaagtggt tcaccggggc gcccttcggg gtgcagagcc acaggtttga catctctgct    120

gtttatccca actggaagaa gttcagcacc ttcactgagg ccccatactc cacgcgttat    180

tctacccaag tgtcccacat aggccctggg acttacagct ccaaagagac ctgcttcagc    240

aagaagaagc tgatgaagga ggtggacaca ggctgggcca aggcccagga agccacgcgg    300

ctgacccagc taccccactt ccagtaccag gccatcatga aagagaagcg gctgaaggag    360

caaaagctgg gccccggctc ctacaacctc aaagacttct tagaacagct gcgggagaaa    420

ccatgtagca cccgggggct gctcagctct ggggaggttc gcttccgagg actcactggg    480

aactactatc caggccctgg aaattatggg gagaagggta acccatacac caagctggag    540

gagaatgcct ggaaccggtc tcattccgag ggcctcatgt gcaggatgag caacaagcca    600

cacccccggc ctcatcaggg gagtggtctg ggacccggca cctacttctt caaaagcgac    660

cttgagacat atgtggcacg atccgtcggc acccgcggcc cctatgacac tttctctggt    720

gatcggagca agccactgcc ttatgggcac tactccatgc agaaaaaaaa gcccagggaa    780

ctgatgaatt tcaagagctt tgtagaagaa cttaactcac atcacaataa gaagcatggg    840

gttttttcta aacttccccg aaacccgaaa acccctacag agaggattta ctgggccaac    900

ctcagccagt gcccccgcac actggccaca tctggcccca gtttctggct tccacaagag    960

aagaaatgca aacccgtcaa ccagccccca ttcctgttga cctccaaggg gtcaggtgca   1020
```

aaggcctgcc agatgattat gggaagctgg aacccagtag gtgtgggccg ctacctcaac 1080
acctggctga tggagacaaa ggacaggcgg cagcgatatc gatccctatt cctgagtgga 1140
tccaaacgct acctctcaga cctggcccgg gacatgctca tgcaaatcag gctgttttgt 1200
tggaaaggcc tagaagtcat caattttggc ctctcaccaa tgtag 1245

<210> SEQ ID NO 29
<211> LENGTH: 1257
<212> TYPE: DNA
<213> ORGANISM: Homo sapiens
<220> FEATURE:
<223> OTHER INFORMATION: C1ORF177 2 (huLEM)
<300> PUBLICATION INFORMATION:
<308> DATABASE ACCESSION NUMBER: NCBI NM_001110533.1
<309> DATABASE ENTRY DATE: 2016-03-27

<400> SEQUENCE: 29
atgagggaaa gccaggatgc cgccggagct catggctgga accgcgtcgg ctccacggcc 60
accaagtggt tcaccggggc gcccttcggg gtgcagagcc acaggtttga catctctgct 120
gtttatccca actggaagaa gttcagcacc ttcactgagg ccccatactc cacgcgttat 180
tctacccaag tgtcccacat aggccctggg acttacagct ccaaagagac ctgcttcagc 240
aagaagaagc tgatgaagga ggtggacaca ggctgggcca aggcccagga agccacgcgg 300
ctgacccagc taccccactt ccagtaccag gccatcatga aagagaagcg gctgaaggag 360
caaaagctgg gccccggctc ctacaacctc aaagacttct tagaacagct gcgggagaaa 420
ccatgtagca cccgggggct gctcagctct ggggaggttc gcttccgagg actcactggg 480
aactactatc caggccctgg aaattatggg gagaagggta acccatacac caagctggag 540
gagaatgcct ggaaccggtc tcattccgag ggcctcatgt gcaggatgag caacaagcca 600
cacccccggc ctcatcaggg gagtggtctg ggacccggca cctacttctt caaaagcgac 660
cttgagacat atgtggcacg atccgtcggc acccgcggcc cctatgacac tttctctggt 720
gatcggagca agccactgcc ttatgggcac tactccatgc agaaaaaaaa gcccagggaa 780
ctgatgaatt tcaagagctt tgtagaagaa cttaactcac atcacaataa gaagcatggg 840 gtttttttcta aacttccccg aaacccgaaa acccctacag agaggattta ctgggccaac 900
ctcagccagt gcccccgcac actggccaca tctggcccca gtttctggct tccacaagag 960
aagaaatgca aacccgtcaa ccagccccca ttcctgttga cctccaaggg gtcaggtgca 1020
aaggcctgcc agatgattat gggaagctgg aacccagtag gtgtgggccg ctacctcaac 1080
acctggctga tggagacaaa ggacaggcgg cagcgatatc gatccctatt cctgagtgga 1140
tccaaacgct acctctcaga cctggcccgg gacatgctca tgcaggaaag gatcacacca 1200
tttactaagg gaaagtgccc tccaactgtg gattacaatt cagatcctac tccttaa 1257

<210> SEQ ID NO 30
<211> LENGTH: 1593
<212> TYPE: DNA
<213> ORGANISM: Homo sapiens
<220> FEATURE:
<223> OTHER INFORMATION: Glycerol kinase (Gyk)
<300> PUBLICATION INFORMATION:
<308> DATABASE ACCESSION NUMBER: RefSeq NG_008178.1
<309> DATABASE ENTRY DATE: 2011-03-01

<400> SEQUENCE: 30
atggcagcct caaagaaggc agttttgggg ccattggtgg gggcggtgga ccagggcacc 60

```
agttcgacgc gctttttggt tttcaattca aaaacagctg aactacttag tcatcatcaa    120
gtagaaataa aacaagagtt cccaagagaa ggatgggtgg aacaggaccc taaggaaatt    180
ctacattctg tctatgagtg tatagagaaa acatgtgaga aacttggaca gctcaatatt    240
gatatttcca acataaaagc tattggtgtc agcaaccaga gggaaaccac tgtagtctgg    300
gacaagataa ctggagagcc tctctacaat gctgtggtgt ggcttgatct aagaacccag    360
tctaccgttg agagtcttag taaaagaatt ccaggaaata ataactttgt caagtccaag    420
acaggccttc cacttagcac ttacttcagt gcagtgaaac ttcgttggct ccttgacaat    480
gtgagaaaag ttcaaaaggc cgttgaagaa aaacgagctc tttttgggac tattgattca    540
tggcttattt ggagtttgac aggaggagtc aatggaggtg tccactgtac agatgtaaca    600
aatgcaagta ggactatgct tttcaacatt cattctttgg aatgggataa acaactctgc    660
gaattttttg gaattccaat ggaaattctt ccaaatgtcc ggagttcttc tgagatctat    720
ggcctaatga aatctctca tagcgtgaaa gctggggcct tggaaggtgt gccaatatct    780
gggtgtttag gggaccagtc tgctgcattg gtgggacaaa tgtgcttcca gattggacaa    840
gccaaaaata cgtatggaac aggatgtttc ttactatgta atacaggcca taagtgtgta    900
ttttctgatc atggccttct caccacagtg gcttacaaac ttggcagaga caaaccagta    960
tattatgctt tggaaggttc tgtagctata gctggtgctg ttattcgctg gctaagagac   1020
aatcttggaa ttataaagac ctcagaagaa attgaaaaac ttgctaaaga agtaggtact   1080
tcttatggct gctacttcgt cccagcattt tcggggttat atgcacctta ttgggagccc   1140
agcgcaagag ggataatctg tggactcact cagttcacca ataaatgcca tattgctttt   1200
gctgcattag aagctgtttg tttccaaact cgagagattt tggatgccat gaatcgagac   1260
tgtggaattc cactcagtca tttgcaggta gatggaggaa tgaccagcaa caaaattctt   1320
atgcagctac aagcagacat tctgtatata ccagtagtga agccctcaat gcccgaaacc   1380
actgcactgg gtgcggctat ggcggcaggg gctgcagaag gagtcggcgt atggagtctc   1440
gaacccgagg atttgtctgc cgtcacgatg gagcggtttg aacctcagat taatgcggag   1500
gaaagtgaaa ttcgttattc tacatggaag aaagctgtga tgaagtcaat gggttgggtt   1560
acaactcaat ctccagaaag tggtattcca taa                                1593
```

<210> SEQ ID NO 31
<211> LENGTH: 1467
<212> TYPE: DNA
<213> ORGANISM: Homo sapiens
<220> FEATURE:
<223> OTHER INFORMATION: DAG O-acetyltransferase 1 (DGAT1)
<300> PUBLICATION INFORMATION:
<308> DATABASE ACCESSION NUMBER: NCBI NM_012079.5
<309> DATABASE ENTRY DATE: 2013-07-19

<400> SEQUENCE: 31

```
atgggcgacc gcggcagctc ccggcgccgg aggacagggt cgcggccctc gagccacggc     60
ggcggcgggc ctgcggcggc ggaagaggag gtgcgggacg ccgctgcggg ccccgacgtg    120
ggagccgcgg gggacgcgcc agccccggcc cccaacaagg acggagacgc cggcgtgggc    180
agcggccact gggagctgag gtgccatcgc ctgcaggatt ctttattcag ctctgacagt    240
ggcttcagca actaccgtgg catcctgaac tggtgtgtgg tgatgctgat cttgagcaat    300
gcccggttat ttctggagaa cctcatcaag tatggcatcc tggtggaccc catccaggtg    360
gtttctctgt tcctgaagga tccctatagc tggcccgccc catgcctggt tattgcggcc    420
```

```
aatgtctttg ctgtggctgc attccaggtt gagaagcgcc tggcggtggg tgccctgacg    480

gagcaggcgg gactgctgct gcacgtggcc aacctggcca ccattctgtg tttcccagcg    540

gctgtggtct tactggttga gtctatcact ccagtgggct ccctgctggc gctgatggcg    600

cacaccatcc tcttcctcaa gctcttctcc taccgcgacg tcaactcatg gtgccgcagg    660

gccagggcca aggctgcctc tgcagggaag aaggccagca gtgctgctgc cccgcacacc    720

gtgagctacc cggacaatct gacctaccgc gatctctact acttcctctt cgcccccacc    780

ttgtgctacg agctcaactt tccccgctct ccccgcatcc ggaagcgctt tctgctgcga    840

cggatccttg agatgctgtt cttcacccag ctccaggtgg ggctgatcca gcagtggatg    900

gtccccacca tccagaactc catgaagccc ttcaaggaca tggactactc acgcatcatc    960

gagcgcctcc tgaagctggc ggtccccaat cacctcatct ggctcatctt cttctactgg   1020

ctcttccact cctgcctgaa tgccgtggct gagctcatgc agtttggaga ccgggagttc   1080

taccgggact ggtggaactc cgagtctgtc acctacttct ggcagaactg gaacatccct   1140

gtgcacaagt ggtgcatcag acacttctac aagcccatgc ttcgacgggg cagcagcaag   1200

tggatggcca ggacaggggt gttcctggcc tcggccttct tccacgagta cctggtgagc   1260

gtccctctgc gaatgttccg cctctgggcg ttcacgggca tgatggctca gatcccactg   1320

gcctggttcg tgggccgctt tttccagggc aactatggca acgcagctgt gtggctgtcg   1380

ctcatcatcg gacagccaat agccgtcctc atgtacgtcc acgactacta cgtgctcaac   1440

tatgaggccc cagcggcaga ggcctga                                       1467
```

<210> SEQ ID NO 32
<211> LENGTH: 2487
<212> TYPE: DNA
<213> ORGANISM: Homo sapiens
<220> FEATURE:
<223> OTHER INFORMATION: Glycerol-3-phosphate acetyltransferase mitochondrial (GPAM)
<300> PUBLICATION INFORMATION:
<308> DATABASE ACCESSION NUMBER: NCBI NM_001244949.1
<309> DATABASE ENTRY DATE: 2011-10-01

<400> SEQUENCE: 32

```
atggatgaat ctgcactgac ccttggtaca atagatgttt cttatctgcc acattcatca     60

gaatacagtg ttggtcgatg taagcacaca agtgaggaat ggggtgagtg tggctttaga    120

cccaccatct tcagatctgc aactttaaaa tggaaagaaa gcctaatgag tcggaaaagg    180

ccatttgttg gaagatgttg ttactcctgc actccccaga gctgggacaa atttttcaac    240

cccagtatcc cgtctttggg tttgcggaat gttatttata tcaatgaaac tcacacaaga    300

caccgcggat ggcttgcaag acgccttttct tacgttcttt ttattcaaga gcgagatgtg   360

cataagggca tgtttgccac caatgtgact gaaaatgtgc tgaacagcag tagagtacaa    420

gaggcaattg cagaagtggc tgctgaatta aaccctgatg gttctgccca gcagcaatca    480

aaagccgtta acaaagtgaa aaagaaagct aaaaggattc ttcaagaaat ggttgccact    540

gtctcaccgg caatgatcag actgactggg tgggtgctgc taaaactgtt caacagcttc    600

ttttggaaca ttcaaattca caaaggtcaa cttgagatgg ttaaagctgc aactgagacg    660

aatttgccgc ttctgtttct accagttcat agatcccata ttgactatct gctgctcact    720

ttcattctct tctgccataa catcaaagca ccatacattg cttcaggcaa taatctcaac    780

atcccaatct tcagtacctt gatccataag cttgggggct tcttcatacg acgaaggctc    840

gatgaaacac cagatggacg gaaagatgtt ctctatagag ctttgctcca tgggcatata    900
```

```
gttgaattac ttcgacagca gcaattcttg gagatcttcc tggaaggcac acgttctagg    960

agtggaaaaa cctcttgtgc tcgggcagga cttttgtcag ttgtggtaga tactctgtct   1020

accaatgtca tcccagacat cttgataata cctgttggaa tctcctatga tcgcattatc   1080

gaaggtcact acaatggtga acaactgggc aaacctaaga agaatgagag cctgtggagt   1140

gtagcaagag gtgttattag aatgttacga aaaaactatg gttgtgtccg agtggatttt   1200

gcacagccat tttccttaaa ggaatattta gaaagccaaa gtcagaaacc ggtgtctgct   1260

ctactttccc tggagcaagc gttgttacca gctatacttc cttcaagacc cagtgatgct   1320

gctgatgaag gtagagacac gtccattaat gagtccagaa atgcaacaga tgaatcccta   1380

cgaaggaggt tgattgcaaa tctggctgag catattctat tcactgctag caagtcctgt   1440

gccattatgt ccacacacat tgtggcttgc ctgctcctct acagacacag gcagggaatt   1500

gatctctcca cattggtcga agacttcttt gtgatgaaag aggaagtcct ggctcgtgat   1560

tttgacctgg ggttctcagg aaattcagaa gatgtagtaa tgcatgccat acagctgctg   1620

ggaaattgtg tcacaatcac ccacactagc aggaacgatg agtttttat caccccccagc   1680

acaactgtcc catcagtctt cgaactcaac ttctacagca atggggtact tcatgtcttt   1740

atcatggagg ccatcatagc ttgcagcctt tatgcagttc tgaacaagag gggactgggg   1800

ggtcccacta gcaccccacc taacctgatc agccaggagc agctggtgcg gaaggcggcc   1860

agcctgtgct accttctctc caatgaaggc accatctcac tgccttgcca gacattttac   1920

caagtctgcc atgaaacagt aggaaagttt atccagtatg gcattcttac agtggcagag   1980

cacgatgacc aggaagatat cagtcctagt cttgctgagc agcagtggga caagaagctt   2040

ccagaacctt tgtcttggag aagtgatgaa gaagatgaag acagtgactt tggggaggaa   2100

cagcgagatt gctacctgaa ggtgagccaa tccaaggagc accagcagtt tatcaccttc   2160

ttacagagac tccttgggcc tttgctggag gcctacagct ctgctgccat ctttgttcac   2220

aacttcagtg gtcctgttcc agaacctgag tatctgcaaa agttgcacaa atacctaata   2280

accagaacag aaagaaatgt tgcagtatat gctgagagtg ccacatattg tcttgtgaag   2340

aatgctgtga aaatgtttaa ggatattggg gttttcaagg agaccaaaca aaagagagtg   2400

tctgttttag aactgagcag cacttttcta cctcaatgca accgacaaaa acttctagaa   2460

tatattctga gttttgtggt gctgtag                                       2487

<210> SEQ ID NO 33
<211> LENGTH: 1008
<212> TYPE: DNA
<213> ORGANISM: Homo sapiens
<220> FEATURE:
<223> OTHER INFORMATION: Monoacylglycerol O-acetyltransferase (MOGAT1)
<300> PUBLICATION INFORMATION:
<308> DATABASE ACCESSION NUMBER: NCBI NM_058165.2
<309> DATABASE ENTRY DATE: 2007-06-09

<400> SEQUENCE: 33

atgaaggtag agtttgcacc gctcaacatc cagctggcgc ggcggctgca gacggtggcc     60

gtgctgcagt gggtcctgaa atacctgctg ctcgggccga tgtccattgg aatcactgtg    120

atgctgatca tacacaacta tttgttcctt tacatcccctt atttgatgtg gctttacttt    180

gactggcata ccccagagcg aggaggcagg agatccagct ggatcaaaaa ttggactctt    240

tggaaacact ttaaggacta ttttccaatt catcttatca aaactcaaga tttggatcca    300

agtcacaact atatatttgg gtttcacccc catggaataa tggcagttgg agcctttggg    360
```

```
aatttttctg taaattattc tgacttcaag gacctgtttc ctggctttac ttcatatctt    420

cacgtgctgc cactttggtt ctggtgtcct gtctttcgag aatatgtgat gagtgttggg    480

ctggtttcag tttccaagaa aagtgtgtcc tacatggtaa gcaaggaggg aggtggaaac    540

atctctgtca ttgtccttgg gggtgcaaaa gaatcactgg atgctcatcc tggaaagttc    600

actctgttca tccgccagcg gaaaggattt gttaaaattg ctttgaccca tggcgcctct    660

ctggtcccag tggtttcttt tggtgaaaat gaactgttta aacaaactga caaccctgaa    720

ggatcatgga ttagaactgt tcagaataaa ctgcagaaga tcatggggtt tgctttgccc    780

ctgtttcatg ccaggggagt tttcagtac aattttggcc taatgaccta taggaaagcc    840

atccacactg ttgttggccg cccgatccct gttcgtcaga ctctgaaccc gacccaggag    900

cagattgagg agttacatca gacctatatg gaggaactta ggaaattgtt tgaggaacac    960

aaaggaaagt atggcattcc agagcacgag actcttgttt taaaatga                1008
```

<210> SEQ ID NO 34
<211> LENGTH: 2481
<212> TYPE: DNA
<213> ORGANISM: Homo sapiens
<220> FEATURE:
<223> OTHER INFORMATION: HIF1alpha
<300> PUBLICATION INFORMATION:
<308> DATABASE ACCESSION NUMBER: NCBI NM_001530.3
<309> DATABASE ENTRY DATE: 2008-07-26

<400> SEQUENCE: 34

```
atggagggcg ccggcggcgc gaacgacaag aaaaagataa gttctgaacg tcgaaaagaa      60

aagtctcgag atgcagccag atctcggcga agtaaagaat ctgaagtttt ttatgagctt     120

gctcatcagt tgccacttcc acataatgtg agttcgcatc ttgataaggc ctctgtgatg     180

aggcttacca tcagctattt gcgtgtgagg aaacttctgg atgctggtga tttggatatt     240

gaagatgaca tgaaagcaca gatgaattgc ttttatttga aagccttgga tggttttgtt     300

atggttctca cagatgatgg tgacatgatt tacatttctg ataatgtgaa caaatacatg     360

ggattaactc agtttgaact aactggacac agtgtgtttg attttactca tccatgtgac     420

catgaggaaa tgagagaaat gcttacacac agaaatggcc ttgtgaaaaa gggtaaagaa     480

caaaacacac agcgaagctt ttttctcaga atgaagtgta ccctaactag ccgaggaaga     540

actatgaaca taaagtctgc aacatggaag gtattgcact gcacaggcca cattcacgta     600

tatgatacca acagtaacca acctcagtgt gggtataaga aaccacctat gacctgcttg     660

gtgctgattt gtgaacccat tcctcaccca tcaaatattg aaattccttt agatagcaag     720

actttcctca gtcgacacag cctggatatg aaattttctt attgtgatga aagaattacc     780

gaattgatgg gatatgagcc agaagaactt ttaggccgct caatttatga atattatcat     840

gctttggact ctgatcatct gaccaaaact catcatgata tgtttactaa aggacaagtc     900

accacaggac agtacaggat gcttgccaaa agaggtggat atgtctgggt tgaaactcaa     960

gcaactgtca tatataacac caagaattct caaccacagt gcattgtatg tgtgaattac    1020

gttgtgagtg gtattattca gcacgacttg attttctccc ttcaacaaac agaatgtgtc    1080

cttaaaccgg ttgaatcttc agatatgaaa atgactcagc tattcaccaa agttgaatca    1140

gaagatacaa gtagcctctt tgacaaactt aagaaggaac ctgatgcttt aactttgctg    1200

gccccagccg ctggagacac aatcatatct ttagattttg gcagcaacga cacagaaact    1260

gatgaccagc aacttgagga agtaccatta tataatgatg taatgctccc ctcacccaac    1320
```

-continued

```
gaaaaattac agaatataaa tttggcaatg tctccattac ccaccgctga aacgccaaag   1380

ccacttcgaa gtagtgctga ccctgcactc aatcaagaag ttgcattaaa attagaacca   1440

aatccagagt cactggaact ttcttttacc atgccccaga ttcaggatca gacacctagt   1500

ccttccgatg gaagcactag acaaagttca cctgagccta atagtcccag tgaatattgt   1560

ttttatgtgg atagtgatat ggtcaatgaa ttcaagttgg aattggtaga aaaacttttt   1620

gctgaagaca cagaagcaaa gaacccattt tctactcagg acacagattt agacttggag   1680

atgttagctc cctatatccc aatggatgat gacttccagt tacgttcctt cgatcagttg   1740

tcaccattag aaagcagttc cgcaagccct gaaagcgcaa gtcctcaaag cacagttaca   1800

gtattccagc agactcaaat acaagaacct actgctaatg ccaccactac cactgccacc   1860

actgatgaat taaaaacagt gacaaaagac cgtatggaag acattaaaat attgattgca   1920

tctccatctc ctacccacat acataaagaa actactagtg ccacatcatc accatataga   1980

gatactcaaa gtcggacagc ctcaccaaac agagcaggaa aaggagtcat agaacagaca   2040

gaaaaatctc atccaagaag ccctaacgtg ttatctgtcg ctttgagtca aagaactaca   2100

gttcctgagg aagaactaaa tccaaagata ctagctttgc agaatgctca gagaaagcga   2160

aaaatggaac atgatggttc acttttttcaa gcagtaggaa ttggaacatt attacagcag   2220

ccagacgatc atgcagctac tacatcactt tcttggaaac gtgtaaaagg atgcaaatct   2280

agtgaacaga atggaatgga gcaaaagaca attattttaa taccctctga tttagcatgt   2340

agactgctgg ggcaatcaat ggatgaaagt ggattaccac agctgaccag ttatgattgt   2400

gaagttaatg ctcctataca aggcagcaga aacctactgc agggtgaaga attactcaga   2460

gctttggatc aagttaactg a                                             2481
```

<210> SEQ ID NO 35
<211> LENGTH: 1869
<212> TYPE: DNA
<213> ORGANISM: Homo sapiens
<220> FEATURE:
<223> OTHER INFORMATION: PCK1
<300> PUBLICATION INFORMATION:
<308> DATABASE ACCESSION NUMBER: NCBI NM_002591.3
<309> DATABASE ENTRY DATE: 2008-05-02

<400> SEQUENCE: 35

```
atgcctcctc agctgcaaaa cggcctgaac ctctcggcca aagttgtcca gggaagcctg     60

gacagcctac cccaggcagt gagggagttt ctcgagaata acgctgagct gtgtcagcct    120

gatcacatcc acatctgtga cggctctgag gaggagaatg ggcggcttct gggccagatg    180

gaggaagagg gcatcctcag gcggctgaag aagtatgaca actgctggtt ggctctcact    240

gaccccaggg atgtggccag gatcgaaagc aagacggtta tcgtcaccca agagcaaaga    300

gacacagtgc ccatccccaa aacaggcctc agccagctcg gtcgctggat gtcagaggag    360

gattttgaga aagcgttcaa tgccaggttc ccagggtgca tgaaaggtcg caccatgtac    420

gtcatcccat tcagcatggg gccgctgggc tcgcctctgt caaagatcgg catcgagctg    480

acggattcac cctacgtggt ggccagcatg cggatcatga cgcggatggg cacgcccgtc    540

ctggaagcag tgggcgatgg ggagtttgtc aaatgcctcc attctgtggg gtgccctctg    600

cctttacaaa agcctttggt caacaactgg ccctgcaacc cggagctgac gctcatcgcc    660

cacctgcctg accgcagaga gatcatctcc tttggcagtg ggtacggcgg gaactcgctg    720

ctcgggaaga agtgctttgc tctcaggatg gccagccggc tggccaagga ggaagggtgg    780
```

```
ctggcagagc acatgctgat tctgggtata accaaccctg agggtgagaa gaagtacctg    840

gcggccgcat ttcccagcgc ctgcgggaag accaacctgg ccatgatgaa ccccagcctc    900

cccgggtgga aggttgagtg cgtcggggat gacattgcct ggatgaagtt tgacgcacaa    960

ggtcatttaa gggccatcaa cccagaaaat ggctttttcg gtgtcgctcc tgggacttca   1020

gtgaagacca accccaatgc catcaagacc atccagaaga acacaatctt taccaatgtg   1080

gccgagacca gcgacggggg cgtttactgg gaaggcattg atgagccgct agcttcaggt   1140

gtcaccatca cgtcctggaa gaataaggag tggagctcag aggatgggga accttgtgcc   1200

caccccaact cgaggttctg caccccctgcc agccagtgcc ccatcattga tgctgcctgg  1260

gagtctccgg aaggtgttcc cattgaaggc attatctttg gaggccgtag acctgctggt   1320

gtccctctag tctatgaagc tctcagctgg caacatggag tctttgtggg ggcggccatg   1380

agatcagagg ccacagcggc tgcagaacat aaaggcaaaa tcatcatgca tgaccccttt   1440

gccatgcggc ccttctttgg ctacaacttc ggcaaatacc tggcccactg gcttagcatg   1500

gcccagcacc cagcagccaa actgcccaag atcttccatg tcaactggtt ccggaaggac   1560

aaggaaggca aattcctctg gccaggcttt ggagagaact ccagggtgct ggagtggatg   1620

ttcaaccgga tcgatggaaa agccagcacc aagctcacgc ccataggcta catccccaag   1680

gaggatgccc tgaacctgaa aggcctgggg cacatcaaca tgatggagct tttcagcatc   1740

tccaaggaat tctgggagaa ggaggtggaa gacatcgaga agtatctgga ggatcaagtc   1800

aatgccgacc tcccctgtga aatcgagaga gagatccttg ccttgaagca aagaataagc   1860

cagatgtaa                                                           1869
```

<210> SEQ ID NO 36
<211> LENGTH: 852
<212> TYPE: DNA
<213> ORGANISM: Homo sapiens
<220> FEATURE:
<223> OTHER INFORMATION: AGPAT1
<300> PUBLICATION INFORMATION:
<308> DATABASE ACCESSION NUMBER: NCBI NM_006411.3
<309> DATABASE ENTRY DATE: 2010-07-27

<400> SEQUENCE: 36

```
atggatttgt ggccaggggc atggatgctg ctgctgctgc tcttcctgct gctgctcttc     60

ctgctgccca ccctgtggtt ctgcagcccc agtgccaagt acttcttcaa gatggccttc    120

tacaatggct ggatcctctt cctggctgtg ctcgccatcc ctgtgtgtgc cgtgcgagga    180

cgcaacgtcg agaacatgaa gatcttgcgt ctaatgctgc tccacatcaa atacctgtac    240

gggatccgag tggaggtgcg aggggctcac cacttccctc cctcgcagcc ctatgttgtt    300

gtctccaacc accagagctc tctcgatctg cttgggatga tggaggtact gccaggccgc    360

tgtgtgccca ttgccaagcg cgagctactg tgggctggct ctgccgggct ggcctgctgg    420

ctggcaggag tcatcttcat cgaccggaag cgcacggggg atgccatcag tgtcatgtct    480

gaggtcgccc agaccctgct cacccaggac gtgagggtct gggtgtttcc tgagggaacg    540

agaaaccaca atggctccat gctgcccttc aaacgtggcg ccttccatct tgcagtgcag    600

gcccaggttc ccattgtccc catagtcatg tcctcctacc aagacttcta ctgcaagaag    660

gagcgtcgct tcacctcggg acaatgtcag gtgcgggtgc tgcccccagt gcccacggaa    720

gggctgacac cagatgacgt cccagctctg gctgacagag tccggcactc catgctcact    780

gttttccggg aaatctccac tgatggccgg ggtggtggtg actatctgaa gaagcctggg    840
```

ggcggtgggt ga 852

<210> SEQ ID NO 37
<211> LENGTH: 837
<212> TYPE: DNA
<213> ORGANISM: Homo sapiens
<220> FEATURE:
<223> OTHER INFORMATION: AGPAT2 isoform alpha precursor
<300> PUBLICATION INFORMATION:
<308> DATABASE ACCESSION NUMBER: NCBI NM_006412.3
<309> DATABASE ENTRY DATE: 2005-07-05

<400> SEQUENCE: 37
atggagctgt ggccgtgtct ggccgcggcg ctgctgttgc tgctgctgct ggtgcagctg 60
agccgcgcgg ccgagttcta cgccaaggtc gccctgtact gcgcgctgtg cttcacggtg 120
tccgccgtgg cctcgctcgt ctgcctgctg cgccacggcg gccggacggt ggagaacatg 180
agcatcatcg gctggttcgt gcgaagcttc aagtactttt acgggctccg cttcgaggtg 240
cgggacccgc gcaggctgca ggaggcccgt ccctgtgtca tcgtctccaa ccaccagagc 300
atcctggaca tgatgggcct catggaggtc cttccggagc gctgcgtgca gatcgccaag 360
cgggagctgc tcttcctggg gcccgtgggc ctcatcatgt acctcggggg cgtcttcttc 420
atcaaccggc agcgctctag cactgccatg acagtgatgg ccgacctggg cgagcgcatg 480
gtcagggaga acctcaaagt gtggatctat cccgagggta ctcgcaacga caatggggac 540
ctgctgcctt ttaagaaggg cgccttctac ctggcagtcc aggcacaggt gcccatcgtc 600
cccgtggtgt actcttcctt ctcctccttc tacaacacca agaagaagtt cttcacttca 660
ggaacagtca cagtgcaggt gctggaagcc atccccacca gcggcctcac tgcggcggac 720
gtccctgcgc tcgtggacac ctgccaccgg gccatgagga ccaccttcct ccacatctcc 780
aagacccccc aggagaacgg ggccactgcg gggtctggcg tgcagccggc ccagtag 837

<210> SEQ ID NO 38
<211> LENGTH: 741
<212> TYPE: DNA
<213> ORGANISM: Homo sapiens
<220> FEATURE:
<223> OTHER INFORMATION: AGPAT2 isoform beta precursor

<400> SEQUENCE: 38
atggagctgt ggccgtgtct ggccgcggcg ctgctgttgc tgctgctgct ggtgcagctg 60
agccgcgcgg ccgagttcta cgccaaggtc gccctgtact gcgcgctgtg cttcacggtg 120
tccgccgtgg cctcgctcgt ctgcctgctg cgccacggcg gccggacggt ggagaacatg 180
agcatcatcg gctggttcgt gcgaagcttc aagtactttt acgggctccg cttcgaggtg 240
cgggacccgc gcaggctgca ggaggcccgt ccctgtgtca tcgtctccaa ccaccagagc 300
atcctggaca tgatgggcct catggaggtc cttccggagc gctgcgtgca gatcgccaag 360
cgggagctgc tcttcctggg gcccgtgggc ctcatcatgt acctcggggg cgtcttcttc 420
atcaaccggc agcgctctag cactgccatg acagtgatgg ccgacctggg cgagcgcatg 480
gtcagggaga acgtgcccat cgtccccgtg gtgtactctt ccttctcctc cttctacaac 540
accaagaaga agttcttcac ttcaggaaca gtcacagtgc aggtgctgga agccatcccc 600
accagcggcc tcactgcggc ggacgtccct gcgctcgtgg acacctgcca ccgggccatg 660
aggaccacct tcctccacat ctccaagacc ccccaggaga acggggccac tgcggggtct 720
ggcgtgcagc cggcccagta g 741

<210> SEQ ID NO 39
<211> LENGTH: 1131
<212> TYPE: DNA
<213> ORGANISM: Homo sapiens
<220> FEATURE:
<223> OTHER INFORMATION: AGPAT3
<300> PUBLICATION INFORMATION:
<308> DATABASE ACCESSION NUMBER: NCBI NM_020132.4
<309> DATABASE ENTRY DATE: 2005-12-05

<400> SEQUENCE: 39
atgggcctgc tggccttcct gaagacccag ttcgtgctgc acctgctggt cggctttgtc 60
ttcgtggtga gtggtctggt catcaacttc gtccagctgt gcacgctggc gctctggccg 120
gtcagcaagc agctctaccg ccgcctcaac tgccgcctcg cctactcact ctggagccaa 180
ctggtcatgc tgctggagtg gtggtcctgc acggagtgta cactgttcac ggaccaggcc 240
acggtagagc gctttgggaa ggagcacgca gtcatcatcc tcaaccacaa cttcgagatc 300
gacttcctct gtgggtggac catgtgtgag cgcttcggag tgctggggag ctccaaggtc 360
ctcgctaaga aggagctgct ctacgtgccc ctcatcggct ggacgtggta ctttctggag 420
attgtgttct gcaagcggaa gtgggaggag gaccgggaca ccgtggtcga agggctgagg 480
cgcctgtcgg actaccccga gtacatgtgg tttctcctgt actgcgaggg gacgcgcttc 540
acggagacca agcaccgcgt tagcatggag gtggcggctg ctaaggggct tcctgtcctc 600
aagtaccacc tgctgccgcg gaccaagggc ttcaccaccg cagtcaagtg cctccggggg 660
acagtcgcag ctgtctatga tgtaaccctg aacttcagag gaaacaagaa cccgtccctg 720
ctggggatcc tctacgggaa gaagtacgag gcggacatgt gcgtgaggag atttcctctg 780
gaagacatcc cgctggatga aaaggaagca gctcagtggc ttcataaact gtaccaggag 840
aaggacgcgc tccaggagat atataatcag aagggcatgt ttccagggga gcagtttaag 900
cctgcccgga ggccgtggac cctcctgaac ttcctgtcct gggccaccat tctcctgtct 960
cccctcttca gttttgtctt gggcgtcttt gccagcggat cacctctcct gatcctgact 1020
ttcttggggt ttgtgggagc agcttccttt ggagttcgca gactgatagg agtaactgag 1080
atagaaaaag gctccagcta cggaaaccaa gagtttaaga aaaaggaata a 1131

<210> SEQ ID NO 40
<211> LENGTH: 1371
<212> TYPE: DNA
<213> ORGANISM: Homo sapiens
<220> FEATURE:
<223> OTHER INFORMATION: AGPAT6 (LPA-MAG PA)
<300> PUBLICATION INFORMATION:
<308> DATABASE ACCESSION NUMBER: NCBI NM_178819.3
<309> DATABASE ENTRY DATE: 2009-02-28

<400> SEQUENCE: 40
atgttcctgt tgctgccttt tgatagcctg attgtcaacc ttctgggcat ctccctgact 60
gtcctcttca ccctccttct cgttttcatc atagtgccag ccatttttgg agtctccttt 120
ggtatccgca aactctacat gaaaagtctg ttaaaaatct ttgcgtgggc taccttgaga 180
atggagcgag gagccaagga gaagaaccac cagctttaca agccctacac caacggaatc 240
attgcaaagg atcccacttc actagaagaa gagatcaaag agattcgtcg aagtggtagt 300
agtaaggctc tggacaacac tccagagttc gagctctctg acattttcta cttttgccgg 360
aaaggaatgg agaccattat ggatgatgag gtgacaaaga gattctcagc agaagaactg 420

```
gagtcctgga acctgctgag cagaaccaat tataacttcc agtacatcag ccttcggctc    480

acggtcctgt gggggttagg agtgctgatt cggtactgct ttctgctgcc gctcaggata    540

gcactggctt tcacagggat tagccttctg gtggtgggca caactgtggt gggatacttg    600

ccaaatggga ggtttaagga gttcatgagt aaacatgttc acttaatgtg ttaccggatc    660

tgcgtgcgag cgctgacagc catcatcacc taccatgaca gggaaaacag accaagaaat    720

ggtggcatct gtgtggccaa tcatacctca ccgatcgatg tgatcatctt ggccagcgat    780

ggctattatg ccatggtggg tcaagtgcac gggggactca tgggtgtgat tcagagagcc    840

atggtgaagg cctgcccaca cgtctggttt gagcgctcgg aagtgaagga tcgccacctg    900

gtggctaaga gactgactga acatgtgcaa gataaaagca agctgcctat cctcatcttc    960

ccagaaggaa cctgcatcaa taatacatcg gtgatgatgt tcaaaaaggg aagttttgaa   1020

attggagcca cagtttaccc tgttgctatc aagtatgacc ctcaatttgg cgatgccttc   1080

tggaacagca gcaaatacgg gatggtgacg tacctgctgc gaatgatgac cagctgggcc   1140

attgtctgca gcgtgtggta cctgcctccc atgactagag aggcagatga agatgctgtc   1200

cagtttgcga atagggtgaa atctgccatt gccaggcagg gaggacttgt ggacctgctg   1260

tgggatgggg gcctgaagag ggagaaggtg aaggacacgt tcaaggagga gcagcagaag   1320

ctgtacagca agatgatcgt ggggaaccac aaggacagga gccgctcctg a            1371
```

```
<210> SEQ ID NO 41
<211> LENGTH: 2388
<212> TYPE: DNA
<213> ORGANISM: Homo sapiens
<220> FEATURE:
<223> OTHER INFORMATION: GPAT2
<300> PUBLICATION INFORMATION:
<308> DATABASE ACCESSION NUMBER: NCBI NM_207328.2
<309> DATABASE ENTRY DATE: 2006-10-28

<400> SEQUENCE: 41
```

```
atggccacca tgttggaagg cagatgccaa actcagccaa ggagcagccc cagtggccga     60

gaggctagcc tgtggtcgtc aggctttggg atgaagctgg aggctgtcac tccattcctg    120

gggaagtatc gcccctttgt gggtcgctgt tgccagacct gcacccccaa gagctgggag    180

tccctcttcc acagaagcat aacggaccta ggcttctgca atgtgatcct ggtgaaggag    240

gagaacacaa ggtttcgggg ctggctggtt cggaggctct gctatttcct gtggtccctg    300

gagcagcaca tccccccctg ccaggatgtc ccacagaaga tcatggaaag caccggggtg    360

cagaacctcc tctcagggag ggtcccagga ggcactgggg aaggccaggt gcctgacctt    420

gtgaagaagg aggtacagcg catcctgggt cacatccagg ccccaccccg tcccttcctg    480

gtcaggctgt tcagctgggc gctgctgagg ttcctgaact gcctgttcct gaatgtgcag    540

ctccacaagg gtcagatgaa gatggtccag aaggccgccc aggcaggctt gccgcttgtc    600

ctcctctcta ctcacaaaac cctcctggat gggatcctgc tgccctttat gctgctctcc    660

cagggcctgg gtgtgcttcg tgtggcctgg gactcccgcg cctgctcccc tgccctcaga    720

gctctgctga ggaagcttgg ggggcttttc ctgcccccag aggccagcct ctccctggac    780

agctctgagg ggctccttgc cagggctgtg gtccaggcgg tcatagagca gctgctggtt    840

agtgggcagc ccctgctcat cttcctggag gaacctcctg ggctctgggg gccacggctg    900

tcagccctgg gccaggcttg ggtggggttt gtggtgcagg cagtccaggt gggcatcgtc    960

ccagatgctc tgctggtacc agtggccgtc acctatgacc tggttccgga tgcaccgtgt   1020
```

-continued

```
gacatagacc atgcctcggc ccccctgggg ctgtggacag gagctctggc tgtcctacgt   1080

agcttgtgga gccgctgggg ctgcagccac cggatctgct cccgggtgca cctagctcag   1140

cccttttccc tgcaggaata catcgtcagt gccagaagct gctggggcgg cagacagacc   1200

ctggagcagc tactgcagcc catcgtgctg ggccaatgta ctgctgtccc agacactgag   1260

aaggagcagg agtggacccc cataactggg cctctcctgg ccctcaagga agaggaccag   1320

ctcctggtca ggagactgag ctgtcatgtc ctgagtgcca gtgtagggag ctctgcggtg   1380

atgagcacgg ccattatggc aacgctgctg ctcttcaagc atcagaagct cctgggggag   1440

ttctcctggc tgacggagga gatactgttg cgtggctttg atgtaggctt ctctgggcag   1500

ctgcggagcc tgctgcagca ctcactgagc ctgctgcggg cgcacgtggc cctgctgcgc   1560

atccgtcagg gtgacttgct ggtggtgccg cagcctggcc caggcctcac acacctggca   1620

caactgagtg ctgagctgct gcccgtcttc ctgagcgagg ctgtgggcgc ctgtgcagtg   1680

cgggggctgc tggcaggcag agtgccgccc caggggccct gggagctgca gggcatattg   1740

ctgctgagcc agaatgagct gtaccgccag atcctgctgc tgatgcacct gctgccgcaa   1800

gacctgctgc tgctaaagcc ctgccagtct tcctactgct actgtcagga ggtgctggac   1860

cggctcatcc aatgcgggct cctggttgct gaggagaccc caggctcccg gccagcctgt   1920

gacacagggc gacagcgatt gagcagaaag ctgctgtgga aaccgagtgg ggactttact   1980

gatagtgaca gtgatgactt cggagaggct gacggccggt acttcaggct cagccagcag   2040

tcacactgcc cagatttctt tcttttcctc tgccgcctgc tcagcccgct gctcaaggcc   2100

tttgcacagg ctgccgcctt cctccgccag ggccagctgc ccgatactga gttgggctac   2160

acagagcagc tgttccagtt cctgcaggcc accgcccagg aagaagggat cttcgagtgt   2220

gcggacccaa agctcgccat cagtgctgtc tggaccttca gagacctagg ggttctgcag   2280

cagacgccga gccctgcagg ccccaggctc cacctgtccc ctacttttgc cagcctggac   2340

aatcaggaaa aactagaaca gttcatccgg cagttcattt gtagctag                2388
```

<210> SEQ ID NO 42
<211> LENGTH: 1005
<212> TYPE: DNA
<213> ORGANISM: Homo sapiens
<220> FEATURE:
<223> OTHER INFORMATION: MOGAT2
<300> PUBLICATION INFORMATION:
<308> DATABASE ACCESSION NUMBER: NCBI NM_025098.2
<309> DATABASE ENTRY DATE: 2003-10-07

<400> SEQUENCE: 42

```
atggtagagt tcgcgccctt gtttatgccg tgggagcgca ggctgcagac acttgctgtc     60

ctacagtttg tcttctcctt cttggcactg gccgagatct gcactgtggg cttcatagcc    120

ctcctgttta caagattctg gctcctcact gtcctgtatg cggcctggtg gtatctggac    180

cgagacaagc cacggcaggg gggccggcac atccaggcca tcaggtgctg gactatatgg    240

aagtacatga aggactattt ccccatctcg ctggtcaaga ctgctgagct ggacccctct    300

cggaactaca ttgcgggctt ccaccccccat ggagtcctgg cagtcggagc ctttgccaac    360

ctgtgcactg agagcacagg cttctcttcg atcttccccg gtatccgccc ccatctgatg    420

atgctgacct tgtggttccg ggcccccttc ttcagagatt acatcatgtc tgcagggttg    480

gtcacatcag aaaaggagag tgctgctcac attctgaaca ggaagggtgg cggaaacttg    540

ctgggcatca ttgtaggggg tgcccaggag gccctggatg ccaggcctgg atccttcacg    600
```

-continued

```
ctgttactgc ggaaccgaaa gggcttcgtc aggctcgccc tgacacacgg ggcacccctg    660

gtgccaatct tctccttcgg ggagaatgac ctatttgacc agattcccaa ctcttctggc    720

tcctggttac gctatatcca gaatcggttg cagaagatca tgggcatctc cctcccactc    780

tttcatggcc gtggtgtctt ccagtacagc tttggtttaa taccctaccg ccggcccatc    840

accactgtgg tggggaagcc catcgaggta cagaagacgc tgcatccctc ggaggaggag    900

gtgaaccagc tgcaccagcg ttatatcaaa gagctgtgca acctcttcga ggcccacaaa    960

cttaagttca acatccctgc tgaccagcac ttggagttct gctga                   1005
```

<210> SEQ ID NO 43
<211> LENGTH: 1167
<212> TYPE: DNA
<213> ORGANISM: Homo sapiens
<220> FEATURE:
<223> OTHER INFORMATION: DGAT2
<300> PUBLICATION INFORMATION:
<308> DATABASE ACCESSION NUMBER: NCBI NM_032564.4
<309> DATABASE ENTRY DATE: 2011-12-09

<400> SEQUENCE: 43

```
atgaagaccc tcatagccgc ctactccggg gtcctgcgcg gcgagcgtca ggccgaggct      60

gaccggagcc agcgctctca cggaggacct gcgctgtcgc gcgaggggtc tgggagatgg    120

ggcactggat ccagcatcct ctccgccctc caggacctct tctctgtcac ctggctcaat    180

aggtccaagg tggaaaagca gctacaggtc atctcagtgc tccagtgggt cctgtccttc    240

cttgtactgg gagtggcctg cagtgccatc ctcatgtaca tattctgcac tgattgctgg    300

ctcatcgctg tgctctactt cacttggctg gtgtttgact ggaacacacc caagaaaggt    360

ggcaggaggt cacagtgggt ccgaaactgg gctgtgtggc gctactttcg agactacttt    420

cccatccagc tggtgaagac acacaacctg ctgaccacca ggaactatat ctttggatac    480

cacccccatg gtatcatggg cctgggtgcc ttctgcaact tcagcacaga ggccacagaa    540

gtgagcaaga agttcccagg catacggcct tacctggcta cactggcagg caacttccga    600

atgcctgtgt tgagggagta cctgatgtct ggaggtatct gccctgtcag ccgggacacc    660

atagactatt tgctttcaaa gaatgggagt ggcaatgcta tcatcatcgt ggtcgggggt    720

gcggctgagt ctctgagctc catgcctggc aagaatgcag tcaccctgcg gaaccgcaag    780

ggctttgtga aactggccct gcgtcatgga gctgacctgg ttcccatcta ctcctttgga    840

gagaatgaag tgtacaagca ggtgatcttc gaggagggct cctggggccg atgggtccag    900

aagaagttcc agaaatacat tggtttcgcc ccatgcatct tccatggtcg aggcctcttc    960

tcctccgaca cctgggggct ggtgccctac tccaagccca tcaccactgt tgtgggagag   1020

cccatcacca tccccaagct ggagcaccca acccagcaag acatcgacct gtaccacacc   1080

atgtacatgg aggccctggt gaagctcttc gacaagcaca agaccaagtt cggcctcccg   1140

gagactgagg tcctggaggt gaactga                                       1167
```

<210> SEQ ID NO 44
<211> LENGTH: 888
<212> TYPE: DNA
<213> ORGANISM: Homo sapiens
<220> FEATURE:
<223> OTHER INFORMATION: AQP9
<300> PUBLICATION INFORMATION:
<308> DATABASE ACCESSION NUMBER: NCBI NM_020980.3
<309> DATABASE ENTRY DATE: 2007-09-14

<400> SEQUENCE: 44
atgcagcctg agggagcaga aaagggaaaa agcttcaagc agagactggt cttgaagagc 60
agcttagcga aagaaaccct ctctgagttc ttgggcacgt tcatcttgat tgtccttgga 120
tgtggctgtg ttgcccaagc tattctcagt cgaggacgtt ttggaggggt catcactatc 180
aatgttggat tttcaatggc agttgcaatg gccatttatg tggctggcgg tgtctctggt 240
ggtcacatca acccagctgt gtctttagca atgtgtctct ttggacggat gaaatggttc 300
aaattgccat tttatgtggg agcccagttc ttgggagcct ttgtgggggc tgcaaccgtc 360
tttggcattt actatgatgg acttatgtcc tttgctggtg gaaaactgct gatcgtggga 420
gaaaatgcaa cagcacacat ttttgcaaca tacccagctc cgtatctatc tctggcgaac 480
gcatttgcag atcaagtggt ggccaccatg atactcctca taatcgtctt tgccatcttt 540
gactccagaa acttgggagc cccagaggc ctagagccca ttgccatcgg cctcctgatt 600
attgtcattg cttcctccct gggactgaac agtggctgtg ccatgaaccc agctcgagac 660
ctgagtccca gacttttcac tgccttggca ggctgggggt ttgaagtctt cagagctgga 720
aacaacttct ggtggattcc tgtagtgggc cctttggttg gtgctgtcat tggaggcctc 780
atctatgttc ttgtcattga aatccaccat ccagagcctg actcagtctt taagacagaa 840
caatctgagg acaaaccaga gaaatatgaa ctcagtgtca tcatgtag 888

<210> SEQ ID NO 45
<211> LENGTH: 2673
<212> TYPE: DNA
<213> ORGANISM: Homo sapiens
<220> FEATURE:
<223> OTHER INFORMATION: LPIN1 (Lipin 1)
<300> PUBLICATION INFORMATION:
<308> DATABASE ACCESSION NUMBER: NCBI NM_145693.2
<309> DATABASE ENTRY DATE: 2012-05-12

<400> SEQUENCE: 45
atgaattacg tggggcagtt agccggccag gtgtttgtca ccgtgaagga gctctacaag 60
gggctgaatc ccgccacact ctcagggtgc attgacatca ttgtcatccg ccagcccaat 120
ggaaacctcc aatgctcccc tttccacgtc cgctttggga agatgggggt cctgcgctcc 180
cgagagaaag tggttgacat agaaatcaat ggggaatctg tggatttgca tatgaaattg 240
ggagataatg gagaagcatt ttttgttcaa gaaacagata atgatcagga agttatccct 300
atgcacctgg ccacctcccc catcctgtca gaaggagctt cgagaatgga atgccagctg 360
aaaaggggct ctgtggacag gatgagaggc ctggacccca gcacgccagc ccaagtgatc 420
gctcccagcg agacgccgtc aagcagctct gtagtaaaga agagaagaaa aaggaggaga 480
aagtcacagc tggacagcct gaagagagat gacaacatga acacatctga ggatgaggac 540
atgttcccca tcgagatgag ctcggatgag gccatggagc tgctggagag cagcagaact 600
cttcctaatg atatacctcc attccaagat gatattcctg aggaaaacct ctccctggct 660
gtgatttacc ctcagtcagc ctcataccct aattcggata gagagtggtc acccactccc 720
agtccttccg gttcccgacc ttcaacacct aaaagtgatt cagaattggt cagcaagtcc 780
acggaaagga cagggcagaa gaacccagaa atgctttggc tgtggggaga gctgccgcag 840
gctgctaagt cttcttctcc acacaagatg aaagagtcca gcccattgag cagtagaaaa 900
atttgtgata aaagtcactt tcaggccatt cacagcgaat cttcagacac ttttagtgac 960
caatcgccaa ctctggtcgg tggggcactt ttggaccaga acaagcctca gacagaaatg 1020
cagtttgtga atgaagaaga cctggagacc ttaggagcag cagcgccact cttgcccatg 1080
atcgaggagc tcaaaccccc ctctgccagt gtagtccaga cagcaaacaa gacggattct 1140
ccttccagga aaagagataa acgaagccga catcttggtg ctgacggcgt ctacttggat 1200
gacctcacag acatggatcc tgaagtggcg gccctgtatt ttcccaaaaa cggagatcct 1260
tccggactcg caaaacatgc aagcgacaac ggagcccggt cagccaacca gtccccgcag 1320
tcggtgggca gctcgggcgt ggacagtggc gtggagagca cctcggacgg gctgagggac 1380
ctcccttcca tcgccatctc cctctgcggg ggcctcagcg accaccggga gatcacgaaa 1440
gatgcattcc tggagcaagc tgtgtcatat caacagtttg tggacaaccc cgctattatc 1500
gatgacccca atctcgtggt aaagattggg agtaaatatt ataactggac aacagcagca 1560
cccctcctcc tggcaatgca ggccttccag aaacctttgc caaaggccac tgtggaatct 1620
atcatgaggg ataaaatgcc caaaaaggga ggaagatggt ggttttcatg gaggggaaga 1680
aacaccacaa tcaaggagga aagtaagcca gagcagtgct tggctggcaa ggcccatagc 1740
accggagagc aaccgccgca gctcagcttg gccaccaggg taaagcatga atcatcctcc 1800
agtgatgagg agcgcgcagc tgccaagcca tcaaacgcag gccacctccc tcttctgcct 1860
aatgtcagct acaagaagac tctccggctg acttccgagc agcttaaaag cttgaagttg 1920
aagaatggcc ccaacgacgt ggttttcagt gtcaccacgc agtaccaagg cacgtgccgc 1980
tgtgagggca ccatctatct gtggaactgg gatgataaag tcatcatttc tgatattgat 2040
gggacaatta ccagatcaga tactcttggc cacattttgc ccacccttgg gaaggattgg 2100
acccatcagg gcatcgctaa gctgtaccat aaagtgagcc agaatggata taaatttctc 2160
tactgttctg cccgtgccat cgggatggcg gacatgacgc ggggctacct gcactgggtc 2220
aacgagaggg gcacggtgct gccccagggg cccctgctgc tgagtcccag cagcctcttc 2280
tctgccctgc acagagaagt gattgaaaag aagccagaaa agtttaaagt ccagtgtttg 2340
acagacatca aaaacctgtt tttccccaac acagaaccct tttatgctgc ttttggaaac 2400
cgaccagctg atgtgtattc atacaagcaa gtaggagtgt ctttgaatag aatatttacc 2460
gtcaacccta aaggagagct ggtacaggaa catgcaaaga ccaacatctc ttcgtatgtg 2520
agactctgtg aagtagtcga ccacgttttc ccgttgctga aaagaagcca ttcttcagac 2580
tttccctgtt cggatacctt cagtaacttc accttttgga gagagccact gccacctttt 2640
gaaaaccagg acattcattc tgcctcagcg taa 2673

<210> SEQ ID NO 46
<211> LENGTH: 669
<212> TYPE: DNA
<213> ORGANISM: Homo sapiens
<220> FEATURE:
<223> OTHER INFORMATION: CRIF1
<300> PUBLICATION INFORMATION:
<308> DATABASE ACCESSION NUMBER: NCBI NM_052850.3
<309> DATABASE ENTRY DATE: 2012-08-04

<400> SEQUENCE: 46
atggcggcgt ccgtgcgaca ggcacgcagc ctactaggtg tggcggcgac cctggccccg 60
ggttcccgtg gctaccgggc gcggccgccc ccgcgccgca ggccgggacc ccggtggcca 120
gaccccgagg acctcctgac cccgcggtgg cagctgggac cgcgctacgc ggctaagcag 180
ttcgcgcgtt acggcgccgc ctccggggtg gtccccggtt cgttatggcc gtcgccggag 240
cagctgcggg agctggaggc cgaagaacgc gaatggtacc cgagcctggc gaccatgcag 300
gagtcgctgc gggtgaagca gctggccgaa gagcagaagc gtcgggagag ggagcagcac 360
atcgcagagt gcatggccaa gatgccacag atgattgtga actggcagca gcagcagcgg 420
gagaactggg agaaggccca ggctgacaag gagaggaggg cccgactgca ggctgaggcc 480
caggagctcc tgggctacca ggtggaccca aggagtgccc gcttccagga gctgctccag 540
gacctagaga agaaggagcg caagcgcctc aaggaggaaa aacagaaacg gaagaaggag 600
gcgcgagctg ctgcattggc tgcagctgtg gctcaagacc cagcagcctc tggggcaccc 660
agctcctga 669

<210> SEQ ID NO 47
<211> LENGTH: 867
<212> TYPE: DNA
<213> ORGANISM: Homo sapiens
<220> FEATURE:
<223> OTHER INFORMATION: PD1
<300> PUBLICATION INFORMATION:
<308> DATABASE ACCESSION NUMBER: GenBank KJ865859.1
<309> DATABASE ENTRY DATE: 2015-09-22

<400> SEQUENCE: 47
atgcagatcc cacaggcgcc ctggccagtc gtctgggcgg tgctacaact gggctggcgg 60
ccaggatggt tcttagactc cccagacagg ccctggaacc cccccacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggcc 240
gccttccccg aggaccgcag ccagcccggc caggactgcc gcttccgtgt cacacaactg 300
cccaacgggc gtgacttcca catgagcgtg gtcagggccc ggcgcaatga cagcggcacc 360
tacctctgtg gggccatctc cctggccccc aaggcgcaga tcaaagagag cctgcgggca 420
gagctcaggg tgacagagag aagggcagaa gtgcccacag cccaccccag cccctcaccc 480
aggccagccg gccagttcca aaccctggtg gttggtgtcg tgggcggcct gctgggcagc 540
ctggtgctgc tagtctgggt cctggccgtc atctgctccc gggccgcacg agggacaata 600
ggagccaggc gcaccggcca gcccctgaag gaggacccct cagccgtgcc tgtgttctct 660
gtggactatg gggagctgga tttccagtgg cgagagaaga ccccggagcc ccccgtgccc 720
tgtgtccctg agcagacgga gtatgccacc attgtctttc ctagcggaat gggcacctca 780
tcccccgccc gcaggggctc agctgacggc cctcggagtg cccagccact gaggcctgag 840
gatggacact gctcttggcc cctctga 867

<210> SEQ ID NO 48
<211> LENGTH: 1245
<212> TYPE: DNA
<213> ORGANISM: Mus musculus
<220> FEATURE:
<223> OTHER INFORMATION: Lymphocyte expansion molecule (LEM)
<300> PUBLICATION INFORMATION:
<308> DATABASE ACCESSION NUMBER: GenBank KP939367.1
<309> DATABASE ENTRY DATE: 2015-04-26

<400> SEQUENCE: 48
atgagacctc gcacccacgg cgcccccccg cgcaacatca tgtccaccat ccccaagtgg 60
ttcaaagggg cgccctttgg ggtgcagagc cacaggtttg atgtctccgc tgtctatccc 120
aaccagaaga aattcagcac cttcacagag gccccatact ccagacatca ttcggtggaa 180
ctgtcccaca taggacctgg gacctataac tccaaggata cctgcttcag caagaagttc 240
ctggaacaga agttgggctc aggatggtcc caggcccacg aagccactcg gctgacccag 300

```
ctaccccact tccactacca ggccatcaag aaggaaaaag agcagcaggt gcacaagcgt    360

ggccctggct cctacaacat caaagacttc ataactgagc tgcagaagaa accacagagc    420

aaacgggggc tgctcagctc tggggagaca cgtttccgag gttttattgg gaattattat    480

cctggccctg gaaattatgg ggagaagggg aacccgtaca cacagctgga ggagaaggcc    540

tggaaccgct cacattctga cggcctgatg tgtagagtgt ctaacaagcc acccttgttt    600

catcagggca gtggcctggg acctggtacc tacaccatca aaagcgatct tgagaccttt    660

gtgaaaaagt ccactggtaa tcgtggcccc tatgacattt tctctggtga acggagcagt    720

cctttgccct atggacatta ctctgtgcag aaaatgaagc ccaaggaact gacagattac    780

aagagctttc tggacgaaat gaactcacaa cacaagaaga aacaaggggt tttctcgaaa    840

tatccccgag atccgaaaca ccccacagag agaattttct ggacaaccct tagtcagtgc    900

cccaaaaata tggatatagc tggccctggt tcttggcttc ctcatgagac ggaacagaaa    960

catgtcaacc ggccaccgtt cctcctggcc tccaaacggt gcggcctaaa ggcctaccag   1020

atgattttgg gaacctggaa cccagttggc gtaggccgct atctcaacac cacgctgatg   1080

gagtccatag accgaaggca gcgataccgt tctctgtaca tgagtgagcc caagcgatac   1140

ctgcaagacc taacccgaga cagactcatg cagaaacgga ttacacctat tacgaagggc   1200

aagtgccgtc caactgtgga ctacaattca gatcctactc cttaa                   1245
```

```
<210> SEQ ID NO 49
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 49

Glu Ser Lys Tyr Gly Pro Pro Cys Pro Pro Cys Pro
1               5                   10


<210> SEQ ID NO 50
<211> LENGTH: 36
<212> TYPE: DNA
<213> ORGANISM: Homo sapiens
<220> FEATURE:
<223> OTHER INFORMATION: Spacer (IgG4hinge)

<400> SEQUENCE: 50

gaatctaagt acggaccgcc ctgcccccct tgccct                               36


<210> SEQ ID NO 51
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 51

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60
```

```
Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 52
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 52

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 53
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 53

Arg Trp Pro Glu Ser Pro Lys Ala Gln Ala Ser Ser Val Pro Thr Ala
1               5                   10                  15
```

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 54
<211> LENGTH: 24
<212> TYPE: PRT
<213> ORGANISM: Artificial Sequence
<220> FEATURE:
<223> OTHER INFORMATION: T2A

<400> SEQUENCE: 54

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 55
<211> LENGTH: 357
<212> TYPE: PRT
<213> ORGANISM: Artificial Sequence
<220> FEATURE:
<223> OTHER INFORMATION: tEGFR

<400> SEQUENCE: 55

Met Leu Leu Leu Val Thr Ser Leu Leu Leu Cys Glu Leu Pro His Pro

-continued

```
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 56
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 56

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 57
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 57

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65
```

<210> SEQ ID NO 58
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 58

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 59
<211> LENGTH: 41
<212> TYPE: PRT
<213> ORGANISM: Homo sapiens
<220> FEATURE:
<223> OTHER INFORMATION: CD28

<400> SEQUENCE: 59

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 60

```
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 60

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 61
<211> LENGTH: 112
<212> TYPE: PRT
<213> ORGANISM: Homo sapiens
<220> FEATURE:
<223> OTHER INFORMATION: CD3 zeta

<400> SEQUENCE: 61

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 62
<211> LENGTH: 112
<212> TYPE: PRT
<213> ORGANISM: Homo sapiens
<220> FEATURE:
<223> OTHER INFORMATION: CD3 zeta

<400> SEQUENCE: 62

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95
```

Thr Lys Asp Thr Tyr Asp Ala Leu His Met Gln Ala Leu Pro Pro Arg
100 105 110

<210> SEQ ID NO 63
<211> LENGTH: 112
<212> TYPE: PRT
<213> ORGANISM: Homo sapiens
<220> FEATURE:
<223> OTHER INFORMATION: CD3 zeta

<400> SEQUENCE: 63

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 64
<211> LENGTH: 18
<212> TYPE: PRT
<213> ORGANISM: Artificial Sequence
<220> FEATURE:
<223> OTHER INFORMATION: T2A

<400> SEQUENCE: 64

Glu Gly Arg Gly Ser Leu Leu Thr Cys Gly Asp Val Glu Glu Asn Pro
1 5 10 15

Gly Pro

<210> SEQ ID NO 65
<211> LENGTH: 22
<212> TYPE: PRT
<213> ORGANISM: Artificial Sequence
<220> FEATURE:
<223> OTHER INFORMATION: P2A

<400> SEQUENCE: 65

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 66
<211> LENGTH: 19
<212> TYPE: PRT
<213> ORGANISM: Artificial Sequence
<220> FEATURE:
<223> OTHER INFORMATION: P2A

<400> SEQUENCE: 66

Ala Thr Asn Phe Ser Leu Leu Lys Gln Ala Gly Asp Val Glu Glu Asn
1 5 10 15

Pro Gly Pro

<210> SEQ ID NO 67
<211> LENGTH: 20
<212> TYPE: PRT
<213> ORGANISM: Artificial Sequence
<220> FEATURE:
<223> OTHER INFORMATION: E2A

<400> SEQUENCE: 67

Gln Cys Thr Asn Tyr Ala Leu Leu Lys Leu Ala Gly Asp Val Glu Ser
1               5                   10                  15

Asn Pro Gly Pro
            20

<210> SEQ ID NO 68
<211> LENGTH: 22
<212> TYPE: PRT
<213> ORGANISM: Artificial Sequence
<220> FEATURE:
<223> OTHER INFORMATION: F2A

<400> SEQUENCE: 68

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 69
<211> LENGTH: 418
<212> TYPE: PRT
<213> ORGANISM: Homo sapiens
<220> FEATURE:
<223> OTHER INFORMATION: Lymphocyte expansion molecule (LEM) isoform 2
<300> PUBLICATION INFORMATION:
<308> DATABASE ACCESSION NUMBER: NCBI NP_001104003.1
<309> DATABASE ENTRY DATE: 2016-03-27

<400> SEQUENCE: 69

Met Arg Glu Ser Gln Asp Ala Ala Gly Ala His Gly Trp Asn Arg Val
1               5                   10                  15

Gly Ser Thr Ala Thr Lys Trp Phe Thr Gly Ala Pro Phe Gly Val Gln
            20                  25                  30

Ser His Arg Phe Asp Ile Ser Ala Val Tyr Pro Asn Trp Lys Lys Phe
        35                  40                  45

Ser Thr Phe Thr Glu Ala Pro Tyr Ser Thr Arg Tyr Ser Thr Gln Val
    50                  55                  60

Ser His Ile Gly Pro Gly Thr Tyr Ser Ser Lys Glu Thr Cys Phe Ser
65                  70                  75                  80

Lys Lys Lys Leu Met Lys Glu Val Asp Thr Gly Trp Ala Lys Ala Gln
                85                  90                  95

Glu Ala Thr Arg Leu Thr Gln Leu Pro His Phe Gln Tyr Gln Ala Ile
            100                 105                 110

Met Lys Glu Lys Arg Leu Lys Glu Gln Lys Leu Gly Pro Gly Ser Tyr
        115                 120                 125

Asn Leu Lys Asp Phe Leu Glu Gln Leu Arg Glu Lys Pro Cys Ser Thr
    130                 135                 140

Arg Gly Leu Leu Ser Ser Gly Glu Val Arg Phe Arg Gly Leu Thr Gly
145                 150                 155                 160

Asn Tyr Tyr Pro Gly Pro Gly Asn Tyr Gly Glu Lys Gly Asn Pro Tyr
                165                 170                 175

```
Thr Lys Leu Glu Glu Asn Ala Trp Asn Arg Ser His Ser Glu Gly Leu
            180                 185                 190

Met Cys Arg Met Ser Asn Lys Pro His Pro Arg Pro His Gln Gly Ser
        195                 200                 205

Gly Leu Gly Pro Gly Thr Tyr Phe Phe Lys Ser Asp Leu Glu Thr Tyr
    210                 215                 220

Val Ala Arg Ser Val Gly Thr Arg Gly Pro Tyr Asp Thr Phe Ser Gly
225                 230                 235                 240

Asp Arg Ser Lys Pro Leu Pro Tyr Gly His Tyr Ser Met Gln Lys Lys
                245                 250                 255

Lys Pro Arg Glu Leu Met Asn Phe Lys Ser Phe Val Glu Glu Leu Asn
            260                 265                 270

Ser His His Asn Lys Lys His Gly Val Phe Ser Lys Leu Pro Arg Asn
        275                 280                 285

Pro Lys Thr Pro Thr Glu Arg Ile Tyr Trp Ala Asn Leu Ser Gln Cys
    290                 295                 300

Pro Arg Thr Leu Ala Thr Ser Gly Pro Ser Phe Trp Leu Pro Gln Glu
305                 310                 315                 320

Lys Lys Cys Lys Pro Val Asn Gln Pro Pro Phe Leu Leu Thr Ser Lys
                325                 330                 335

Gly Ser Gly Ala Lys Ala Cys Gln Met Ile Met Gly Ser Trp Asn Pro
            340                 345                 350

Val Gly Val Gly Arg Tyr Leu Asn Thr Trp Leu Met Glu Thr Lys Asp
        355                 360                 365

Arg Arg Gln Arg Tyr Arg Ser Leu Phe Leu Ser Gly Ser Lys Arg Tyr
    370                 375                 380

Leu Ser Asp Leu Ala Arg Asp Met Leu Met Gln Glu Arg Ile Thr Pro
385                 390                 395                 400

Phe Thr Lys Gly Lys Cys Pro Pro Thr Val Asp Tyr Asn Ser Asp Pro
                405                 410                 415

Thr Pro
```

<210> SEQ ID NO 70
<211> LENGTH: 1254
<212> TYPE: DNA
<213> ORGANISM: Homo sapiens
<220> FEATURE:
<223> OTHER INFORMATION: Lymphocyte expansion molecule (LEM) isoform 2
<300> PUBLICATION INFORMATION:
<308> DATABASE ACCESSION NUMBER: NCBI NM_001110533.1
<309> DATABASE ENTRY DATE: 2016-03-27

<400> SEQUENCE: 70

```
atgagggaaa gccaggatgc cgccggagct catggctgga accgcgtcgg ctccacggcc      60

accaagtggt tcaccggggc gcccttcggg gtgcagagcc acaggtttga catctctgct     120

gtttatccca actggaagaa gttcagcacc ttcactgagg ccccatactc cacgcgttat     180

tctacccaag tgtcccacat aggccctggg acttacagct ccaaagagac ctgcttcagc     240

aagaagaagc tgatgaagga ggtggacaca ggctgggcca aggcccagga agccacgcgg     300

ctgacccagc taccccactt ccagtaccag gccatcatga aagagaagcg gctgaaggag     360

caaaagctgg gccccggctc ctacaacctc aaagacttct tagaacagct gcgggagaaa     420

ccatgtagca cccgggggct gctcagctct ggggaggttc gcttccgagg actcactggg     480

aactactatc caggccctgg aaattatggg gagaagggta acccatacac caagctggag     540

gagaatgcct ggaaccggtc tcattccgag ggcctcatgt gcaggatgag caacaagcca     600
```

```
caccccggc ctcatcaggg gagtggtctg ggacccggca cctacttctt caaaagcgac     660

cttgagacat atgtggcacg atccgtcggc acccgcggcc cctatgacac tttctctggt    720

gatcggagca agccactgcc ttatgggcac tactccatgc agaaaaaaaa gcccagggaa    780

ctgatgaatt tcaagagctt tgtagaagaa cttaactcac atcacaataa gaagcatggg    840

gttttttcta aacttccccg aaacccgaaa acccctacag agaggattta ctgggccaac    900

ctcagccagt gcccccgcac actggccaca tctggcccca gtttctggct tccacaagag    960

aagaaatgca aacccgtcaa ccagcccccca ttcctgttga cctccaaggg gtcaggtgca   1020

aaggcctgcc agatgattat gggaagctgg aacccagtag gtgtgggccg ctacctcaac   1080

acctggctga tggagacaaa ggacaggcgg cagcgatatc gatccctatt cctgagtgga   1140

tccaaacgct acctctcaga cctggcccgg gacatgctca tgcaggaaag gatcacacca   1200

tttactaagg gaaagtgccc tccaactgtg gattacaatt cagatcctac tcct         1254
```

<210> SEQ ID NO 71
<211> LENGTH: 72
<212> TYPE: DNA
<213> ORGANISM: Artificial Sequence
<220> FEATURE:
<223> OTHER INFORMATION: T2A

<400> SEQUENCE: 71

```
ctcgagggcg gcggagaggg cagaggaagt cttctaacat gcggtgacgt ggaggagaat     60

cccggcccta gg                                                          72
```

<210> SEQ ID NO 72
<211> LENGTH: 22
<212> TYPE: PRT
<213> ORGANISM: Homo sapiens
<220> FEATURE:
<223> OTHER INFORMATION: GMCSFR alpha chain signal sequence
<300> PUBLICATION INFORMATION:
<308> DATABASE ACCESSION NUMBER: UniProt P15509
<309> DATABASE ENTRY DATE: 1990-04-01

<400> SEQUENCE: 72

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 73
<211> LENGTH: 66
<212> TYPE: DNA
<213> ORGANISM: Homo sapiens
<220> FEATURE:
<223> OTHER INFORMATION: GMCSFR alpha chain signal  sequence

<400> SEQUENCE: 73

```
atgcttctcc tggtgacaag ccttctgctc tgtgagttac cacacccagc attcctcctg     60

atccca                                                                 66
```

<210> SEQ ID NO 74
<211> LENGTH: 363
<212> TYPE: DNA
<213> ORGANISM: Artificial Sequence
<220> FEATURE:
<223> OTHER INFORMATION: Modified Her2t

<400> SEQUENCE: 74

```
tgccaccctg agtgtcagcc ccagaatggc tcagtgacct gttttggacc ggaggctgac     60

cagtgtgtgg cctgtgccca ctataaggac cctcccttct gcgtggcccg ctgccccagc    120

ggtgtgaaac ctgacctctc ctacatgccc atctggaagt ttccagatga ggagggcgca    180

tgccagcctt gccccatcaa ctgcacccac tcctgtgtgg acctggatga caagggctgc    240

cccgccgagc agagagccag ccctctgacg ggtggaggaa gcggaggtgg cagctccatc    300

atctctgcgg tggttggcat tctgctggtc gtggtcttgg gggtggtctt tgggatcctc    360

atc                                                                  363
```

<210> SEQ ID NO 75
<211> LENGTH: 121
<212> TYPE: PRT
<213> ORGANISM: Artificial Sequence
<220> FEATURE:
<223> OTHER INFORMATION: Modified Her2t

<400> SEQUENCE: 75

```
Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala Arg Cys Pro Ser Gly Val Lys Pro Asp Leu Ser Tyr
        35                  40                  45

Met Pro Ile Trp Lys Phe Pro Asp Glu Glu Gly Ala Cys Gln Pro Cys
    50                  55                  60

Pro Ile Asn Cys Thr His Ser Cys Val Asp Leu Asp Asp Lys Gly Cys
65                  70                  75                  80

Pro Ala Glu Gln Arg Ala Ser Pro Leu Thr Gly Gly Gly Ser Gly Gly
                85                  90                  95

Gly Ser Ser Ile Ile Ser Ala Val Val Gly Ile Leu Leu Val Val Val
            100                 105                 110

Leu Gly Val Val Phe Gly Ile Leu Ile
        115                 120
```

<210> SEQ ID NO 76
<211> LENGTH: 1464
<212> TYPE: DNA
<213> ORGANISM: Artificial Sequence
<220> FEATURE:
<223> OTHER INFORMATION: DAG O-acetyltransferase 1 (DGAT1)

<400> SEQUENCE: 76

```
atgggcgatc gcggcagctc ccggagaagg cgcaccggca gccggccctc tagccacggc     60

ggcggcggcc ctgctgccgc cgaggaggag gtgcgcgacg ccgccgccgg ccctgatgtg    120

ggagcagcag gcgacgcacc agcacctgcc ccaaacaagg acggcgatgc aggagtggga    180

agcggacact gggagctgag atgccacagg ctgcaggatt ccctgttctc ctctgacagc    240

ggcttttcca actacagagg catcctgaat tggtgcgtgg tcatgctgat cctgtccaac    300

gccaggctgt tcctggagaa tctgatcaag tacggcatcc tggtggatcc tatccaggtg    360

gtgagcctgt ttctgaagga cccatattcc tggccagcac cttgcctggt catcgcagca    420

aacgtgttcg cagtggcagc ctttcaggtg gagaagcggc tggccgtggg cgccctgacc    480

gagcaggcag gcctgctgct gcacgtggcc aatctggcca caatcctgtg cttcccagca    540

gcagtggtgc tgctggtgga gtctatcacc cctgtgggaa gcctgctggc cctgatggca    600
```

```
cacacaatcc tgttcctgaa gctgttttcc tacagagacg tgaattcttg gtgtaggaga    660
gcaagggcaa aggcagcctc tgccggcaag aaggccagca gcgccgccgc ccctcacacc    720
gtgagctacc cagataacct gacatataga gacctgtact atttcctgtt tgccccccacc   780
ctgtgctatg agctgaattt cccaaggtcc cccaggatcc gcaagcggtt tctgctgagg    840
cgcatcctgg agatgctgtt ctttacccag ctgcaagtgg gcctgatcca gcagtggatg    900
gtgccaacaa tccagaactc catgaagccc ttcaaggaca tggattactc tagaatcatc    960
gagaggctgc tgaagctggc cgtgcccaac cacctgatct ggctgatctt cttttattgg   1020
ctgtttcact cttgcctgaa tgccgtggcc gagctgatgc agttcggcga tcgcgagttt   1080
taccgggact ggtggaattc cgagtctgtg acatatttct ggcagaactg gaatatccca   1140
gtgcacaagt ggtgtatccg ccacttttac aagcccatgc tgcggagagg ctctagcaag   1200
tggatggcca gaaccggcgt gttcctggcc tctgccttct ttcacgagta tctggtgagc   1260
gtgcctctgc gcatgttccg gctgtgggcc tttacaggca tgatggccca gatcccactg   1320
gcctggtttg tgggccggtt ctttcagggc aactacggca atgccgccgt gtggctgagc   1380
ctgatcatcg gccagcccat cgccgtgctg atgtacgtgc acgattacta tgtgctgaac   1440
tatgaggccc ctgccgccga ggcc                                          1464
```

<210> SEQ ID NO 77
<211> LENGTH: 1677
<212> TYPE: DNA
<213> ORGANISM: Artificial Sequence
<220> FEATURE:
<223> OTHER INFORMATION: Glycerol kinase (Gyk)

<400> SEQUENCE: 77

```
atggcagcca gcaagaaggc cgtgctgggc ccactggtgg gagcagtgga ccagggcacc     60
agctccacaa ggttcctggt gtttaatagc aagaccgcag agctgctgtc ccaccaccag    120
gtggagatca agcaggagtt tccaagggag ggatgggtgg agcaggaccc aaaggagatc    180
ctgcactccg tgtacgagtg catcgagaag acctgtgaga agctgggcca gctgaatatc    240
gacatcagca acatcaaggc catcggcgtg tccaatcagc gggagaccac agtggtgtgg    300
gacaagatca caggcgagcc cctgtataac gccgtggtgt ggctggatct gaggacccag    360
agcacagtgg agtccctgtc taagcgcatc cctggcaaca ataactttgt gaagtccaag    420
accggcctgc cactgtccac atatttctct gccgtgaagc tgaggtggct gctggacaat    480
gtgcgcaagg tgcagaaggc cgtggaggag aagagggccc tgtttggcac catcgattct    540
tggctgatct ggagcctgac aggaggagtg aacggaggcg tgcactgcac cgacgtgaca    600
aatgcctctc ggaccatgct gttcaacatc cacagcctgg agtgggataa gcagctgtgc    660
gagttctttg gcatccctat ggagatcctg ccaaacgtga gatctagctc cgagatctat    720
ggcctgatga agatcagcca ctccgtgaag gcaggcgccc tggagggagt gcctatctct    780
ggatgcctgg gcgaccagag cgccgccctg gtgggacaga tgtgcttcca gatcggccag    840
gccaagaata cctacggcac aggctgcttt ctgctgtgca acaccggcca caagtgcgtg    900
ttcagcgacc acggcctgct gaccacagtg gcctataagc tgggcaggga taagcccgtg    960
tactatgcac tggagggatc tgtggcaatc gcaggagccg tgatcaggtg gctgagagat   1020
aatctgggca tcatcaagac cagcgaggag atcgagaagc tggccaagga agtgggcaca   1080
tcctacggct gttatttcgt gcctgccttt tctggcctgt acgcaccata ttgggagcca   1140
agcgccaggg gaatcatctg cggcctgacc cagttcacaa acaagtgtca catcgccttt   1200
```

gccgccctgg aggccgtgtg cttccagacc cgggagatcc tggacgccat gaatagagat 1260
tgtggcatcc ctctgtccca cctgcaggtg gacggaggca tgacatctaa caagatcctg 1320
atgcagctgc aggccgacat cctgtatatc ccagtggtga agccctccat gcctgagacc 1380
acagccctgg gagcagcaat ggcagcagga gcagccgagg gcgtgggcgt gtggtccctg 1440
gagccagagg acctgtctgc cgtgaccatg gagcggtttg agcctcagat caatgccgag 1500
gagtccgaga tcagatactc tacatggaag aaggccgtga tgaagtccat gggctgggtg 1560
accacacagt ctcccgagag cggcgatcct agcatcttct gctccctgcc actgggcttc 1620
tttatcgtgt ctagcatggt catgctgatc ggcgcccggt atatctctgg catcccc 1677

<210> SEQ ID NO 78
<211> LENGTH: 2484
<212> TYPE: DNA
<213> ORGANISM: Artificial Sequence
<220> FEATURE:
<223> OTHER INFORMATION: Glycerol-3-phosphate acetyltransferase mitochondrial (GPAM)

<400> SEQUENCE: 78
atggacgagt ccgccctgac actgggcacc atcgacgtga gctacctgcc acacagctcc 60
gagtattctg tgggcaggtg caagcacaca agcgaggagt ggggagagtg tggcttccgg 120
ccaacaatct ttagatccgc caccctgaag tggaaggaga gcctgatgtc ccggaagaga 180
ccattcgtgg gccggtgctg ttactcctgc accccccagt cttgggacaa gttctttaac 240
ccttctatcc caagcctggg cctgagaaac gtgatctaca tcaatgagac ccacacaagg 300
cacaggggat ggctggcccg gagactgagc tatgtgctgt tcatccagga gagggacgtg 360
cacaagggca tgtttgccac aaatgtgacc gagaacgtgc tgaattctag ccgcgtgcag 420
gaggcaatcg cagaggtggc agcagagctg aaccctgatg gaagcgccca gcagcagtcc 480
aaggcagtga ataaggtgaa gaagaaggcc aagcggatcc tgcaggagat ggtggccaca 540
gtgtccccag ccatgatcag actgaccggc tgggtgctgc tgaagctgtt caactctttc 600
ttttggaata tccagatcca caagggccag ctggagatgg tgaaggccgc caccgagaca 660
aacctgccac tgctgtttct gcccgtgcac cgcagccaca tcgattacct gctgctgacc 720
ttcatcctgt tttgtcacaa catcaaggcc ccttatatcg ccagcggcaa caatctgaat 780
atcccaatct tctccacact gatccacaag ctgggcggct tctttatcag gcgccggctg 840
gatgagaccc ctgacggcag gaaggatgtg ctgtaccgcg ccctgctgca cggacacatc 900
gtggagctgc tgaggcagca gcagttcctg gagatctttc tggagggcac acggtctaga 960
agcggcaaga cctcctgcgc aagggcagga ctgctgtccg tggtggtgga cacactgtct 1020
accaacgtga tccccgacat cctgatcatc cctgtgggca tctcttacga ccggatcatc 1080
gagggccact ataacggcga gcagctgggc aagcccaaga agaatgagtc cctgtggtct 1140
gtggccaggg gcgtgatccg gatgctgaga aagaattacg gatgcgtgcg ggtggatttc 1200
gcacagcctt tttccctgaa ggagtatctg gagtcccagt ctcagaagcc cgtgagcgcc 1260
ctgctgtccc tggagcaggc cctgctgcct gcaatcctgc caagcagacc ttccgatgca 1320
gcagacgagg gaagggacac atctatcaac gagagcagaa atgccaccga tgagagcctg 1380
agaaggcgcc tgatcgccaa cctggccgag cacatcctgt tcacagccag caagtcctgc 1440
gccatcatga gcacccacat cgtggcctgt ctgctgctgt accggcacag gcagggaatc 1500
gacctgtcca cactggtgga ggatttcttt gtgatgaagg aggaggtgct ggccagggac 1560

```
ttcgatctgg gcttttctgg caatagcgag gacgtggtca tgcacgccat ccagctgctg   1620

ggcaactgcg tgaccatcac acacacctcc cgcaatgatg agttctttat caccccttct   1680

accacagtgc caagcgtgtt cgagctgaac ttttactcta atggcgtgct gcacgtgttt   1740

atcatggagg ccatcatcgc ctgcagcctg tatgccgtgc tgaacaagag gggactgggc   1800

ggcccaacaa gcaccccccc taatctgatc tcccaggagc agctggtgag aaaggccgcc   1860

tccctgtgct atctgctgtc taacgagggc acaatcagcc tgccctgcca gaccttctac   1920

caggtgtgcc acgagacagt gggcaagttt atccagtatg gcatcctgac cgtggccgag   1980

cacgacgatc aggaggacat ctctcctagc ctggccgagc agcagtggga taagaagctg   2040

ccagagcccc tgtcctggag gtctgacgag gaggacgagg atagcgactt cggcgaggag   2100

cagcgcgatt gttacctgaa ggtgtcccag tctaaggagc accagcagtt catcaccttt   2160

ctgcagcggc tgctgggccc actgctggag gcctattcct ctgccgccat cttcgtgcac   2220

aacttttccg gccctgtgcc agagccagag tacctgcaga agctgcacaa gtatctgatc   2280

acaaggaccg agaggaacgt ggccgtgtac gcagagagcg ccacctattg cctggtgaag   2340

aatgccgtga agatgttcaa ggacatcggc gtgtttaagg agacaaagca gaagcgggtg   2400

tctgtgctgg agctgagctc caccttcctg ccccagtgta atagacagaa gctgctggag   2460

tacatcctga gctttgtggt gctg                                          2484
```

<210> SEQ ID NO 79
<211> LENGTH: 2478
<212> TYPE: DNA
<213> ORGANISM: Artificial Sequence
<220> FEATURE:
<223> OTHER INFORMATION: HIF1alpha

<400> SEQUENCE: 79

```
atggagggcg ccggcggcgc caacgataag aagaagatca gctccgagcg gagaaaggag     60

aagagcaggg acgcagcacg ctctaggcgc agcaaggagt ccgaggtgtt ctacgagctg    120

gcccaccagc tgccactgcc acacaacgtg tctagccacc tggataaggc cagcgtgatg    180

cggctgacca tctcctatct gcgggtgaga aagctgctgg acgccggcga tctggacatc    240

gaggacgata tgaaggccca gatgaattgc ttctacctga aggccctgga cggctttgtg    300

atggtgctga ccgacgatgg cgacatgatc tacatctccg ataacgtgaa taagtatatg    360

ggcctgaccc agtttgagct gacaggccac agcgtgttcg actttaccca cccctgcgat    420

cacgaggaga tgagggagat gctgacacac cgcaacggcc tggtgaagaa gggcaaggag    480

cagaataccc agcggtcttt ctttctgaga atgaagtgta ccctgacaag caggggccgc    540

accatgaaca tcaagtccgc cacatggaag gtgctgcact gcaccggcca catccacgtg    600

tacgatacca actccaatca gccacagtgt ggctataaga agccccctat gacatgcctg    660

gtgctgatct gtgagcctat cccacacccc tctaatatcg agatccccct ggacagcaag    720

accttcctgt ctcggcacag cctggacatg aagtttagct actgcgatga gagaatcaca    780

gagctgatgg gctatgagcc tgaggagctg ctgggcagat ctatctacga gtactatcac    840

gccctggata gcgaccacct gaccaagaca caccacgaca tgttcaccaa gggccaggtg    900

accacaggcc agtacaggat gctggccaag aggggaggat acgtgtgggt ggagacccag    960

gccacagtga tctataacac caagaatagc cagccccagt gcatcgtgtg cgtgaactac   1020

gtggtgtccg gcatcatcca gcacgatctg atcttttctc tgcagcagac cgagtgcgtg   1080
```

```
ctgaagcctg tggagtcctc tgacatgaag atgacccagc tgttcacaaa ggtggagtcc   1140

gaggacacaa gctccctgtt tgataagctg aagaaggagc cagacgcact gaccctgctg   1200

gccccagcag caggcgatac aatcatctct ctggacttcg gcagcaatga taccgagaca   1260

gacgatcagc agctggagga ggtgcctctg tataacgatg tgatgctgcc ttctccaaat   1320

gagaagctgc agaacatcaa tctggcaatg agcccactgc ctaccgcaga gacaccaaag   1380

ccactgaggt ctagcgccga cccagccctg aaccaggagg tggccctgaa gctggagcct   1440

aatccagagt ccctggagct gtcttttaca atgccacaga tccaggacca gaccccatcc   1500

ccttctgatg gcagcacacg ccagtcctct ccagagccca acagcccttc cgagtactgc   1560

ttctatgtgg attccgacat ggtgaatgag ttcaagctgg agctggtgga gaagctgttt   1620

gccgaggata ccgaggccaa gaaccccttc agcacccagg atacagacct ggatctggag   1680

atgctggccc cctatatccc tatggacgat gacttccagc tgcggtcctt tgaccagctg   1740

tctcctctgg agagctcctc tgcctcccct gagtctgcca gcccacagtc taccgtgaca   1800

gtgttccagc agacccagat ccaggagcca acagccaatg ccaccacaac cacagccacc   1860

acagatgagc tgaagaccgt gacaaaggac cggatggagg acatcaagat cctgatcgcc   1920

tccccttctc caacccacat ccacaaggag accacatccg ccacaagctc cccttaccgg   1980

gacacccaga gcagaacagc ctccccaaac agagccggca agggcgtgat cgagcagacc   2040

gagaagtctc acccaaggag ccccaatgtg ctgtccgtgg ccctgtctca gcgcaccaca   2100

gtgcccgagg aggagctgaa ccctaagatc ctggccctgc agaatgccca gcggaagaga   2160

aagatggagc acgatggaag cctgttccag gcagtgggaa tcggcaccct gctgcagcag   2220

ccagatgacc acgccgccac cacaagcctg tcctggaaga gggtgaaggg ctgtaagtct   2280

agcgagcaga acggcatgga gcagaagacc atcatcctga tcccatccga cctggcatgc   2340

aggctgctgg gccagagcat ggatgagtcc ggcctgcccc agctgacaag ctacgactgt   2400

gaggtgaacg cccctatcca gggctcccgg aatctgctgc agggcgagga gctgctgaga   2460

gccctggacc aggtgaat                                                 2478
```

<210> SEQ ID NO 80
<211> LENGTH: 1005
<212> TYPE: DNA
<213> ORGANISM: Artificial Sequence
<220> FEATURE:
<223> OTHER INFORMATION: MOGAT1

<400> SEQUENCE: 80

```
atgaaggtgg agttcgcccc tctgaacatc cagctggccc ggagactgca gaccgtggcc     60

gtgctgcagt gggtgctgaa gtacctgctg ctgggcccaa tgtccatcgg catcacagtg    120

atgctgatca tccacaatta cctgttcctg tatatcccct atctgatgtg gctgtatttt    180

gactggcaca cccctgagag gggcggcagg cgcagctcct ggatcaagaa ctggacactg    240

tggaagcact tcaaggatta ctttccaatc cacctgatca agacccagga cctggatcct    300

tctcacaatt atatcttcgg ctttcaccca cacggaatca tggcagtggg agccttcggc    360

aactttagcg tgaattactc cgacttcaag gatctgttcc ccggctttac cagctatctg    420

cacgtgctgc cactgtggtt ctggtgcccc gtgtttagag agtacgtgat gtccgtgggc    480

ctggtgtctg tgagcaagaa gtccgtgtct tatatggtgt ccaaggaggg cggcggcaac    540

atctctgtga tcgtgctggg aggagcaaag gagtctctgg acgcccaccc tggcaagttc    600

accctgttta tccggcagag aaagggcttt gtgaagatcg ccctgacaca cggagcctct    660
```

```
ctggtgccag tggtgagctt cggcgagaac gagctgttta agcagaccga taatcccgag     720

ggcagctgga tcaggacagt gcagaacaag ctgcagaaga tcatgggctt cgcactgcca     780

ctgtttcacg caaggggcgt gttccagtac aattttggcc tgatgaccta tagaaaggcc     840

atccacacag tggtgggcag gcccatccct gtgcgccaga ccctgaatcc cacacaggag     900

cagatcgagg agctgcacca gacctacatg gaggagctgc gcaagctgtt cgaggagcac     960

aagggcaagt atggcatccc tgagcacgag acactggtgc tgaag                    1005
```

<210> SEQ ID NO 81
<211> LENGTH: 1866
<212> TYPE: DNA
<213> ORGANISM: Artificial Sequence
<220> FEATURE:
<223> OTHER INFORMATION: PCK1

<400> SEQUENCE: 81

```
atgccccctc agctgcagaa cggcctgaat ctgtccgcca aggtggtgca gggctccctg      60

gactctctgc ctcaggccgt gagggagttt ctggagaaca atgccgagct gtgccagcca     120

gaccacatcc acatctgtga tggctctgag gaggagaacg gccgcctgct gggacagatg     180

gaggaggagg gcatcctgcg gagactgaag aagtacgata attgctggct ggccctgacc     240

gacccaaggg atgtggcacg catcgagagc aagaccgtga tcgtgacaca ggagcagagg     300

gacaccgtgc caatccccaa gacaggcctg tctcagctgg gccgctggat gagcgaggag     360

gatttcgaga aggcctttaa cgcccggttc cctggctgta tgaagggcag aaccatgtac     420

gtgatcccct tcagcatggg acctctggga agcccactgt ccaagatcgg catcgagctg     480

acagactccc catatgtggt ggcctctatg cggatcatga ccagaatggg aacacccgtg     540

ctggaggcag tgggcgatgg cgagttcgtg aagtgcctgc actccgtggg ctgtcctctg     600

ccactgcaga agcccctggt gaacaattgg ccctgcaacc ctgagctgac cctgatcgca     660

cacctgcctg acaggaggga gatcatctct tttggcagcg gctacggcgg caatagcctg     720

ctgggcaaga agtgtttcgc actgaggatg gcctcccgcc tggccaagga ggagggatgg     780

ctggccgagc acatgctgat cctgggcatc accaatcccg agggcgagaa gaagtatctg     840

gctgccgcct ttccttctgc ctgcggcaag acaaacctgg ccatgatgaa tccaagcctg     900

ccaggatgga aggtggagtg cgtgggcgac gacatcgcct ggatgaagtt cgatgcacag     960

ggacacctga gggccatcaa cccagagaat ggcttctttg gcgtggcccc aggcacctct    1020

gtgaagacaa accccaatgc catcaagacc atccagaaga acaccatctt tacaaatgtg    1080

gccgagacaa gcgacggagg cgtgtactgg gagggaatcg atgagcccct ggccagcggc    1140

gtgaccatca catcctggaa gaacaaggag tggagctccg aggacggaga gccatgcgca    1200

caccctaatt ccagattctg cacccccgcc tctcagtgtc ctatcatcga tgcagcatgg    1260

gagtctccag agggagtgcc aatcgagggc atcatctttg gcggccggag acctgcagga    1320

gtgccactgg tgtatgaggc cctgtcctgg cagcacggcg tgttcgtggg agcagcaatg    1380

cggtctgagg caacagctgc cgccgagcac aagggcaaga tcatcatgca cgacccattt    1440

gccatgagac ccttctttgg ctacaacttc ggcaagtatc tggcacactg gctgtccatg    1500

gcacagcacc ctgcagcaaa gctgccaaag atctttcacg tgaattggtt caggaaggat    1560

aaggagggca agtttctgtg gcctggcttc ggcgagaaca gcagggtgct ggagtggatg    1620

ttcaatcgca tcgacggcaa ggcctccacc aagctgacac ccatcggcta catccctaag    1680
```

```
gaggatgccc tgaacctgaa gggcctgggc cacatcaata tgatggagct gttttctatc   1740

agcaaggagt tctgggagaa ggaggtggag gacatcgaga agtatctgga ggaccaggtg   1800

aacgccgatc tgccctgtga gatcgagcgg gagatcctgg ccctgaagca gagaatctcc   1860

cagatg                                                              1866


<210> SEQ ID NO 82
<211> LENGTH: 8
<212> TYPE: PRT
<213> ORGANISM: Artificial Sequence
<220> FEATURE:
<223> OTHER INFORMATION: Linker

<400> SEQUENCE: 82

Gly Gly Gly Ser Gly Gly Gly Ser
1               5


<210> SEQ ID NO 83
<211> LENGTH: 335
<212> TYPE: PRT
<213> ORGANISM: Artificial Sequence
<220> FEATURE:
<223> OTHER INFORMATION: tEGFR

<400> SEQUENCE: 83

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255
```

```
His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

<210> SEQ ID NO 84
<211> LENGTH: 1755
<212> TYPE: DNA
<213> ORGANISM: Artificial Sequence
<220> FEATURE:
<223> OTHER INFORMATION: huLEM-T2A-Her2t

<400> SEQUENCE: 84

```
atgagggaaa gccaggatgc cgccggagct catggctgga accgcgtcgg ctccacggcc     60

accaagtggt tcaccggggc gcccttcggg gtgcagagcc acaggtttga catctctgct    120

gtttatccca actggaagaa gttcagcacc ttcactgagg ccccatactc cacgcgttat    180

tctacccaag tgtcccacat aggccctggg acttacagct ccaaagagac ctgcttcagc    240

aagaagaagc tgatgaagga ggtggacaca ggctgggcca aggcccagga agccacgcgg    300

ctgacccagc taccccactt ccagtaccag gccatcatga aagagaagcg gctgaaggag    360

caaaagctgg gccccggctc ctacaacctc aaagacttct tagaacagct gcgggagaaa    420

ccatgtagca cccgggggct gctcagctct ggggaggttc gcttccgagg actcactggg    480

aactactatc caggccctgg aaattatggg gagaagggta acccatacac caagctggag    540

gagaatgcct ggaaccggtc tcattccgag ggcctcatgt gcaggatgag caacaagcca    600

cacccccggc ctcatcaggg gagtggtctg ggacccggca cctacttctt caaaagcgac    660

cttgagacat atgtggcacg atccgtcggc acccgcggcc cctatgacac tttctctggt    720

gatcggagca agccactgcc ttatgggcac tactccatgc agaaaaaaaa gcccagggaa    780

ctgatgaatt tcaagagctt tgtagaagaa cttaactcac atcacaataa gaagcatggg    840

gtttttttcta aacttccccg aaacccgaaa acccctacag agaggattta ctgggccaac    900

ctcagccagt gcccccgcac actggccaca tctggcccca gtttctggct tccacaagag    960

aagaaatgca aacccgtcaa ccagccccca ttcctgttga cctccaaggg gtcaggtgca   1020

aaggcctgcc agatgattat gggaagctgg aacccagtag gtgtgggccg ctacctcaac   1080

acctggctga tggagacaaa ggacaggcgg cagcgatatc gatccctatt cctgagtgga   1140

tccaaacgct acctctcaga cctggcccgg gacatgctca tgcaggaaag gatcacacca   1200

tttactaagg gaaagtgccc tccaactgtg gattacaatt cagatcctac tcctctcgag   1260

ggcggcggag agggcagagg aagtcttcta acatgcggtg acgtggagga gaatcccggc   1320

cctaggatgc ttctcctggt gacaagcctt ctgctctgtg agttaccaca cccagcattc   1380

ctcctgatcc catgccaccc tgagtgtcag ccccagaatg gctcagtgac ctgttttgga   1440

ccggaggctg accagtgtgt ggcctgtgcc cactataagg accctccctt ctgcgtggcc   1500

cgctgcccca gcggtgtgaa acctgacctc tcctacatgc ccatctggaa gtttccagat   1560

gaggagggcg catgccagcc ttgccccatc aactgcaccc actcctgtgt ggacctggat   1620
```

-continued

```
gacaagggct gccccgccga gcagagagcc agccctctga cgggtggagg aagcggaggt   1680

ggcagctcca tcatctctgc ggtggttggc attctgctgg tcgtggtctt gggggtggtc   1740

tttgggatcc tcatc                                                    1755


<210> SEQ ID NO 85
<211> LENGTH: 585
<212> TYPE: PRT
<213> ORGANISM: Artificial Sequence
<220> FEATURE:
<223> OTHER INFORMATION: huLEM-T2A-Her2t

<400> SEQUENCE: 85

Met Arg Glu Ser Gln Asp Ala Ala Gly Ala His Gly Trp Asn Arg Val
1               5                   10                  15

Gly Ser Thr Ala Thr Lys Trp Phe Thr Gly Ala Pro Phe Gly Val Gln
            20                  25                  30

Ser His Arg Phe Asp Ile Ser Ala Val Tyr Pro Asn Trp Lys Lys Phe
        35                  40                  45

Ser Thr Phe Thr Glu Ala Pro Tyr Ser Thr Arg Tyr Ser Thr Gln Val
    50                  55                  60

Ser His Ile Gly Pro Gly Thr Tyr Ser Ser Lys Glu Thr Cys Phe Ser
65                  70                  75                  80

Lys Lys Lys Leu Met Lys Glu Val Asp Thr Gly Trp Ala Lys Ala Gln
                85                  90                  95

Glu Ala Thr Arg Leu Thr Gln Leu Pro His Phe Gln Tyr Gln Ala Ile
            100                 105                 110

Met Lys Glu Lys Arg Leu Lys Glu Gln Lys Leu Gly Pro Gly Ser Tyr
        115                 120                 125

Asn Leu Lys Asp Phe Leu Glu Gln Leu Arg Glu Lys Pro Cys Ser Thr
    130                 135                 140

Arg Gly Leu Leu Ser Ser Gly Glu Val Arg Phe Arg Gly Leu Thr Gly
145                 150                 155                 160

Asn Tyr Tyr Pro Gly Pro Gly Asn Tyr Gly Glu Lys Gly Asn Pro Tyr
                165                 170                 175

Thr Lys Leu Glu Glu Asn Ala Trp Asn Arg Ser His Ser Glu Gly Leu
            180                 185                 190

Met Cys Arg Met Ser Asn Lys Pro His Pro Arg Pro His Gln Gly Ser
        195                 200                 205

Gly Leu Gly Pro Gly Thr Tyr Phe Phe Lys Ser Asp Leu Glu Thr Tyr
    210                 215                 220

Val Ala Arg Ser Val Gly Thr Arg Gly Pro Tyr Asp Thr Phe Ser Gly
225                 230                 235                 240

Asp Arg Ser Lys Pro Leu Pro Tyr Gly His Tyr Ser Met Gln Lys Lys
                245                 250                 255

Lys Pro Arg Glu Leu Met Asn Phe Lys Ser Phe Val Glu Glu Leu Asn
            260                 265                 270

Ser His His Asn Lys Lys His Gly Val Phe Ser Lys Leu Pro Arg Asn
        275                 280                 285

Pro Lys Thr Pro Thr Glu Arg Ile Tyr Trp Ala Asn Leu Ser Gln Cys
    290                 295                 300

Pro Arg Thr Leu Ala Thr Ser Gly Pro Ser Phe Trp Leu Pro Gln Glu
305                 310                 315                 320

Lys Lys Cys Lys Pro Val Asn Gln Pro Pro Phe Leu Leu Thr Ser Lys
                325                 330                 335
```

```
Gly Ser Gly Ala Lys Ala Cys Gln Met Ile Met Gly Ser Trp Asn Pro
            340                 345                 350

Val Gly Val Gly Arg Tyr Leu Asn Thr Trp Leu Met Glu Thr Lys Asp
        355                 360                 365

Arg Arg Gln Arg Tyr Arg Ser Leu Phe Leu Ser Gly Ser Lys Arg Tyr
    370                 375                 380

Leu Ser Asp Leu Ala Arg Asp Met Leu Met Gln Glu Arg Ile Thr Pro
385                 390                 395                 400

Phe Thr Lys Gly Lys Cys Pro Pro Thr Val Asp Tyr Asn Ser Asp Pro
                405                 410                 415

Thr Pro Leu Glu Gly Gly Gly Glu Gly Arg Gly Ser Leu Leu Thr Cys
            420                 425                 430

Gly Asp Val Glu Glu Asn Pro Gly Pro Arg Met Leu Leu Leu Val Thr
        435                 440                 445

Ser Leu Leu Leu Cys Glu Leu Pro His Pro Ala Phe Leu Leu Ile Pro
    450                 455                 460

Cys His Pro Glu Cys Gln Pro Gln Asn Gly Ser Val Thr Cys Phe Gly
465                 470                 475                 480

Pro Glu Ala Asp Gln Cys Val Ala Cys Ala His Tyr Lys Asp Pro Pro
                485                 490                 495

Phe Cys Val Ala Arg Cys Pro Ser Gly Val Lys Pro Asp Leu Ser Tyr
            500                 505                 510

Met Pro Ile Trp Lys Phe Pro Asp Glu Glu Gly Ala Cys Gln Pro Cys
        515                 520                 525

Pro Ile Asn Cys Thr His Ser Cys Val Asp Leu Asp Asp Lys Gly Cys
    530                 535                 540

Pro Ala Glu Gln Arg Ala Ser Pro Leu Thr Gly Gly Gly Ser Gly Gly
545                 550                 555                 560

Gly Ser Ser Ile Ile Ser Ala Val Val Gly Ile Leu Leu Val Val Val
                565                 570                 575

Leu Gly Val Val Phe Gly Ile Leu Ile
            580                 585
```

<210> SEQ ID NO 86
<211> LENGTH: 1965
<212> TYPE: DNA
<213> ORGANISM: Artificial Sequence
<220> FEATURE:
<223> OTHER INFORMATION: DGAT1-T2A-Her2t

<400> SEQUENCE: 86

```
atgggcgatc gcggcagctc ccggagaagg cgcaccggca gccggccctc tagccacggc      60

ggcggcggcc ctgctgccgc cgaggaggag gtgcgcgacg ccgccgccgg ccctgatgtg     120

ggagcagcag gcgacgcacc agcacctgcc ccaaacaagg acggcgatgc aggagtggga     180

agcggacact gggagctgag atgccacagg ctgcaggatt ccctgttctc ctctgacagc     240

ggcttttcca actacagagg catcctgaat tggtgcgtgg tcatgctgat cctgtccaac     300

gccaggctgt tcctggagaa tctgatcaag tacggcatcc tggtggatcc tatccaggtg     360

gtgagcctgt ttctgaagga cccatattcc tggccagcac cttgcctggt catcgcagca     420

aacgtgttcg cagtggcagc ctttcaggtg gagaagcggc tggccgtggg cgccctgacc     480

gagcaggcag gcctgctgct gcacgtggcc aatctggcca caatcctgtg cttcccagca     540

gcagtggtgc tgctggtgga gtctatcacc cctgtgggaa gcctgctggc cctgatggca     600

cacacaatcc tgttcctgaa gctgttttcc tacagagacg tgaattcttg gtgtaggaga     660
```

```
gcaagggcaa aggcagcctc tgccggcaag aaggccagca gcgccgccgc ccctcacacc    720

gtgagctacc cagataacct gacatataga gacctgtact atttcctgtt tgcccccacc    780

ctgtgctatg agctgaattt cccaaggtcc cccaggatcc gcaagcggtt tctgctgagg    840

cgcatcctgg agatgctgtt ctttacccag ctgcaagtgg gcctgatcca gcagtggatg    900

gtgccaacaa tccagaactc catgaagccc ttcaaggaca tggattactc tagaatcatc    960

gagaggctgc tgaagctggc cgtgcccaac cacctgatct ggctgatctt cttttattgg   1020

ctgtttcact cttgcctgaa tgccgtggcc gagctgatgc agttcggcga tcgcgagttt   1080

taccgggact ggtggaattc cgagtctgtg acatatttct ggcagaactg gaatatccca   1140

gtgcacaagt ggtgtatccg ccacttttac aagcccatgc tgcggagagg ctctagcaag   1200

tggatggcca gaaccggcgt gttcctggcc tctgccttct ttcacgagta tctggtgagc   1260

gtgcctctgc gcatgttccg gctgtgggcc tttacaggca tgatggccca gatcccactg   1320

gcctggtttg tgggccggtt ctttcagggc aactacggca atgccgccgt gtggctgagc   1380

ctgatcatcg gccagcccat cgccgtgctg atgtacgtgc acgattacta tgtgctgaac   1440

tatgaggccc ctgccgccga ggccctcgag ggcggcggag agggcagagg aagtcttcta   1500

acatgcggtg acgtggagga gaatcccggc cctaggatgc ttctcctggt gacaagcctt   1560

ctgctctgtg agttaccaca cccagcattc ctcctgatcc catgccaccc tgagtgtcag   1620

ccccagaatg gctcagtgac ctgttttgga ccggaggctg accagtgtgt ggcctgtgcc   1680

cactataagg accctccctt ctgcgtggcc cgctgcccca gcggtgtgaa acctgacctc   1740

tcctacatgc ccatctggaa gtttccagat gaggagggcg catgccagcc ttgccccatc   1800

aactgcaccc actcctgtgt ggacctggat gacaagggct gccccgccga gcagagagcc   1860

agccctctga cgggtggagg aagcggaggt ggcagctcca tcatctctgc ggtggttggc   1920

attctgctgg tcgtggtctt gggggtggtc tttgggatcc tcatc                   1965
```

<210> SEQ ID NO 87
<211> LENGTH: 655
<212> TYPE: PRT
<213> ORGANISM: Artificial Sequence
<220> FEATURE:
<223> OTHER INFORMATION: DGAT1-T2A-Her2t

<400> SEQUENCE: 87

```
Met Gly Asp Arg Gly Ser Ser Arg Arg Arg Arg Thr Gly Ser Arg Pro
1               5                   10                  15

Ser Ser His Gly Gly Gly Gly Pro Ala Ala Ala Glu Glu Glu Val Arg
            20                  25                  30

Asp Ala Ala Ala Gly Pro Asp Val Gly Ala Ala Gly Asp Ala Pro Ala
        35                  40                  45

Pro Ala Pro Asn Lys Asp Gly Asp Ala Gly Val Gly Ser Gly His Trp
    50                  55                  60

Glu Leu Arg Cys His Arg Leu Gln Asp Ser Leu Phe Ser Ser Asp Ser
65                  70                  75                  80

Gly Phe Ser Asn Tyr Arg Gly Ile Leu Asn Trp Cys Val Val Met Leu
                85                  90                  95

Ile Leu Ser Asn Ala Arg Leu Phe Leu Glu Asn Leu Ile Lys Tyr Gly
            100                 105                 110

Ile Leu Val Asp Pro Ile Gln Val Val Ser Leu Phe Leu Lys Asp Pro
        115                 120                 125
```

-continued

```
Tyr Ser Trp Pro Ala Pro Cys Leu Val Ile Ala Ala Asn Val Phe Ala
    130                 135                 140

Val Ala Ala Phe Gln Val Glu Lys Arg Leu Ala Val Gly Ala Leu Thr
145                 150                 155                 160

Glu Gln Ala Gly Leu Leu Leu His Val Ala Asn Leu Ala Thr Ile Leu
                165                 170                 175

Cys Phe Pro Ala Ala Val Val Leu Leu Val Glu Ser Ile Thr Pro Val
            180                 185                 190

Gly Ser Leu Leu Ala Leu Met Ala His Thr Ile Leu Phe Leu Lys Leu
        195                 200                 205

Phe Ser Tyr Arg Asp Val Asn Ser Trp Cys Arg Arg Ala Arg Ala Lys
    210                 215                 220

Ala Ala Ser Ala Gly Lys Lys Ala Ser Ser Ala Ala Ala Pro His Thr
225                 230                 235                 240

Val Ser Tyr Pro Asp Asn Leu Thr Tyr Arg Asp Leu Tyr Tyr Phe Leu
                245                 250                 255

Phe Ala Pro Thr Leu Cys Tyr Glu Leu Asn Phe Pro Arg Ser Pro Arg
            260                 265                 270

Ile Arg Lys Arg Phe Leu Leu Arg Arg Ile Leu Glu Met Leu Phe Phe
        275                 280                 285

Thr Gln Leu Gln Val Gly Leu Ile Gln Gln Trp Met Val Pro Thr Ile
    290                 295                 300

Gln Asn Ser Met Lys Pro Phe Lys Asp Met Asp Tyr Ser Arg Ile Ile
305                 310                 315                 320

Glu Arg Leu Leu Lys Leu Ala Val Pro Asn His Leu Ile Trp Leu Ile
                325                 330                 335

Phe Phe Tyr Trp Leu Phe His Ser Cys Leu Asn Ala Val Ala Glu Leu
            340                 345                 350

Met Gln Phe Gly Asp Arg Glu Phe Tyr Arg Asp Trp Trp Asn Ser Glu
        355                 360                 365

Ser Val Thr Tyr Phe Trp Gln Asn Trp Asn Ile Pro Val His Lys Trp
    370                 375                 380

Cys Ile Arg His Phe Tyr Lys Pro Met Leu Arg Arg Gly Ser Ser Lys
385                 390                 395                 400

Trp Met Ala Arg Thr Gly Val Phe Leu Ala Ser Ala Phe Phe His Glu
                405                 410                 415

Tyr Leu Val Ser Val Pro Leu Arg Met Phe Arg Leu Trp Ala Phe Thr
            420                 425                 430

Gly Met Met Ala Gln Ile Pro Leu Ala Trp Phe Val Gly Arg Phe Phe
        435                 440                 445

Gln Gly Asn Tyr Gly Asn Ala Ala Val Trp Leu Ser Leu Ile Ile Gly
    450                 455                 460

Gln Pro Ile Ala Val Leu Met Tyr Val His Asp Tyr Tyr Val Leu Asn
465                 470                 475                 480

Tyr Glu Ala Pro Ala Ala Glu Ala Leu Glu Gly Gly Gly Glu Gly Arg
                485                 490                 495

Gly Ser Leu Leu Thr Cys Gly Asp Val Glu Glu Asn Pro Gly Pro Arg
            500                 505                 510

Met Leu Leu Leu Val Thr Ser Leu Leu Leu Cys Glu Leu Pro His Pro
        515                 520                 525

Ala Phe Leu Leu Ile Pro Cys His Pro Glu Cys Gln Pro Gln Asn Gly
    530                 535                 540

Ser Val Thr Cys Phe Gly Pro Glu Ala Asp Gln Cys Val Ala Cys Ala
```

-continued

```
545                 550                 555                 560

His Tyr Lys Asp Pro Pro Phe Cys Val Ala Arg Cys Pro Ser Gly Val
                565                 570                 575

Lys Pro Asp Leu Ser Tyr Met Pro Ile Trp Lys Phe Pro Asp Glu Glu
            580                 585                 590

Gly Ala Cys Gln Pro Cys Pro Ile Asn Cys Thr His Ser Cys Val Asp
        595                 600                 605

Leu Asp Asp Lys Gly Cys Pro Ala Glu Gln Arg Ala Ser Pro Leu Thr
    610                 615                 620

Gly Gly Gly Ser Gly Gly Gly Ser Ser Ile Ile Ser Ala Val Val Gly
625                 630                 635                 640

Ile Leu Leu Val Val Val Leu Gly Val Val Phe Gly Ile Leu Ile
                645                 650                 655


<210> SEQ ID NO 88
<211> LENGTH: 2178
<212> TYPE: DNA
<213> ORGANISM: Artificial Sequence
<220> FEATURE:
<223> OTHER INFORMATION: GYK-T2A-Her2t

<400> SEQUENCE: 88

atggcagcca gcaagaaggc cgtgctgggc ccactggtgg gagcagtgga ccagggcacc      60

agctccacaa ggttcctggt gtttaatagc aagaccgcag agctgctgtc ccaccaccag     120

gtggagatca agcaggagtt tccaagggag ggatgggtgg agcaggaccc aaaggagatc     180

ctgcactccg tgtacgagtg catcgagaag acctgtgaga agctgggcca gctgaatatc     240

gacatcagca acatcaaggc catcggcgtg tccaatcagc gggagaccac agtggtgtgg     300

gacaagatca caggcgagcc cctgtataac gccgtggtgt ggctggatct gaggacccag     360

agcacagtgg agtccctgtc taagcgcatc cctggcaaca ataactttgt gaagtccaag     420

accggcctgc cactgtccac atatttctct gccgtgaagc tgaggtggct gctggacaat     480

gtgcgcaagg tgcagaaggc cgtggaggag aagagggccc tgtttggcac catcgattct     540

tggctgatct ggagcctgac aggaggagtg aacggaggcg tgcactgcac cgacgtgaca     600

aatgcctctc ggaccatgct gttcaacatc cacagcctgg agtgggataa gcagctgtgc     660

gagttctttg gcatccctat ggagatcctg ccaaacgtga gatctagctc cgagatctat     720

ggcctgatga agatcagcca ctccgtgaag gcaggcgccc tggagggagt gcctatctct     780

ggatgcctgg gcgaccagag cgccgccctg gtgggacaga tgtgcttcca gatcggccag     840

gccaagaata cctacggcac aggctgcttt ctgctgtgca acaccggcca caagtgcgtg     900

ttcagcgacc acggcctgct gaccacagtg gcctataagc tgggcaggga taagcccgtg     960

tactatgcac tggagggatc tgtggcaatc gcaggagccg tgatcaggtg gctgagagat    1020

aatctgggca tcatcaagac cagcgaggag atcgagaagc tggccaagga agtgggcaca    1080

tcctacggct gttatttcgt gcctgccttt tctggcctgt acgcaccata ttgggagcca    1140

agcgccaggg gaatcatctg cggcctgacc cagttcacaa acaagtgtca catcgccttt    1200

gccgccctgg aggccgtgtg cttccagacc cgggagatcc tggacgccat gaatagagat    1260

tgtggcatcc ctctgtccca cctgcaggtg gacggaggca tgacatctaa caagatcctg    1320

atgcagctgc aggccgacat cctgtatatc ccagtggtga agccctccat gcctgagacc    1380

acagccctgg gagcagcaat ggcagcagga gcagccgagg gcgtgggcgt gtggtccctg    1440

gagccagagg acctgtctgc cgtgaccatg gagcggtttg agcctcagat caatgccgag    1500
```

gagtccgaga tcagatactc tacatggaag aaggccgtga tgaagtccat gggctgggtg 1560
accacacagt ctcccgagag cggcgatcct agcatcttct gctccctgcc actgggcttc 1620
tttatcgtgt ctagcatggt catgctgatc ggcgcccggt atatctctgg catccccctc 1680
gagggcggcg gagagggcag aggaagtctt ctaacatgcg gtgacgtgga ggagaatccc 1740
ggccctagga tgcttctcct ggtgacaagc cttctgctct gtgagttacc acacccagca 1800
ttcctcctga tcccatgcca ccctgagtgt cagccccaga atggctcagt gacctgtttt 1860
ggaccggagg ctgaccagtg tgtggcctgt gcccactata aggaccctcc cttctgcgtg 1920
gcccgctgcc ccagcggtgt gaaacctgac ctctcctaca tgcccatctg gaagtttcca 1980
gatgaggagg gcgcatgcca gccttgcccc atcaactgca cccactcctg tgtggacctg 2040
gatgacaagg gctgccccgc cgagcagaga gccagccctc tgacgggtgg aggaagcgga 2100
ggtggcagct ccatcatctc tgcggtggtt ggcattctgc tggtcgtggt cttgggggtg 2160
gtctttggga tcctcatc 2178

<210> SEQ ID NO 89
<211> LENGTH: 726
<212> TYPE: PRT
<213> ORGANISM: Artificial Sequence
<220> FEATURE:
<223> OTHER INFORMATION: GYK-T2A-Her2t

<400> SEQUENCE: 89

Met Ala Ala Ser Lys Lys Ala Val Leu Gly Pro Leu Val Gly Ala Val
1 5 10 15

Asp Gln Gly Thr Ser Ser Thr Arg Phe Leu Val Phe Asn Ser Lys Thr
20 25 30

Ala Glu Leu Leu Ser His His Gln Val Glu Ile Lys Gln Glu Phe Pro
35 40 45

Arg Glu Gly Trp Val Glu Gln Asp Pro Lys Glu Ile Leu His Ser Val
50 55 60

Tyr Glu Cys Ile Glu Lys Thr Cys Glu Lys Leu Gly Gln Leu Asn Ile
65 70 75 80

Asp Ile Ser Asn Ile Lys Ala Ile Gly Val Ser Asn Gln Arg Glu Thr
85 90 95

Thr Val Val Trp Asp Lys Ile Thr Gly Glu Pro Leu Tyr Asn Ala Val
100 105 110

Val Trp Leu Asp Leu Arg Thr Gln Ser Thr Val Glu Ser Leu Ser Lys
115 120 125

Arg Ile Pro Gly Asn Asn Asn Phe Val Lys Ser Lys Thr Gly Leu Pro
130 135 140

Leu Ser Thr Tyr Phe Ser Ala Val Lys Leu Arg Trp Leu Leu Asp Asn
145 150 155 160

Val Arg Lys Val Gln Lys Ala Val Glu Glu Lys Arg Ala Leu Phe Gly
165 170 175

Thr Ile Asp Ser Trp Leu Ile Trp Ser Leu Thr Gly Gly Val Asn Gly
180 185 190

Gly Val His Cys Thr Asp Val Thr Asn Ala Ser Arg Thr Met Leu Phe
195 200 205

Asn Ile His Ser Leu Glu Trp Asp Lys Gln Leu Cys Glu Phe Phe Gly
210 215 220

Ile Pro Met Glu Ile Leu Pro Asn Val Arg Ser Ser Ser Glu Ile Tyr
225 230 235 240

-continued

```
Gly Leu Met Lys Ile Ser His Ser Val Lys Ala Gly Ala Leu Glu Gly
                245                 250                 255

Val Pro Ile Ser Gly Cys Leu Gly Asp Gln Ser Ala Ala Leu Val Gly
            260                 265                 270

Gln Met Cys Phe Gln Ile Gly Gln Ala Lys Asn Thr Tyr Gly Thr Gly
        275                 280                 285

Cys Phe Leu Leu Cys Asn Thr Gly His Lys Cys Val Phe Ser Asp His
    290                 295                 300

Gly Leu Leu Thr Thr Val Ala Tyr Lys Leu Gly Arg Asp Lys Pro Val
305                 310                 315                 320

Tyr Tyr Ala Leu Glu Gly Ser Val Ala Ile Ala Gly Ala Val Ile Arg
                325                 330                 335

Trp Leu Arg Asp Asn Leu Gly Ile Ile Lys Thr Ser Glu Glu Ile Glu
            340                 345                 350

Lys Leu Ala Lys Glu Val Gly Thr Ser Tyr Gly Cys Tyr Phe Val Pro
        355                 360                 365

Ala Phe Ser Gly Leu Tyr Ala Pro Tyr Trp Glu Pro Ser Ala Arg Gly
    370                 375                 380

Ile Ile Cys Gly Leu Thr Gln Phe Thr Asn Lys Cys His Ile Ala Phe
385                 390                 395                 400

Ala Ala Leu Glu Ala Val Cys Phe Gln Thr Arg Glu Ile Leu Asp Ala
                405                 410                 415

Met Asn Arg Asp Cys Gly Ile Pro Leu Ser His Leu Gln Val Asp Gly
            420                 425                 430

Gly Met Thr Ser Asn Lys Ile Leu Met Gln Leu Gln Ala Asp Ile Leu
        435                 440                 445

Tyr Ile Pro Val Val Lys Pro Ser Met Pro Glu Thr Thr Ala Leu Gly
    450                 455                 460

Ala Ala Met Ala Ala Gly Ala Ala Glu Gly Val Gly Val Trp Ser Leu
465                 470                 475                 480

Glu Pro Glu Asp Leu Ser Ala Val Thr Met Glu Arg Phe Glu Pro Gln
                485                 490                 495

Ile Asn Ala Glu Glu Ser Glu Ile Arg Tyr Ser Thr Trp Lys Lys Ala
            500                 505                 510

Val Met Lys Ser Met Gly Trp Val Thr Thr Gln Ser Pro Glu Ser Gly
        515                 520                 525

Asp Pro Ser Ile Phe Cys Ser Leu Pro Leu Gly Phe Phe Ile Val Ser
    530                 535                 540

Ser Met Val Met Leu Ile Gly Ala Arg Tyr Ile Ser Gly Ile Pro Leu
545                 550                 555                 560

Glu Gly Gly Gly Glu Gly Arg Gly Ser Leu Leu Thr Cys Gly Asp Val
                565                 570                 575

Glu Glu Asn Pro Gly Pro Arg Met Leu Leu Leu Val Thr Ser Leu Leu
            580                 585                 590

Leu Cys Glu Leu Pro His Pro Ala Phe Leu Leu Ile Pro Cys His Pro
        595                 600                 605

Glu Cys Gln Pro Gln Asn Gly Ser Val Thr Cys Phe Gly Pro Glu Ala
    610                 615                 620

Asp Gln Cys Val Ala Cys Ala His Tyr Lys Asp Pro Pro Phe Cys Val
625                 630                 635                 640

Ala Arg Cys Pro Ser Gly Val Lys Pro Asp Leu Ser Tyr Met Pro Ile
                645                 650                 655
```

```
Trp Lys Phe Pro Asp Glu Glu Gly Ala Cys Gln Pro Cys Pro Ile Asn
            660                 665                 670

Cys Thr His Ser Cys Val Asp Leu Asp Asp Lys Gly Cys Pro Ala Glu
        675                 680                 685

Gln Arg Ala Ser Pro Leu Thr Gly Gly Gly Ser Gly Gly Gly Ser Ser
    690                 695                 700

Ile Ile Ser Ala Val Val Gly Ile Leu Leu Val Val Val Leu Gly Val
705                 710                 715                 720

Val Phe Gly Ile Leu Ile
                725


<210> SEQ ID NO 90
<211> LENGTH: 2985
<212> TYPE: DNA
<213> ORGANISM: Artificial Sequence
<220> FEATURE:
<223> OTHER INFORMATION: GPAM-T2A-Her2t

<400> SEQUENCE: 90

atggacgagt ccgccctgac actgggcacc atcgacgtga gctacctgcc acacagctcc      60

gagtattctg tgggcaggtg caagcacaca agcgaggagt ggggagagtg tggcttccgg     120

ccaacaatct ttagatccgc caccctgaag tggaaggaga gcctgatgtc ccggaagaga     180

ccattcgtgg gccggtgctg ttactcctgc accccccagt cttgggacaa gttctttaac     240

ccttctatcc caagcctggg cctgagaaac gtgatctaca tcaatgagac ccacacaagg     300

cacaggggat ggctggcccg gagactgagc tatgtgctgt tcatccagga gagggacgtg     360

cacaagggca tgtttgccac aaatgtgacc gagaacgtgc tgaattctag ccgcgtgcag     420

gaggcaatcg cagaggtggc agcagagctg aaccctgatg gaagcgccca gcagcagtcc     480

aaggcagtga ataaggtgaa gaagaaggcc aagcggatcc tgcaggagat ggtggccaca     540

gtgtccccag ccatgatcag actgaccggc tgggtgctgc tgaagctgtt caactctttc     600

ttttggaata tccagatcca caagggccag ctggagatgg tgaaggccgc caccgagaca     660

aacctgccac tgctgtttct gcccgtgcac cgcagccaca tcgattacct gctgctgacc     720

ttcatcctgt tttgtcacaa catcaaggcc ccttatatcg ccagcggcaa caatctgaat     780

atcccaatct tctccacact gatccacaag ctgggcggct tctttatcag gcgccggctg     840

gatgagaccc ctgacggcag gaaggatgtg ctgtaccgcg ccctgctgca cggacacatc     900

gtggagctgc tgaggcagca gcagttcctg gagatctttc tggagggcac acggtctaga     960

agcggcaaga cctcctgcgc aagggcagga ctgctgtccg tggtggtgga cacactgtct    1020

accaacgtga tccccgacat cctgatcatc cctgtgggca tctcttacga ccggatcatc    1080

gagggccact ataacggcga gcagctgggc aagcccaaga agaatgagtc cctgtggtct    1140

gtggccaggg gcgtgatccg gatgctgaga aagaattacg gatgcgtgcg ggtggatttc    1200

gcacagcctt tttccctgaa ggagtatctg gagtcccagt ctcagaagcc cgtgagcgcc    1260

ctgctgtccc tggagcaggc cctgctgcct gcaatcctgc caagcagacc ttccgatgca    1320

gcagacgagg gaagggacac atctatcaac gagagcagaa atgccaccga tgagagcctg    1380

agaaggcgcc tgatcgccaa cctggccgag cacatcctgt tcacagccag caagtcctgc    1440

gccatcatga gcacccacat cgtggcctgt ctgctgctgt accggcacag gcagggaatc    1500

gacctgtcca cactggtgga ggatttcttt gtgatgaagg aggaggtgct ggccagggac    1560

ttcgatctgg gcttttctgg caatagcgag gacgtggtca tgcacgccat ccagctgctg    1620
```

ggcaactgcg tgaccatcac acacacctcc cgcaatgatg agttctttat cacccctttct 1680 accacagtgc caagcgtgtt cgagctgaac ttttactcta atggcgtgct gcacgtgttt 1740
atcatggagg ccatcatcgc ctgcagcctg tatgccgtgc tgaacaagag gggactgggc 1800
ggcccaacaa gcaccccccc taatctgatc tcccaggagc agctggtgag aaaggccgcc 1860
tccctgtgct atctgctgtc taacgagggc acaatcagcc tgccctgcca gaccttctac 1920
caggtgtgcc acgagacagt gggcaagttt atccagtatg gcatcctgac cgtggccgag 1980
cacgacgatc aggaggacat ctctcctagc ctggccgagc agcagtggga taagaagctg 2040
ccagagcccc tgtcctggag gtctgacgag gaggacgagg atagcgactt cggcgaggag 2100
cagcgcgatt gttacctgaa ggtgtcccag tctaaggagc accagcagtt catcaccttt 2160
ctgcagcggc tgctgggccc actgctggag gcctattcct ctgccgccat cttcgtgcac 2220
aacttttccg gccctgtgcc agagccagag tacctgcaga agctgcacaa gtatctgatc 2280
acaaggaccg agaggaacgt ggccgtgtac gcagagagcg ccacctattg cctggtgaag 2340
aatgccgtga agatgttcaa ggacatcggc gtgtttaagg agacaaagca gaagcgggtg 2400
tctgtgctgg agctgagctc caccttcctg ccccagtgta atagacagaa gctgctggag 2460
tacatcctga gctttgtggt gctgctcgag ggcggcggag agggcagagg aagtcttcta 2520
acatgcggtg acgtggagga gaatcccggc cctaggatgc ttctcctggt gacaagcctt 2580
ctgctctgtg agttaccaca cccagcattc ctcctgatcc catgccaccc tgagtgtcag 2640
ccccagaatg gctcagtgac ctgttttgga ccggaggctg accagtgtgt ggcctgtgcc 2700
cactataagg accctccctt ctgcgtggcc cgctgcccca gcggtgtgaa acctgacctc 2760
tcctacatgc ccatctggaa gtttccagat gaggagggcg catgccagcc ttgccccatc 2820
aactgcaccc actcctgtgt ggacctggat gacaagggct gccccgccga gcagagagcc 2880
agccctctga cgggtggagg aagcggaggt ggcagctcca tcatctctgc ggtggttggc 2940
attctgctgg tcgtggtctt gggggtggtc tttgggatcc tcatc 2985

<210> SEQ ID NO 91
<211> LENGTH: 995
<212> TYPE: PRT
<213> ORGANISM: Artificial Sequence
<220> FEATURE:
<223> OTHER INFORMATION: GPAM-T2A-Her2t

<400> SEQUENCE: 91

Met Asp Glu Ser Ala Leu Thr Leu Gly Thr Ile Asp Val Ser Tyr Leu
1 5 10 15

Pro His Ser Ser Glu Tyr Ser Val Gly Arg Cys Lys His Thr Ser Glu
20 25 30

Glu Trp Gly Glu Cys Gly Phe Arg Pro Thr Ile Phe Arg Ser Ala Thr
35 40 45

Leu Lys Trp Lys Glu Ser Leu Met Ser Arg Lys Arg Pro Phe Val Gly
50 55 60

Arg Cys Cys Tyr Ser Cys Thr Pro Gln Ser Trp Asp Lys Phe Phe Asn
65 70 75 80

Pro Ser Ile Pro Ser Leu Gly Leu Arg Asn Val Ile Tyr Ile Asn Glu
85 90 95

Thr His Thr Arg His Arg Gly Trp Leu Ala Arg Arg Leu Ser Tyr Val
100 105 110

Leu Phe Ile Gln Glu Arg Asp Val His Lys Gly Met Phe Ala Thr Asn
115 120 125

```
Val Thr Glu Asn Val Leu Asn Ser Ser Arg Val Gln Glu Ala Ile Ala
    130                 135                 140

Glu Val Ala Ala Glu Leu Asn Pro Asp Gly Ser Ala Gln Gln Gln Ser
145                 150                 155                 160

Lys Ala Val Asn Lys Val Lys Lys Lys Ala Lys Arg Ile Leu Gln Glu
                165                 170                 175

Met Val Ala Thr Val Ser Pro Ala Met Ile Arg Leu Thr Gly Trp Val
            180                 185                 190

Leu Leu Lys Leu Phe Asn Ser Phe Phe Trp Asn Ile Gln Ile His Lys
        195                 200                 205

Gly Gln Leu Glu Met Val Lys Ala Ala Thr Glu Thr Asn Leu Pro Leu
    210                 215                 220

Leu Phe Leu Pro Val His Arg Ser His Ile Asp Tyr Leu Leu Leu Thr
225                 230                 235                 240

Phe Ile Leu Phe Cys His Asn Ile Lys Ala Pro Tyr Ile Ala Ser Gly
                245                 250                 255

Asn Asn Leu Asn Ile Pro Ile Phe Ser Thr Leu Ile His Lys Leu Gly
            260                 265                 270

Gly Phe Phe Ile Arg Arg Arg Leu Asp Glu Thr Pro Asp Gly Arg Lys
        275                 280                 285

Asp Val Leu Tyr Arg Ala Leu Leu His Gly His Ile Val Glu Leu Leu
    290                 295                 300

Arg Gln Gln Gln Phe Leu Glu Ile Phe Leu Glu Gly Thr Arg Ser Arg
305                 310                 315                 320

Ser Gly Lys Thr Ser Cys Ala Arg Ala Gly Leu Leu Ser Val Val Val
                325                 330                 335

Asp Thr Leu Ser Thr Asn Val Ile Pro Asp Ile Leu Ile Ile Pro Val
            340                 345                 350

Gly Ile Ser Tyr Asp Arg Ile Ile Glu Gly His Tyr Asn Gly Glu Gln
        355                 360                 365

Leu Gly Lys Pro Lys Lys Asn Glu Ser Leu Trp Ser Val Ala Arg Gly
    370                 375                 380

Val Ile Arg Met Leu Arg Lys Asn Tyr Gly Cys Val Arg Val Asp Phe
385                 390                 395                 400

Ala Gln Pro Phe Ser Leu Lys Glu Tyr Leu Glu Ser Gln Ser Gln Lys
                405                 410                 415

Pro Val Ser Ala Leu Leu Ser Leu Glu Gln Ala Leu Leu Pro Ala Ile
            420                 425                 430

Leu Pro Ser Arg Pro Ser Asp Ala Ala Asp Glu Gly Arg Asp Thr Ser
        435                 440                 445

Ile Asn Glu Ser Arg Asn Ala Thr Asp Glu Ser Leu Arg Arg Arg Leu
    450                 455                 460

Ile Ala Asn Leu Ala Glu His Ile Leu Phe Thr Ala Ser Lys Ser Cys
465                 470                 475                 480

Ala Ile Met Ser Thr His Ile Val Ala Cys Leu Leu Leu Tyr Arg His
                485                 490                 495

Arg Gln Gly Ile Asp Leu Ser Thr Leu Val Glu Asp Phe Phe Val Met
            500                 505                 510

Lys Glu Glu Val Leu Ala Arg Asp Phe Asp Leu Gly Phe Ser Gly Asn
        515                 520                 525

Ser Glu Asp Val Val Met His Ala Ile Gln Leu Leu Gly Asn Cys Val
    530                 535                 540
```

-continued

```
Thr Ile Thr His Thr Ser Arg Asn Asp Glu Phe Phe Ile Thr Pro Ser
545                 550                 555                 560

Thr Thr Val Pro Ser Val Phe Glu Leu Asn Phe Tyr Ser Asn Gly Val
                565                 570                 575

Leu His Val Phe Ile Met Glu Ala Ile Ile Ala Cys Ser Leu Tyr Ala
            580                 585                 590

Val Leu Asn Lys Arg Gly Leu Gly Gly Pro Thr Ser Thr Pro Pro Asn
        595                 600                 605

Leu Ile Ser Gln Glu Gln Leu Val Arg Lys Ala Ala Ser Leu Cys Tyr
    610                 615                 620

Leu Leu Ser Asn Glu Gly Thr Ile Ser Leu Pro Cys Gln Thr Phe Tyr
625                 630                 635                 640

Gln Val Cys His Glu Thr Val Gly Lys Phe Ile Gln Tyr Gly Ile Leu
                645                 650                 655

Thr Val Ala Glu His Asp Asp Gln Glu Asp Ile Ser Pro Ser Leu Ala
            660                 665                 670

Glu Gln Gln Trp Asp Lys Lys Leu Pro Glu Pro Leu Ser Trp Arg Ser
        675                 680                 685

Asp Glu Glu Asp Glu Asp Ser Asp Phe Gly Glu Glu Gln Arg Asp Cys
    690                 695                 700

Tyr Leu Lys Val Ser Gln Ser Lys Glu His Gln Gln Phe Ile Thr Phe
705                 710                 715                 720

Leu Gln Arg Leu Leu Gly Pro Leu Leu Glu Ala Tyr Ser Ser Ala Ala
                725                 730                 735

Ile Phe Val His Asn Phe Ser Gly Pro Val Pro Glu Pro Glu Tyr Leu
            740                 745                 750

Gln Lys Leu His Lys Tyr Leu Ile Thr Arg Thr Glu Arg Asn Val Ala
        755                 760                 765

Val Tyr Ala Glu Ser Ala Thr Tyr Cys Leu Val Lys Asn Ala Val Lys
    770                 775                 780

Met Phe Lys Asp Ile Gly Val Phe Lys Glu Thr Lys Gln Lys Arg Val
785                 790                 795                 800

Ser Val Leu Glu Leu Ser Ser Thr Phe Leu Pro Gln Cys Asn Arg Gln
                805                 810                 815

Lys Leu Leu Glu Tyr Ile Leu Ser Phe Val Val Leu Leu Glu Gly Gly
            820                 825                 830

Gly Glu Gly Arg Gly Ser Leu Leu Thr Cys Gly Asp Val Glu Glu Asn
        835                 840                 845

Pro Gly Pro Arg Met Leu Leu Leu Val Thr Ser Leu Leu Leu Cys Glu
    850                 855                 860

Leu Pro His Pro Ala Phe Leu Leu Ile Pro Cys His Pro Glu Cys Gln
865                 870                 875                 880

Pro Gln Asn Gly Ser Val Thr Cys Phe Gly Pro Glu Ala Asp Gln Cys
                885                 890                 895

Val Ala Cys Ala His Tyr Lys Asp Pro Pro Phe Cys Val Ala Arg Cys
            900                 905                 910

Pro Ser Gly Val Lys Pro Asp Leu Ser Tyr Met Pro Ile Trp Lys Phe
        915                 920                 925

Pro Asp Glu Glu Gly Ala Cys Gln Pro Cys Pro Ile Asn Cys Thr His
    930                 935                 940

Ser Cys Val Asp Leu Asp Asp Lys Gly Cys Pro Ala Glu Gln Arg Ala
945                 950                 955                 960

Ser Pro Leu Thr Gly Gly Gly Ser Gly Gly Gly Ser Ser Ile Ile Ser
```

```
                965                 970                 975

Ala Val Val Gly Ile Leu Leu Val Val Val Leu Gly Val Val Phe Gly
            980                 985                 990

Ile Leu Ile
        995


<210> SEQ ID NO 92
<211> LENGTH: 2979
<212> TYPE: DNA
<213> ORGANISM: Artificial Sequence
<220> FEATURE:
<223> OTHER INFORMATION: HIF1a-T2A-Her2t

<400> SEQUENCE: 92

atggagggcg ccggcggcgc caacgataag aagaagatca gctccgagcg gagaaaggag     60

aagagcaggg acgcagcacg ctctaggcgc agcaaggagt ccgaggtgtt ctacgagctg    120

gcccaccagc tgccactgcc acacaacgtg tctagccacc tggataaggc cagcgtgatg    180

cggctgacca tctcctatct gcgggtgaga aagctgctgg acgccggcga tctggacatc    240

gaggacgata tgaaggccca gatgaattgc ttctacctga aggccctgga cggctttgtg    300

atggtgctga ccgacgatgg cgacatgatc tacatctccg ataacgtgaa taagtatatg    360

ggcctgaccc agtttgagct gacaggccac agcgtgttcg actttaccca cccctgcgat    420

cacgaggaga tgagggagat gctgacacac cgcaacggcc tggtgaagaa gggcaaggag    480

cagaataccc agcggtcttt ctttctgaga atgaagtgta ccctgacaag caggggccgc    540

accatgaaca tcaagtccgc cacatggaag gtgctgcact gcaccggcca catccacgtg    600

tacgatacca actccaatca gccacagtgt ggctataaga agccccctat gacatgcctg    660

gtgctgatct gtgagcctat cccacacccc tctaatatcg agatccccct ggacagcaag    720

accttcctgt ctcggcacag cctggacatg aagtttagct actgcgatga gagaatcaca    780

gagctgatgg gctatgagcc tgaggagctg ctgggcagat ctatctacga gtactatcac    840

gccctggata gcgaccacct gaccaagaca caccacgaca tgttcaccaa gggccaggtg    900

accacaggcc agtacaggat gctggccaag aggggaggat acgtgtgggt ggagacccag    960

gccacagtga tctataacac caagaatagc cagccccagt gcatcgtgtg cgtgaactac   1020

gtggtgtccg gcatcatcca gcacgatctg atcttttctc tgcagcagac cgagtgcgtg   1080

ctgaagcctg tggagtcctc tgacatgaag atgacccagc tgttcacaaa ggtggagtcc   1140

gaggacacaa gctccctgtt tgataagctg aagaaggagc cagacgcact gaccctgctg   1200

gccccagcag caggcgatac aatcatctct ctggacttcg gcagcaatga taccgagaca   1260

gacgatcagc agctggagga ggtgcctctg tataacgatg tgatgctgcc ttctccaaat   1320

gagaagctgc agaacatcaa tctggcaatg agcccactgc ctaccgcaga gacaccaaag   1380

ccactgaggt ctagcgccga cccagccctg aaccaggagg tggccctgaa gctggagcct   1440

aatccagagt ccctggagct gtcttttaca atgccacaga tccaggacca gaccccatcc   1500

ccttctgatg gcagcacacg ccagtcctct ccagagccca acagcccttc cgagtactgc   1560

ttctatgtgg attccgacat ggtgaatgag ttcaagctgg agctggtgga gaagctgttt   1620

gccgaggata ccgaggccaa gaacccmttc agcacccagg atacagacct ggatctggag   1680

atgctggccc cctatatccc tatggacgat gacttccagc tgcggtcctt tgaccagctg   1740

tctcctctgg agagctcctc tgcctcccct gagtctgcca gcccacagtc taccgtgaca   1800

gtgttccagc agacccagat ccaggagcca acagccaatg ccaccacaac cacagccacc   1860
```

acagatgagc tgaagaccgt gacaaaggac cggatggagg acatcaagat cctgatcgcc 1920
tccccttctc caacccacat ccacaaggag accacatccg ccacaagctc cccttaccgg 1980
gacacccaga gcagaacagc ctccccaaac agagccggca agggcgtgat cgagcagacc 2040
gagaagtctc acccaaggag ccccaatgtg ctgtccgtgg ccctgtctca gcgcaccaca 2100
gtgcccgagg aggagctgaa ccctaagatc ctggccctgc agaatgccca gcggaagaga 2160
aagatggagc acgatggaag cctgttccag gcagtgggaa tcggcaccct gctgcagcag 2220
ccagatgacc acgccgccac cacaagcctg tcctggaaga gggtgaaggg ctgtaagtct 2280
agcgagcaga acggcatgga gcagaagacc atcatcctga tcccatccga cctggcatgc 2340
aggctgctgg gccagagcat ggatgagtcc ggcctgcccc agctgacaag ctacgactgt 2400
gaggtgaacg cccctatcca gggctcccgg aatctgctgc agggcgagga gctgctgaga 2460
gccctggacc aggtgaatct cgagggcggc ggagagggca gaggaagtct tctaacatgc 2520
ggtgacgtgg aggagaatcc cggccctagg atgcttctcc tggtgacaag ccttctgctc 2580
tgtgagttac cacacccagc attcctcctg atcccatgcc accctgagtg tcagccccag 2640
aatggctcag tgacctgttt tggaccggag gctgaccagt gtgtggcctg tgcccactat 2700
aaggaccctc ccttctgcgt ggcccgctgc cccagcggtg tgaaacctga cctctcctac 2760
atgcccatct ggaagtttcc agatgaggag ggcgcatgcc agccttgccc catcaactgc 2820
acccactcct gtgtggacct ggatgacaag ggctgccccg ccgagcagag agccagccct 2880
ctgacgggtg gaggaagcgg aggtggcagc tccatcatct ctgcggtggt tggcattctg 2940
ctggtcgtgg tcttgggggt ggtctttggg atcctcatc 2979

<210> SEQ ID NO 93
<211> LENGTH: 993
<212> TYPE: PRT
<213> ORGANISM: Artificial Sequence
<220> FEATURE:
<223> OTHER INFORMATION: HIF1a-T2A-Her2t

<400> SEQUENCE: 93

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

```
Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
```

```
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn Leu Glu Gly Gly Gly Glu
            820                 825                 830

Gly Arg Gly Ser Leu Leu Thr Cys Gly Asp Val Glu Glu Asn Pro Gly
        835                 840                 845

Pro Arg Met Leu Leu Leu Val Thr Ser Leu Leu Leu Cys Glu Leu Pro
    850                 855                 860

His Pro Ala Phe Leu Leu Ile Pro Cys His Pro Glu Cys Gln Pro Gln
865                 870                 875                 880

Asn Gly Ser Val Thr Cys Phe Gly Pro Glu Ala Asp Gln Cys Val Ala
                885                 890                 895

Cys Ala His Tyr Lys Asp Pro Pro Phe Cys Val Ala Arg Cys Pro Ser
            900                 905                 910

Gly Val Lys Pro Asp Leu Ser Tyr Met Pro Ile Trp Lys Phe Pro Asp
        915                 920                 925

Glu Glu Gly Ala Cys Gln Pro Cys Pro Ile Asn Cys Thr His Ser Cys
    930                 935                 940

Val Asp Leu Asp Asp Lys Gly Cys Pro Ala Glu Gln Arg Ala Ser Pro
945                 950                 955                 960

Leu Thr Gly Gly Gly Ser Gly Gly Gly Ser Ser Ile Ile Ser Ala Val
                965                 970                 975

Val Gly Ile Leu Leu Val Val Val Leu Gly Val Val Phe Gly Ile Leu
            980                 985                 990

Ile
```

<210> SEQ ID NO 94
<211> LENGTH: 1506
<212> TYPE: DNA
<213> ORGANISM: Artificial Sequence
<220> FEATURE:
<223> OTHER INFORMATION: MOGAT1-T2A-Her2t

<400> SEQUENCE: 94

```
atgaaggtgg agttcgcccc tctgaacatc cagctggccc ggagactgca gaccgtggcc     60

gtgctgcagt gggtgctgaa gtacctgctg ctgggcccaa tgtccatcgg catcacagtg    120

atgctgatca tccacaatta cctgttcctg tatatcccct atctgatgtg gctgtatttt    180

gactggcaca cccctgagag gggcggcagg cgcagctcct ggatcaagaa ctggacactg    240

tggaagcact tcaaggatta ctttccaatc cacctgatca agacccagga cctggatcct    300

tctcacaatt atatcttcgg ctttcaccca cacggaatca tggcagtggg agccttcggc    360

aactttagcg tgaattactc cgacttcaag gatctgttcc ccggctttac cagctatctg    420

cacgtgctgc cactgtggtt ctggtgcccc gtgtttagag agtacgtgat gtccgtgggc    480

ctggtgtctg tgagcaagaa gtccgtgtct tatatggtgt ccaaggaggg cggcggcaac    540

atctctgtga tcgtgctggg aggagcaaag gagtctctgg acgcccaccc tggcaagttc    600

accctgttta tccggcagag aaagggcttt gtgaagatcg ccctgacaca cggagcctct    660

ctggtgccag tggtgagctt cggcgagaac gagctgttta agcagaccga taatcccgag    720

ggcagctgga tcaggacagt gcagaacaag ctgcagaaga tcatgggctt cgcactgcca    780

ctgtttcacg caaggggcgt gttccagtac aattttggcc tgatgaccta tagaaaggcc    840

atccacacag tggtgggcag gcccatccct gtgcgccaga ccctgaatcc cacacaggag    900

cagatcgagg agctgcacca gacctacatg gaggagctgc gcaagctgtt cgaggagcac    960

aagggcaagt atggcatccc tgagcacgag acactggtgc tgaagctcga gggcggcgga   1020

gagggcagag gaagtcttct aacatgcggt gacgtggagg agaatcccgg ccctaggatg   1080

cttctcctgg tgacaagcct tctgctctgt gagttaccac acccagcatt cctcctgatc   1140

ccatgccacc ctgagtgtca gccccagaat ggctcagtga cctgttttgg accggaggct   1200

gaccagtgtg tggcctgtgc ccactataag gaccctccct tctgcgtggc ccgctgcccc   1260

agcggtgtga aacctgacct ctcctacatg cccatctgga agtttccaga tgaggagggc   1320

gcatgccagc cttgccccat caactgcacc cactcctgtg tggacctgga tgacaagggc   1380

tgccccgccg agcagagagc cagccctctg acgggtggag gaagcggagg tggcagctcc   1440

atcatctctg cggtggttgg cattctgctg gtcgtggtct tgggggtggt ctttgggatc   1500

ctcatc                                                               1506
```

<210> SEQ ID NO 95
<211> LENGTH: 502
<212> TYPE: PRT
<213> ORGANISM: Artificial Sequence
<220> FEATURE:
<223> OTHER INFORMATION: MOGAT1-T2A-Her2t

<400> SEQUENCE: 95

```
Met Lys Val Glu Phe Ala Pro Leu Asn Ile Gln Leu Ala Arg Arg Leu
1               5                   10                  15

Gln Thr Val Ala Val Leu Gln Trp Val Leu Lys Tyr Leu Leu Leu Gly
            20                  25                  30

Pro Met Ser Ile Gly Ile Thr Val Met Leu Ile Ile His Asn Tyr Leu
```

-continued

```
        35                  40                  45

Phe Leu Tyr Ile Pro Tyr Leu Met Trp Leu Tyr Phe Asp Trp His Thr
    50                  55                  60

Pro Glu Arg Gly Gly Arg Arg Ser Ser Trp Ile Lys Asn Trp Thr Leu
65                  70                  75                  80

Trp Lys His Phe Lys Asp Tyr Phe Pro Ile His Leu Ile Lys Thr Gln
                85                  90                  95

Asp Leu Asp Pro Ser His Asn Tyr Ile Phe Gly Phe His Pro His Gly
            100                 105                 110

Ile Met Ala Val Gly Ala Phe Gly Asn Phe Ser Val Asn Tyr Ser Asp
        115                 120                 125

Phe Lys Asp Leu Phe Pro Gly Phe Thr Ser Tyr Leu His Val Leu Pro
    130                 135                 140

Leu Trp Phe Trp Cys Pro Val Phe Arg Glu Tyr Val Met Ser Val Gly
145                 150                 155                 160

Leu Val Ser Val Ser Lys Lys Ser Val Ser Tyr Met Val Ser Lys Glu
                165                 170                 175

Gly Gly Gly Asn Ile Ser Val Ile Val Leu Gly Gly Ala Lys Glu Ser
            180                 185                 190

Leu Asp Ala His Pro Gly Lys Phe Thr Leu Phe Ile Arg Gln Arg Lys
        195                 200                 205

Gly Phe Val Lys Ile Ala Leu Thr His Gly Ala Ser Leu Val Pro Val
    210                 215                 220

Val Ser Phe Gly Glu Asn Glu Leu Phe Lys Gln Thr Asp Asn Pro Glu
225                 230                 235                 240

Gly Ser Trp Ile Arg Thr Val Gln Asn Lys Leu Gln Lys Ile Met Gly
                245                 250                 255

Phe Ala Leu Pro Leu Phe His Ala Arg Gly Val Phe Gln Tyr Asn Phe
            260                 265                 270

Gly Leu Met Thr Tyr Arg Lys Ala Ile His Thr Val Val Gly Arg Pro
        275                 280                 285

Ile Pro Val Arg Gln Thr Leu Asn Pro Thr Gln Glu Gln Ile Glu Glu
    290                 295                 300

Leu His Gln Thr Tyr Met Glu Glu Leu Arg Lys Leu Phe Glu Glu His
305                 310                 315                 320

Lys Gly Lys Tyr Gly Ile Pro Glu His Glu Thr Leu Val Leu Lys Leu
                325                 330                 335

Glu Gly Gly Gly Glu Gly Arg Gly Ser Leu Leu Thr Cys Gly Asp Val
            340                 345                 350

Glu Glu Asn Pro Gly Pro Arg Met Leu Leu Leu Val Thr Ser Leu Leu
        355                 360                 365

Leu Cys Glu Leu Pro His Pro Ala Phe Leu Leu Ile Pro Cys His Pro
    370                 375                 380

Glu Cys Gln Pro Gln Asn Gly Ser Val Thr Cys Phe Gly Pro Glu Ala
385                 390                 395                 400

Asp Gln Cys Val Ala Cys Ala His Tyr Lys Asp Pro Pro Phe Cys Val
                405                 410                 415

Ala Arg Cys Pro Ser Gly Val Lys Pro Asp Leu Ser Tyr Met Pro Ile
            420                 425                 430

Trp Lys Phe Pro Asp Glu Glu Gly Ala Cys Gln Pro Cys Pro Ile Asn
        435                 440                 445

Cys Thr His Ser Cys Val Asp Leu Asp Asp Lys Gly Cys Pro Ala Glu
    450                 455                 460
```

Gln Arg Ala Ser Pro Leu Thr Gly Gly Gly Ser Gly Gly Gly Ser Ser
465 470 475 480

Ile Ile Ser Ala Val Val Gly Ile Leu Leu Val Val Val Leu Gly Val
485 490 495

Val Phe Gly Ile Leu Ile
500

<210> SEQ ID NO 96
<211> LENGTH: 2367
<212> TYPE: DNA
<213> ORGANISM: Artificial Sequence
<220> FEATURE:
<223> OTHER INFORMATION: PCK1-T2A-Her2t

<400> SEQUENCE: 96
atgccccctc agctgcagaa cggcctgaat ctgtccgcca aggtggtgca gggctccctg 60
gactctctgc ctcaggccgt gagggagttt ctggagaaca atgccgagct gtgccagcca 120
gaccacatcc acatctgtga tggctctgag gaggagaacg gccgcctgct gggacagatg 180
gaggaggagg gcatcctgcg gagactgaag aagtacgata attgctggct ggccctgacc 240
gacccaaggg atgtggcacg catcgagagc aagaccgtga tcgtgacaca ggagcagagg 300
gacaccgtgc caatccccaa gacaggcctg tctcagctgg gccgctggat gagcgaggag 360
gatttcgaga aggcctttaa cgcccggttc cctggctgta tgaagggcag aaccatgtac 420
gtgatcccct tcagcatggg acctctggga agcccactgt ccaagatcgg catcgagctg 480
acagactccc catatgtggt ggcctctatg cggatcatga ccagaatggg aacacccgtg 540
ctggaggcag tgggcgatgg cgagttcgtg aagtgcctgc actccgtggg ctgtcctctg 600
ccactgcaga agcccctggt gaacaattgg ccctgcaacc ctgagctgac cctgatcgca 660
cacctgcctg acaggaggga gatcatctct tttggcagcg gctacggcgg caatagcctg 720
ctgggcaaga agtgtttcgc actgaggatg gcctcccgcc tggccaagga ggagggatgg 780
ctggccgagc acatgctgat cctgggcatc accaatcccg agggcgagaa gaagtatctg 840
gctgccgcct ttccttctgc ctgcggcaag acaaacctgg ccatgatgaa tccaagcctg 900
ccaggatgga aggtggagtg cgtgggcgac gacatcgcct ggatgaagtt cgatgcacag 960
ggacacctga gggccatcaa cccagagaat ggcttctttg gcgtggcccc aggcacctct 1020
gtgaagacaa accccaatgc catcaagacc atccagaaga acaccatctt tacaaatgtg 1080
gccgagacaa gcgacggagg cgtgtactgg gagggaatcg atgagcccct ggccagcggc 1140
gtgaccatca catcctggaa gaacaaggag tggagctccg aggacggaga gccatgcgca 1200
caccctaatt ccagattctg caccccccgcc tctcagtgtc ctatcatcga tgcagcatgg 1260
gagtctccag agggagtgcc aatcgagggc atcatctttg gcggccggag acctgcagga 1320
gtgccactgg tgtatgaggc cctgtcctgg cagcacggcg tgttcgtggg agcagcaatg 1380
cggtctgagg caacagctgc cgccgagcac aagggcaaga tcatcatgca cgacccattt 1440
gccatgagac ccttctttgg ctacaacttc ggcaagtatc tggcacactg gctgtccatg 1500
gcacagcacc ctgcagcaaa gctgccaaag atctttcacg tgaattggtt caggaaggat 1560
aaggagggca agtttctgtg gcctggcttc ggcgagaaca gcagggtgct ggagtggatg 1620
ttcaatcgca tcgacggcaa ggcctccacc aagctgacac ccatcggcta catccctaag 1680
gaggatgccc tgaacctgaa gggcctgggc cacatcaata tgatggagct gttttctatc 1740
agcaaggagt tctgggagaa ggaggtggag gacatcgaga agtatctgga ggaccaggtg 1800
aacgccgatc tgccctgtga gatcgagcgg gagatcctgg ccctgaagca gagaatctcc 1860
cagatgctcg agggcggcgg agagggcaga ggaagtcttc taacatgcgg tgacgtggag 1920
gagaatcccg gccctaggat gcttctcctg gtgacaagcc ttctgctctg tgagttacca 1980
cacccagcat tcctcctgat cccatgccac cctgagtgtc agccccagaa tggctcagtg 2040
acctgttttg gaccggaggc tgaccagtgt gtggcctgtg cccactataa ggaccctccc 2100
ttctgcgtgg cccgctgccc cagcggtgtg aaacctgacc tctcctacat gcccatctgg 2160
aagtttccag atgaggaggg cgcatgccag ccttgcccca tcaactgcac ccactcctgt 2220
gtggacctgg atgacaaggg ctgccccgcc gagcagagag ccagccctct gacgggtgga 2280
ggaagcggag gtggcagctc catcatctct gcggtggttg gcattctgct ggtcgtggtc 2340
ttgggggtgg tctttgggat cctcatc 2367

<210> SEQ ID NO 97
<211> LENGTH: 789
<212> TYPE: PRT
<213> ORGANISM: Artificial Sequence
<220> FEATURE:
<223> OTHER INFORMATION: PCK1-T2A-Her2t

<400> SEQUENCE: 97

Met Pro Pro Gln Leu Gln Asn Gly Leu Asn Leu Ser Ala Lys Val Val
1 5 10 15

Gln Gly Ser Leu Asp Ser Leu Pro Gln Ala Val Arg Glu Phe Leu Glu
20 25 30

Asn Asn Ala Glu Leu Cys Gln Pro Asp His Ile His Ile Cys Asp Gly
35 40 45

Ser Glu Glu Glu Asn Gly Arg Leu Leu Gly Gln Met Glu Glu Glu Gly
50 55 60

Ile Leu Arg Arg Leu Lys Lys Tyr Asp Asn Cys Trp Leu Ala Leu Thr
65 70 75 80

Asp Pro Arg Asp Val Ala Arg Ile Glu Ser Lys Thr Val Ile Val Thr
85 90 95

Gln Glu Gln Arg Asp Thr Val Pro Ile Pro Lys Thr Gly Leu Ser Gln
100 105 110

Leu Gly Arg Trp Met Ser Glu Glu Asp Phe Glu Lys Ala Phe Asn Ala
115 120 125

Arg Phe Pro Gly Cys Met Lys Gly Arg Thr Met Tyr Val Ile Pro Phe
130 135 140

Ser Met Gly Pro Leu Gly Ser Pro Leu Ser Lys Ile Gly Ile Glu Leu
145 150 155 160

Thr Asp Ser Pro Tyr Val Val Ala Ser Met Arg Ile Met Thr Arg Met
165 170 175

Gly Thr Pro Val Leu Glu Ala Val Gly Asp Gly Glu Phe Val Lys Cys
180 185 190

Leu His Ser Val Gly Cys Pro Leu Pro Leu Gln Lys Pro Leu Val Asn
195 200 205

Asn Trp Pro Cys Asn Pro Glu Leu Thr Leu Ile Ala His Leu Pro Asp
210 215 220

Arg Arg Glu Ile Ile Ser Phe Gly Ser Gly Tyr Gly Gly Asn Ser Leu
225 230 235 240

Leu Gly Lys Lys Cys Phe Ala Leu Arg Met Ala Ser Arg Leu Ala Lys
245 250 255

```
Glu Glu Gly Trp Leu Ala Glu His Met Leu Ile Leu Gly Ile Thr Asn
            260                 265                 270

Pro Glu Gly Glu Lys Lys Tyr Leu Ala Ala Ala Phe Pro Ser Ala Cys
        275                 280                 285

Gly Lys Thr Asn Leu Ala Met Met Asn Pro Ser Leu Pro Gly Trp Lys
    290                 295                 300

Val Glu Cys Val Gly Asp Asp Ile Ala Trp Met Lys Phe Asp Ala Gln
305                 310                 315                 320

Gly His Leu Arg Ala Ile Asn Pro Glu Asn Gly Phe Phe Gly Val Ala
                325                 330                 335

Pro Gly Thr Ser Val Lys Thr Asn Pro Asn Ala Ile Lys Thr Ile Gln
            340                 345                 350

Lys Asn Thr Ile Phe Thr Asn Val Ala Glu Thr Ser Asp Gly Gly Val
        355                 360                 365

Tyr Trp Glu Gly Ile Asp Glu Pro Leu Ala Ser Gly Val Thr Ile Thr
    370                 375                 380

Ser Trp Lys Asn Lys Glu Trp Ser Ser Glu Asp Gly Glu Pro Cys Ala
385                 390                 395                 400

His Pro Asn Ser Arg Phe Cys Thr Pro Ala Ser Gln Cys Pro Ile Ile
                405                 410                 415

Asp Ala Ala Trp Glu Ser Pro Glu Gly Val Pro Ile Glu Gly Ile Ile
            420                 425                 430

Phe Gly Gly Arg Arg Pro Ala Gly Val Pro Leu Val Tyr Glu Ala Leu
        435                 440                 445

Ser Trp Gln His Gly Val Phe Val Gly Ala Ala Met Arg Ser Glu Ala
    450                 455                 460

Thr Ala Ala Ala Glu His Lys Gly Lys Ile Ile Met His Asp Pro Phe
465                 470                 475                 480

Ala Met Arg Pro Phe Phe Gly Tyr Asn Phe Gly Lys Tyr Leu Ala His
                485                 490                 495

Trp Leu Ser Met Ala Gln His Pro Ala Ala Lys Leu Pro Lys Ile Phe
            500                 505                 510

His Val Asn Trp Phe Arg Lys Asp Lys Glu Gly Lys Phe Leu Trp Pro
        515                 520                 525

Gly Phe Gly Glu Asn Ser Arg Val Leu Glu Trp Met Phe Asn Arg Ile
    530                 535                 540

Asp Gly Lys Ala Ser Thr Lys Leu Thr Pro Ile Gly Tyr Ile Pro Lys
545                 550                 555                 560

Glu Asp Ala Leu Asn Leu Lys Gly Leu Gly His Ile Asn Met Met Glu
                565                 570                 575

Leu Phe Ser Ile Ser Lys Glu Phe Trp Glu Lys Glu Val Glu Asp Ile
            580                 585                 590

Glu Lys Tyr Leu Glu Asp Gln Val Asn Ala Asp Leu Pro Cys Glu Ile
        595                 600                 605

Glu Arg Glu Ile Leu Ala Leu Lys Gln Arg Ile Ser Gln Met Leu Glu
    610                 615                 620

Gly Gly Gly Glu Gly Arg Gly Ser Leu Leu Thr Cys Gly Asp Val Glu
625                 630                 635                 640

Glu Asn Pro Gly Pro Arg Met Leu Leu Leu Val Thr Ser Leu Leu Leu
                645                 650                 655

Cys Glu Leu Pro His Pro Ala Phe Leu Leu Ile Pro Cys His Pro Glu
            660                 665                 670

Cys Gln Pro Gln Asn Gly Ser Val Thr Cys Phe Gly Pro Glu Ala Asp
```

-continued

```
        675                 680                 685

Gln Cys Val Ala Cys Ala His Tyr Lys Asp Pro Pro Phe Cys Val Ala
    690                 695                 700

Arg Cys Pro Ser Gly Val Lys Pro Asp Leu Ser Tyr Met Pro Ile Trp
705                 710                 715                 720

Lys Phe Pro Asp Glu Glu Gly Ala Cys Gln Pro Cys Pro Ile Asn Cys
                725                 730                 735

Thr His Ser Cys Val Asp Leu Asp Asp Lys Gly Cys Pro Ala Glu Gln
            740                 745                 750

Arg Ala Ser Pro Leu Thr Gly Gly Gly Ser Gly Gly Gly Ser Ser Ile
        755                 760                 765

Ile Ser Ala Val Val Gly Ile Leu Leu Val Val Val Leu Gly Val Val
    770                 775                 780

Phe Gly Ile Leu Ile
785
```

VECTORS AND GENETICALLY ENGINEERED IMMUNE CELLS EXPRESSING METABOLIC PATHWAY MODULATORS AND USES IN ADOPTIVE CELL THERAPY

CROSS-REFERENCE TO RELATED APPLICATIONS

This application is a U.S. National Stage of International Application No. PCT/US2016/060734 filed Nov. 4, 2016, which claims priority from U.S. provisional application No. 62/251,615 filed Nov. 5, 2015, entitled "Vectors and Genetically Engineered Immune Cells Expressing Metabolic Pathway Modulators and Uses in Adoptive Cell Therapy," the contents of which are incorporated by reference in its their entirety.

INCORPORATION BY REFERENCE OF SEQUENCE LISTING

The present application is being filed with a Sequence Listing in electronic format. The Sequence Listing is provided as a file entitled 735042003700SeqList.txt, created on Apr. 27, 2018, which is 248,039 bytes in size. The information in electronic format of the Sequence Listing is incorporated by reference in its entirety.

FIELD

Provided are cells, e.g., engineered immune cells, expressing recombinant or engineered molecules that promote desirable effects and outcomes upon administration of such cells in adoptive cell therapy, for example, in treatment of tumors. Such molecules generally are molecules involved in metabolic pathways, such as those that promote or inhibit one or more metabolic steps, reactions, or pathways, for example, in T cells. Such molecules include those that induce or repress a particular functional outcome or metabolic event, for example, one that promotes differentiation or reprogramming into a particular phenotypic state, such as memory, long-lived, activated or activatable, non-exhausted, phenotype or stem-like phenotype. The cells generally further express an immune receptor, such as an antigen receptor, which may be an engineered receptor, such as a CAR or recombinant TCR, or may be a natural immune receptor. Also provided are cells, such as T cells, expressing such molecules and combinations thereof, compositions comprising such cells, nucleic acids such as vectors encoding the same, and methods of administration to subjects in adoptive cell therapy.

BACKGROUND

Various strategies are available for producing and administering engineered cells for adoptive therapy. For example, strategies are available for engineering immune cells expressing genetically engineered antigen receptors, such as CARs, and administering compositions containing such cells to subjects. Improved strategies are needed to improve efficacy of the cells, for example, improving the persistence and/or survival of the cells upon administration to subjects. Provided are methods, cells, compositions, kits, and systems that meet such needs.

SUMMARY

Provided are cells, e.g., engineered cells, such as engineered immune cells, generally T cells or NK cells or cells engineered to contain signaling components involved in antigen or target recognition, and/or the delivery of signals thereby, by T cells or NK cells. The cells may be derived from an immune cell compartment such as blood or peripheral blood mononuclear cell (PBMC) sample and optionally selection or enrichment, and/or may be generated via differentiation from less differentiated cells such as HSC or iPSC populations. The cells are generally primary cells from a subject to be treated or a subject of the same species.

The cells generally are engineered to express a recombinant, non-natural, engineered or ectopically expressed molecule, or a functional or catalytically active portion and/or variant of such molecule. The molecule (and/or portion or variant thereof) may be a protein, polypeptide or nucleic acid molecule. In some embodiments, the protein is an enzyme, such as an enzyme that catalyzes one or more metabolic reactions and/or an adapter or other molecule that interacts with or recruits or directs localization of such a molecule. The molecule which plays a role in or interacts with component(s) of one or more metabolic pathways or steps or reactions thereof or events.

The cells generally further include a receptor, such as an antigen receptor or other ligand-binding receptor, such as a natural or endogenously expressed receptor and/or a recombinant or engineered receptor. The receptor may be a TCR or chimeric receptor, such as a chimeric antigen receptor (CAR). The cells may be tumor infiltrating lymphocytes or contain TCRs derived therefrom and optionally modified, e.g., to enhance their recognition or function. In some embodiments, the cells are useful in adoptive cell therapy or other treatment, such as for tumors, cancers, or other proliferative or dysplastic disorders or diseases, and/or infectious disease or autoimmunity.

The molecule (e.g., recombinant, engineered, exogenous or ectopically expressed molecule or variant or portion thereof) in some embodiments is involved with, e.g., promotes or inhibits or otherwise influences, a metabolic event, pathway, reaction, or step, and/or interacts with a molecule involved in such pathway or a metabolite thereof. In some embodiments, the molecule is capable of promoting said metabolic pathway or step or reaction thereof or a metabolic event, directly or indirectly. In some embodiments, the molecule is capable of inhibiting said metabolic pathway. In some embodiments, the molecule is or comprises an enzyme; and/or wherein the recombinant molecule is or comprises an adapter or other molecule that is capable of interacting with a component of the pathway or reaction. The molecule may comprise more than one such molecule, e.g., two or more such molecules, which may impact or be involved with one or more such pathway.

In some embodiments, the metabolic pathway or event comprises lipid metabolism. The molecule is involved in fatty acid synthesis, fatty acid storage and/or fatty acid uptake; and/or the metabolic pathway or event or reaction or step comprises fatty acid uptake, fatty acid synthesis (FAS), and/or fatty acid oxidation (FAO).

In some embodiments, the metabolic pathway or event comprises oxidative phosphorylation (OXPHOS). In some embodiments, it comprises a reactive oxygen species (ROS)-induced signal.

In some embodiments, the pathway or event or step comprises or involves glycolysis or a component or metabolite thereof.

In some embodiments, the pathway or event or step comprises or involves mitochondrial biogenesis.

In some embodiments, the pathway or event or step comprises or involves generation of energy or ATP in a process that occurs within the mitochondria or via mitochondrial proteins, or occurs independently of glucose, or occurs via a pathway other than glycolysis.

In some embodiments, the pathway or event or step comprises or involves the generation of ATP in a glucose-low environment, in a nutrient-poor environment, in a hypoxic environment.

In some embodiments, the pathway or event or step comprises or involves e.g., the molecule influences, e.g., promotes, a catabolic molecular profile, optionally in the engineered cell, as compared to a reference cell substantially similar to the engineered cell but not comprising the recombinant molecule.

In some embodiments, the pathway or event or step comprises or involves, e.g., the molecule influences, e.g., promotes an anabolic molecular profile, optionally in the engineered cell, as compared to a reference cell substantially similar to the engineered cell but not comprising the recombinant molecule.

In some embodiments, the pathway or event or step comprises or involves, e.g., the molecule influences wherein the metabolic pathway or event comprises glutaminolysis, TCA cycle, glucose metabolism, amino acid or nucleotide metabolism, or beta-oxidation.

In some embodiments, the molecule promotes or enhances FAS or FAO or fatty acid storage, and/or TAG synthesis or storage, or glycerol import.

In some embodiments, the pay, event or step or reaction is or comprises triacylglyceride (TAG) synthesis, TAG storage, glycerol phosphate pathway, glycerophospholipid synthesis and/or glycerol uptake.

In some embodiments, the molecule is involved in and/or is capable of promoting glycerol transport, is or comprises a glycerol transporter, is a TAG synthase molecule, is or comprises a glycerol kinase, or is or comprises an acyltransferase.

In some embodiment, the molecule is or comprises a Glycerol kinase (GYK).

In some embodiment, the molecule is or comprises a Glycerol-3-phosphate acetyltransferase mitochondrial (GPAT). In some embodiments, the molecule is or comprises a GPAT1.

In some aspects, the molecule is or comprises a GYK.

In some embodiment, the molecule is or comprises a Monoacylglycerol O-acetyltransferase (MOGAT). In some aspects, it comprises a MOGAT1.

In some embodiment, the molecule is or comprises a DAG O-acetyltransferase (DGAT). In some aspects, the molecule is a DGAT1.

In some embodiment, the molecule is or comprises an acylglycerolphosphate acyltransferase (AGPAT).

In some embodiment, the molecule is or comprises a Lipin. In some aspects, it includes a Lipin 1.

In some embodiments, the molecule is or comprises or interacts with a GPAT2, an AGPAT1, an AGPAT2, an AGPAT3, an AGPAT6, a MOGAT2, a Lipin1, and/or a DGAT2.

In some embodiments, the molecule comprises an amino acid sequence selected from among any of SEQ ID NO: 4, 7, 8 and 9; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 4, 7, 8 and 9. In some embodiments, the molecule comprises an amino acid sequence encoded by a nucleotide sequence selected from among any of SEQ ID NO: 76, 77, 78 and 80; and a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 76, 77, 78 and 80 that encodes a functional protein, variant, or fragment thereof.

In some embodiments, the molecule is or comprises a glycerol transporter or functional portion thereof. In some aspects the molecule is or comprises an AQP, such as an APQ9

In some embodiments, the molecule is a molecule that encodes or inhibits or promotes or stabilizes or destabilizes expression or activity any of the foregoing molecules. In some embodiments, it is a molecule that interacts with directly or indirectly, acts downstream of or compensates for, any of the aforementioned molecules.

In some embodiments, the molecule is or comprises a palmitoyltransferase. In some aspects, such a molecule is or comprises a carnitine palmitoyltransferase (CPT), such as CPTI.

In some embodiments, the metabolic pathway or event comprises oxidative phosphorylation (OXPHOS), generation or accumulation of reactive oxygen species (ROS), cellular respiration, spare respiratory capacity (SPC) and/or mitochondrial respiratory capacity.

In some of any of the foregoing embodiments, the molecule does not promote or enhance glycolysis, for example, does not promote or enhance glycolysis in T cells or a particular subtype thereof. In some aspects, the recombinant molecule does not promote or enhance glycolysis under conditions under which the molecule promotes or enhances FAS, FAO, OXPHOS, ROS accumulation or generation, cellular respiration, or respiratory capacity.

In some embodiments, the recombinant molecule is capable of binding to or interacting with an OXPHOS complex protein, is capable of binding to or interacting with a mitochondrial membrane protein, promotes, acts upstream of, or is required for, optionally in lymphocytes, optionally in a population of T cells, the translation and/or insertion of one or more OXPHOS proteins into a mitochondrial membrane.

In some embodiments, the molecule comprises a mitochondrial protein.

The engineered immune cell of any of claims 1-19, wherein the recombinant molecule is capable of interacting with or associating with, directly or indirectly, a CR6 interacting factor (CRIF), optionally CRIF1, a LEM or a 39S subunit, optionally MRPL23.

In some embodiments, the molecule is or comprises a lymphocyte enhancer molecule (LEM).

In some embodiments, the molecule comprises an amino acid sequence set forth in SEQ ID NO:69 or a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO:69. In some embodiments, the molecule comprises an amino acid sequence encoded by a nucleotide sequence set forth in SEQ ID NO:70 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:70 that encodes a functional protein, variant, or fragment thereof.

In some embodiments, the molecule is or comprises CRIF, e.g., CRIF1 optionally, CRIF1.

In some embodiments, the molecule is capable of promoting or enhancing the metabolic pathway, reaction or step under conditions of hypoxia, low glucose, poor vascularization, and/or ROS;

In some embodiments, the recombinant molecule is capable of promoting or enhancing the metabolic pathway, reaction or step in the engineered cell under conditions of hypoxia, low glucose, poor vascularization, and/or ROS, at a level increased as compared to a reference cell, substantially identical to the engineered cell but not comprising the molecule.

In some embodiments, the molecule is or comprises NADH ubiquinone oxidoreductase chain (ND), such as ND chain 1 (ND1), a ubiquinol cytochrome c oxidoreductase chain (UQRC), e.g., chain 2 (UQRC2), and/or a cytochrome c oxidoreductase (COX), such as COX1.

In some embodiments, the molecule is involved in or promotes a pathway resulting in the generation of energy or ATP, which optionally is independent of the presence of glucose or independent of glycolysis.

In some embodiments, the metabolic pathway, step, reaction, or event is or comprises a glycolysis pathway, a reaction thereof, and/or a reaction or pathway that metabolizes a metabolite of the glycolysis pathway, optionally under glucose-low, hypoxic, or nutrient-deprived conditions.

In some embodiments, the recombinant molecule is a molecule that is upregulated or activated in response to a particular signal, such as for example, antigen-receptor signaling, IL-17-mediated signaling, IL-15-mediated signaling, TRAF-mediated signaling, TRAF6-mediated signaling, IL-7-mediated signaling, IL-21-mediated signaling, low-oxygen conditions, succinate, release of reactive oxygen species (ROS), mTOR-induced signaling, or a functional variant thereof, and/or is differentially expressed or activated under nutrient-rich versus nutrient-poor conditions, or under hypoxic vs. normoxic conditions, or in effector or vs naïve or central memory T cells and/or in exhausted vs non-exhausted T cells, and/or in terminally differentiated T cells vs. non-terminally differentiated T cells.

In some embodiments, the recombinant molecule comprises a hypoxia-induced factor (HIF), for example, a HIF1-alpha.

In some embodiments, the molecule comprises an amino acid sequence set forth in SEQ ID NO:10 or a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO:10. In some embodiments, the molecule comprises an amino acid sequence encoded by a nucleotide sequence set forth in SEQ ID NO:79 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:79 that encodes a functional protein, variant, or fragment thereof.

In some embodiments, the molecule is capable of promoting generation of a glycolysis metabolite, such as PEP.

In some embodiments, the recombinant molecule comprises a phosphoenolpyruvate carboxykinase 1 (PCK1).

In some embodiments, the molecule comprises an amino acid sequence set forth in SEQ ID NO:12 or a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO:12. In some embodiments, the molecule comprises an amino acid sequence encoded by a nucleotide sequence set forth in SEQ ID NO:81 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:81 that encodes a functional protein, variant, or fragment thereof.

In some embodiments, the recombinant molecule is or interacts with GLUT4. In some embodiments, the recombinant molecule is or interacts with SGK1.

Also provided are vectors for producing the cells, such as vectors encoding the recombinant receptor and/or the molecule, and combinations of such vectors and compositions containing the same.

In some embodiments, the engineered cells exhibit increased generation of said glycolysis metabolite compared to reference cells substantially identical to the engineered cells but not expressing the recombinant molecule, under the same conditions.

In some embodiments, he molecule is capable of promoting said metabolic pathway, event, or step or reaction; the molecule is capable of inhibiting said metabolic pathway, event, or step or reaction; in some embodiments, the pathway, event or step or reaction is enhanced in the engineered cell compared to a reference cell substantially identical to the engineered cell, but not expressing the recombinant molecule; in some embodiments, the molecule is capable of inhibiting said metabolic pathway, event, or step or reaction.

In some embodiments, an outcome of the metabolic pathway, event, or step is inhibited or reduced in the engineered cell compared to a reference cell substantially identical to the engineered cell, but not expressing the molecule.

In some embodiments, the molecule, e.g. recombinant molecule, is a nucleic acid or protein capable of interfering with expression, activity, or stability of a negative regulator of the metabolic pathway or event or step or reaction, or a molecule that stabilizes the expression or longevity of a molecule that promotes said pathway, event, step or reaction. In some aspects, it is or comprises an RNAi, siRNA, or shRNA molecule.

In some embodiments, the cell further contains a disruption in expression and/or function of an immune checkpoint molecule, wherein the disruption or expression thereby promotes activation, proliferation, expansion, or reduced exhaustion, of the immune cell and/or is capable of reducing generation of or longevity of memory T cells or central memory T cells. The engineered immune cell of claim 31, wherein the checkpoint molecule comprises a PD-1, PD-L1, TIM3, CTLA4 or an adenosine receptor.

In some embodiments, persistence of the engineered cell and/or of reprogramming in favor of memory T cell, central memory T cell, Tscm, and/or undifferentiated phenotype cells, and/or reduction in exhaustion phenotype, and/or reduction in regulatory T cells, is enhanced or increased in the cell as compared to a cell substantially the same as the engineered cell without the recombinant molecule, under the same conditions.

In some embodiments, such conditions comprise one or more of activation via an antigen receptor, such as an artificial or natural receptor, a TCR, an ITAM-containing signaling molecule, cytokine signaling, TNFR signaling, and/or adoptive transfer to a subject containing cells expressing the ligand.

The cells in some embodiments are T cells, such as CD8+ and/or CD4+ T cells. In some embodiments, the molecule is different depending on whether the cell is CD4+ or CD8+. In some embodiments, the composition comprising the cells contains the molecule only in a certain subset of cells, such as in CD8+ T cells and not in CD4+ T cells, for example, for a molecule involved in a pathway known to be important for metabolic signature in CD8+ cells.

The cells generally contain a ligand-binding receptor such as an antigen-receptor, which may be natural or recombinant or engineered or artificially or ectopically expressed. In some embodiments, the ligand-binding receptor is an antigen receptor such as a non-TCR such as a chimeric antigen receptor the ligand-binding receptor and/or is a TCR, such as a functional portion thereof.

In some embodiments, the cells also include or express a recombinant truncated cell surface receptor. In some embodiments, the cell surface receptor is selected from among a modified and/or truncated form of EGFR (tEGFR), ErbB2/HER2/neu (Her2t), CD34 and/or NGFR. In some embodiments, the cell surface receptor comprises an amino acid sequence selected from among: any of SEQ ID NO: 55, 74 and 83; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 55, 74 and 83. In some embodiments, the cell surface marker comprises an amino acid sequence encoded by a nucleotide sequence set forth in SEQ ID NO:74 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:74 that encodes a functional protein, variant, or fragment thereof.

Also provided are nucleic acid molecules that encode the recombinant receptor and/or the molecule, and vectors containing said nucleic acid molecules. For example, in some embodiment, the nucleic acid molecule includes the nucleotide sequence set forth in any of SEQ ID NOS: 85, 87, 89, 91, 93, 95 and 97 or a sequence of nucleotides that has at least 85%, 86%, 87%, 88%, 89%, 90%, 91%, 92%, 93%, 94%, 95%, 96%, 97%, 98%, 99% or more sequence identity to 85, 87, 89, 91, 93, 95 and 97 that encodes a functional protein, variant, or fragment thereof.

In some embodiments, provided herein are a nucleic acid molecule(s), that include a nucleotide sequence encoding a genetically engineered receptor that specifically binds to a ligand; and a nucleotide sequence encoding a molecule that is involved in or capable of modulating a metabolic pathway or a functional and/or catalytically-active portion or variant thereof. In some embodiments, the encoded genetically engineered receptor and encoded molecule involved in or capable of modulating a metabolic pathway are any as present in any of the cells provided herein. In some embodiments, the nucleic acid molecule is a single polynucleotide.

In some embodiments, the nucleic acid molecule further includes at least one promoter operatively linked to control expression of the genetically engineered receptor and the molecule involved in or capable of modulating a metabolic pathway. For example, in some embodiments, the nucleotide sequence encoding the genetically engineered receptor is operatively linked to a first promoter and the nucleotide sequence encoding the molecule involved in or capable of modulating a metabolic pathway is operatively linked to a second promoter, which first and second promoter can be the same or different.

In some embodiments, the nucleotide sequence encoding the genetically engineered receptor and the nucleotide sequence encoding the molecule involved in or capable of modulating a metabolic pathway are separated by an internal ribosome entry site (IRES), a self-cleaving peptide or a peptide that causes ribosome skipping, optionally a T2A, P2A, E2A and/or F2A peptide, and the first and second chimeric receptor are expressed under the control of the same promoter. In some embodiments, the peptide that causes ribosome skipping comprises an amino acid sequence selected from among: any of SEQ ID NO: 54 and 64-68; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 54 and 64-68. In some embodiments, nucleotide sequence encoding the peptide that causes ribosome skipping is selected from among a nucleotide sequence set forth in SEQ ID NO:71 and a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:71 that encodes a functional protein, variant, or fragment thereof.

In some embodiments, exemplary encoded molecule that is involved in or capable of modulating a metabolic pathway include an amino acid sequence selected from among: any of SEQ ID NO: 4, 7-10, 12 and 69; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 4, 7-10, 12 and 69. In some embodiments, the nucleotide sequence encoding the molecule that is involved in or capable of modulating a metabolic pathway is selected from among: any of SEQ ID NO: 70 and 76-81; and a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 70 and 76-81 that encodes a functional protein, variant, or fragment thereof.

In some embodiments, the nucleic acid molecule can further include a nucleotide sequence encoding a recombinant truncated cell surface receptor. In some embodiments, the cell surface receptor is selected from among a modified and/or truncated form of EGFR (tEGFR), ErbB2/HER2/neu (Her2t), CD34 and/or NGFR, such as those having an amino acid sequence selected from among: any of SEQ ID NO: 55, 74 and 83; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 55, 74 and 83. In some embodiments, the nucleotide sequence encoding the cell surface receptor is set forth in SEQ ID NO:74 or is a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:74 that encodes a functional protein, variant, or fragment thereof.

In some embodiments, the nucleotide sequence provided herein encodes an amino acid sequence selected from among: any of SEQ ID NO: 85, 87, 89, 91, 93, 95 and 97; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 85, 87, 89, 91, 93, 95 and 97. In some embodiments, the nucleotide sequence is selected from among: any of SEQ ID NO: 84, 86, 88, 90, 92, 94 and 96; and a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 84, 86, 88, 90, 92, 94 and 96 that encodes a functional protein, variant, or fragment thereof.

Also provided herein are vectors that include any of the nucleic acid molecules provided herein. In some embodiments, the vector is a viral vector, such as a retroviral vector, a lentiviral vector or a gammaretroviral vector. Also provided herein are engineered cells, e.g., engineered immune cells, that contain any of the nucleic acid molecules described herein or any of the vectors described herein.

Also provided are compositions containing any of the engineered cells provided herein. In some embodiments, the cells are CD4+ or CD8+ cells. In some embodiments, the cells are CD4+ cells and the composition further comprises CD8+ cells that are genetically engineered with the ligand-binding receptor but do not express the recombinant molecule. In some embodiments, the cells are CD4+ cells and the composition further comprises CD8+ cells that are genetically engineered with the ligand-binding receptor and express the recombinant molecule. In some embodiments, the cells are CD8+ cells and the composition further comprises CD4+ cells that are genetically engineered with the ligand-binding receptor but do not express the recombinant molecule. In some embodiments, the cells are CD8+ cells and the composition further comprises CD4+ cells that are genetically engineered with the ligand-binding receptor and express the recombinant molecule. In some embodiments, the CD4+ cells express a different ligand-binding receptor than the CD8+ cells. In some embodiments, the only difference in the ligand-binding receptor expressed in the CD4+ cell compared to the CD8+ cell is the different costimulatory signaling domain. In some embodiments, the different costimulatory signaling domain is or comprises a cytoplasmic signaling domain of a CD28, a 4-1BB, or an ICOS molecule, or is a functional variant of a signaling portion thereof.

Also provided are methods of treatment that includes administering any of the engineered cells provided or any of the compositions provided herein, to a subject having a disease or condition. In some embodiments, the engineered cells employed in the methods contain ligand-binding receptor that specifically binds to a ligand or antigen associated with the disease or condition. In some embodiments, the disease or condition is a cancer, a tumor, an autoimmune disease or disorder, or an infectious disease.

In some embodiments, the engineered cells exhibit increased or longer expansion and/or persistence in the subject than in a subject administered the same or about the same dosage amount of a reference cell composition. In some embodiments, there is an increase or greater number of memory T cells or a memory T cell subset and/or an increased or longer persistence of memory T cells or a memory T cell subset in the subject derived from the administered the engineered cells compared to the number or persistence of the memory T cells or memory T cell subset in a subject derived from a reference cell composition administered at the same or about the same dosage.

In some embodiments, the memory T cells or memory T cell subset are CD62L+. In some embodiments, the memory T cells or memory T cell subset are central memory T cells (TCM), long-lived memory T cells or T memory stem cells (Tscm). In some embodiments, the memory T cells or memory T cell subset also exhibit a phenotyp that includes CD127+; and/or any one or more of CD45RA+, CD45RO−, CCR7+ and CD27+ and any one or more of t-betlow, IL-7Ra+, CD95+, IL-2Rβ+, CXCR3+ and LFA-1+.

In some embodiments, the memory T cells or memory T cell subset are CD8+.

In some embodiments, the number of memory T cells or a memory T cell subset derived from the administered genetically engineered cells comprises an increase or greater percentage of central memory T cells (Tcm), long-lived memory T cells or T memory stem cells (Tscm) compared to the number of such cells derived from a reference cell composition administered at the same or about the same dosage.

In some embodiments, there is an increase or greater number of non-terminally differentiated T cells in the subject derived from the administered genetically engineered T cells compared to the number of the non-terminally differentiated cells in a subject derived from a reference cell composition administered at the same or about the same dosage amount.

In some embodiments, the genetically engineered cells in the subject derived from the administered genetically engineered cells exhibit an increase in activation or proliferation upon restimulation ex vivo in the presence of a stimulatory agent or agent compared to the activation or proliferation of genetically engineered cells in a subject derived from a reference cell composition administered at the same or about the same dosage when restimulated ex vivo in the presence of the same stimulatory agent or agents. In some embodiments, the stimulatory agent or agents comprise an antigen, an anti-CD3/anti-CD28 antibody or comprises an IL-2, IL-15 and/or IL-7 cytokine. In some embodiments, the increase is at least 1.2-fold, 1.5-fold, 2-fold, 3-fold, 4-fold, or 5-fold.

In some embodiments, there is a decreased or reduced expression of an exhaustion marker genetically engineered cells in the subject derived from the administered genetically engineered T cells compared to the expression of the exhaustion marker in genetically engineered cells in a subject administered the same or about the same dosage amount of a reference cell composition. In some embodiments, the exhaustion marker is selected from among CD244, CD160 and PD-1. In some embodiments, the expression is decreased or reduced 1.2-fold, 1.5-fold, 2.0-fold, 3-fold, 4-fold, 5-fold, 6-fold, 7-fold, 8-fold, 9-fold, 10-fold or more.

In some embodiments, the increase or decrease is observed or is present within a month, within two months, within six months or within one year of administering the cells.

Also provided are methods for making and using the cells and/or compositions, such as uses in adoptive cell therapy, in a subject in need thereof, such as in a subject having a tumor. The cell therapy may be autologous or allogeneic. In some embodiments, the compositions and/or engineered cells are used in treating a disease or a condition is a subject. In some embodiments, the engineered cells or the engineered cells in the composition contain a ligand-binding receptor that specifically binds to a ligand or antigen associated with the disease or condition. In some embodiments, the disease or condition is a cancer, a tumor, an autoimmune disease or disorder, or an infectious disease. In some embodiments, the cancer or tumor may be a solid tumor and/or a blood tumor such as a leukemia or lymphoma.

Expression of the molecule may be constitutive and/or conditional, e.g., inducible and/or repressible expression, such as inducible upon activation, stress, hypoxia, decreased vasculature, TME, checkpoint molecule upregulation, proliferation, expression of activation marker, low glucose, or other conditions.

DETAILED DESCRIPTION

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Engineered Cells Expressing Metabolic Pathway-Modulating Molecules

Provided are cells, including immune cells, which cells are engineered to express or contain molecules, such as recombinant, engineered and/or ectopically expressed molecules or a functional and/or catalytically-active portion or variant thereof, which are involved in or capable of modulating, e.g., promoting, inducing, enhancing, inhibiting, preventing, or carrying out or facilitating, a metabolic pathway or event, or a step or reaction thereof, or capable of associating with a metabolite or component of such pathway.

Adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory.

In some contexts, optimal efficacy can depend on the ability of the administered cells to recognize and bind to a target, e.g., target antigen, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states (such as effector, long-lived memory, less-differentiated, and effector states), to provide effective, robust, and rapid recall responses, e.g., following clearance, rest, and subsequent re-exposure to target ligand or antigen, and avoid or reduce exhaustion, anergy, terminal differentiation, and/or differentiation into a suppressive state.

Maximizing exposure (including by improving expansion and persistence) of the cell product in the subject, disease, or condition can improve efficacy and therapeutic outcomes. For example, greater and/or longer degree of exposure to the CAR-expressing cells can improve treatment outcomes, including patient survival and remission, even in individuals with severe or significant tumor burden. Nonetheless, exposure can be limited by host immune responses against the recombinant receptors expressed by the administered cells, which may prematurely eliminate the cells. Once such a host immune response develops, either acquired or innate, it may not be feasible or effective to attempt to increase exposure or provide retreatment of subjects by administering a subsequent dose of cells expressing the same recombinant receptor. Once such an immune response has developed against the receptor, administration of such a second or subsequent dose of cells expressing the same receptor or one with similar immunogenic epitopes may result in rapid elimination of the cells before they have had a chance to expand and/or persist to an effective or substantial degree. Provided are embodiments that address these challenges.

In the context of certain diseases such as tumors, particularly solid tumors, optimal efficacy can further depend on the cells' ability to achieve such outcomes even in the context of various environmental factors in locations such as in locations other than immune organs and/or within environments or microenvironments of certain tissues, such as within a tumor microenvironment (TME), which are often unfavorable.

Such environmental factors and conditions can include various metabolic and immunosuppressive signatures, biosensors, and conditions, including nutrient-poor, immunosuppressive, and hypoxic conditions, increased expression of immune checkpoint molecules, increased numbers of regulatory cells, altered availability of certain various metabolites, growth factors, and nutrients (such as lactate, which may be increased in the context of hypoxic conditions, glucose, amino acids (e.g., decreased in the context of amino acid starvation), nucleic acids, acetyl-CoA and NAD+, citrate, post-translational modification, reactive oxygen species (ROS), ATP, lipids, glycogen), increased expression of amino acid-catabolic enzymes such as IDO, TDO, ARG-1, depletion of certain amino acids, poor vascularization, increased or decreased levels of inflammatory cells, cytokines and other factors.

Alterations in metabolism and metabolic pathways and signatures can impact the ability of T cells to properly engage in activation, proliferation, differentiation, homeostasis, persistence, dedifferentiation, and transition or reprogramming into various desirable states such as long-lived memory and undifferentiated populations, such as central memory T ($T_{CM}$) cells and T memory stem cells ($T_{SCM}$) cells, and the ability to avoid terminal differentiation, anergy, and exhaustion. In addition to adopting different cell surface expression and other phenotypic profiles (e.g., different expression levels of various activation, differentiation and checkpoint markers and differing levels of secretion of various factors), as T cells at different phenotypic states exhibit distinct metabolic profiles. See, e.g., Wang & Green, 2012 *Nature Immunology* 13(10) 907-15; Mockler et al., 2012, *Fronteirs in Oncology,* 4(107), Buck et al., 2015 *J. Exp. Med.,* 212(9) 1345-60, O'Sullivan & Pearce, 2014 *Trends in Immunology,* 36(2) 71-80.

For example, in some contexts, memory, e.g., CD8+, long-lived, and/or central memory T cells, as compared to other subtypes, memory T cells, exhibit distinct metabolic signatures and/or engage in different responses to various metabolism-related signals and conditions. Such memory cells generally differ in the pathways preferentially involved in the generation of ATP and/or energy. The same may be true in comparing other subtypes. For example, whereas naïve T cells generally do not exhibit considerable net growth and thus do not engage in substantial nutrient uptake or glycolysis, upon activation, activated and effector T cells generally grow considerably and exhibit increased nutrient uptake and glycolysis. Exhaustion or anergy, on the other hand, may be linked to an inability to take up certain nutrients and/or to enter glycolysis, steps thereof, or other energy-generating metabolic events or pathways.

Memory cells, and particularly long-lived and less differentiated memory phenotype cells, generally do not engage in aerobic glycolysis as highly as other subtypes, and instead may preferentially rely on other pathways as primary sources of energy, such as those carried out within mitochondria, e.g., OXPHOS.

They may also drive such pathways in part via lipids produced by their increased catabolism of intracellular fatty acids, via fatty acid oxidation (FAO), in the mitochondria. Such cells in some contexts engage in a comparatively high level of biosynthesis of lipids for use in such reactions, e.g., fatty acid synthesis (FAS), such as events generally observed in adipose cells, such as triacylglyceride (TAG) synthesis. This process may be driven in some contexts via signals that promote importation of glycerol into the mitochondria, mitochondrial biosynthesis, or other components of such pathways. In some contexts, such events are induced by signals known to promote memory- or long-lived phenotypes, such as certain cytokines and other stimuli. Memory T cells may also maintain substantial spare respiratory capacity (SRC) and have increased mitochondrial mass, both of which confer a metabolic advantage for survival and recall following antigenic challenge. The molecule in some embodiments is involved with or interacts with one or more components or metabolites of a lipid metabolism pathway or step or reaction thereof, for example, lipid synthesis, lipid oxidation, and/or lipid storage. For example, it may include fatty acid uptake, fatty acid synthesis (FAS), and/or fatty acid oxidation (FAO). In some embodiments, the metabolic pathway, event, step or reaction is or comprises triacylglyceride (TAG) synthesis, TAG storage, glycerol phosphate pathway, glycerophospholipid synthesis and/or glycerol uptake.

A mutation stabilizing a molecule, lymphocyte activating molecule (LEM) that associated and/or promoted OXPHOS outcomes in T cells was shown to enhance both expansion without terminal differentiation/exhaustion and the emergence and/or persistence of functional CD8+ memory cells, which exhibited functional recall responses, e.g., following clearance and rechallenge with antigen. Okoye et al. Science. 2015 May 29; 348(6238):995-1001. In some embodiments, the provided molecule is a molecule involved in OXPHOS or related pathways or molecules. T cell subsets and different T cell activation/differentiation states also differ in their ability to respond or the types of responses exhibited in environments of particular metabolite levels, such as those observed in a tumor microenvironment, e.g., hypoxia, nutrient deprivation, glucose-poor condition, or poor vasculature. The ability to reprogram or differentiate into one or more T cell phenotypic states may also depend upon the ability to react or react in a desirable way to such conditions. For example, the inability to induce glycolysis or generation of glycolysis metabolites can result in exhaustion or anergy in response to stimulation through the TCR. For example, deficiencies in pathways involving hypoxia-induced factors, such as HIF1-alpha-related pathways and components thereof, have been linked to preference towards an exhausted phenotype in nutrient-poor or hypoxic conditions, whereas expression of certain molecules involved in such pathways can inhibit exhaustion and promote persistent expansion and survival of effector cells, rather than terminal differentiation. Doedens et al. *Nat Immunol.* 2013 November; 14(11):1173-82. In some embodiments, the molecule is involved with or interacts with a molecule involved with a pathway or metabolic signature induced by or that compensates for hypoxic environment.

Glucose-depravation, such as in the TME, can dampen glycolysis and thereby limit the ability of T cells to effectively respond, proliferate, and adopt effector phenotypes in response to antigen. Insufficient levels of the glycolysis metabolite phosphoenolpyruvate (PEP) can lead to insufficient NFAT and calcium signaling. Expression of molecules involved in promoting the generation of such metabolites such as phosphoenolpyruvate carboxykinase 1 (PCK1) can rescue such events and avoid exhaustion. See Ho et al. *Cell.* 2015 Sep. 10; 162(6):1217-28. Signals received via the antigen receptor and other signaling molecules such as cytokines and costimulatory molecules can promote pathways that allow these events even in such poor conditions. Such signals can be dampened or prevented by signaling through certain immune checkpoint molecules such as PD-1 (e.g., amino acid sequence set forth in SEQ ID NO:26, nucleic acid sequence set forth in SEQ ID NO:47). Yet the deletion or genetic absence of PD-1 or other such molecules in T cells in vivo may in some contexts—despite preventing an exhausted phenotype and permitting primary expansion and activation and other effector functions—may also negatively impact the long-lived memory compartment, either by preventing reprogramming or persistence. In some embodiments, provided are cells expressing molecules that inhibit exhaustion and promote expansion, while also enhancing or promoting persistence and the generation of functional long-lived memory cells and survival thereof. In some embodiments, the molecule is involved with or interacts with component(s) of glycolysis or PEP-mediated signaling or generation or pathways induced, e.g., in response to glucose-depravation.

The metabolic pathways and events and reactions may include one or more of a lipid metabolism pathway or step or reaction thereof, for example, lipid synthesis, lipid oxidation, and/or lipid storage. For example, it may include fatty acid uptake, fatty acid synthesis (FAS), and/or fatty acid oxidation (FAO). In some embodiments, the metabolic pathway, event, step or reaction is or comprises triacylglyceride (TAG) synthesis, TAG storage, glycerol phosphate pathway, glycerophospholipid synthesis and/or glycerol uptake.

In some embodiments, the metabolic pathway or event is or comprises lipid metabolism, oxidative phosphorylation (OXPHOS), a reactive oxygen species (ROS)-induced signal, glycolysis, or mitochondrial biogenesis. In some aspects, the metabolic pathway or event is or comprises generation of energy or ATP in a process that occurs within the mitochondria or via mitochondrial proteins, or occurs independently of glucose or via a pathway other than glycolysis. In some embodiments, the metabolic pathway, step, reaction, or event is or comprises a glycolysis pathway, a reaction thereof, or a reaction or pathway that metabolizes a metabolite of the glycolysis pathway, such as under glucose-low, hypoxic, or nutrient-deprived conditions. In some aspects, the metabolic pathway or event is or comprises the generation of ATP in a glucose-low environment, in a nutrient-poor environment, or in a hypoxic environment. In some embodiments, the metabolic pathway or event comprises glutaminolysis, TCA cycle, glucose metabolism, amino acid or nucleotide metabolism, or beta-oxidation.

In some embodiments, the metabolic pathway or event, reaction or step comprises oxidative phosphorylation (OXPHOS), generation or accumulation of reactive oxygen species (ROS), cellular respiration, spare respiratory capacity (SPC) or mitochondrial respiratory capacity.

In some embodiments, the molecule is capable of promoting the metabolic pathway or step or reaction thereof or a metabolic event, directly or indirectly. In some aspects, the molecule is capable of inhibiting the metabolic pathway. In some embodiments, the molecule promotes a catabolic molecular profile. In some aspects, the molecule promotes an anabolic molecular profile. In some embodiments, the molecule is not directly involved in the pathway but is capable of associating with a component thereof.

In some embodiments, the molecule is involved in or promotes a pathway resulting in the generation of energy or ATP, which may be independent of the presence of glucose or independent of glycolysis. In some embodiments, the molecule does not promote or enhance glycolysis, does not promote or enhance glycolysis in T cells, or does not promote or enhance glycolysis under conditions under which the molecule promotes or enhances FAS, FAO, OXPHOS, ROS accumulation or generation, cellular respiration, or respiratory capacity. In some embodiments, the molecule is capable of binding to or interacting with an OXPHOS complex protein or is capable of binding to or interacting with a mitochondrial membrane protein. In some aspects, the molecule promotes, acts upstream of, or is required for, such as in lymphocytes or a population of T cells, the translation or insertion of one or more OXPHOS proteins into a mitochondrial membrane. In some embodiments, the molecule is capable of promoting or enhancing the metabolic pathway, reaction or step under conditions of hypoxia, low glucose, poor vascularization, or ROS. In some embodiments, the molecule is capable of promoting generation of a glycolysis metabolite, such as PEP.

In some embodiments, the molecule is or comprises an enzyme. In some aspects, the molecule is or comprises an adapter. In some embodiments, the molecule is involved in fatty acid synthesis, fatty acid storage or fatty acid uptake. In some embodiments, the molecule promotes or enhances FAS or FAO. In some embodiments, the molecule is involved in or is capable of promoting glycerol transport, is or comprises a glycerol transporter, a TAG synthase molecule, a glycerol kinase, or an acyltransferase.

In some embodiments, the molecule comprises a mitochondrial protein. In some embodiments, the molecule is or comprises a Glycerol kinase (GYK), a Glycerol-3-phosphate acetyltransferase mitochondrial (GPAT), a Monoacylglycerol O-acetyltransferase (MOGAT), a DAG O-acetyltransferase (DGAT), an acylglycerolphosphate acyltransferase (AGPAT), or a Lipin. In some aspects, the molecule is any described in Takeuchi et al. *Am J Physiol Endocrinol Metab.* 2009 June; 296(6): E1195-E1209. In some embodiments, the molecule is or comprises a glycerol transporter or functional portion thereof. In some embodiments, the molecule is or comprises a palmitoyltransferase, such as carnitine palmitoyltransferase (CPT), such as CPTI. In some embodiments, the molecule is or comprises NADH ubiquinone oxidoreductase chain (ND), such as ND chain 1 (ND1), a ubiquinol cytochrome c oxidoreductase chain (UQRC), e.g., chain 2 (UQRC2), or a cytochrome c oxidoreductase (COX), such as COX1.

In some embodiments, molecule is capable of interacting with or associating with, directly or indirectly, a CR6 interacting factor (CRIF), a LEM or a 39S subunit, such as MRPL23. In some embodiments, the molecule in the metabolic pathway is or comprises lymphocyte expansion molecule (LEM), glycerol kinase (Gyk), diacylglycerol O-acetyltransferase 1 (DGAT1) or 2 (DGAT2), glycerol-3-phosphate acetyltransferase mitochondrial (GPAM), monoacylglycerol O-acetyltransferase 1 (MOGAT1) or 2 (MOGAT2), hypoxia-inducible factor alpha (HIF1$\alpha$), PCK1, AGPAT1, AGPAT2, AGPAT3, AGPAT 6 (LPA-MAG PA), GPAT1, GPAT2, AQP9, LPIN1, or CRIF1.

II. Recombinant Receptors

In some embodiments, the provided cells express and/or are engineered to express receptors, such as recombinant receptors, including those containing ligand-binding domains or binding fragments thereof, and T cell receptors (TCRs) and components thereof, and/or functional non-TCR antigen receptors, such as chimeric antigen receptors (CARs). In some embodiments, the recombinant receptor contains an extracellular ligand-binding domain that specifically binds to an antigen. In some embodiments, the recombinant receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.,* 2012 October; 24(5): 633-39; Wu et al., *Cancer,* 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

The recombinant receptor, such as a CAR, generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

A. Ligand-Binding Domain

In some embodiments, the recombinant receptor includes a ligand-binding domain that binds, such as specifically binds, to an antigen (or a ligand). Among the antigens targeted by the recombinant receptors are those expressed in the context of a disease, condition, or cell type to be targeted via the adoptive cell therapy. In some embodiments, the disease or condition is a tumor, such as a solid tumor, lymphoma, leukemia, blood tumor, metastatic tumor, or other cancer or tumor type. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen associated with the disease or disorder is selected from the group consisting of orphan tyrosine kinase receptor ROR1, tEGFR, Her2, L1-CAM, CD19, CD20, CD22, BCMA, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the antigen is a pathogen-specific antigen. In some embodiments, the antigen is a viral antigen (such as a viral antigen from HIV, HCV, HBV, etc.), bacterial antigens, and/or parasitic antigens.

1. Antigen Receptor

In some embodiments, the recombinant receptor includes a CAR. In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150:880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the CAR contains an antibody or an antigen-binding fragment (e.g. scFv) that specifically recognizes an antigen, such as an intact antigen, expressed on the surface of a cell.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated (32 microglobulin. Generally, MHC class II molecules are composed of two transmembrane glycoproteins, a and (3, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

The term "peptide antigen" or "peptide epitope" refers to a peptide of a polypeptide that can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFV or other antibody forms can be generated, for example, in which members of the library are mutated at one or more residues of a CDR or CDRs. Exemplary of such methods are known in the art (see e.g. US published application No. US20020150914, US2014/0294841; and Cohen C J. et al. (2003) *J Mol. Recogn.* 16:324-332).

2. TCR

In some embodiments, the recombinant receptors include recombinant T cell receptors (TCRs) and/or TCRs cloned from naturally occurring T cells.

A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al., *Immunobiology: The Immune System in Health and Disease,* 3$^{rd}$ Ed., Current Biology Publications, p. 4:33, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_\alpha$, or $V_\beta$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contain a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) *Nat*

*Med.* 14:1390-1395 and Li (2005) *Nat Biotechnol.* 23:349-354. In some embodiments, the TCR or antigen-binding portion thereof can be synthetically generated from knowledge of the sequence of the TCR.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpressed. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

B. Intracellular Signaling Domain

In some aspects, the ligand-binding domain, such as an antigen-specific binding, or recognition component is linked to one or more transmembrane and intracellular signaling domains.

In some embodiments, the recombinant receptor, such as a CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some aspects, the portion of the constant region serves as a spacer region between the ligand-binding domain, such as the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.,* 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 49), and is encoded by the sequence set forth in SEQ ID NO: 50. In some embodiments, the spacer has the sequence set forth in SEQ ID NO: 51. In some embodiments, the spacer has the sequence set forth in SEQ ID NO: 52. In some embodiments, the constant region or portion is of IgD. In some embodiments, the spacer has the sequence set forth in SEQ ID NO:53. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOs: 49, 51, 52 or 53.

The ligand-binding domain, such as antigen recognition domain, generally is linked to one or more intracellular signaling components, such as signaling components that mimic activation through an antigen receptor complex, such as a TCR complex, in the case of a CAR, and/or signal via another cell surface receptor. Thus, in some embodiments, the ligand-binding domain (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154, and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. In some embodiments the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the CD19-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, or ICOS, or CD27. In some aspects, the same CAR includes both the activating and costimulatory components.

In some embodiments, the activating domain (e.g. CD3 zeta) is included within one CAR, whereas the costimulatory component (e.g. CD28 or 4-1BB) is provided by another CAR recognizing another antigen. In some embodiments, the CARs include activating or stimulatory CARs, costimulatory CARs, both expressed on the same cell (see WO2014/055668). In some aspects, the CD19-targeting CAR is the stimulatory or activating CAR; in other aspects, it is the costimulatory CAR. In some embodiments, the cells further include inhibitory CARs (iCARs, see Fedorov et al., *Sci. Transl. Medicine,* 5(215) (December, 2013), such as a CAR recognizing an antigen other than CD19, whereby an activating signal delivered through the CD19-targeting CAR is diminished or inhibited by binding of the inhibitory CAR to its ligand, e.g., to reduce off-target effects.

In some embodiments, the intracellular signaling component of the recombinant receptor, such as CAR, comprises a CD3 zeta intracellular domain and a costimulatory signaling region. In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and/or CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor, or the engineered cell expressing the same, further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR) or a functional variant thereof. In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 55 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 55, or the mature form thereof set forth in SEQ ID NO: 83 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 83. An exemplary T2A linker sequence comprises the sequence of amino acids set forth in SEQ ID NO: 54, and is encoded by the sequence set forth in SEQ ID NO: 71, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 54, or the sequence of amino acids set forth in SEQ ID NO: 64 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 64. In some embodiments, the linker sequence comprise P2A, E2A or F2A cleavable linker sequence or other linkers, such as those set forth in SEQ ID NOS: 65-68 and 82, or the sequence of amino acids set forth in SEQ ID NO: 64 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 65-68 and 82.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as “self” by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the receptor, e.g., chimeric antigen receptor, includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, as provided herein, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, as provided herein, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 56 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 56; in some embodiments, the transmembrane-domain containing portion of the recombinant receptor comprises the sequence of amino acids set forth in SEQ ID NO: 57 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 58 or 59 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 58 or 59. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 60 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 60.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or 8,911,993. For example, in some embodiments, the intracellular signaling domain comprises the sequence of amino acids set forth in SEQ ID NO: 61, 62 or 63 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 61, 62 or 63.

In some aspects, the spacer contains only a hinge region of an IgG, such as only a hinge of IgG4 or IgG1, such as the hinge only spacer set forth in SEQ ID NO: 49. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 52. In some embodiments, the spacer is an Ig hinge, e.g., an IgG4 hinge, linked to a CH3 domain only, such as set forth in SEQ ID NO: 51. In some embodiments, the spacer is or comprises a glycine-serine rich sequence or other flexible linker such as known flexible linkers, such as set forth in SEQ ID NO:82.

For example, in some embodiments, the CAR includes an anti-CD19 antibody such as an anti-CD19 antibody fragment, such as any of the provided human anti-CD19 antibodies, e.g., single-chain antibodies including scFvs, described herein, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an anti-CD19 antibody or fragment, such as any of the human anti-CD19 antibodies, including scFvs described herein, a spacer such as any of the Ig-hinge containing spacers, a CD28-derived transmembrane domain, a 4-1BB-derived intracellular signaling domain, and a CD3 zeta-derived signaling domain.

In some embodiments, such CAR constructs further includes a T2A ribosomal skip element and/or a tEGFR sequence, e.g., downstream of the CAR, such as set forth in SEQ ID NO: 54 or 64 and/or 55 or 83, respectively, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 54 or 64 and/or 55 or 83.

III. Molecules Involved in Metabolic Pathway

In some embodiments, the molecule, e.g., recombinant molecule, which can be exogenous or heterologous, or a functional and/or catalytically-active portion or variant thereof, is involved in or capable of modulating a metabolic pathway. In some embodiments, provided are engineered cells, such as recombinant receptor-expressing engineered cells, that are modified by recombinant, engineered and/or ectopic expression of one or more metabolic pathway-modulating molecule, such as those described herein. In some embodiments, expression of the metabolic pathway-modulating molecule is under the control of a heterologous promoter or enhancer, such as is under the control of an inducible promoter. In some embodiments, a nucleic acid molecule, e.g. vector, encoding the metabolic pathway-modulating molecule is introduced into the cell, which introduction can occur simultaneously or sequentially with introduction of the nucleic acid encoding the transgenic receptor, such as the CAR. Exemplary nucleic acid constructs for engineering cells are provided.

In some embodiments, the metabolic pathway or event is or comprises lipid metabolism, oxidative phosphorylation (OXPHOS), a reactive oxygen species (ROS)-induced signal, glycolysis, or mitochondrial biogenesis. In some aspects, the metabolic pathway or event is or comprises generation of energy or ATP in a process that occurs within the mitochondria or via mitochondrial proteins, or occurs independently of glucose or via a pathway other than glycolysis. In some embodiments, the metabolic pathway, step, reaction, or event is or comprises a glycolysis pathway, a reaction thereof, or a reaction or pathway that metabolizes a metabolite of the glycolysis pathway, such as under glucose-low, hypoxic, or nutrient-deprived conditions. In some aspects, the metabolic pathway or event is or comprises the generation of ATP in a glucose-low environment, in a nutrient-poor environment, or in a hypoxic environment. In some embodiments, the metabolic pathway or event comprises glutaminolysis, TCA cycle, glucose metabolism, amino acid or nucleotide metabolism, or beta-oxidation.

In some embodiments, the metabolic pathway or event, reaction or step comprises fatty acid uptake, fatty acid synthesis (FAS), and/or fatty acid oxidation (FAO). In some embodiments, the metabolic pathway, event, step or reaction is or comprises triacylglyceride (TAG) synthesis, TAG storage, glycerol phosphate pathway, glycerophospholipid synthesis and/or glycerol uptake. In some aspects, the metabolic pathway or event comprises oxidative phosphorylation (OXPHOS), generation or accumulation of reactive oxygen species (ROS), cellular respiration, spare respiratory capacity (SPC) or mitochondrial respiratory capacity.

In some embodiments, the molecule is capable of promoting the metabolic pathway or step or reaction thereof or a metabolic event, directly or indirectly. In some aspects, the molecule is capable of inhibiting the metabolic pathway. In some embodiments, the molecule promotes a catabolic molecular profile. In some aspects, the molecule promotes an anabolic molecular profile.

In some embodiments, the molecule is involved in or promotes a pathway resulting in the generation of energy or ATP, which may be independent of the presence of glucose or independent of glycolysis. In some embodiments, the molecule does not promote or enhance glycolysis, does not promote or enhance glycolysis in T cells, or does not promote or enhance glycolysis under conditions under which the molecule promotes or enhances FAS, FAO, OXPHOS, ROS accumulation or generation, cellular respiration, or respiratory capacity. In some embodiments, the molecule is capable of binding to or interacting with an OXPHOS complex protein or is capable of binding to or interacting with a mitochondrial membrane protein. In some aspects, the molecule promotes, acts upstream of, or is required for, such as in lymphocytes or a population of T cells, the translation or insertion of one or more OXPHOS proteins into a mitochondrial membrane. In some embodiments, the molecule is capable of promoting or enhancing the metabolic pathway, reaction or step under conditions of hypoxia, low glucose, poor vascularization, or ROS. In some embodiments, the molecule is capable of promoting generation of a glycolysis metabolite, such as PEP.

In some embodiments, the molecule is or comprises an enzyme. In some aspects, the molecule is or comprises an adapter. In some embodiments, the molecule is involved in fatty acid synthesis, fatty acid storage or fatty acid uptake. In some embodiments, the molecule promotes or enhances FAS or FAO. In some embodiments, the molecule is involved in or is capable of promoting glycerol transport, is or comprises a glycerol transporter, a TAG synthase molecule, a glycerol kinase, or an acyltransferase.

In some embodiments, the molecule comprises a mitochondrial protein. In some embodiments, the molecule is or comprises a Glycerol kinase (GYK), a Glycerol-3-phosphate acetyltransferase mitochondrial (GPAT), a Monoacylglycerol O-acetyltransferase (MOGAT), a DAG O-acetyltransferase (DGAT), an acylglycerolphosphate acyltransferase (AGPAT), or a Lipin. In some aspects, the molecule is any described in Takeuchi et al. Am J Physiol Endocrinol Metab. 2009 June; 296(6): E1195-E1209. In some embodiments, the molecule is or comprises a glycerol transporter or functional portion thereof. In some embodiments, the molecule is or comprises a palmitoyltransferase, such as carnitine palmitoyltransferase (CPT), such as CPTI. In some embodiments, the molecule is or comprises NADH ubiquinone oxidoreductase chain (ND), such as ND chain 1 (ND1), a ubiquinol cytochrome c oxidoreductase chain (UQRC), e.g., chain 2 (UQRC2), or a cytochrome c oxidoreductase (COX), such as COX1.

In some embodiments, molecule is capable of interacting with or associating with, directly or indirectly, a CR6 interacting factor (CRIF), a LEM or a 39S subunit, such as MRPL23. In some embodiments, the molecule in the metabolic pathway is or comprises lymphocyte expansion molecule (LEM), glycerol kinase (Gyk), diacylglycerol 0-acetyltransferase 1 (DGAT1) or 2 (DGAT2), glycerol-3-phosphate acetyltransferase mitochondrial (GPAM), monoacylglycerol O-acetyltransferase 1 (MOGAT1) or 2 (MOGAT2), hypoxia-inducible factor alpha (HIF1α), PCK1, AGPAT1, AGPAT2, AGPAT3, AGPAT 6 (LPA-MAG PA), GPAT1, GPAT2, AQP9, LPIN1, or CRIF1.

In some embodiments, the molecule involved in the metabolic pathway is or comprises lymphocyte expansion molecule (LEM) or a functional fragment or functional variant thereof, such as a functional fragment or functional variant that is catalytically active and/or that exhibits an activity to modulate a metabolic pathway. In some embodiments, LEM comprises the sequence of amino acids set forth in any of SEQ ID NOs: 1-3, 27 or 69, or is a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOs: 1-3, 27 or 69, or is a functional fragment thereof. In some embodiments, LEM lacks or does not contain a prodomain and/or is a mature or catalytically active protein. In some embodiments, LEM is encoded by a sequence of nucleotides that comprises the sequence of nucleotides set forth in any of SEQ ID NOs: 28, 29, 48 or 70, or a sequence of nucleotides that exhibits at least 85%, 86%, 87%, 88%, 89%, 90%, 91%, 92%, 93%, 94%, 95%, 96%, 97%, 98%, 99% or more sequence identity to any of SEQ ID NOs: 28, 29, 48 or 70, and that encodes a functional protein, variant, or fragment thereof. In some embodiments, the LEM-encoding nucleic acid molecule comprises a signal sequence. In some embodiments, LEM is a human protein. In some embodiments, LEM comprises a sequence of human LEM (huLEM or C1ORF177) set forth in NCBI Reference Sequence: NP 689820.2, NCBI Reference Sequence: NP_001104003.1, or UniProt accession number Q3ZCV2, is encoded by a sequence or coding portion of a sequence set forth in NCBI Reference Sequence: NM_152607.2, NCBI Reference Sequence: NM_001110533.1 or is described in Okoye et al. *Science*. 2015 May 29; 348(6238):995-1001. In some embodiments, LEM is a mouse LEM set forth in SEQ ID NO:27, GenBank: AKD95359.1 or a functional protein, variant, or fragment thereof, or is encoded by the sequence of nucleotides set forth in SEQ ID NO:48, or a sequence of nucleotides that exhibits at least 85%, 86%, 87%, 88%, 89%, 90%, 91%, 92%, 93%, 94%, 95%, 96%, 97%, 98%, 99% or more sequence identity to any of SEQ ID NOs: 48, and that encodes a functional protein, variant, or fragment thereof.

In some embodiments, the molecule involved in the metabolic pathway is or comprises glycerol kinase (Gyk) or a functional fragment or functional variant thereof, such as a functional fragment or functional variant that is catalytically active and/or that exhibits an activity to modulate a metabolic pathway. In some embodiments, Gyk comprises the sequence of amino acids set forth in any of SEQ ID NOs: 4-6, or is a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOs: 4-6, or is a functional fragment thereof. In some embodiments, Gyk lacks or does not contain a prodomain and/or is a mature or catalytically active protein. In some embodiments, Gyk is encoded by a sequence of nucleotides that comprises the sequence of nucleotides set forth in SEQ ID NO: 30 or 77, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 30 or 77, and that encodes a functional protein, variant, or fragment thereof. In some embodiments, the Gyk-encoding nucleic acid molecule comprises a signal sequence. In some embodiments, Gyk is a human protein. In some embodiments, Gyk comprises a sequence set forth in UniProt accession number Q14410, GenBank: CAA55365.1, or GenBank: CAA55364.1, or is encoded by a sequence or coding portion of a sequence set forth in NG_008178.1 RefSeqGene.

In some embodiments, the molecule involved in the metabolic pathway is or comprises Diacylglycerol O-acetyltransferase 1 (DGAT1) or a functional fragment or functional variant thereof, such as a functional fragment or functional variant that is catalytically active and/or that exhibits an activity to modulate a metabolic pathway. In some embodiments, DGAT1 comprises the sequence of amino acids set forth in SEQ ID NO: 7 or 11, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 11, or is a functional fragment thereof. In some embodiments, DGAT1 lacks or does not contain a prodomain and/or is a mature or catalytically active protein. In some embodiments, DGAT1 is encoded by a sequence of nucleotides that comprises the sequence of nucleotides set forth in SEQ ID NO: 31 or 76, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 31 or 76, and that encodes a functional protein, variant, or fragment thereof. In some embodiments, the DGAT1-encoding nucleic acid molecule comprises a signal sequence. In some embodiments, DGAT1 is a human protein. In some embodiments, DGAT1 comprises a sequence set forth in UniProt accession number 075907 or NCBI Reference Sequence: NP_036211.2, or is encoded by a sequence or coding portion of a sequence set forth in NCBI Reference Sequence: NM_012079.5.

In some embodiments, the molecule involved in the metabolic pathway is or comprises Glycerol-3-phosphate acetyltransferase mitochondrial (GPAM) or a functional fragment or functional variant thereof, such as a functional fragment or functional variant that is catalytically active and/or that exhibits an activity to modulate a metabolic pathway. In some embodiments, GPAM comprises the sequence of amino acids set forth in SEQ ID NO: 8, or is a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8, or is a functional fragment thereof. In some embodiments, GPAM lacks or does not contain a prodomain and/or is a mature or catalytically active protein. In some embodiments, GPAM is encoded by a sequence of nucleotides that comprises the sequence of nucleotides set forth in SEQ ID NO: 32 or 78, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 32 or 78, and that encodes a functional protein, variant, or fragment thereof. In some embodiments, the GPAM-encoding nucleic acid molecule comprises a signal sequence. In some embodiments, GPAM is a human protein. In some embodiments, GPAM comprises a sequence set forth in UniProt accession number Q9HCL2 or NCBI Reference Sequence: NP_001231878.1, or is encoded by a sequence or coding portion of a sequence set forth in NCBI Reference Sequence: NM_001244949.1.

In some embodiments, the molecule involved in the metabolic pathway is or comprises Monoacylglycerol O-acetyltransferase (MOGAT1) or a functional fragment or functional variant thereof, such as a functional fragment or functional variant that is catalytically active and/or that exhibits an activity to modulate a metabolic pathway. In some embodiments, MOGAT1 comprises the sequence of amino acids set forth in SEQ ID NO: 9, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 9, or is a functional fragment thereof. In some embodiments, MOGAT1 lacks or does not contain a prodomain and/or is a mature or catalytically active protein. In some embodiments, MOGAT1 is encoded by a sequence of nucleotides that comprises the sequence of nucleotides set forth in SEQ ID NO: 33 or 80, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 33 or 80, and that encodes a functional protein, variant, or fragment thereof. In some embodiments, the MOGAT1-encoding nucleic acid molecule comprises a signal sequence. In some embodiments, MOGAT1 is a human protein. In some embodiments, MOGAT1 comprises a sequence set forth in UniProt accession number Q96PD6 or NCBI Reference Sequence: NP_477513.2, or is encoded by a sequence or coding portion of a sequence set forth in NCBI Reference Sequence: NM_058165.2.

In some embodiments, the molecule involved in the metabolic pathway is or comprises hypoxia-inducible factor alpha (HIF1α) or a functional fragment or functional variant thereof, such as a functional fragment or functional variant that is catalytically active and/or that exhibits an activity to modulate a metabolic pathway. In some embodiments, HIF1α comprises the sequence of amino acids set forth in SEQ ID NO: 10, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10, or is a functional fragment thereof. In some embodiments, HIF1α lacks or does not contain a prodomain and/or is a mature or catalytically active protein. In some embodiments, HIF1α is encoded by a sequence of nucleotides that comprises the sequence of nucleotides set forth in SEQ ID NO: 34 or 79, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 34 or 79, and that encodes a functional protein, variant, or fragment thereof. In some embodiments, the HIF1α-encoding nucleic acid molecule comprises a signal sequence. In some embodiments, HIF1α is a human protein. In some embodiments, HIF1α comprises a sequence set forth in UniProt accession number Q16665 or NCBI Reference Sequence: NP_036211.2, is encoded by a sequence or coding portion of a sequence set forth in NCBI Reference Sequence: NM_001530.3, or is described in Doedens et al. *Nat Immunol.* 2013 November; 14(11):1173-82.

In some embodiments, the molecule involved in the metabolic pathway is or comprises PCK1 or a functional fragment or functional variant thereof, such as a functional fragment or functional variant that is catalytically active and/or that exhibits an activity to modulate a metabolic pathway. In some embodiments, PCK1 comprises the sequence of amino acids set forth in SEQ ID NO: 12, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12, or is a functional fragment thereof. In some embodiments, PCK1 lacks or does not contain a prodomain and/or is a mature or catalytically active protein. In some embodiments, PCK1 is encoded by a sequence of nucleotides that comprises the sequence of nucleotides set forth in SEQ ID NO: 35 or 81, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 35 or 81, and that encodes a functional protein, variant, or fragment thereof. In some embodiments, the PCK1-encoding nucleic acid molecule comprises a signal sequence. In some embodiments, PCK1 is a human protein. In some embodiments, PCK1 comprises a sequence set forth in UniProt accession number P35558 or NCBI Reference Sequence: NP_002582.3, is encoded by a sequence or coding portion of a sequence set forth in NCBI Reference Sequence: NM_002591.3, or is described in Ho et al. *Cell.* 2015 Sep. 10; 162(6):1217-28.

In some embodiments, the molecule involved in the metabolic pathway is or comprises AGPAT1 or a functional fragment or functional variant thereof, such as a functional fragment or functional variant that is catalytically active and/or that exhibits an activity to modulate a metabolic pathway. In some embodiments, AGPAT1 comprises the sequence of amino acids set forth in SEQ ID NO: 13, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, or is a functional fragment thereof. In some embodiments, AGPAT1 lacks or does not contain a prodomain and/or is a mature or catalytically active protein. In some embodiments, AGPAT1 is encoded by a sequence of nucleotides that comprises the sequence of nucleotides set forth in SEQ ID NO: 36, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 36, and that encodes a functional protein, variant, or fragment thereof. In some embodiments, the AGPAT1-encoding nucleic acid molecule comprises a signal sequence. In some embodiments, AGPAT1 is a human protein. In some embodiments, AGPAT1 comprises a sequence set forth in amino acids 27-283 of UniProt accession number Q99943 or NCBI Reference Sequence: XP_011546679.1, or is encoded by a sequence or coding portion of a sequence set forth in NCBI Reference Sequence: NM_006411.3.

In some embodiments, the molecule involved in the metabolic pathway is or comprises AGPAT2 or a functional fragment or functional variant thereof, such as a functional fragment or functional variant that is catalytically active and/or that exhibits an activity to modulate a metabolic pathway. In some embodiments, AGPAT2 comprises the sequence of amino acids set forth in SEQ ID NO: 14 or 15, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 14 or 15, or is a functional fragment thereof. In some embodiments, AGPAT2 lacks or does not contain a prodomain and/or is a mature or catalytically active protein. In some embodiments, AGPAT2 is encoded by a sequence of nucleotides that comprises the sequence of nucleotides set forth in SEQ ID NO: 37 or 38, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 37 or 38, and that encodes a functional protein, variant, or fragment thereof. In some embodiments, the AGPAT2-encoding nucleic acid molecule comprises a signal sequence. In some embodiments, AGPAT2 is a human protein. In some embodiments, AGPAT2 comprises a sequence or portion of a sequence set forth in UniProt accession number 015120, NCBI Reference Sequence: NP_006403.2, or NCBI Reference Sequence: NP_001012745.1, or is encoded by a sequence or coding portion of a sequence set forth in NCBI Reference Sequence: NM_006412.3 or NCBI Reference Sequence: NM_001012727.1.

In some embodiments, the molecule involved in the metabolic pathway is or comprises AGPAT3 or a functional fragment or functional variant thereof, such as a functional fragment or functional variant that is catalytically active and/or that exhibits an activity to modulate a metabolic pathway. In some embodiments, AGPAT3 comprises the sequence of amino acids set forth in SEQ ID NO: 16 or 17, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 16 or 17, or is a functional fragment thereof. In some embodiments, AGPAT3 lacks or does not contain a prodomain and/or is a mature or catalytically active protein. In some embodiments, AGPAT3 is encoded by a sequence of nucleotides that comprises the sequence of nucleotides set forth in SEQ ID NO: 39, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 39, and that encodes a functional protein, variant, or fragment thereof. In some embodiments, the AGPAT3-encoding nucleic acid molecule comprises a signal sequence. In some embodiments, AGPAT3 is a human protein. In some embodiments, AGPAT3 comprises a sequence or portion of a sequence set forth in NCBI Reference Sequence: NP_001012745.1, UniProt accession number Q9NRZ7, or NCBI Reference Sequence: NP_001032642.1, or is encoded by a sequence or coding portion of a sequence set forth in NCBI Reference Sequence: NM_006412.3.

In some embodiments, the molecule involved in the metabolic pathway is or comprises AGPAT6 (LPA-MAG PA) or a functional fragment or functional variant thereof, such as a functional fragment or functional variant that is catalytically active and/or that exhibits an activity to modulate a metabolic pathway. In some embodiments, AGPAT6 comprises the sequence of amino acids set forth in SEQ ID NO: 18, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 18, or is a functional fragment thereof. In some embodiments, AGPAT6 lacks or does not contain a prodomain and/or is a mature or catalytically active protein. In some embodiments, AGPAT6 is encoded by a sequence of nucleotides that comprises the sequence of nucleotides set forth in SEQ ID NO: 40, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 40, and that encodes a functional protein, variant, or fragment thereof. In some embodiments, the AGPAT6-encoding nucleic acid molecule comprises a signal sequence. In some embodiments, AGPAT6 is a human protein. In some embodiments, AGPAT6 comprises a sequence or portion of a sequence set forth in UniProt accession number Q86UL3, or is encoded by a sequence or coding portion of a sequence set forth in NCBI Reference Sequence: NM_178819.3.

In some embodiments, the molecule involved in the metabolic pathway is or comprises GPAT2 or a functional fragment or functional variant thereof, such as a functional fragment or functional variant that is catalytically active and/or that exhibits an activity to modulate a metabolic pathway. In some embodiments, GPAT2 comprises the sequence of amino acids set forth in SEQ ID NO: 19, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 19, or is a functional fragment thereof. In some embodiments, GPAT2 lacks or does not contain a prodomain and/or is a mature or catalytically active protein. In some embodiments, GPAT2 is encoded by a sequence of nucleotides that comprises the sequence of nucleotides set forth in SEQ ID NO: 41, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 41, and that encodes a functional protein, variant, or fragment thereof. In some embodiments, the GPAT2-encoding nucleic acid molecule comprises a signal sequence. In some embodiments, GPAT2 is a human protein. In some embodiments, GPAT2 comprises a sequence or portion of a sequence set forth in UniProt accession number Q86UL3, or is encoded by a sequence or coding portion of a sequence set forth in NCBI Reference Sequence: NM_178819.3.

In some embodiments, the molecule involved in the metabolic pathway is or comprises MOGAT2 or a functional fragment or functional variant thereof, such as a functional fragment or functional variant that is catalytically active and/or that exhibits an activity to modulate a metabolic pathway. In some embodiments, MOGAT2 comprises the sequence of amino acids set forth in SEQ ID NO: 20 or 21, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 20 or 21, or is a functional fragment thereof. In some embodiments, MOGAT2 lacks or does not contain a prodomain and/or is a mature or catalytically active protein. In some embodiments, MOGAT2 is encoded by a sequence of nucleotides that comprises the sequence of nucleotides set forth in SEQ ID NO: 42, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 42, and that encodes a functional protein, variant, or fragment thereof. In some embodiments, the MOGAT2-encoding nucleic acid molecule comprises a signal sequence. In some embodiments, MOGAT2 is a human protein. In some embodiments, MOGAT2 comprises a sequence or portion of a sequence set forth in UniProt accession number Q3SYC2 or GenBank: AA103879.1, or is encoded by a sequence or coding portion of a sequence set forth in NCBI Reference Sequence: NM_025098.2.

In some embodiments, the molecule involved in the metabolic pathway is or comprises DGAT2 or a functional fragment or functional variant thereof, such as a functional fragment or functional variant that is catalytically active and/or that exhibits an activity to modulate a metabolic pathway. In some embodiments, DGAT2 comprises the sequence of amino acids set forth in SEQ ID NO: 22, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 22, or is a functional fragment thereof. In some embodiments, DGAT2 lacks or does not contain a prodomain and/or is a mature or catalytically active protein. In some embodiments, DGAT2 is encoded by a sequence of nucleotides that comprises the sequence of nucleotides set forth in SEQ ID NO: 43, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 43, and that encodes a functional protein, variant, or fragment thereof. In some embodiments, the DGAT2-encoding nucleic acid molecule comprises a signal sequence. In some embodiments, DGAT2 is a human protein. In some embodiments, DGAT2 comprises a sequence or portion of a sequence set forth in UniProt accession number Q96PD7 or GenBank: AAQ88896.1, or is encoded by a sequence or coding portion of a sequence set forth in NCBI Reference Sequence: NM_032564.4.

In some embodiments, the molecule involved in the metabolic pathway is or comprises AQP9 or a functional fragment or functional variant thereof, such as a functional fragment or functional variant that is catalytically active and/or that exhibits an activity to modulate a metabolic pathway. In some embodiments, AQP9 comprises the sequence of amino acids set forth in SEQ ID NO: 23, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 23, or is a functional fragment thereof. In some embodiments, AQP9 lacks or does not contain a prodomain and/or is a mature or catalytically active protein. In some embodiments, AQP9 is encoded by a sequence of nucleotides that comprises the sequence of nucleotides set forth in SEQ ID NO: 44, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 44, and that encodes a functional protein, variant, or fragment thereof. In some embodiments, the AQP9-encoding nucleic acid molecule comprises a signal sequence. In some embodiments, AQP9 is a human protein. In some embodiments, AQP9 comprises a sequence or portion of a sequence set forth in UniProt accession number 043315 or GenBank: AAH26258.1, is encoded by a sequence or coding portion of a sequence set forth in NCBI Reference Sequence: NM_020980.3, or is described in Cui et al. Cell. 2015 May 7; 161(4):750-61.

In some embodiments, the molecule involved in the metabolic pathway is or comprises LPIN1 or a functional fragment or functional variant thereof, such as a functional fragment or functional variant that is catalytically active and/or that exhibits an activity to modulate a metabolic pathway. In some embodiments, LPIN1 comprises the sequence of amino acids set forth in SEQ ID NO: 24, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 24, or is a functional fragment thereof. In some embodiments, LPIN1 lacks or does not contain a prodomain and/or is a mature or catalytically active protein. In some embodiments, LPIN1 is encoded by a sequence of nucleotides that comprises the sequence of nucleotides set forth in SEQ ID NO: 45, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 45, and that encodes a functional protein, variant, or fragment thereof. In some embodiments, the LPIN1-encoding nucleic acid molecule comprises a signal sequence. In some embodiments, LPIN1 is a human protein. In some embodiments, LPIN1 comprises a sequence or portion of a sequence set forth in UniProt accession number 043315 or GenBank: AAH26258.1, or is encoded by a sequence or coding portion of a sequence set forth in NCBI Reference Sequence: NM_145693.2.

In some embodiments, the molecule involved in the metabolic pathway is or comprises CRIF1 or a functional fragment or functional variant thereof, such as a functional fragment or functional variant that is catalytically active and/or that exhibits an activity to modulate a metabolic pathway. In some embodiments, CRIF1 comprises the sequence of amino acids set forth in SEQ ID NO: 25, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 25, or is a functional fragment thereof. In some embodiments, CRIF1 lacks or does not contain a prodomain and/or is a mature or catalytically active protein. In some embodiments, CRIF1 is encoded by a sequence of nucleotides that comprises the sequence of nucleotides set forth in SEQ ID NO: 46, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 46, and that encodes a functional protein, variant, or fragment thereof. In some embodiments, the CRIF1-encoding nucleic acid molecule comprises a signal sequence. In some embodiments, CRIF1 is a human protein. In some embodiments, CRIF1 comprises a sequence or portion of a sequence set forth in UniProt accession number Q8TAE8, or is encoded by a sequence or coding portion of a sequence set forth in NCBI Reference Sequence: NM_052850.3.

In some embodiments, the molecule is selected from among huLEM, DGAT1, GYK, GPAM, HIF1α, MOGAT1 and PCK1, In some embodiments, the molecule comprises a sequence of amino acids set forth in any of SEQ ID NOS: 4, 7-10, 12 and 69, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 4, 7-10, 12 and 69, or is a functional fragment thereof. In some embodiments, the molecule is encoded by a sequence of nucleotides that comprises the sequence of nucleotides set forth in any of SEQ ID NOS: 70 and 76-81, or a sequence of nucleotides that exhibits at least 85%, 86%, 87%, 88%, 89%, 90%, 91%, 92%, 93%, 94%, 95%, 96%, 97%, 98%, 99% or more sequence identity to any of SEQ ID NOS: 70 and 76-81, and that encodes a functional protein, variant, or fragment thereof.

IV. Nucleic Acids and Engineered Cells

Provided are methods, nucleic acids, compositions, and kits for producing the genetically engineered cells. The genetic engineering generally involves introduction of a nucleic acid encoding the recombinant receptor into a composition containing the cultured cells, such as by retroviral transduction, transfection, or transformation.

Also provided are cells such as cells that contain an engineered recombinant receptor, such as described herein. Also provided are populations of such cells, compositions containing such cells and/or enriched for such cells, such as in which cells expressing the recombinant receptor make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the recombinant receptors e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

A. Preparation of Cells for Engineering

In some embodiments, preparation of the engineered cells includes one or more culture and/or preparation steps. The cells for introduction of the recombinant receptor, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher © Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

B. Nucleic Acids, Vectors and Methods for Genetic Engineering

Also provided are nucleic acids and vectors encoding the receptors and/or molecules of any of the provided embodiments, and combinations thereof, as well as cells and compositions containing the same. The vectors may be viral or non-viral, such as gammaretroviral, lentiviral, and/or use transposon-based systems such as Sleeping Beauty or PiggyBac systems. Various methods for the introduction of genetically engineered components, e.g., antigen receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation. Transfer of genetic material in the vectors may be achieved by a number of known methods, via transduction, transformation, electroporation, and/or any known method.

1. Nucleic Acids and Promoters

In some embodiments, a nucleic acid encodes a genetically engineered receptor that specifically binds to a ligand, such as a recombinant, e.g., chimeric, receptor, and a molecule involved in a metabolic pathway, or functional portion thereof. In some embodiments, the molecule involved in a metabolic pathway is a recombinant molecule, including an exogenous or heterologous molecule. In some embodiments, the molecule involved in a metabolic pathway is a protein, including a recombinant protein, including an exogenous or heterologous protein. In some embodiments, the genetically engineered receptor and the molecule involved in a metabolic pathway are encoded by one nucleic acid. In some embodiments, the genetically engineered receptor and the molecule involved in a metabolic pathway are encoded by two or more different nucleic acids. In some embodiments, a first nucleic acid encodes the genetically engineered receptor that specifically binds to a ligand and a second nucleic acid encodes the molecule involved in a metabolic pathway. In some embodiments, the nucleic acid or acids encoding the genetically engineered receptor that specifically binds to a ligand and the molecule involved in a metabolic pathway are expressed in the same or different vectors. The vectors can be any of the vectors described herein, including viral vectors and expression vectors.

In some embodiments, the nucleic acid is multicistronic, such as bicistronic or otherwise permits the coexpression of multiple, separate peptide chains, such as two or more, from the same promoter. The transcript in some embodiments has the potential to code for more than one final product, such as two final products. In some embodiments, at least one of the nucleic acids contains an internal ribosome binding site (IRES) separating the encoded molecules such that the genetically engineered receptor and the molecule involved in a metabolic pathway are expressed under the control of the same promoter. As used herein, an “internal ribosome entry site” (IRES) refers to a nucleotide sequence that allows for translation initiation in the middle of a messenger RNA (mRNA) sequence as part of protein synthesis. In some embodiments, the nucleic acid includes one or more ribosomal skip sequences, such as picornavirus 2A ribosomal skip peptide, so that the two or more peptide chains or other products may be expressed in operable linkage with the same promoter, but produced as separate chains.

In some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 68), equine rhinitis A virus (E2A, e.g., SEQ ID NO: 67), Thosea asigna virus (T2A, e.g., SEQ ID NO: 54 or 64), and porcine teschovirus-1 (P2A, e.g., SEQ ID NO: 65 or 66) as described in U.S. Patent Publication No. 20070116690.

In some embodiments, expression or activity of the genetically engineered or recombinant receptor and/or of the recombinant or engineered molecule involved in a metabolic pathway is constitutive; in some embodiments, one or more of such expression or activity is engineered to be conditional, for example, induced or repressed by one or more natural or non-natural events or molecules.

In some embodiments, the genetically engineered receptor and the molecule involved in a metabolic pathway are operably linked to the same promoter or other inducing or repressing element, such as one or more enhancer(s), and/or transactivator(s) or repressors or other sequences or molecules for control of expression, e.g., via control of transcription or translation. In other embodiments, they are operably linked to different promoters and/or such other elements, for example, such that expression thereof is controlled via different mechanisms or events.

In some embodiments, expression of the receptor and/or the molecule is under the control of a constitutive promoter, enhancer, or transactivator. In some embodiments, the expression is under the control of a conditional promoter, enhancer or transactivator. In some embodiments, expression of the genetically engineered receptor is under the control of a constitutive promoter and expression of the molecule involved in a metabolic pathway is under the control of a conditional promoter. In some embodiments, expression of the genetically engineered receptor is under the control of a conditional promoter and expression of the molecule involved in a metabolic pathway is under the control of a constitutive promoter.

In some embodiments, the expression is under the control of a conditional promoter, enhancer or transactivator. In some embodiments, the conditional promoter, enhancer or transactivator is an inducible promoter, enhancer or transactivator, a repressible promoter, enhancer or transactivator, or a tissue-specific promoter, enhancer or transactivator.

Exemplary tissue specific promoters include, but are not limited to, those that are active in heart, lung, esophagus, muscle, intestine, breast, prostate, stomach, bladder, liver, spleen, pancreas, kidney, neurons, myocytes, leukocytes, immortalized cells, neoplastic cells, tumor cells, cancer cells, duodenum, jejunum, ileum, cecum, colon, rectum, salivary glands, gall bladder, urinary bladder, trachea, larynx, pharynx, aorta, arteries capillaries, veins, thymus, mandibular lymph nodes, mesenteric lymph node, bone marrow, pituitary gland, thyroid gland, parathyroid glands, adrenal glands, brain, cerebrum, cerebellum, medulla, pons, spinal cord, sciatic nerve, skeletal muscle, smooth muscle, bone, testes, epididymis, prostate, seminal vesicles, penis, ovaries, uterus, mammary glands, vagina, skin, eyes or optic nerve.

Exemplary cell specific promoters include T cells, such as the CD4 mini-promoter/enhancer described in Zhao-Emonet, et al. (2000) *J. Gene. Med.,* 2: 416-425.

In some embodiments, the expression of the molecule or receptor, generally the molecule, is conditional upon (e.g., is induced or repressed by, such as via an inducible promoter or other element) by one or more specific conditions, events, or molecules found or found at relatively higher levels in particular, regions of the body, disease, activation state, or tissues. For example, the in some embodiments the promoter can be inducible or suppressible by hypoxia, glucose-poor or other nutrient-poor conditions, deficiencies in metabolites such as amino acids or nucleic acids or lipids, elements of the tumor microenvironment, or other elements of metabolic pathways or metabolites or levels thereof. See, e.g. Cao, et al. (2001) *Gene Ther.,* 8: 1357-1362 and Dachs, et al. (2000) *Eur. J. Cancer,* 36:1649-1660, and Greco et al., (2002) *Gene Ther.,* 9:1403-1411. In some embodiments, expression is conditioned upon activation signals or pathways, or signaling via a particular receptor, such as a cytokine or antigen receptor. In some embodiments, expression is regulated by activation or proliferative events. Exemplary inducible systems are those activatable by NFκB, NFAT or Nur77.

In some embodiments, expression of any of the peptides or nucleic acids described herein may be externally controlled by treating the cell with a modulating factor, such as doxycycline, tetracycline or analogues thereof. Analogues of tetracycline include, for example, chlortetracycline, oxytetracycline, demethylchloro-tetracycline, methacycline, doxycycline and minocycline.

In some embodiments, inducible transcription and/or expression can be implemented using a transactivator together with a transactivator induced promoter. In some embodiments, such a transactivator induced promoter comprises control elements for the enhancement or repression of transcription of the transgene or nucleic acid of interest. Control elements include, without limitation, operators, enhancers and promoters. In some embodiments, a transactivator inducible promoter is transcriptionally active when bound to a transactivator, which in turn is activated under a specific set of conditions, for example, in the presence or in the absence of a particular combination of chemical signals, for example, by a modulating factor selected for example from the previous list.

The transactivator induced promoter may be any promoter herein mentioned which has been modified to incorporate transactivator binding sequences, such as several tet-operator sequences, for example 3, 4, 5, 6, 7, 8, 9, or 10 tet-operator sequences. In some embodiments, the tet-operator sequences are in tandem. Such sequences can for example replace the functional recognition sites for Staf and Oct-1 in the distal sequence element (DSE) of the U6 promoter, including the human U6 promoter.

Specific examples of transcription modulator domains that induce expression in the presence of modulating factor include, but are not limited to, the transcription modulator domains found in the following transcription modulators: the Tet-On transcription modulator; and the Tet-On Advanced transcription modulator and the Tet-On 3G transcription modulator; all of which are available from Clontech Laboratories, Mountain View, Calif. Specific examples of transcription modulator domains that induce expression in the absence of modulating factor include, but are not limited to, the transcription modulator domains found in the following transcription modulators: the Tet-off transcription modulator and the Tet-Off Advanced transcription modulator, both of which are available from Clontech Laboratories, Mountain View, Calif. These systems can be adapted and used according to procedures that are well known in the art and that will be familiar to the ordinarily skilled artisan.

In some embodiments, the transactivator induced promoter comprises a plurality of transactivator binding sequences operatively linked to the inhibitory nucleic acid molecule.

The transactivator may be provided by a nucleic acid sequence, in the same expression vector or in a different expression vector, comprising a modulating factor-dependent promoter operatively linked to a sequence encoding the transactivator. The term "different expression vector" is intended to include any vehicle for delivery of a nucleic acid, for example, a virus, plasmid, cosmid or transposon. Suitable promoters for use in said nucleic acid sequence include, for example, constitutive, regulated, tissue-specific or ubiquitous promoters, which may be of cellular, viral or synthetic origin, such as CMV, RSV, PGK, EF1α, NSE, synapsin, β-actin, GFAP.

An exemplary transactivator according to some embodiments is the rtTA-Oct.2 transactivator composed of the DNA binding domain of rtTA2-M2 and of the Oct-2Q(Q→A) activation domain. Another exemplary transactivator according to some embodiments is the rtTA-Oct.3 transactivator composed of the DNA binding domain of the Tet-repressor protein (*E. coli*) and of the Oct-2Q(Q→A) activation domain. Both are described in patent application WO 2007/004062.

In some embodiments, the molecule involved in a metabolic pathway is an inhibitory nucleic acid that inhibits expression of a molecule involved in a metabolic pathway. In some embodiments, expression is reduced or eliminated using small-hairpin RNAs (shRNAs) that target nucleic acids encoding, molecule involved in a metabolic pathway. In some embodiments, shRNA and siRNA segments may further comprise stop and/or polyadenylation sequences. Suitable shRNA sequences for the knock down of a given target gene or nucleic acid sequence are well known in the art or can readily be determined by a person skilled in the art.

Expression of shRNAs in mammalian cells, such as T cells, can be achieved using any conventional expression system, e.g., a lentiviral expression system. In some embodiments, the RNA can be a component of a viral vector, or a shRNA encoded by a viral vector. In some embodiments, the viral vector comprises an oligonucleotide that inhibits expression of a molecule involved in a metabolic pathway, or encodes a shRNA having such capability. In some embodiments, the viral vector is a lentivirus vector. In some embodiments, the lentivirus vector is an integrating lentivirus vector.

In some embodiments, suitable promoters include, for example, RNA polymerase (pol) III promoters including, but not limited to, the (human and murine) U6 promoters, the (human and murine) H1 promoters, and the (human and murine) 7SK promoters, including conditional variants thereof. In some embodiments, a hybrid promoter also can be prepared that contains elements derived from, for example, distinct types of RNA polymerase (pol) III promoters. In some embodiments, modified promoters that contain sequence elements derived from two or more naturally occurring promoter sequences can be combined by the skilled person to effect transcription under a desired set of conditions or in a specific context. For example, the human and murine U6 RNA polymerase (pol) III and H1 RNA pol III promoters are well characterized. One skilled in the art will be able to select and/or modify the promoter that is most effective for the desired application and cell type so as to optimize modulation of the expression of one or more genes. In some embodiments, the promoter sequence can be one that does not occur in nature, so long as it functions in a eukaryotic cell, such as, for example, a mammalian cell.

2. Vectors and Introduction

Introduction of the molecules encoding the receptor and/or molecule involved with metabolism may be carried out using any of a number of known vectors. Such vectors include viral and non-viral systems, including lentiviral and gammaretroviral systems, as well as transposon-based systems such as PiggyBac or Sleeping Beauty-based gene transfer systems.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) Blood. 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990));

and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR) and/or a metabolic pathway-modulating molecule. This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, introduction of the receptor and/or molecule involved with metabolism into a population of cells are carried out separately, such as by co-transfection or transduction of a vector encoding each. Such introduction can be performed simulataneously or sequentially in any order. In some embodiments, the introduction of the receptor and/or molecule involved with metabolism into a population of cells are carried out together, such as by introduction of a vector encoding both the receptor and the molecule involved with metabolism.

In some embodiments, in the nucleic acid molecule is a single polynucleotide encoding a plurality of different polypeptide chains, such as the genetically engineered receptor and the molecule involved in a metabolic pathway. For example, in some embodiments, the polynucleotide contains at least one promoter operatively linked to control expression of the recombinant receptor and the metabolic pathway-modulating molecule. In some embodiments, the coding sequences encoding each of the different polypeptide chains can be operatively linked to a promoter, which can be the same or different. In some embodiments, the nucleic acid molecule can contain a promoter that drives the expression of the recombinant receptor and the metabolic pathway-modulating molecule. In some embodiments, such nucleic acid molecules can be multicistronic (bicistronic or tricistronic) For example, in some embodiments, the sequence of nucleotides encoding the genetically engineered receptor and the sequence of nucleotides encoding the metabolic pathway-modulating molecule are separated by an internal ribosome entry site (IRES), a self-cleaving peptide or a peptide that causes ribosome skipping, optionally a T2A, F2A, E2A or P2A peptide, e.g., any ribosome skipping peptides described herein, and the first and second chimeric receptor are expressed under the control of the same promoter. In some embodiments, two, three or more separate polypeptide chains can be encoded in one nucleic acid molecule, separated from one another by sequences encoding a self-cleavage peptide (e.g., 2A sequences) or a protease recognition site (e.g., furin). For example, in some embodiments, one nucleic acid molecule can encode multiple polypeptide chains: the genetically engineered receptor, the sequence of nucleotides encoding the metabolic pathway-modulating molecule and one or more surface markers. In some embodiments, the nucleotide sequences encoding the polypeptide chains can be operatively linked to one or more separate promoter, such as any of the promoters described herein, and/or can be separated by any IRES, self-cleaving peptide, ribosome skipping peptide and/or protease sites, such as any described herein.

In some embodiments, nucleic acid molecules encoding the recombinant receptor, e.g., CAR and/or the metabolic pathway-modulating molecules provided herein can be engineered using the same method or different methods. In some embodiments, the recombinant receptor, e.g., CAR and the metabolic pathway-modulating molecule provided herein can be introduced as two separate nucleic acid molecules. In some embodiments, one nucleic acid molecule, e.g., a viral vector, can contain nucleic acids encoding the recombinant receptor, e.g., CAR, and the metabolic pathway-modulating molecule. In some examples, the recombinant receptor and metabolic pathway-modulating molecule are encoded by one nucleic acid molecule, and are transcribed into one transcript, as described above. In other examples, the recombinant receptor and metabolic pathway-modulating molecule provided herein are encoded by one nucleic acid molecule, and are transcribed into two or more transcripts. In some embodiments, the recombinant receptor and metabolic pathway-modulating molecule are encoded by one nucleic acid molecule, and are transcribed into one transcript, which is translated into one polypeptide, then are separated, e.g., cleaved, in a post-translational manner.

In other embodiments, the recombinant receptor and metabolic pathway-modulating molecule are encoded by two or more different nucleic acid molecules, e.g., viral vectors. For example, recombinant receptor, e.g. CAR is encoded by one nucleic acid molecule, and the metabolic pathway-modulating molecule can be encoded by a separate nucleic acid molecule. In some embodiments, one or more of the nucleic acid molecules can further contain nucleotide sequences encoding a cell surface marker, e.g., any of those described herein, that can be used to confirm introduction of particular nucleic acid molecules into cells and/or transduction and/or engineering of cells.

In some embodiments, the recombinant receptor and metabolic pathway-modulating molecule are encoded by same types of vectors. In other embodiments, the recombinant receptor and metabolic pathway-modulating molecule are encoded by different types of vectors. In some embodiments, the recombinant receptor and metabolic pathway-modulating molecule are engineered into a cell using the same methods, e.g., viral transduction. In other embodiments, the recombinant receptor and metabolic pathway-modulating molecule are engineered into a cell using different methods.

3. Exemplary Constructs

Provided herein are expression vectors, such as viral vectors, e.g. lentiviral vectors encoding a metabolic pathway modulating molecule. In some embodiments, the vector comprises a nucleotide sequence encoding any of the metabolic pathway modulators as described in Section III. In some embodiments, the vector comprises a nucleotide sequence encoding a molecule selected from among huLEM, DGAT1, GYK, GPAM, HIF1α, MOGAT1 and PCK1. In some embodiments, the nucleotide sequence encodes a molecule comprising a sequence of amino acids set forth in any of SEQ ID NOS: 4, 7-10, 12 and 69, or a functional variant thereof comprising a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 4, 7-10, 12 and 69, or is a functional fragment thereof. In some embodiments, the nucleotide sequence comprises the sequence of nucleotides set forth in any of SEQ ID NOS: 70 and 76-81, or a sequence of nucleotides that exhibits at least 85%, 86%, 87%, 88%, 89%, 90%, 91%, 92%, 93%, 94%, 95%, 96%, 97%, 98%, 99% or more sequence identity to any of SEQ ID NOS: 70 and 76-81, and that encodes a functional protein, variant, or fragment thereof.

In some embodiments, such expression vectors can further encode a recombinant receptor, such as a CAR, e.g. any as described. In some embodiments, CAR contains a sequence of nucleotides encoding a genetically engineered receptor that specifically binds to a ligand, a marker, a transmembrane portion of a costimulatory receptor, a signal peptide, a activating domain (e.g. CD3 zeta), and a 2A element. Exemplary CD3 zeta sequences are set forth in SEQ ID NOs: 61-63. Exemplary signaling domain and/or transmembrane portion of a costimulatory receptor include CD28, 4-1BB, OX40, DAP10, ICOS, or CD27.

In some aspects, the nucleic acid molecule can be modified for use in the constructs described herein. In some cases, the sequences can be designed to contain terminal restriction site sequences for purposes of cloning into vectors. In some cases, the sequences can be modified by codon optimization. Codon optimization involves balancing the percentages of codons selected with the published abundance of human transfer RNAs so that none is overloaded or limiting. This may be necessary in some cases because most amino acids are encoded by more than one codon, and codon usage varies from organism to organism. Differences in codon usage between transfected genes and host cells can have effects on protein expression and immunogenicity of a nucleic acid construct. In general, for codon optimization, codons are chosen to select for those codons that are in balance with human usage frequency. Typically, the redundancy of the codons for amino acids is such that different codons code for one amino acid. In some embodiments, in selecting a codon for replacement, it may be desired that the resulting mutation is a silent mutation such that the codon change does not affect the amino acid sequence. Generally, the last nucleotide of the codon can remain unchanged without affecting the amino acid sequence.

In some embodiments, the nucleic acid(s) that encodes a genetically engineered receptor and/or and a molecule involved in a metabolic pathway, or functional portion thereof further comprises a marker, such as a cell surface marker, that can be used to confirm introduction of the nucleic acid(s) into the cell. Exemplary markers, such as a cell surface marker, which may be used to confirm transduction or engineering of the cell to express the receptor and/or the molecule involved in a metabolic pathway, include truncated and/or modified versions of a cell surface receptor, such as all or part (e.g., truncated form) of CD34, a NGFR, epidermal growth factor receptor (e.g., tEGFR), ErbB2/HER2/neu (e.g., modified Her2t) or a functional variant thereof. In some specific embodiments, exemplary markers include tEGFR (sequences set forth in SEQ ID NO:55 or 83) and modified Her2t (sequence set forth in SEQ ID NO:75 and encoded by the nucleic acid sequences set forth in SEQ ID NO:74). In some embodiments, the nucleic acid encoding the marker is operably linked to a polynucleotide encoding for a linker sequence, such as a cleavable linker sequence. For example, a marker, and optionally a linker sequence, can be any as disclosed in published patent application No. WO2014031687.

Exemplary markers include tEGFR sequences set forth in SEQ ID NO:55 or 83, and modified Her2t sequence set forth in SEQ ID NO:75 and encoded by the nucleic acid sequences set forth in SEQ ID NO:74, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NOs: 55, 83 or 75, or encoded by a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 74 and encodes a functional protein, variant, or fragment.

In some embodiments, a nucleic acids encoding one or more cell surface markers is operatively linked to a promoter, such as any described herein, to control expression of the cell surface marker. In some embodiments, a nucleic acids encoding one or more cell surface markers is linked to nucleic acids encoding the genetically engineered receptor and/or the molecule involved in a metabolic pathway, separated from one another by sequences encoding a ribosome-skipping peptide or a self-cleavage peptide, such as any described herein. Exemplary 2A elements include F2A, E2A, T2A, and P2A (set forth in SEQ ID NOs: 54 and 64-68).

In some cases, the sequence of nucleotides encoding the genetically engineered receptor, the recombinant, engineered or ectopically expressed molecule and/or the surface marker contains a signal sequence that encodes a signal peptide. In some aspects, the signal sequence may encode a signal peptide derived from the native cell surface molecule. In other aspects, the signal sequence may encode a heterologous or non-native signal peptide, such as the exemplary signal peptide of the GMCSFR alpha chain set forth in SEQ ID NO: 72 and encoded by the nucleotide sequence set forth in SEQ ID NO:73. In some cases, the nucleic acid sequence encoding the chimeric antigen receptor (CAR) and/or a cell surface marker contains a signal sequence that encodes a signal peptide. Non-limiting exemplary examples of signal peptides include, for example, the GMCSFR alpha chain signal peptide set forth in SEQ ID NO:72.

In some embodiments, exemplary provided nucleic acid molecule include those that encode an amino acid sequence selected from among: any of SEQ ID NO: 85, 87, 89, 91, 93, 95 and 97; and a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 85, 87, 89, 91, 93, 95 and 97. In some embodiments, the nucleic acid molecule contains the nucleotide sequence is selected from among: any of SEQ ID NO: 84, 86, 88, 90, 92, 94 and 96; and a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 84, 86, 88, 90, 92, 94 and 96 that encodes a functional protein, variant, or fragment thereof. In some embodiments, such nucleic acid molecules encoding a metabolic pathway molecule can be co-expressed in a cell with a recombinant receptor, e.g., CAR. In some embodiments, such nucleic acid molecules can further comprise a sequence encoding a recombinant receptor, e.g. CAR.

Also provided are vectors encoding any of the provided nucleic acid constructs. The vectors can include any as described above, including lentiviral vectors, e.g. retroviral or gammaretroviral vectors. Also provided are cells encoding any of the provided nucleic acid constructs. The cells include any of the cells as described above. In some embodiments, the cells are T cell, such as CD4+ or CD8+ T cells. In some embodiments, the T cells are primary T cells obtained from a subject.

V. Compositions, Formulations and Methods of Administration

Also provided are compositions containing the recombinant receptor, such as CAR or TCR, and compositions containing the engineered cells, including pharmaceutical compositions and formulations. Also provided are methods of using and uses of the compositions, such as in the treatment of diseases, conditions, and disorders in which the antigen is expressed, or in detection, diagnostic, and prognostic methods.

A. Compositions/Formulations

The term “pharmaceutical formulation” refers to a preparation which is in such form as to permit the biological activity of an active ingredient contained therein to be effective, and which contains no additional components which are unacceptably toxic to a subject to which the formulation would be administered.

A “pharmaceutically acceptable carrier” refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington’s Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

B. Methods of Administration

Provided are methods of administering the cells, populations, and compositions, and uses of such cells, populations, and compositions to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various time-points, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments. In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

VI. Exemplary Embodiments

Among the embodiments provided herein are:

1. An engineered immune cell, comprising:

(a) a genetically engineered receptor that specifically binds to a ligand; and (b) a recombinant, engineered and/or ectopically expressed molecule or a functional and/or catalytically-active portion or variant thereof, which recombinant molecule is involved in or capable of modulating a metabolic pathway.

2. The engineered immune cell of embodiment 1, wherein the recombinant molecule is capable of promoting said metabolic pathway or step or reaction thereof or a metabolic event, directly or indirectly.

3. The engineered immune cell of embodiment 1, wherein the recombinant molecule is capable of inhibiting said metabolic pathway.

4. The engineered immune cell of any of embodiments 1-3, wherein the recombinant molecule is or comprises an enzyme; and/or wherein the recombinant molecule is or comprises an adapter.

5. The engineered immune cell of any of embodiments 1-4, wherein the metabolic pathway or event comprises lipid metabolism;

wherein the metabolic pathway or event comprises oxidative phosphorylation (OXPHOS);

wherein the metabolic pathway or event comprises a reactive oxygen species (ROS)-induced signal, event or pathway; and/or wherein the metabolic pathway or event comprises glycolysis, wherein the metabolic pathway or event comprises mitochondrial biogenesis; and/or wherein the metabolic pathway or event comprises generation of energy or ATP in a process that occurs within the mitochondria or via mitochondrial proteins, or occurs independently of glucose, or occurs via a pathway other than glycolysis;

wherein the metabolic pathway or event comprises the generation of ATP in a glucose-low environment, in a nutrient-poor environment, in a hypoxic environment, wherein the molecule promotes a catabolic molecular profile, optionally in the engineered cell, as compared to a reference cell substantially similar to the engineered cell but not comprising the recombinant molecule; and/or wherein the molecule promotes an anabolic molecular profile, optionally in the engineered cell, as compared to a reference cell substantially similar to the engineered cell but not comprising the recombinant molecule.

6. The engineered immune cell of any of embodiments 1-5, wherein the metabolic pathway or event comprises glutaminolysis, TCA cycle, glucose metabolism, amino acid or nucleotide metabolism, or beta-oxidation.

7. The engineered immune cell of any of embodiments 1-6, wherein the molecule is involved in fatty acid synthesis, fatty acid storage and/or fatty acid uptake; and/or the metabolic pathway or event or reaction or step comprises fatty acid uptake, fatty acid synthesis (FAS), and/or fatty acid oxidation (FAO).

8. The engineered immune cell of embodiment 7, wherein the molecule promotes or enhances FAS or FAO.

9. The engineered immune cell of embodiment 7 or embodiment 8, wherein the metabolic pathway, event or step or reaction is or comprises triacylglyceride (TAG) synthesis, TAG storage, glycerol phosphate pathway, glycerophospholipid synthesis and/or glycerol uptake.

10. The engineered immune cell of any of embodiments 7-9, wherein the recombinant molecule is involved in and/or is capable of promoting glycerol transport, is or comprises a glycerol transporter, is a TAG synthase molecule, is or comprises a glycerol kinase, or is or comprises an acyltransferase.

11. The engineered immune cell of any of embodiments 1-10, wherein the molecule is or comprises a Glycerol kinase (GYK), a Glycerol-3-phosphate acetyltransferase mitochondrial (GPAT), a Monoacylglycerol O-acetyltransferase (MOGAT), a DAG O-acetyltransferase (DGAT), an acylglycerolphosphate acyltransferase (AGPAT), or a Lipin.

12. The engineered immune cell of embodiment 11, wherein the molecule is or comprises a GYK, a GPAT1, a MOGAT1, or a DGAT1.

13. The engineered immune cell of embodiment 11 or embodiment 12, wherein the molecule comprises an amino acid sequence selected from among:

(i) any of SEQ ID NO: 4, 7, 8 and 9; and (ii) a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 4, 7, 8 and 9.

14. The engineered immune cell of any of embodiments 11-13, wherein the molecule comprises an amino acid sequence encoded by a nucleotide sequence selected from among:

(i) any of SEQ ID NO: 76, 77, 78 and 80; and (ii) a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 76, 77, 78 and 80 that encodes a functional protein, variant, or fragment thereof.

15. The engineered immune cell of any of embodiments 1-14, wherein the molecule is or comprises a glycerol transporter or functional portion thereof.

16. The engineered immune cell of embodiment 15, wherein the molecule is or comprises an AQP9.

17. The engineered immune cell of any of embodiments 1-16, wherein the recombinant molecule is or comprises a palmitoyltransferase, which optionally is carnitine palmitoyltransferase (CPT), which optionally is CPTI.

18. The engineered immune cell of any of embodiments 1-17, wherein the metabolic pathway or event comprises oxidative phosphorylation (OXPHOS), generation or accumulation of reactive oxygen species (ROS), cellular respiration, spare respiratory capacity (SPC) and/or mitochondrial respiratory capacity.

19. The engineered immune cell of any of embodiments 1-18, wherein the recombinant molecule does not promote or enhance glycolysis;

wherein the recombinant molecule does not promote or enhance glycolysis in T cells;

wherein the recombinant molecule does not promote or enhance and/or does not promote or enhance glycolysis under conditions under which the molecule promotes or enhances FAS, FAO, OXPHOS, ROS accumulation or generation, cellular respiration, or respiratory capacity.

20. The engineered immune cell of any of embodiments 1-19, wherein the recombinant molecule is capable of binding to or interacting with an OXPHOS complex protein, is capable of binding to or interacting with a mitochondrial membrane protein, promotes, acts upstream of, or is required for, optionally in lymphocytes, optionally in a population of T cells, the translation and/or insertion of one or more OXPHOS proteins into a mitochondrial membrane.

21. The engineered immune cell of any of embodiments 1-20, wherein the recombinant molecule comprises a mitochondrial protein.

22. The engineered immune cell of any of embodiments 1-21, wherein the recombinant molecule is capable of interacting with or associating with, directly or indirectly, a CR6 interacting factor (CRIF), optionally CRIF1, a LEM or a 39S subunit, optionally MRPL23.

23. The engineered immune cell of any of embodiments 1-22, wherein the recombinant molecule is or comprises a lymphocyte enhancer molecule (LEM).

24. The engineered immune cell of embodiment 22 or embodiment 23, wherein the molecule comprises an amino acid sequence set forth in SEQ ID NO:69 or a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO:69.

25. The engineered immune cell of any of embodiments 22-24, wherein the molecule comprises an amino acid sequence encoded by a nucleotide sequence set forth in SEQ ID NO:70 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:70 that encodes a functional protein, variant, or fragment thereof.

26. The engineered immune cell of any of embodiments 1-25, wherein the recombinant molecule is or comprises CRIF, e.g., CRIF1 optionally, CRIF1.

27. The engineered immune cell of any of embodiments 1-26, wherein:

the recombinant molecule is capable of promoting or enhancing the metabolic pathway, reaction or step under conditions of hypoxia, low glucose, poor vascularization, and/or ROS;

the recombinant molecule is capable of promoting or enhancing the metabolic pathway, reaction or step in the engineered cell under conditions of hypoxia, low glucose, poor vascularization, and/or ROS, at a level increased as compared to a reference cell, substantially identical to the engineered cell but not comprising the molecule.

28. The engineered immune cell of any of embodiments 1-27, wherein the recombinant molecule is involved in or promotes a pathway resulting in the generation of energy or ATP, which optionally is independent of the presence of glucose or independent of glycolysis.

29. The engineered immune cell of any of embodiments 1-28, wherein the metabolic pathway, step, reaction, or event is or comprises a glycolysis pathway, a reaction thereof, and/or a reaction or pathway that metabolizes a metabolite of the glycolysis pathway, optionally under glucose-low, hypoxic, or nutrient-deprived conditions.

30. The engineered immune cell of any of embodiments 1-29, wherein the recombinant molecule is a molecule that is upregulated or activated in response to antigen-receptor signaling, IL-17-mediated signaling, IL-15-mediated signaling, TRAF-mediated signaling, TRAF6-mediated signaling, IL-7-mediated signaling, IL-21-mediated signaling, low-oxygen conditions, succinate, release of reactive oxygen species (ROS), mTOR-induced signaling, or a functional variant thereof, and/or is differentially expressed or activated under nutrient-rich versus nutrient-poor conditions, or under hypoxic vs. normoxic conditions, or in effector or vs naïve or central memory T cells and/or in exhausted vs non-exhausted T cells, and/or in terminally differentiated T cells vs. non-terminally differentiated T cells.

31. The engineered immune cell of any of embodiments 1-30, wherein the recombinant molecule comprises a hypoxia-induced factor (HIF).

32. The engineered immune cell of embodiment 31, wherein the recombinant molecule comprises a HIF1-alpha.

33. The engineered immune cell of embodiment 31 or embodiment 32, wherein the molecule comprises an amino acid sequence set forth in SEQ ID NO:10 or a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO:10.

34. The engineered immune cell of any of embodiments 31-33, wherein the molecule comprises an amino acid sequence encoded by a nucleotide sequence set forth in SEQ ID NO:79 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:79 that encodes a functional protein, variant, or fragment thereof.

35. The engineered immune cell of any of embodiments 1-34, wherein:

the recombinant molecule is capable of promoting generation of a glycolysis metabolite, which optionally is PEP, and/or the engineered cells exhibit increased generation of said glycolysis metabolite compared to reference cells substantially identical to the engineered cells but not expressing the recombinant molecule, under the same conditions.

36. The engineered immune cell of any of embodiments 1-35, wherein the recombinant molecule comprises a phosphoenolpyruvate carboxykinase 1 (PCK1).

37. The engineered immune cell of embodiment 35 or embodiment 36, wherein the molecule comprises an amino acid sequence set forth in SEQ ID NO:12 or a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to SEQ ID NO:12.

38. The engineered immune cell of any of embodiments 35-37, wherein the molecule comprises an amino acid sequence encoded by a nucleotide sequence set forth in SEQ ID NO:81 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:81 that encodes a functional protein, variant, or fragment thereof.

39. The engineered immune cell of any of embodiments 1-24, wherein the recombinant molecule is or interacts with GLUT4.

40. The engineered immune cell of any of embodiments 1-24, wherein the recombinant molecule is or interacts with SGK1.

41. The engineered cell of any of embodiments 1-40, wherein the molecule is capable of promoting said metabolic pathway, event, or step or reaction;

wherein the molecule is capable of inhibiting said metabolic pathway, event, or step or reaction;

wherein an outcome of the metabolic pathway, event, or step or reaction is enhanced in the engineered cell compared to a reference cell substantially identical to the engineered cell, but not expressing the recombinant molecule;

wherein the molecule is capable of inhibiting said metabolic pathway, event, or step or reaction; and/or wherein an outcome of the metabolic pathway, event, or step is inhibited or reduced in the engineered cell compared to a reference cell substantially identical to the engineered cell, but not expressing the recombinant molecule.

42. The engineered cell of any of embodiments 1-40, wherein the recombinant molecule is a nucleic acid or protein capable of interfering with expression, activity, or stability of a negative regulator of the metabolic pathway or event or step or reaction, or a molecule that stabilizes the expression or longevity of a molecule that promotes said pathway, event, step or reaction.

43. The engineered cell of embodiment 42, wherein the nucleic acid or protein is an RNAi, siRNA, or shRNA molecule.

44. The engineered immune cell of any of embodiments 1-43, further comprising a disruption in expression or function of an immune checkpoint molecule, wherein the disruption or expression thereby promotes activation, proliferation, expansion, or reduced exhaustion, of the immune cell and/or is capable of reducing generation of or longevity of memory T cells or central memory T cells.

45. The engineered immune cell of embodiment 44, wherein the checkpoint molecule comprises a PD-1, PD-L1, TIM3, CTLA4 or an adenosine receptor.

46. The engineered cell of any of embodiments 1-45, wherein persistence of the engineered cell and/or of reprograming in favor of memory T cell, central memory T cell, Tscm, and/or undifferentiated phenotype cells, and/or reduction in exhaustion phenotype, and/or reduction in regulatory T cells, is enhanced or increased in the cell as compared to a cell substantially the same as the engineered cell without the recombinant molecule, under the same conditions.

47. The engineered cell of embodiment 46, wherein the conditions comprise activation via an antigen receptor, a TCR, an ITAM-containing signaling molecule, cytokine signaling, TNFR signaling, and/or adoptive transfer to a subject containing cells expressing the ligand.

48. The engineered cell of any of embodiments 1-47, wherein the cell is a T cell.

49. The engineered cell of embodiment 48, wherein the T cell is a CD8+ T cell.

50. The engineered cell of embodiment 48, wherein the T cell is a CD4+ T cell.

51. The engineered cell of any of embodiments 1-47, wherein the cell is a natural killer (NK) cell.

52. The engineered cell of any of embodiments 1-47, wherein the cell is an iPS-derived cell.

53. The engineered cell of any of embodiments 1-52, wherein the genetically engineered receptor that specifically binds to a ligand is a functional non-T cell receptor.

54. The engineered cell of any of embodiments 1-53, wherein the genetically engineered receptor that specifically binds to a ligand is a chimeric antigen receptor (CAR).

55. The engineered cell of embodiment 54, wherein the CAR comprises an extracellular antigen-recognition domain that specifically binds to the antigen and an intracellular signaling domain comprising an ITAM.

56. The engineered cell of embodiment 55, wherein the intracellular signaling domain comprises an intracellular domain of a CD3-zeta (CD3ζ) chain.

57. The engineered cell of embodiment 55 or embodiment 56, wherein the CAR further comprises a costimulatory signaling region.

58. The engineered cell of embodiment 57, wherein the costimulatory signaling region comprises a signaling domain of CD28 or 4-1BB.

59. The engineered cell of embodiment 57 or embodiment 58, wherein the costimulatory domain is CD28.

60. The engineered cell of any of embodiments 1-52, wherein the genetically engineered receptor that specifically binds to a ligand is a recombinant receptor.

61. The engineered cell of any of embodiments 1-52, wherein the genetically engineered receptor that specifically binds to a ligand is a transgenic T cell receptor (TCR).

62. The engineered cell of any of embodiments 1-61, wherein expression of the molecule in the cell is under the control of a conditional promoter or enhancer or transactivator.

63. The engineered cell of embodiment 62, wherein the conditional promoter or enhancer or transactivator is an inducible promoter, enhancer, or transactivator or a repressible promoter, enhancer, or transactivator.

64. The engineered cell of embodiment 62 or embodiment 63, wherein the promoter is selected from among an RNA pol I, pol II or pol III promoter.

65. The engineered cell of embodiment 64, wherein the promoter is selected from: a pol III promoter that is a U6 or H1 promoter; or a pol II promoter that is a CMV, SV40 early region or adenovirus major late promoter.

66. The engineered cell of any of embodiments 62-65, wherein the promoter is an inducible promoter.

67. The engineered cell of embodiment 66, wherein the promoter comprises a Lac operator sequence, a tetracycline operator sequence, a galactose operator sequence or a doxycycline operator sequence, or is an analog thereof.

68. The engineered cell of any of embodiments 62-65, wherein the promoter is a repressible promoter.

69. The engineered cell of embodiment 68, wherein the promoter comprises a Lac repressor or a tetracycline repressor, or is an analog thereof.

70. The engineered immune cell of any of embodiments 1-69, further comprising a recombinant truncated cell surface receptor.

71. The engineered immune cell of embodiment 70, wherein the cell surface receptor is selected from among a modified and/or truncated form of EGFR (tEGFR), ErbB2/HER2/neu (Her2t), CD34 and/or NGFR.

72. The engineered immune cell of embodiment 70 or embodiment 71, wherein the cell surface receptor comprises an amino acid sequence selected from among:

(i) any of SEQ ID NO: 55, 74 and 83; and (ii) a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 55, 74 and 83.

73. The engineered immune cell of any of embodiments 70-72, wherein the cell surface marker comprises an amino acid sequence encoded by a nucleotide sequence set forth in SEQ ID NO:74 or a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:74 that encodes a functional protein, variant, or fragment thereof.

74. A nucleic acid molecule, comprising the nucleotide sequence set forth in any of SEQ ID NOS: 85, 87, 89, 91, 93, 95 and 97 or a sequence of nucleotides that has at least 85%, 86%, 87%, 88%, 89%, 90%, 91%, 92%, 93%, 94%, 95%, 96%, 97%, 98%, 99% or more sequence identity to 85, 87, 89, 91, 93, 95 and 97 that encodes a functional protein, variant, or fragment thereof.

75. A nucleic acid molecule(s), comprising:

a nucleotide sequence encoding a genetically engineered receptor that specifically binds to a ligand; and a nucleotide sequence encoding a molecule that is involved in or capable of modulating a metabolic pathway or a functional and/or catalytically-active portion or variant thereof.

76. The nucleic acid molecule of embodiment 75, wherein the encoded genetically engineered receptor and encoded molecule involved in or capable of modulating a metabolic pathway are any as present in cells as forth in embodiments 1-58.

77. The nucleic acid molecule of embodiment 75 or embodiment 76 that is a single polynucleotide.

78. The nucleic acid molecule of any of embodiments 75-77, further comprising at least one promoter operatively linked to control expression of the genetically engineered receptor and the molecule involved in or capable of modulating a metabolic pathway.

79. The nucleic acid molecule of any of embodiments 75-78, wherein the nucleotide sequence encoding the genetically engineered receptor is operatively linked to a first promoter and the nucleotide sequence encoding the molecule involved in or capable of modulating a metabolic pathway is operatively linked to a second promoter, which first and second promoter can be the same or different.

80. The nucleic acid molecule of embodiment 78 or embodiment 79, wherein the nucleotide sequence encoding the genetically engineered receptor and the nucleotide sequence encoding the molecule involved in or capable of modulating a metabolic pathway are separated by an internal ribosome entry site (IRES), a self-cleaving peptide or a peptide that causes ribosome skipping, optionally a T2A, P2A, E2A and/or F2A peptide, and the first and second chimeric receptor are expressed under the control of the same promoter.

81. The nucleic acid molecule of embodiment 80, wherein the peptide that causes ribosome skipping comprises an amino acid sequence selected from among:

(i) any of SEQ ID NO: 54 and 64-68; and (ii) a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 54 and 64-68.

82. The nucleic acid molecule of embodiment 80 or embodiment 81, wherein nucleotide sequence encoding the peptide that causes ribosome skipping is selected from among a nucleotide sequence set forth in SEQ ID NO:71 and a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:71 that encodes a functional protein, variant, or fragment thereof.

83. The nucleic acid molecule of any of embodiments 75-82, wherein the encoded molecule that is involved in or capable of modulating a metabolic pathway comprises an amino acid sequence selected from among:

(i) any of SEQ ID NO: 4, 7-10, 12 and 69; and (ii) a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 4, 7-10, 12 and 69.

84. The nucleic acid molecule of any of embodiments 75-83, wherein the nucleotide sequence encoding the molecule that is involved in or capable of modulating a metabolic pathway is selected from among:

(i) any of SEQ ID NO: 70 and 76-81; and (ii) a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 70 and 76-81 that encodes a functional protein, variant, or fragment thereof.

85. The nucleic acid molecule of any of embodiments 75-84, further comprising a nucleotide sequence encoding a recombinant truncated cell surface receptor.

86. The nucleic acid molecule of embodiment 85, wherein the cell surface receptor is selected from among a modified and/or truncated form of EGFR (tEGFR), ErbB2/HER2/neu (Her2t), CD34 and/or NGFR.

87. The nucleic acid molecule of embodiment 85 or embodiment 86, wherein the cell surface receptor comprises an amino acid sequence selected from among:

(i) any of SEQ ID NO: 55, 74 and 83; and (ii) a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 55, 74 and 83.

88. The nucleic acid molecule of any of embodiments 85-87, wherein the nucleotide sequence encoding the cell surface receptor is set forth in SEQ ID NO:74 or is a nucleotide sequence that exhibits at least 85%, 86%, 87%, 88%, 89%, 90%, 91%, 92%, 93%, 94%, 95%, 96%, 97%, 98%, 99% or more sequence identity to SEQ ID NO:74 that encodes a functional protein, variant, or fragment thereof.

89. The nucleic acid molecule of any of embodiments 75-88, wherein the nucleotide sequence encodes an amino acid sequence selected from among:

(i) any of SEQ ID NO: 85, 87, 89, 91, 93, 95 and 97; and (ii) a functional variant comprising an amino acid sequence that exhibits at least 85%, 86%, 87%, 88%, 89%, 90%, 91%, 92%, 93%, 94%, 95%, 96%, 97%, 98%, 99% or more sequence identity to any of SEQ ID NO: 85, 87, 89, 91, 93, 95 and 97.

90. The nucleic acid molecule of any of embodiments 75-89, wherein the nucleotide sequence is selected from among:

(i) any of SEQ ID NO: 84, 86, 88, 90, 92, 94 and 96; and (ii) a nucleotide sequence that exhibits at least 85%, 86%, 87%, 88%, 89%, 90%, 91%, 92%, 93%, 94%, 95%, 96%, 97%, 98%, 99% or more sequence identity to any of SEQ ID NO: 84, 86, 88, 90, 92, 94 and 96 that encodes a functional protein, variant, or fragment thereof.

91. A vector, comprising the nucleic acid molecule of any of embodiments 74-90.

92. The vector of embodiment 91 that is a viral vector.

93. The vector of embodiment 91 or embodiment 92 that is a retroviral vector.

94. The vector of any of embodiments 91-93 that is a lentiviral vector or a gammaretroviral vector.

95. An engineered cell, comprising the nucleic acid molecules(s) of any of embodiments 74-90 or the vector of any of embodiments 91-94.

96. The engineered cell of embodiment 95, wherein the cell is a T cell.

97. The engineered cell of embodiment 96, wherein the T cell is a CD8+ T cell.

98. The engineered cell of embodiment 96, wherein the T cell is a CD4+ T cell.

99. The engineered cell of embodiment 95, wherein the cell is a natural killer (NK) cell.

100. The engineered cell of embodiment 95, wherein the cell is an iPS-derived cell.

101. The engineered cell of any of embodiments 95-98, wherein the genetically engineered receptor that specifically binds to a ligand is a functional non-T cell receptor.

102. The engineered cell of any of embodiments 95-99, wherein the genetically engineered receptor that specifically binds to a ligand is a chimeric antigen receptor (CAR).

103. The engineered cell of embodiment 102, wherein the CAR comprises an extracellular antigen-recognition domain that specifically binds to the antigen and an intracellular signaling domain comprising an ITAM.

104. The engineered cell of embodiment 103, wherein the intracellular signaling domain comprises an intracellular domain of a CD3-zeta (CD3ζ) chain.

105. The engineered cell of embodiment 103 or embodiment 104, wherein the CAR further comprises a costimulatory signaling region.

106. The engineered cell of embodiment 105, wherein the costimulatory signaling region comprises a signaling domain of CD28 or 4-1BB.

107. The engineered cell of embodiment 105 or embodiment 106, wherein the costimulatory domain is CD28.

108. The engineered cell of any of embodiments 95-107, wherein the genetically engineered receptor that specifically binds to a ligand is a recombinant receptor.

109. The engineered cell of any of embodiments 95-108, wherein the genetically engineered receptor that specifically binds to a ligand is a transgenic T cell receptor (TCR).

110. The engineered cell of any of embodiments 1-73 and 95-109, wherein the recombinant molecule is inducible upon activation, stress, hypoxia, decreased vasculature, alterations in tumor microenvironment, checkpoint molecule upregulation, proliferation, expression of an activation marker, or exposure to low glucose conditions.

111. A composition comprising the engineered cell of any of embodiments 1-73 and 95-110.

112. The composition of embodiment 111, wherein the cells are CD4+ or CD8+ cells.

113. The composition of embodiment 112, wherein the cells are CD4+ cells and the composition further comprises CD8+ cells that are genetically engineered with the ligand-binding receptor but do not express the recombinant molecule.

114. The composition of embodiment 112, wherein the cells are CD4+ cells and the composition further comprises CD8+ cells that are genetically engineered with the ligand-binding receptor and express the recombinant molecule.

115. The composition of embodiment 112, wherein the cells are CD8+ cells and the composition further comprises CD4+ cells that are genetically engineered with the ligand-binding receptor but do not express the recombinant molecule.

116. The composition of embodiment 112, wherein the cells are CD8+ cells and the composition further comprises CD4+ cells that are genetically engineered with the ligand-binding receptor and express the recombinant molecule.

117. The composition of any of embodiments 112-116, wherein the CD4+ cells express a different ligand-binding receptor than the CD8+ cells.

118. The composition of embodiment 117, wherein the only difference in the ligand-binding receptor expressed in the CD4+ cell compared to the CD8+ cell is the different costimulatory signaling domain.

119. The composition of embodiment 118, wherein the different costimulatory signaling domain is or comprises a cytoplasmic signaling domain of a CD28, a 4-1BB, or an ICOS molecule, or is a functional variant of a signaling portion thereof.

120. A method of treatment, comprising administering the engineered cell of any of embodiments 1-73 and 95-110 or the composition of any of embodiments 111-119 to a subject having a disease or condition.

121. The method of embodiment 120, wherein the ligand-binding receptor specifically binds to a ligand or antigen associated with the disease or condition.

122. The method of embodiment 120 or embodiment 121, wherein the disease or condition is a cancer, a tumor, an autoimmune disease or disorder, or an infectious disease.

123. The method of any of embodiments 120-122, wherein the engineered cells exhibit increased or longer expansion and/or persistence in the subject than in a subject administered the same or about the same dosage amount of a reference cell composition.

124. The method of any of embodiments 120-123, wherein there is an increase or greater number of memory T cells or a memory T cell subset and/or an increased or longer persistence of memory T cells or a memory T cell subset in the subject derived from the administered the engineered cells compared to the number or persistence of the memory T cells or memory T cell subset in a subject derived from a reference cell composition administered at the same or about the same dosage.

125. The method of embodiment 124, wherein the memory T cells or memory T cell subset are CD62L+.

126. The method of embodiment 124 or embodiment 125, wherein the memory T cells or memory T cell subset are central memory T cells (Tcm), long-lived memory T cells or T memory stem cells (Tscm).

127. The method of any of embodiments 124-126, wherein the memory T cells or memory T cell subset further comprises a phenotype comprising:

a) CD127+; and/or b) any one or more of CD45RA+, CD45RO−, CCR7+ and CD27+ and any one or more of t-bet$^{low}$, IL-7Ra+, CD95+, IL-2Rβ+, CXCR3+ and LFA-1+.

128. The method of any of embodiments 120-127, wherein the memory T cells or memory T cell subset are CD8+.

129. The method of any of embodiments 120-128, wherein the number of memory T cells or a memory T cell subset derived from the administered genetically engineered cells comprises an increase or greater percentage of central memory T cells (Tcm), long-lived memory T cells or T memory stem cells (Tscm) compared to the number of such cells derived from a reference cell composition administered at the same or about the same dosage.

130. The method of any of embodiments 120-129, wherein there is an increase or greater number of non-terminally differentiated T cells in the subject derived from the administered genetically engineered T cells compared to the number of the non-terminally differentiated cells in a subject derived from a reference cell composition administered at the same or about the same dosage amount.

131. The method of any of embodiments 120-130, wherein the genetically engineered cells in the subject derived from the administered genetically engineered cells exhibit an increase in activation or proliferation upon restimulation ex vivo in the presence of a stimulatory agent or agent compared to the activation or proliferation of genetically engineered cells in a subject derived from a reference cell composition administered at the same or about the same dosage when restimulated ex vivo in the presence of the same stimulatory agent or agents.

132. The method of embodiment 131, wherein the stimulatory agent or agents comprise an antigen, an anti-CD3/anti-CD28 antibody or comprises an IL-2, IL-15 and/or IL-7 cytokine.

133. The method of any of embodiments 123-132, wherein the increase is at least 1.2-fold, 1.5-fold, 2-fold, 3-fold, 4-fold, or 5-fold.

134. The method of any of embodiments 120-133, wherein there is a decreased or reduced expression of an exhaustion marker genetically engineered cells in the subject derived from the administered genetically engineered T cells compared to the expression of the exhaustion marker in genetically engineered cells in a subject administered the same or about the same dosage amount of a reference cell composition.

135. The method of embodiment 134, wherein the exhaustion marker is selected from among CD244, CD160 and PD-1.

136. The method of embodiment 134 or embodiment 135, wherein the expression is decreased or reduced 1.2-fold, 1.5-fold, 2.0-fold, 3-fold, 4-fold, 5-fold, 6-fold, 7-fold, 8-fold, 9-fold, 10-fold or more.

137. The method of any of embodiments 120-136, wherein the increase or decrease is observed or is present within a month, within two months, within six months or within one year of administering the cells.

138. The composition of any of embodiments 111-119 or the method of any of embodiments 120-137, wherein the reference cell composition contains genetically engineered cells that are substantially the same except the expressed chimeric receptor comprises a different costimulatory molecule and/or comprises a costimulatory domain of CD28, 4-1BB or ICOS.

139. A composition of any of embodiments 111-119 for use in treating a disease or condition in a subject having a disease or condition.

140. Use of a composition of any of embodiments 111-119 for treating a disease or condition in a subject having a disease or condition.

141. Use of a composition of any of embodiments 111-119 for the manufacture of a medicament for treating a disease or condition in a subject having a disease or condition.

142. The composition for use of embodiment 139 or the use of embodiment 140 or embodiment 141, wherein the ligand-binding receptor specifically binds to a ligand or antigen associated with the disease or condition.

143. The composition for use of embodiment 139 or the use of embodiment 140 or embodiment 141 or the composition for use or the use of embodiment 142, wherein the disease or condition is a cancer, a tumor, an autoimmune disease or disorder, or an infectious disease.

VII. Definitions

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

As used herein, a subject includes any living organism, such as humans and other mammals. Mammals include, but are not limited to, humans, and non-human animals, including farm animals, sport animals, rodents and pets.

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, "operably linked" or "operatively linked" refers to the association of components, such as a DNA sequence, e.g. a heterologous nucleic acid and a regulatory sequence(s), in such a way as to permit gene expression when the appropriate molecules (e.g. transcriptional activator proteins) are bound to the regulatory sequence. Hence, it means that the components described are in a relationship permitting them to function in their intended manner and/or in which there is a functional linkage of at least two sequences. For example, operably linked includes linkage between a promoter and a second sequence, wherein the promoter sequence initiates and mediates transcription of the DNA sequence corresponding to the second sequence. Operably associated includes linkage between an inducing or repressing element and a promoter, wherein the inducing or repressing element acts as a transcriptional activator of the promoter.

As used herein, "percent (%) sequence identity" and "percent identity" when used with respect to a nucleotide sequence (reference nucleotide sequence) or amino acid sequence (reference amino acid sequence) is defined as the percentage of nucleotide residues or amino acid residues, respectively, in a candidate sequence that are identical with the residues in the reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as lentiviral vectors.

VIII. Examples

The following examples are included for illustrative purposes only and are not intended to limit the scope of the invention.

Example 1: Generation of Nucleic Acid Constructs Encoding Metabolic Pathway-Modulating Molecules Various exemplary nucleic acid molecule constructs were generated encoding a metabolic pathway-modulating molecule that included either: (1) nucleotides set forth in SEQ ID NO:70 encoding lymphocyte expansion molecule (LEM) isoform 2 set forth in SEQ ID NO:69; (2) nucleotides set forth in SEQ ID NO: 76 encoding DAG O-acetyltransferase 1 (DGAT1) set forth in SEQ ID NO:7; (3) nucleotides set forth in SEQ ID NO: 77 encoding Glycerol kinase (Gyk) set forth in SEQ ID NO: 4; (4) nucleotides set forth in SEQ ID NO: 78 encoding Glycerol-3-phosphate acetyltransferase mitochondrial (GPAM) set forth in SEQ ID NO:8; (5) nucleotides set forth in SEQ ID NO: 79 encoding HIF1α set forth in SEQ ID NO: 10; (6) nucleotides set forth in SEQ ID NO: 80 encoding MOGAT1 set forth in SEQ ID NO:9; (7) nucleotides set forth in SEQ ID NO: 81 encoding PCK1 set forth in SEQ ID NO: 12.

Each nucleic acid construct also included a nucleic acid molecule encoding a truncated Her2 (Her2t, SEQ ID NO: 75, nucleotides set forth in SEQ ID NO: 74) for use as a transduction marker separated from the nucleic acid molecule encoding the metabolic pathway-modulating molecule by a self-cleaving T2A peptide (SEQ ID NO: 54, nucleotides set forth in SEQ ID NO: 71). The nucleic acid molecule was also designed to encode an N-terminal signal sequence derived from GMCSFR (SEQ ID NO: 72, nucleotides set forth in SEQ ID NO: 73).

Nucleic acid sequences of exemplary constructs are set forth in SEQ ID NOS: 84, 86, 88, 90, 92, 94 and 96 and encode the sequences set forth in SEQ ID NOS: 85, 87, 89, 91, 93, 95 and 97, respectively. The nucleic acid molecules were cloned into a lentiviral vector for transduction of primary T cells.

Example 2: Assessment of Proliferation, Anti-Tumor Efficacy, and Expansion of Engineered T Cells Co-Expressing a CAR and a Metabolic Pathway-Modulating Molecule T cells are isolated by immunoaffinity-based enrichment from human donor subjects and cells from each donor are activated and co-transduced with a lentiviral vector encoding a chimeric antigen receptor (CAR) and a lentiviral vector encoding a metabolic pathway-modulating molecule as described in Example 1. An exemplary CAR contains an anti-CD19 scFv, an Ig-derived spacer, a human CD28-derived transmembrane domain, a human 4-1BB-derived intracellular signaling domain and a human CD3 zeta-derived signaling domain. An alternative exemplary CAR may be substantially similar to the aforementioned CAR, but may comprise a human CD28-derived intracellular signaling domain. As a control, T cells also were generated by transduction with the CAR only, with the metabolic pathway-modulating molecule only or with an empty vector.

The genetically engineered T cells, including CAR-expressing cells and/or cells ectopically expressing a metabolic pathway-modulating molecule, produced as described above, are assessed for various responses following co-culture with CD19-expressing cells. In vitro assays to assess CAR-T cell activity were conducted using K562 cells transduced with CD19 (K562-CD19) as target cells.

To assess cell expansion and proliferation K562-CD19 target cells are incubated with the various genetically engineered T cells (at various effector:target ratios). The fold change in total number of cells at Day 0 prior to stimulation compared to Day 5 post-stimulation is determined for T cells co-expressing a CAR and a metabolic pathway-modulating molecule and compared to the fold change of T cells expressing only the CAR. In some cases, proliferation of the various genetically engineered cells following incubation with CD19-expressing target cells is assessed by flow cytometry. Genetically engineered T cells are labeled with 0.2 μM carboxyfluorescein succinmidyl ester (CFSE). Cells are washed and incubated for 72 hours in triplicate with target cells (K562-CD19) in serum-containing medium without exogenous cytokines. Division of live T cells is indicated by CFSE dilution, as assessed by flow cytometry.

To assess T cell killing activity, CD19-expressing K562-CD19 target cells are co-cultured with the various genetically engineered T cells at various E:T ratios (e.g. from 1:1 to 9:1). Cell lysis is monitored in real-time over a 0 to about 110-hour time course by adding an IncuCyte™ fluorescent Caspase 3/7 Reagent to the co-cultures to detect apoptotic cells. Target cell death is quantitated by automated image analysis over time. The area under the curve (AUC) of fluorescent signal over time for each concentration is determined and a killing index is determined using the formula: 1/AUC. The cell killing achieved with T cells expressing both a CAR and a metabolic pathway-modulating molecule is compared with control T cells.

Cytokine release is assessed from supernatants following incubation of the various genetically engineered cells with antigen-expressing K562-CD19 target cells at various E:T ratios (e.g. from 1:1 to 9:1). The presence of cytokines, such as TNF-α, IFNγ, GM-CSF and IL-2, in culture supernatants is assessed using an ELISA or other immunoassay method. The concentration of various cytokines in the supernatants from co-cultures incubated with T cells expressing both a CAR and a metabolic pathway-modulating molecule is compared with control T cells.

The ability of cells to expand ex vivo following repeated stimulations in some aspects can indicate capacity of CAR-T cells to persist (e.g. following initial activation) and/or is indicative of function in vivo (Zhao et al. (2015) Cancer Cell, 28:415-28). To assess expansion following restimulation in a serial stimulation assay, CAR-T cells are plated on 96 well Poly-D-Lysine coated plates to which irradiated target cells (K562-CD19) are added at various effector to target ratios (e.g. from 1:1 to 9:1). Cells are stimulated, harvested every 3-4 days and counted, and restimulated with new target cells using the same culture conditions after resetting cell number to initial seeding density for each round. Multiple rounds of stimulation during a 14 to 28 day culture period are carried out. For each round of stimulation, the number of doublings of the cell population is determined for T cells expressing both a CAR and a metabolic pathway-modulating molecule and compared to control T cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | MRESQDAAGAHGWNRVGSTATKWFTGAPFGVQSHREDISAVYPNWKKFSTFTEAP<br>YSTRYSTQVSHIGPGTYSSKETCFSKKKLMKEVDTGWAKAQEATRLTQLPHFQYQ<br>AIMKEKRLKEQKLGPGSYNLKDFLEQLREKPCSTRGLLSSGEVRFRGLTGNYYPG<br>PGNYGEKGNPYTKLEENAWNRSHSEGLMCRMSNKPHPRPHQGSGLGPGTYFEKSD<br>LETYVARSVGTRGPYDTFSGDRSKPLPYGHYSMQKKKPRELMNEKSFVEELNSHH<br>NKKHGVESKLPRNPKTPTERIYWANLSQCPRTLATSGPSEWLPQEKKCKPVNQPP<br>FLLTSKGSGAKACQMIMGSWNPVGVGRYLNTWLMETKDRRQRYRSLELSGSKRYL<br>SDLARDMLMQIRLFCWKGLEVINFGLSPM | C1ORF177 isoform 1(huLEM)<br>*Homo sapiens*<br>NCCBI Reference Sequence:<br>NP_689820.2 |
| 2 | MRESQDAAGAHGWNRVGSTATKWFTGAPFGVQSHREDISAVYPNWKKFSTFTEAP<br>YSTRYSTQVSHIGPGTYSSKETCFSKKKLMKEVDTGWAKAQEATRLTQLPHFQYQ<br>AIMKEKRLKEQKLGPGSYNLKDFLEQLREKPCSTRGLLSSGEVRFRGLTGNYYPG<br>PGNYGEKGNPYTKLEENAWNRSHSEGLMCRMSNKPHPRPYQGSGLGPGTYFEKSD<br>LETYVARSVGTRGPYDTFSGDRSKPLPYGHYSMQKKKPRELMNEKSFVEELNSHH<br>NKKHGVESKLPRNPKTPTERIYWANLSQCPRTLATSGPSEWLPQEKKCKPVNQPP<br>FLLTSKGSGAKACQMIMGSWNPVGVGRYLNTWLMETKDRRQRYRSLELSGSKRYL<br>SDLARDMLMQERITPFTKGKCPPTVDYNSDPTP | C1ORF177<br>isoform2 (huLEM)<br>*Homo sapiens*<br>UniProt accession<br>number Q3ZCV2 |
| 3 | MRESQDAAGAHGWNRVGSTATKWFTGAPFGVQSHREDISAVYPNWKKFSTFTEAP<br>YSTRYSTQVSHIGPGTYSSKETCFSKKKLMKEVDTGWAKAQEATRLTQLPHFQYQ<br>AIMKEKRLKEQKLGPGSYNLKDFLEQLREKPCSTRGLLSSGEVRFRGLTGNYYPG<br>PGNYGEKGNPYTKLEENAWNRSHSEGLMCRMSNKPHPRPHQGSGLGPGTYFEKSD<br>LETYVARSVGTRGPYDTFSGDRSKPLPYGHYSMQKKKPRELMNEKSFVEELNSHH<br>NKKHGVESKLPRNPKTPTERIYWANLSQCPRTLATSGPSEWLPQEKKCKPVNQPP<br>FLLTSKGSGAKACQMIMGSWNPVGVGRYLNTWLMETKDRRQRYRSLELSGSKRYL<br>SDLARDMLMQ | C1ORF177 isoform 1(huLEM)<br>*Homo sapiens* |
| 4 | MAASKKAVLGPLVGAVDQGTSSTRELVENSKTAELLSHHQVEIKQEFPREGWVEQ<br>DPKEILHSVYECIEKTCEKLGQLNIDISNIKAIGVSNQRETTVVWDKITGEPLYN<br>AVVWLDLRTQSTVESLSKRIPGNNNEVKSKTGLPLSTYFSAVKLRWLLDNVRKVQ<br>KAVEEKRALFGTIDSWLIWSLTGGVNGGVHCTDVTNASRTMLFNIHSLEWDKQLC<br>EFFGIPMEILPNVRSSSEIYGLMKISHSVKAGALEGVPISGCLGDQSAALVGQMC<br>FQIGQAKNTYGTGCELLCNTGHKCVESDHGLLTTVAYKLGRDKPVYYALEGSVAI | Glycerol kinase<br>(Gyk)<br>*Homo sapiens*<br>UniProt accession<br>number Q14410 |

-continued

SEQUENCES

| SEQ ID NO. | SEQUENCE | DESCRIPTION |
|---|---|---|
| | AGAVIRWLRDNLGIIKTSEEIEKLAKEVGTSYGCYFVPAFSGLYAPYWEPSARGI<br>ICGLTQFTNKCHIAFAALEAVCFQTREILDAMNRDCGIPLSHLQVDGGMTSNKIL<br>MQLQADILYIPVVKPSMPETTALGAAMAAGAAEGVGVWSLEPEDLSAVTMERFEP<br>QINAEESEIRYSTWKKAVMKSMGWVTTQSPESGDPSIFCSLPLGFFIVSSMVMLI<br>GARYISGIP | |
| 5 | MAAPKTAAVGPLVGAVVQGTNSTRELVENSKTAELLSHHKVELTQEFPKEGWVEQ<br>DPKEILQSVYECIARTCEKLDELNIDISNIKAVGVSNQRETTVIWDKLTGEPLYN<br>AVVWLDLRTQTTVEDLSKKIPGNSNEVKSKTGLPLSTYFSAVKLRWMLDNVRNVQ<br>KAVEEGRALFGTIDSWLIWSLTGGVNGGVHCTDVTNASRTMLFNIHSLEWDKELC<br>DFFEIPMDLLPNVFSSSEIYGLIKTGALEGVPISGCLGDQCAALVGQMCFQEGQA<br>KNTYGTGCELLCNTGRKCVESEHGLLTTVAYKLGREKPAYYALEGSVAIAGAVIR<br>WLRDNLGIIETSGDIERLAKEVGTSYGCYFVPAFSGLYAPYWEPSARGILCGLTQ<br>FTNKCHIAFAALEAVCFQTREILEAMNRDCGIPLRHLQVDGGMTNNKVLMQLQAD<br>ILHIPVIKPFMPETTALGAAMAAGAAEGVSVWSLEPQALSVLRMERFEPQIQATE<br>SEIRYATWKKAVMKSMGWVTSQSPEGGDPSIFCSLPLGFFIVSSMVMLIGARYIS<br>GVP | Glycerol kinase<br>(Gyk)<br>*Homo sapiens*<br>GenBank:<br>CAA55365.1 |
| 6 | MAASKKAVLGPLVGAVDQGTSSTRELVENSRTAELLSHHQVEIKQEFPREGWVEQ<br>DPKEILHSVYECIEKTCEKLGQLNIGISNIKAIGVSNQRETTVAWDKITGEPLYN<br>AVVWLDLRTQSTVESLSKRIPGNNNEVKSKTGLPLSTYFSAVKLRWLLDNVRKVQ<br>KAVEEKRALFGTIDSWLIWSLTGGVNGGVHCTDVTNASRTMLFNIHSLEWDKQLC<br>EFFGIPMEILPHVRSSSEIYGLMKAGALEGVPISGCLGDQSAALVGQMCFQIGQA<br>KNTYGTGCELLCNTGHKCVESDHGLLTTVAYKLGRDKPVYYALEGSVAIAGAVIR<br>WLRDNLGIIKTSEEIEKLAKEVGTSYGCYFVPAFSGLYAPYWEPSARGIICGLTQ<br>FTNKCHIAFAALEAVCFQTREILDAMNRDCGIPLSHLQVDGGMTSNKILMQLQAD<br>ILYIPVVKPLMPETTALGAAMAAGAAEGVDVWSLEPEDLSAVTMERFEPQINAEE<br>SEIRYSTWKKAVMKSMGWVTTQSPEGGDPSVFCSLPLGEFIVSSMAMLIGARYIS<br>GIP | Glycerol kinase<br>(Gyk)<br>*Homo sapiens*<br>GenBank:<br>CAA55364.1 |
| 7 | MGDRGSSRRRRTGSRPSSHGGGGPAAAEEEVRDAAAGPDVGAAGDAPAPAPNKDG<br>DAGVGSGHWELRCHRLQDSLFSSDSGFSNYRGILNWCVVMLILSNARLFLENLIK<br>YGILVDPIQVVSLFLKDPYSWPAPCLVIAANVFAVAAFQVEKRLAVGALTEQAGL<br>LLHVANLATILCFPAAVVLLVESITPVGSLLALMAHTILELKLESYRDVNSWCRR<br>ARAKAASAGKKASSAAAPHTVSYPDNLTYRDLYYFLFAPTLCYELNFPRSPRIRK<br>RFLLRRILEMLFFTQLQVGLIQQWMVPTIQNSMKPFKDMDYSRIIERLLKLAVPN<br>HLIWLIFFYWLFHSCLNAVAELMQFGDREFYRDWWNSESVTYFWQNWNIPVHKWC<br>IRHFYKPMLRRGSSKWMARTGVFLASAFFHEYLVSVPLRMFRLWAFTGMMAQIPL<br>AWFVGRFFQGNYGNAAVWLSLIIGQPIAVLMYVHDYYVLNYEAPAAEA | DAG O-<br>acetyltransferase 1<br>(DGAT1)<br>*Homo sapiens*<br>UniProt accession<br>number 075907<br>NCBI Reference<br>Sequence:<br>NP_036211.2 |
| 8 | MDESALTLGTIDVSYLPHSSEYSVGRCKHTSEEWGECGFRPTIFRSATLKWKESL<br>MSRKRPFVGRCCYSCTPQSWDKFFNPSIPSLGLRNVIYINETHTRHRGWLARRLS<br>YVLFIQERDVHKGMFATNVTENVLNSSRVQEAIAEVAAELNPDGSAQQQSKAVNK<br>VKKKAKRILQEMVATVSPAMIRLTGWVLLKLENSFEWNIQIHKGQLEMVKAATET<br>NLPLLFLPVHRSHIDYLLLTFILFCHNIKAPYIASGNNLNIPIFSTLIHKLGGFF<br>IRRRLDETPDGRKDVLYRALLHGHIVELLRQQQFLEIFLEGTRSRSGKTSCARAG<br>LLSVVVDTLSTNVIPDILIIPVGISYDRIIEGHYNGEQLGKPKKNESLWSVARGV<br>IRMLRKNYGCVRVDFAQPFSLKEYLESQSQKPVSALLSLEQALLPAILPSRPSDA<br>ADEGRDTSINESRNATDESLRRRLIANLAEHILFTASKSCAIMSTHIVACLLLYR<br>HRQGIDLSTLVEDFFVMKEEVLARDFDLGFSGNSEDVVMHAIQLLGNCVTITHTS<br>RNDEFFITPSTTVPSVFELNEYSNGVLHVFIMEAIIACSLYAVLNKRGLGGPTST<br>PPNLISQEQLVRKAASLCYLLSNEGTISLPCQTFYQVCHETVGKFIQYGILTVAE<br>HDDQEDISPSLAEQQWDKKLPEPLSWRSDEEDEDSDFGEEQRDCYLKVSQSKEHQ<br>QFITFLQRLLGPLLEAYSSAAIFVHNFSGPVPEPEYLQKLHKYLITRTERNVAVY<br>AESATYCLVKNAVKMFKDIGVFKETKQKRVSVLELSSTFLPQCNRQKLLEYILSF<br>VVL | Glycerol-3-<br>phosphate<br>acetyltransferase<br>mitochondrial<br>(GPAM)<br>*Homo sapiens*<br>UniProt accession<br>number Q9HCL2<br>NCBI Reference<br>Sequence:<br>NP_001231878.1 |
| 9 | MKVEFAPLNIQLARRLQTVAVLQWVLKYLLLGPMSIGITVMLIIHNYLFLYIPYL<br>MWLYEDWHTPERGGRRSSWIKNWTLWKHEKDYFPIHLIKTQDLDPSHNYIFGFHP<br>HGIMAVGAFGNESVNYSDEKDLFPGFTSYLHVLPLWFWCPVEREYVMSVGLVSVS<br>KKSVSYMVSKEGGGNISVIVLGGAKESLDAHPGKFTLFIRQRKGFVKIALTHGAS<br>LVPVVSFGENELFKQTDNPEGSWIRTVQNKLQKIMGFALPLFHARGVFQYNEGLM<br>TYRKAIHTVVGRPIPVRQTLNPTQEQIEELHQTYMEELRKLFEEHKGKYGIPEHE<br>TLVLK | Monoacylglycerol<br>O-acetyltransferase<br>(MOGAT1)<br>*Homo sapiens*<br>UniProt accession<br>number Q96PD6<br>NCBI Reference<br>Sequence:<br>NP_477513.2 |
| 10 | MEGAGGANDKKKISSERRKEKSRDAARSRRSKESEVFYELAHQLPLPHNVSSHLD<br>KASVMRLTISYLRVRKLLDAGDLDIEDDMKAQMNCFYLKALDGFVMVLTDDGDMI<br>YISDNVNKYMGLTQFELTGHSVEDFTHPCDHEEMREMLTHRNGLVKKGKEQNTQR<br>SFFLRMKCTLTSRGRTMNIKSATWKVLHCTGHIHVYDTNSNQPQCGYKKPPMTCL<br>VLICEPIPHPSNIEIPLDSKTFLSRHSLDMKFSYCDERITELMGYEPEELLGRSI<br>YEYYHALDSDHLTKTHHDMFTKGQVTTGQYRMLAKRGGYVWVETQATVIYNTKNS<br>QPQCIVCVNYVVSGIIQHDLIFSLQQTECVLKPVESSDMKMTQLFTKVESEDTSS | HIF1α<br>*Homo sapiens*<br>UniProt accession<br>number Q16665 |

-continued

SEQUENCES

| SEQ ID NO. | SEQUENCE | DESCRIPTION |
|---|---|---|
| | LFDKLKKEPDALTLLAPAAGDTIISLDFGSNDTETDDQQLEEVPLYNDVMLPSPN EKLQNINLAMSPLPTAETPKPLRSSADPALNQEVALKLEPNPESLELSFTMPQIQ DQTPSPSDGSTRQSSPEPNSPSEYCFYVDSDMVNEFKLELVEKLFAEDTEAKNPF STQDTDLDLEMLAPYIPMDDDEQLRSEDQLSPLESSSASPESASPQSTVTVFQQT QIQEPTANATTTTATTDELKTVTKDRMEDIKILIASPSPTHIHKETTSATSSPYR DTQSRTASPNRAGKGVIEQTEKSHPRSPNVLSVALSQRTTVPEEELNPKILALQN AQRKRKMEHDGSLFQAVGIGTLLQQPDDHAATTSLSWKRVKGCKSSEQNGMEQKT IILIPSDLACRLLGQSMDESGLPQLTSYDCEVNAPIQGSRNLLQGEELLRALDQV N | |
| 11 | MGDRGSSRRRRTGSRPSSHGGGGPAAAEEEVRDAAAGPDVGAAGDAPAPAPNKDG DAGVGSGHWELRCHRLQDSLFSSDSGFSNYRGILNWCVVMLILSNARLFLENLIK YGILVDPIQVVSLFLKDPYSWPAPCLVIAANVFAVAAFQVEKRLAVGALTEQAGL LLHVANLATILCFPAAVVLLVESITPVGSLLALMAHTILFLKLFSYRDVNSWCRR ARAKAASAGKKASSAAAPHTVSYPDNLTYRDLYYFLFAPTLCYELNFPRSPRIRK RFLLRRILEMLFFTQLQVGLIQQWMVPTIQNSMKPFKDMDYSRIIERLLKLAVPN HLIWLIFFYWLFHSCLNAVAELMQFGDREFYRDWWNSESVTYFWQNWNIPVHKWC IRHFYKPMLRRGSSKWMARTGVFLASAFFHEYLVSVPLRMFRLWAFTGMMAQIPL AWFVGRFFQGNYGNAAVWLSLIIGQPIAVLMYVHDYYVLNYEAPAAEA | DAG O-acetyltransferase 1 (DGAT1) *Homo sapiens* NCBI Reference Sequence: NP_036211.2 |
| 12 | MPPQLQNGLNLSAKVVQGSLDSLPQAVREFLENNAELCQPDHIHICDGSEEENGR LLGQMEEEGILRRLKKYDNCWLALTDPRDVARIESKTVIVTQEQRDTVPIPKTGL SQLGRWMSEEDFEKAFNARFPGCMKGRTMYVIPFSMGPLGSPLSKIGIELTDSPY VVASMRIMTRMGTPVLEAVGDGEFVKCLHSVGCPLPLQKPLVNNWPCNPELTLIA HLPDRREIISFGSGYGGNSLLGKKCFALRMASRLAKEEGWLAEHMLILGITNPEG EKKYLAAAFPSACGKTNLAMMNPSLPGWKVECVGDDIAWMKFDAQGHLRAINPEN GFFGVAPGTSVKTNPNAIKTIQKNTIFTNVAETSDGGVYWEGIDEPLASGVTITS WKNKEWSSEDGEPCAHPNSRFCTPASQCPIIDAAWESPEGVPIEGIIFGGRRPAG VPLVYEALSWQHGVFVGAAMRSEATAAAEHKGKIIMHDPFAMRPFFGYNFGKYLA HWLSMAQHPAAKLPKIFHVNWFRKDKEGKFLWPGFGENSRVLEWMFNRIDGKAST KLTPIGYIPKEDALNLKGLGHINMMELFSISKEFWEKEVEDIEKYLEDQVNADLP CEIEREILALKQRISQM | PCK1 *Homo sapiens* UniProt accession number P35558 NCBI Reference Sequence: NP_002582.3 |
| 13 | FCSPSAKYFFKMAFYNGWILFLAVLAIPVCAVRGRNVENMKILRLMLLHIKYLYG IRVEVRGAHHFPPSQPYVVVSNHQSSLDLLGMMEVLPGRCVPIAKRELLWAGSAG LACWLAGVIFIDRKRTGDAISVMSEVAQTLLTQDVRVWVFPEGTRNHNGSMLPFK RGAFHLAVQAQVPIVPIVMSSYQDFYCKKERRFTSGQCQVRVLPPVPTEGLTPDD VPALADRVRHSMLTVFREISTDGRGGGDYLKKPGGGG | AGPAT1 *Homo sapiens* Amino acids 27-283 of UniProt accession number Q99943 and NCBI Reference Sequence: XP_011546679.1 |
| 14 | AEFYAKVALYCALCFTVSAVASLVCLLRHGGRTVENMSIIGWFVRSFKYFYGLRF EVRDPRRLQEARPCVIVSNHQSILDMMGLMEVLPERCVQIAKRELLFLGPVGLIM YLGGVFFINRQRSSTAMTVMADLGERMVRENLKVWIYPEGTRNDNGDLLPFKKGA FYLAVQAQVPIVPVVYSSFSSFYNTKKKFFTSGTVTVQVLEAIPTSGLTAADVPA LVDTCHRAMRTTFLHISKTPQENGATAGSGVQPAQ | AGPAT2 isoform α precursor *Homo sapiens* Amino acids 24-278 of UniProt accession number O15120 and NCBI Reference Sequence: NP_006403.2 |
| 15 | AEFYAKVALYCALCFTVSAVASLVCLLRHGGRTVENMSIIGWFVRSFKYFYGLRF EVRDPRRLQEARPCVIVSNHQSILDMMGLMEVLPERCVQIAKRELLFLGPVGLIM YLGGVFFINRQRSSTAMTVMADLGERMVRENVPIVPVVYSSFSSFYNTKKKFFTS GTVTVQVLEAIPTSGLTAADVPALVDTCHRAMRTTFLHISKTPQENGATAGSGVQ PAQ | AGPAT2 isoform β precursor Amino acids 24-246 of NCBI Reference Sequence: NP_001012745.1 *Homo sapiens* |
| 16 | MGLLAFLKTQFVLHLLVGFVFVVSGLVINFVQLCTLALWPVSKQLYRRLNCRLAY SLWSQLVMLLEWWSCTECTLFTDQATVERFGKEHAVIILNHNFEIDFLCGWTMCE RFGVLGSSKVLAKKELLYVPLIGWTWYFLEIVFCKRKWEEDRDTVVEGLRRLSDY PEYMWFLLYCEGTRFTETKHRVSMEVAAAKGLPVLKYHLLPRTKGFTTAVKCLRG TVAAVYDVTLNFRGNKNPSLLGILYGKKYEADMCVRRFPLEDIPLDEKEAAQWLH KLYQEKDALQEIYNQKGMFPGEQFKPARRPWTLLNFLSWATILLSPLFSFVLGVF ASGSPLLILTFLGFVGAASFGVRRLIGVTEIEKGSSYGNQEFKKKE | AGPAT3 *Homo sapiens* UniProt accession number Q9NRZ7 NCBI Reference Sequence: NP_001032642.1 |
| 17 | MCLLAFLKTQFVLHLLVGFVFVVSGLVINFVQLCTLALWPVSKQLYRRLNCRLAY SLWSQLVMLLEWWSCTECTLFTDQATVERFGKEHAVIILNHNFEIDFLCGWTMCE RFGVLGSSKVLAKKELLYVPLIGWTWYFLEIVFCKRKWEEDRDTVVEGLRRLSDY | AGPAT3 *Homo sapiens* GenBank: |

-continued

SEQUENCES

| SEQ ID NO. | SEQUENCE | DESCRIPTION |
|---|---|---|
| | PEYMWFLLYCEGTRFTETKHRVSMEVAAAKGLPVLKYHLLPRTKGFTTAVKCLRGTVAAVYDVTLNFRGNKNPSLLGILYGKKYEADMCVRRFPLEDIPLDEKEAAQWLHKLYQEKDALQEIYNQKGMFPGEQFKPARRPWTLLNFLSWATILLSPLFSFVLGVFASGSPLLILTFLGFVGAASFGVRRLIGESLEPGRWRLQ | AAQ89067.1 |
| 18 | VSFGIRKLYMKSLLKIFAWATLRMERGAKEKNHQLYKPYTNGIIAKDPTSLEEEIKEIRRSGSSKALDNTPEFELSDIFYFCRKGMETIMDDEVTKRFSAEELESWNLLSRTNYNFQYISLRLTVLWGLGVLIRYCFLLPLRIALAFTGISLLVVGTTVVGYLPNGRFKEFMSKHVHLMCYRICVRALTAIITYHDRENRPRNGGICVANHTSPIDVIILASDGYYAMVGQVHGGLMGVIQRAMVKACPHVWFERSEVKDRHLVAKRLTEHVQDKSKLPILIFPEGTCINNTSVMMFKKGSFEIGATVYPVAIKYDPQFGDAFWNSSKYGMVTYLLRMMTSWAIVCSVWYLPPMTREADEDAVQFANRVKSAIARQGGLVDLLWDGGLKREKVKDTFKEEQQKLYSKMIVGNHKDRSRS | AGPAT6 (LPA-MAG PA) *Homo sapiens* Amino acids 38-456 of UniProt accession number Q86UL3 |
| 19 | MATMLEGRCQTQPRSSPSCREASLWSSGFGMKLEAVTPFLGKYRPFVGRCCQTCTPKSWESLFHRSITDLGFCNVILVKEENTRFRGWLVRRLCYFLWSLEQHIPPCQDVPQKIMESTGVQNLLSGRVPGGTGEGQVPDLVKKEVQRILGHIQAPPRPFLVRLFSWALLRFLNCLFLNVQLHKGQMKMVQKAAQAGLPLVLLSTHKTLLDGILLPFMLLSQGLGVLRVAWDSRACSPALRALLRKLGGLFLPPEASLSLDSSEGLLARAVVQAVIEQLLVSGQPLLIFLEEPPGALGPRLSALGQAWVGFVVQAVQVGIVPDALLVPVAVTYDLVPDAPCDIDHASAPLGLWTGALAVLRSLWSRWGCSHRICSRVHLAQPFSLQEYIVSARSCWGGRQTLEQLLQPIVLGQCTAVPDTEKEQEWTPITGPLLALKEEDQLLVRRLSCHVLSASVGSSAVMSTAIMATLLLFKHQKLLGEFSWLTEEILLRGFDVGFSGQLRSLLQHSLSLLRAHVALLRIRQGDLLVVPQPGPGLTHLAQLSAELLPVFLSEAVGACAVRGLLAGRVPPQGPWELQGILLLSQNELYRQILLLMHLLPQDLLLLKPCQSSYCYCQEVLDRLIQCGLLVAEETPGSRPACDTGRQRLSRKLLWKPSGDFTDSDSDDFGEADGRYFRLSQQSHCPDFFLFLCRLLSPLLKAFAQAAAFLRQGQLPDTELGYTEQLFQFLQATAQEEGIFECADPKLAISAVWTFRDLGVLQQTPSPAGPRLHLSPTFASLDNQEKLEQFIRQFICS | GPAT2 *Homo sapiens* UniProt accession number Q6NUI2 NCBI Reference Sequence: NP_997211.2 |
| 20 | MVEFAPLFMPWERRLQTLAVLQFVFSFLALAEICTVGFIALLFTRFWLLTVLYAAWWYLDRDKPRQGGRHIQAIRCWTIWKYMKDYFPISLVKTAELDPSRNYIAGFHPHGVLAVGAFANLCTESTGFSSIFPGIRPHLMMLTLWFRAPFFRDYIMSAGLVTSEKESAAHILNRKGGGNLLGIIVGGAQEALDARPGSFTLLLRNRKGFVRLALTHGAPLVPIFSFGENDLFDQIPNSSGSWLRYIQNRLQKIMGISLPLFHGRGVFQYSFGLIPYRRPITTVVGKPIEVQKTLHPSEEEVNQLHQRYIKELCNLFEAHKLKFNIPADQHLEFC | MOGAT2 *Homo sapiens* UniProt accession number Q3SYC2 |
| 21 | MVEFAPLFMPWERRLQTLAVLQFVFSFLALAEICTVGFIALLFTRFWLLTVLYAAWWYLDRDKPRQGGRHIQAIRCWTIWKYMKDYFPISLVKTAELDPSRNYIAGFHPHGVLAVGAFANLCTESTGFSSIFPGIRPHLMMLTLWFRAPFFRDYIMSAGLVTSEKESAAHILNRKGGGNLLGIIVGGAQEALDARPGSFTLLLRNRKGFVRLALTHGYQASGKSTLGSVGNWQGFYFGGKMAETNADSILVEIFSPFTIKIIFWCLMPKYLEKFPQRRLSDLRN | MOGAT2 *Homo sapiens* GenBank: AAI03879.1 |
| 22 | MKTLIAAYSGVLRGERQAEADRSQRSHGGPALSREGSGRWGTGSSILSALQDLFSVTWLNRSKVEKQLQVISVLQWVLSFLVLGVACSAILMYIFCTDCWLIAVLYFTWLVFDWNTPKKGGRRSQWVRNWAVWRYFRDYFPIQLVKTHNLLTTRNYIFGYHPHGIMGLGAFCNFSTEATEVSKKFPGIRPYLATLAGNFRMPVLREYLMSGGICPVSRDTIDYLLSKNGSGNAIIIVVGGAAESLSSMPGKNAVTLRNRKGFVKLALRHGADLVPIYSFGENEVYKQVIFEEGSWGRWVQKKFQKYIGFAPCIFHGRGLFSSDTWGLVPYSKPITTVVGEPITIPKLEHPTQQDIDLYHTMYMEALVKLFDKHKTKFGLPETEVLEVN | DGAT2 *Homo sapiens* UniProt accession number Q96PD7 GenBank: AAQ88896.1 |
| 23 | MQPECAEKGKSFKQRLVLKSSLAKETLSEFLGTFILIVLGCCCVAQAILSRGRFCGVITINVGFSMAVAMAIYVAGGVSGGHINPAVSLAMCLFGRMKWFKLPFYVGAQFLGAFVGAATVFGIYYDGLMSFAGGKLLIVGENATAHIFATYPAPYLSLANAFADQVVATMILLIIVFAIFDSRNLGAPRGLEPIAIGLLIIVIASSLGLNSGCAMNPARDLSPRLFTALAGWGFEVFRAGNNFWWIPVVGPLVGAVIGGLIYVLVIEIHHPEPDSVFKTEQSEDKPEKYELSVIM | AQP9 *Homo sapiens* UniProt accession number 043315 GenBank: AAH26258.1 |
| 24 | MNYVGQLAGQVFVTVKELYKGLNPATLSGCIDIIVIRQPNGNLQCSPFHVRFGKMGVLRSREKVVDIEINGESVDLHMKLGDNGEAFFVQETDNDQEVIPMHLATSPILSEGASRMECQLKRGSVDRMRGLDPSTPAQVIAPSETPSSSSVVKKRRKRRRKSQLDSLKRDDNMNTSEDEDMFPIEMSSDEAMELLESSRTLPNDIPPFQDDIPEENLSLAVIYPQSASYPNSDREWSPTPSPSGSRPSTPKSDSELVSKSTERTGQKNPEMLWLWGELPQAAKSSSPHKMKESSPLSSRKICDKSHFQAIHSESSDTFSDQSPTLVGGALLDQNKPQTEMQFVNEEDLETLGAAAPLLPMIEELKPPSASVVQTANKTDSPSRKRDKRSRHLGADGVYLDDLTDMDPEVAALYFPKNGDPSGLAKHASDNGARSANQSPQSVGSSGVDSGVESTSDGLRDLPSIAISLCGGLSDHREITKDAFLEQAVSYQQFVDNPAIIDDPNLVVKIGSKYYNWTTAAPLLLAMQAFQKPLPKATVESIMRDKMPKKGGRWWFSWRGRNTTIKEESKPEQCLAGKAHSTGEQPPQLSLATRVKHESSSSDEERAAAKPSNAGHLPLLPNVSYKKTLRLTSEQLKSLKLKNGPNDVVFSVTTQYQGTCRCEGTIYLWNWDDKVIISDIDGTITRSDTLGHILPTLGKDWTHQGIAKLYHKVSQN | LPIN1 (Lipin 1) *Homo sapiens* UniProt accession number Q14693 |

-continued

SEQUENCES

| SEQ ID NO. | SEQUENCE | DESCRIPTION |
|---|---|---|
| | GYKFLYCSARAIGMADMTRGYLHWVNERGTVLPQGPLLLSPSSLFSALHREVIEK KPEKFKVQCLTDIKNLFFPNTEPFYAAFGNRPADVYSYKQVGVSLNRIFTVNPKG ELVQEHAKTNISSYVRLCEVVDHVFPLLKRSHSSDFPCSDTFSNFTFWREPLPPF ENQDIHSASA | |
| 25 | MAASVRQARSLLGVAATLAPGSRGYRARPPPRRRPGPRWPDPEDLLTPRWQLGPR YAAKQFARYGAASGVVPGSLWPSPEQLRELEAEEREWYPSLATMQESLRVKQLAE EQKRREREQHIAECMAKMPQMIVNWQQQQRENWEKAQADKERRARLQAEAQELLG YQVDPRSARFQELLQDLEKKERKRLKEEKQKRKKEARAAALAAAVAQDPAASGAP SS | CRIF1 *Homo sapiens* UniProt accession number Q8TAE8 |
| 26 | PGWFLDSPDRPWNPPTFSPALLVVTEGDNATFTCSFSNTSESFVLNWYRMSPSN4 TDKLAAFPEDRSQPGQDCRFRVTQLPNGRDFHMSVVRARRNDSGTYLCGAISLAP KAQIKESLRAELRVTERRAEVPTAHPSPSPRPAGQFQTLVVGVVGGLLGSLVLLV WVLAVICSRAARGTIGARRTGQPLKEDPSAVPVFSVDYGELDFQWREKTPEPPVP CVPEQTEYATIVFPSGMGTSSPARRGSADGPRSAQPLRPEDGHCSWPL | PD1 *Homo sapiens* Amino acids 21-288 of UniProt accession number Q15116 |
| 27 | MRPRTHGAPPRNIMSTIPKWFKGAPFGVQSHRFDVSAVYPNQKKFSTFTEAPYSR HHSVELSHIGPGTYNSKDTCFSKKFLEQKLGSGWSQAHEATRLTQLPHFHYQAIK KEKEQQVHKRGPGSYNIKDFITELQKKPQSKRGLLSSGETRFRGFIGNYYPGPGN YGEKGNPYTQLEEKAWNRSHSDGLMCRVSNKPPLFHQGSGLGPGTYTIKSDLETF VKKSTGNRGPYDIFSGERSSPLPYGHYSVQKMKPKELTDYKSFLDEMNSQHKKKQ GVFSKYPRDPKHPTERIFWTTLSQCPKNMDIAGPGSWLPHETEQKHVNRPPFLLA SKRCGLKAYQMILGTWNPVGVGRYLNTTLMESIDRRQRYRSLYMSEPKRYLQDLT RDRLMQKRITPITKGKCRPTVDYNSDPTP | Lymphocyte expansion molecule (LEM) Mus musculus GenBank: AKD95359.1 |
| 28 | ATGAGGGAAAGCCAGGATGCCGCCGGAGCTCATGGCTGGAACCGCGTCGGCTCCA CGGCCACCAAGTGGTTCACCGGGGCGCCCTTCGGGGTGCAGAGCCACAGGTTTGA CATCTCTGCTGTTTATCCCAACTGGAAGAAGTTCAGCACCTTCACTGAGGCCCCA TACTCCACGCGTTATTCTACCCAAGTGTCCCACATAGGCCCTGGGACTTACAGCT CCAAAGAGACCTGCTTCAGCAAGAAGAAGCTGATGAAGGAGGTGGACACAGGCTG GGCCAAGGCCCAGGAAGCCACGCGGCTGACCCAGCTACCCCACTTCCAGTACCAG GCCATCATGAAAGAGAAGCGGCTGAAGGAGCAAAAGCTGGGCCCCGGCTCCTACA ACCTCAAAGACTTCTTAGAACAGCTGCGGGAGAAACCATGTAGCACCCGGGGGCT GCTCAGCTCTGGGGAGGTTCGCTTCCGAGGACTCACTGGGAACTACTATCCAGGC CCTGGAAATTATGGGGAGAAGGGTAACCCATACACCAAGCTGGAGGAGAATGCCT GGAACCGGTCTCATTCCGAGGGCCTCATGTGCAGGATGAGCAACAAGCCACACCC CCGGCCTCATCAGGGGAGTGGTCTGGGACCCGGCACCTACTTCTTCAAAAGCGAC CTTGAGACATATGTGGCACGATCCGTCGGCACCCGCGGCCCCTATGACACTTTCT CTGGTGATCGGAGCAAGCCACTGCCTTATGGGCACTACTCCATGCAGAAAAAAAA GCCCAGGGAACTGATGAATTTCAAGAGCTTTGTAGAAGAACTTAACTCACATCAC AATAAGAAGCATGGGGTTTTTTCTAAACTTCCCCGAAACCCGAAAACCCCCTACAG AGAGGATTTACTGGGCCAACCTCAGCCAGTGCCCCCGCACACTGGCCACATCTGG CCCCAGTTTCTGGCTTCCACAAGAGAAGAAATGCAAACCCGTCAACCAGCCCCCA TTCCTGTTGACCTCCAAGGGGTCAGGTGCAAAGGCCTGCCAGATGATTATGGGAA GCTGGAACCCAGTAGGTGTGGGCCGCTACCTCAACACCTGGCTGATGGAGACAAA GGACAGGCGGCAGCGATATCGATCCCTATTCCTGAGTGGATCCAAACGCTACCTC TCAGACCTGGCCCGGGACATGCTCATGCAAATCAGGCTGTTTTGTTGGAAAGGCC TAGAAGTCATCAATTTTGGCCTCTCACCAATGTAG | C1ORF177 1 (huLEM) *Homo sapiens* Coding sequence NCBI Reference Sequence: NM_152607.2 |
| 29 | ATGAGGGAAAGCCAGGATGCCGCCGGAGCTCATGGCTGGAACCGCGTCGGCTCCA CGGCCACCAAGTGGTTCACCGGGGCGCCCTTCGGGGTGCAGAGCCACAGGTTTGA CATCTCTGCTGTTTATCCCAACTGGAAGAAGTTCAGCACCTTCACTGAGGCCCCA TACTCCACGCGTTATTCTACCCAAGTGTCCCACATAGGCCCTGGGACTTACAGCT CCAAAGAGACCTGCTTCAGCAAGAAGAAGCTGATGAAGGAGGTGGACACAGGCTG GGCCAAGGCCCAGGAAGCCACGCGGCTGACCCAGCTACCCCACTTCCAGTACCAG GCCATCATGAAAGAGAAGCGGCTGAAGGAGCAAAAGCTGGGCCCCGGCTCCTACA ACCTCAAAGACTTCTTAGAACAGCTGCGGGAGAAACCATGTAGCACCCGGGGGCT GCTCAGCTCTGGGGAGGTTCGCTTCCGAGGACTCACTGGGAACTACTATCCAGGC CCTGGAAATTATGGGGAGAAGGGTAACCCATACACCAAGCTGGAGGAGAATGCCT GGAACCGGTCTCATTCCGAGGGCCTCATGTGCAGGATGAGCAACAAGCCACACCC CCGGCCTCATCAGGGGAGTGGTCTGGGACCCGGCACCTACTTCTTCAAAAGCGAC CTTGAGACATATGTGGCACGATCCGTCGGCACCCGCGGCCCCTATGACACTTTCT CTGGTGATCGGAGCAAGCCACTGCCTTATGGGCACTACTCCATGCAGAAAAAAAA GCCCAGGGAACTGATGAATTTCAAGAGCTTTGTAGAAGAACTTAACTCACATCAC AATAAGAAGCATGGGGTTTTTTCTAAACTTCCCCGAAACCCGAAAACCCCCTACAG AGAGGATTTACTGGGCCAACCTCAGCCAGTGCCCCCGCACACTGGCCACATCTGG CCCCAGTTTCTGGCTTCCACAAGAGAAGAAATGCAAACCCGTCAACCAGCCCCCA TTCCTGTTGACCTCCAAGGGGTCAGGTGCAAAGGCCTGCCAGATGATTATGGGAA GCTGGAACCCAGTAGGTGTGGGCCGCTACCTCAACACCTGGCTGATGGAGACAAA GGACAGGCGGCAGCGATATCGATCCCTATTCCTGAGTGGATCCAAACGCTACCTC TCAGACCTGGCCCGGGACATGCTCATGCAGGAAAGGATCACACCATTTACTAAGG GAAAGTGCCCTCCAACTGTGGATTACAATTCAGATCCTACTCCTTAA | C1ORF177 2 (huLEM) *Homo sapiens* Coding sequence of NCBI Reference Sequence: NM_001110533.1 |

-continued

SEQUENCES

| SEQ ID NO. | SEQUENCE | DESCRIPTION |
|---|---|---|
| 30 | ATGGCAGCCTCAAAGAAGGCAGTTTTGGGGCCATTGGTGGGGGCGGTGGACCAGG<br>GCACCAGTTCGACGCGCTTTTTGGTTTTCAATTCAAAAACAGCTGAACTACTTAG<br>TCATCATCAAGTAGAAATAAAACAAGAGTTCCCAAGAGAAGGATGGGTGGAACAG<br>GACCCTAAGGAAATTCTACATTCTGTCTATGAGTGTATAGAGAAAACATGTGAGA<br>AACTTGGACAGCTCAATATTGATATTTCCAACATAAAAGCTATTGGTGTCAGCAA<br>CCAGAGGGAAACCACTGTAGTCTGGGACAAGATAACTGGAGAGCCTCTCTACAAT<br>GCTGTGGTGTGGCTTGATCTAAGAACCCAGTCTACCGTTGAGAGTCTTAGTAAAA<br>GAATTCCAGGAAATAATAACTTTGTCAAGTCCAAGACAGGCCTTCCACTTAGCAC<br>TTACTTCAGTGCAGTGAAACTTCGTTGGCTCCTTGACAATGTGAGAAAAGTTCAA<br>AAGGCCGTTGAAGAAAAACGAGCTCTTTTTGGGACTATTGATTCATGGCTTATTT<br>GGAGTTTGACAGGAGGAGTCAATGGAGGTGTCCACTGTACAGATGTAACAAATGC<br>AAGTAGGACTATGCTTTTCAACATTCATTCTTTGGAATGGGATAAACAACTCTGC<br>GAATTTTTTGGAATTCCAATGGAAATTCTTCCAAATGTCCGGAGTTCTTCTGAGA<br>TCTATGGCCTAATGAAAATCTCTCATAGCGTGAAAGCTGGGGCCTTGGAAGGTGT<br>GCCAATATCTGGGTGTTTAGGGGACCAGTCTGCTGCATTGGTGGGACAAATGTGC<br>TTCCAGATTGGACAAGCCAAAAATACGTATGGAACAGGATGTTTCTTACTATGTA<br>ATACAGGCCATAAGTGTGTATTTTCTGATCATGGCCTTCTCACCACAGTGGCTTA<br>CAAACTTGGCAGAGACAAACCAGTATATTATGCTTTGGAAGGTTCTGTAGCTATA<br>GCTGGTGCTGTTATTCGCTGGCTAAGAGACAATCTTGGAATTATAAAGACCTCAG<br>AAGAAATTGAAAAACTTGCTAAAGAAGTAGGTACTTCTTATGGCTGCTACTTCGT<br>CCCAGCATTTTCGGGGTTATATGCACCTTATTGGGAGCCCAGCGCAAGAGGGATA<br>ATCTGTGGACTCACTCAGTTCACCAATAAATGCCATATTGCTTTTGCTGCATTAG<br>AAGCTGTTTGTTTCCAAACTCGAGAGATTTTGGATGCCATGAATCGAGACTGTGG<br>AATTCCACTCAGTCATTTGCAGGTAGATGGAGGAATGACCAGCAACAAAATTCTT<br>ATGCAGCTACAAGCAGACATTCTGTATATACCAGTAGTGAAGCCCTCAATGCCCG<br>AAACCACTGCACTGGGTGCGGCTATGGCGGCAGGGGCTGCAGAAGGAGTCGGCGT<br>ATGGAGTCTCGAACCCGAGGATTTGTCTGCCGTCACGATGGAGCGGTTTGAACCT<br>CAGATTAATGCGGAGGAAAGTGAAATTCGTTATTCTACATGGAAGAAAGCTGTGA<br>TGAAGTCAATGGGTTGGGTTACAACTCAATCTCCAGAAAGTGGTATTCCATAA | Glycerol kinase<br>(Gyk)<br>*Homo sapiens*<br>NG_008178.1<br>RefSeqGene |
| 31 | ATGGGCGACCGCGGCAGCTCCCGGCGCCGGAGGACAGGGTCGCGGCCCTCGAGCC<br>ACGGCGGCGGCGGGCCTGCGGCGGCGGAAGAGGAGGTGCGGGACGCCGCTGCGGG<br>CCCCGACGTGGGAGCCGCGGGGGACGCGCCAGCCCCGGCCCCCAACAAGGACGGA<br>GACGCCGGCGTGGGCAGCGGCCACTGGGAGCTGAGGTGCCATCGCCTGCAGGATT<br>CTTTATTCAGCTCTGACAGTGGCTTCAGCAACTACCGTGGCATCCTGAACTGGTG<br>TGTGGTGATGCTGATCTTGAGCAATGCCCGGTTATTTCTGGAGAACCTCATCAAG<br>TATGGCATCCTGGTGGACCCCATCCAGGTGGTTTCTCTGTTCCTGAAGGATCCCT<br>ATAGCTGGCCCGCCCCATGCCTGGTTATTGCGGCCAATGTCTTTGCTGTGGCTGC<br>ATTCCAGGTTGAGAAGCGCCTGGCGGTGGGTGCCCTGACGGAGCAGGCGGGACTG<br>CTGCTGCACGTGGCCAACCTGGCCACCATTCTGTGTTTCCCAGCGGCTGTGGTCT<br>TACTGGTTGAGTCTATCACTCCAGTGGGCTCCCTGCTGGCGCTGATGGCGCACAC<br>CATCCTCTTCCTCAAGCTCTTCTCCTACCGCGACGTCAACTCATGGTGCCGCAGG<br>GCCAGGGCCAAGGCTGCCTCTGCAGGGAAGAAGGCCAGCAGTGCTGCTGCCCCGC<br>ACACCGTGAGCTACCCGGACAATCTGACCTACCGCGATCTCTACTACTTCCTCTT<br>CGCCCCCACCTTGTGCTACGAGCTCAACTTTCCCCGCTCTCCCCGCATCCGGAAG<br>CGCTTTCTGCTGCGACGGATCCTTGAGATGCTGTTCTTCACCCAGCTCCAGGTGG<br>GGCTGATCCAGCAGTGGATGGTCCCCACCATCCAGAACTCCATGAAGCCCTTCAA<br>GGACATGGACTACTCACGCATCATCGAGCGCCTCCTGAAGCTGGCGGTCCCCAAT<br>CACCTCATCTGGCTCATCTTCTTCTACTGGCTCTTCCACTCCTGCCTGAATGCCG<br>TGGCTGAGCTCATGCAGTTTGGAGACCGGGAGTTCTACCGGGACTGGTGGAACTC<br>CGAGTCTGTCACCTACTTCTGGCAGAACTGGAACATCCCTGTGCACAAGTGGTGC<br>ATCAGACACTTCTACAAGCCCATGCTTCGACGGGGCAGCAGCAAGTGGATGGCCA<br>GGACAGGGGTGTTCCTGGCCTCGGCCTTCTTCCACGAGTACCTGGTGAGCGTCCC<br>TCTGCGAATGTTCCGCCTCTGGGCGTTCACGGGCATGATGGCTCAGATCCCACTG<br>GCCTGGTTCGTGGGCCGCTTTTTCCAGGGCAACTATGGCAACGCAGCTGTGTGGC<br>TGTCGCTCATCATCGGACAGCCAATAGCCGTCCTCATGTACGTCCACGACTACTA<br>CGTGCTCAACTATGAGGCCCCAGCGGCAGAGGCCTGA | DAG O-<br>acetyltransferase 1<br>(DGAT1)<br>*Homo sapiens*<br>Coding sequence of<br>NCBI Reference<br>Sequence:<br>NM_012079.5 |
| 32 | ATGGATGAATCTGCACTGACCCTTGGTACAATAGATGTTTCTTATCTGCCACATT<br>CATCAGAATACAGTGTTGGTCGATGTAAGCACACAAGTGAGGAATGGGGTGAGTG<br>TGGCTTTAGACCCACCATCTTCAGATCTGCAACTTTAAAATGGAAAGAAAGCCTA<br>ATGAGTCGGAAAAGGCCATTTGTTGGAAGATGTTGTTACTCCTGCACTCCCCAGA<br>GCTGGGACAAATTTTTCAACCCCAGTATCCCGTCTTTGGGTTTGCGGAATGTTAT<br>TTATATCAATGAAACTCACACAAGACACCGCGGATGGCTTGCAAGACGCCTTTCT<br>TACGTTCTTTTTATTCAAGAGCGAGATGTGCATAAGGGCATGTTTGCCACCAATG<br>TGACTGAAAATGTGCTGAACAGCAGTAGAGTACAAGAGGCAATTGCAGAAGTGGC<br>TGCTGAATTAAACCCTGATGGTTCTGCCCAGCAGCAATCAAAAGCCGTTAACAAA<br>GTGAAAAAGAAAGCTAAAAGGATTCTTCAAGAAATGGTTGCCACTGTCTCACCGG<br>CAATGATCAGACTGACTGGGTGGGTGCTGCTAAAACTGTTCAACAGCTTCTTTTG<br>GAACATTCAAATTCACAAAGGTCAACTTGAGATGGTTAAAGCTGCAACTGAGACG<br>AATTTGCCGCTTCTGTTTCTACCAGTTCATAGATCCCATATTGACTATCTGCTGC<br>TCACTTTCATTCTCTTCTGCCATAACATCAAAGCACCATACATTGCTTCAGGCAA<br>TAATCTCAACATCCCAATCTTCAGTACCTTGATCCATAAGCTTGGGGGCTTCTTC | Glycerol-3-<br>phosphate<br>acetyltransferase<br>mitochondrial<br>(GPAM)<br>*Homo sapiens*<br>Coding sequence of<br>NCBI Reference<br>Sequence:<br>NM_001244949.1 |

-continued

SEQUENCES

| SEQ ID NO. | SEQUENCE | DESCRIPTION |
|---|---|---|
| | ATACGACGAAGGCTCGATGAAACACCAGATGGACGGAAAGATGTTCTCTATAGAG<br>CTTTGCTCCATGGGCATATAGTTGAATTACTTCGACAGCAGCAATTCTTGGAGAT<br>CTTCCTGGAAGGCACACGTTCTAGGAGTGGAAAAACCTCTTGTGCTCGGGCAGGA<br>CTTTTGTCAGTTGTGGTAGATACTCTGTCTACCAATGTCATCCCAGACATCTTGA<br>TAATACCTGTTGGAATCTCCTATGATCGCATTATCGAAGGTCACTACAATGGTGA<br>ACAACTGGGCAAACCTAAGAAGAATGAGAGCCTGTGGAGTGTAGCAAGAGGTGTT<br>ATTAGAATGTTACGAAAAAACTATGGTTGTGTCCGAGTGGATTTTGCACAGCCAT<br>TTTCCTTAAAGGAATATTTAGAAAGCCAAAGTCAGAAACCGGTGTCTGCTCTACT<br>TTCCCTGGAGCAAGCGTTGTTACCAGCTATACTTCCTTCAAGACCCAGTGATGCT<br>GCTGATGAAGGTAGAGACACGTCCATTAATGAGTCCAGAAATGCAACAGATGAAT<br>CCCTACGAAGGAGGTTGATTGCAAATCTGGCTGAGCATATTCTATTCACTGCTAG<br>CAAGTCCTGTGCCATTATGTCCACACACATTGTGGCTTGCCTGCTCCTCTACAGA<br>CACAGGCAGGGAATTGATCTCTCCACATTGGTCGAAGACTTCTTTGTGATGAAAG<br>AGGAAGTCCTGGCTCGTGATTTTGACCTGGGGTTCTCAGGAAATTCAGAAGATGT<br>AGTAATGCATGCCATACAGCTGCTGGGAAATTGTGTCACAATCACCCACACTAGC<br>AGGAACGATGAGTTTTTATCACCCCCAGCACAACTGTCCCATCAGTCTTCGAAC<br>TCAACTTCTACAGCAATGGGGTACTTCATGTCTTTATCATGGAGGCCATCATAGC<br>TTGCAGCCTTTATGCAGTTCTGAACAAGAGGGGACTGGGGGGTCCCACTAGCACC<br>CCACCTAACCTGATCAGCCAGGAGCAGCTGGTGCGGAAGGCGGCCAGCCTGTGCT<br>ACCTTCTCTCCAATGAAGGCACCATCTCACTGCCTTGCCAGACATTTTACCAAGT<br>CTGCCATGAAACAGTAGGAAAGTTTATCCAGTATGGCATTCTTACAGTGGCAGAG<br>CACGATGACCAGGAAGATATCAGTCCTAGTCTTGCTGAGCAGCAGTGGGACAAGA<br>AGCTTCCAGAACCTTTGTCTTGGAGAAGTGATGAAGAAGATGAAGACAGTGACTT<br>TGGGGAGGAACAGCGAGATTGCTACCTGAAGGTGAGCCAATCCAAGGAGCACCAG<br>CAGTTTATCACCTTCTTACAGAGACTCCTTGGGCCTTTGCTGGAGGCCTACAGCT<br>CTGCTGCCATCTTTGTTCACAACTTCAGTGGTCCTGTTCCAGAACCTGAGTATCT<br>GCAAAAGTTGCACAAATACCTAATAACCAGAACAGAAAGAAATGTTGCAGTATAT<br>GCTGAGAGTGCCACATATTGTCTTGTGAAGAATGCTGTGAAAATGTTTAAGGATA<br>TTGGGGTTTTCAAGGAGACCAAACAAAAGAGAGTGTCTGTTTTAGAACTGAGCAG<br>CACTTTTCTACCTCAATGCAACCGACAAAAACTTCTAGAATATATTCTGAGTTTT<br>GTGGTGCTGTAG | |
| 33 | ATGAAGGTAGAGTTTGCACCGCTCAACATCCAGCTGGCGCGGCGGCTGCAGACGG<br>TGGCCGTGCTGCAGTGGGTCCTGAAATACCTGCTGCTCGGGCCGATGTCCATTGG<br>AATCACTGTGATGCTGATCATACACAACTATTTGTTCCTTTACATCCCTTATTTG<br>ATGTGGCTTTACTTTGACTGGCATACCCCAGAGCGAGGAGGCAGGAGATCCAGCT<br>GGATCAAAAATTGGACTCTTTGGAAACACTTTAAGGACTATTTTCCAATTCATCT<br>TATCAAAACTCAAGATTTGGATCCAAGTCACAACTATATATTTGGGTTTCACCCC<br>CATGGAATAATGGCAGTTGGAGCCTTTGGGAATTTTTCTGTAAATTATTCTGACT<br>TCAAGGACCTGTTTCCTGGCTTTACTTCATATCTTCACGTGCTGCCACTTTGGTT<br>CTGGTGTCCTGTCTTTCGAGAATATGTGATGAGTGTTGGGCTGGTTTCAGTTTCC<br>AAGAAAAGTGTGTCCTACATGGTAAGCAAGGAGGGAGGTGGAAACATCTCTGTCA<br>TTGTCCTTGGGGGTGCAAAAGAATCACTGGATGCTCATCCTGGAAAGTTCACTCT<br>GTTCATCCGCCAGCGGAAAGGATTTGTTAAAATTGCTTTGACCCATGGCGCCTCT<br>CTGGTCCCAGTGGTTTCTTTTGGTGAAAATGAACTGTTTAAACAAACTGACAACC<br>CTGAAGGATCATGGATTAGAACTGTTCAGAATAAACTGCAGAAGATCATGGGGTT<br>TGCTTTGCCCCTGTTTCATGCCAGGGGAGTTTTTCAGTACAATTTTGGCCTAATG<br>ACCTATAGGAAAGCCATCCACACTGTTGTTGGCCGCCCGATCCCTGTTCGTCAGA<br>CTCTGAACCCGACCCAGGAGCAGATTGAGGAGTTACATCAGACCTATATGGAGGA<br>ACTTAGGAAATTGTTTGAGGAACACAAAGGAAAGTATGGCATTCCAGAGCACGAG<br>ACTCTTGTTTTAAAATGA | Monoacylglycerol<br>O-acetyltransferase<br>(MOGAT1)<br>*Homo sapiens*<br>Coding sequence of<br>NCBI Reference<br>Sequence:<br>NM_058165.2 |
| 34 | ATGGAGGGCGCCGGCGGCGCGAACGACAAGAAAAAGATAAGTTCTGAACGTCGAA<br>AAGAAAAGTCTCGAGATGCAGCCAGATCTCGGCGAAGTAAAGAATCTGAAGTTTT<br>TTATGAGCTTGCTCATCAGTTGCCACTTCCACATAATGTGAGTTCGCATCTTGAT<br>AAGGCCTCTGTGATGAGGCTTACCATCAGCTATTTGCGTGTGAGGAAACTTCTGG<br>ATGCTGGTGATTTGGATATTGAAGATGACATGAAAGCACAGATGAATTGCTTTTA<br>TTTGAAAGCCTTGGATGGTTTTGTTATGGTTCTCACAGATGATGGTGACATGATT<br>TACATTTCTGATAATGTGAACAAATACATGGGATTAACTCAGTTTGAACTAACTG<br>GACACAGTGTGTTTGATTTTACTCATCCATGTGACCATGAGGAAATGAGAGAAAT<br>GCTTACACACAGAAATGGCCTTGTGAAAAAGGGTAAAGAACAAAACACACAGCGA<br>AGCTTTTTTCTCAGAATGAAGTGTACCCTAACTAGCCGAGGAAGAACTATGAACA<br>TAAAGTCTGCAACATGGAAGGTATTGCACTGCACAGGCCACATTCACGTATATGA<br>TACCAACAGTAACCAACCTCAGTGTGGGTATAAGAAACCACCTATGACCTGCTTG<br>GTGCTGATTTGTGAACCCATTCCTCACCCATCAAATATTGAAATTCCTTTAGATA<br>GCAAGACTTTCCTCAGTCGACACAGCCTGGATATGAAATTTTCTTATTGTGATGA<br>AAGAATTACCGAATTGATGGGATATGAGCCAGAAGAACTTTTAGGCCGCTCAATT<br>TATGAATATTATCATGCTTTGGACTCTGATCATCTGACCAAAACTCATCATGATA<br>TGTTTACTAAAGGACAAGTCACCACAGGACAGTACAGGATGCTTGCCAAAAGAGG<br>TGGATATGTCTGGGTTGAAACTCAAGCAACTGTCATATATAACACCAAGAATTCT<br>CAACCACAGTGCATTGTATGTGTGAATTACGTTGTGAGTGGTATTATTCAGCACG<br>ACTTGATTTTCTCCCTTCAACAAACAGAATGTGTCCTTAAACCGGTTGAATCTTC<br>AGATATGAAAATGACTCAGCTATTCACCAAAGTTGAATCAGAAGATACAAGTAGC<br>CTCTTTGACAAACTTAAGAAGGAACCTGATGCTTTAACTTTGCTGGCCCCAGCCG | HIF1α<br>*Homo sapiens*<br>Coding sequence of<br>NCBI Reference<br>Sequence:<br>NM_001530.3 |

-continued

SEQUENCES

| SEQ ID NO. | SEQUENCE | DESCRIPTION |
|---|---|---|
| | CTGGAGACACAATCATATCTTTAGATTTTGGCAGCAACGACACAGAAACTGATGA<br>CCAGCAACTTGAGGAAGTACCATTATATAATGATGTAATGCTCCCCTCACCCAAC<br>GAAAAATTACAGAATATAAATTTGGCAATGTCTCCATTACCCACCGCTGAAACGC<br>CAAAGCCACTTCGAAGTAGTGCTGACCCTGCACTCAATCAAGAAGTTGCATTAAA<br>ATTAGAACCAAATCCAGAGTCACTGGAACTTTCTTTTACCATGCCCCAGATTCAG<br>GATCAGACACCTAGTCCTTCCGATGGAAGCACTAGACAAAGTTCACCTGAGCCTA<br>ATAGTCCCAGTGAATATTGTTTTTATGTGGATAGTGATATGGTCAATGAATTCAA<br>GTTGGAATTGGTAGAAAAACTTTTTGCTGAAGACACAGAAGCAAAGAACCCATTT<br>TCTACTCAGGACACAGATTTAGACTTGGAGATGTTAGCTCCCTATATCCCAATGG<br>ATGATGACTTCCAGTTACGTTCCTTCGATCAGTTGTCACCATTAGAAAGCAGTTC<br>CGCAAGCCCTGAAAGCGCAAGTCCTCAAAGCACAGTTACAGTATTCCAGCAGACT<br>CAAATACAAGAACCTACTGCTAATGCCACCACTACCACTGCCACCACTGATGAAT<br>TAAAAACAGTGACAAAAGACCGTATGGAAGACATTAAAATATTGATTGCATCTCC<br>ATCTCCTACCCACATACATAAAGAAACTACTAGTGCCACATCATCACCATATAGA<br>GATACTCAAAGTCGGACAGCCTCACCAAACAGAGCAGGAAAAGGAGTCATAGAAC<br>AGACAGAAAAATCTCATCCAAGAAGCCCTAACGTGTTATCTGTCGCTTTGAGTCA<br>AAGAACTACAGTTCCTGAGGAAGAACTAAATCCAAAGATACTAGCTTTGCAGAAT<br>GCTCAGAGAAAGCGAAAAATGGAACATGATGGTTCACTTTTTCAAGCAGTAGGAA<br>TTGGAACATTATTACAGCAGCCAGACGATCATGCAGCTACTACATCACTTTCTTG<br>GAAACGTGTAAAAGGATGCAAATCTAGTGAACAGAATGGAATGGAGCAAAAGACA<br>ATTATTTTAATACCCTCTGATTTAGCATGTAGACTGCTGGGGCAATCAATGGATG<br>AAAGTGGATTACCACAGCTGACCAGTTATGATTGTGAAGTTAATGCTCCTATACA<br>AGGCAGCAGAAACCTACTGCAGGGTGAAGAATTACTCAGAGCTTTGGATCAAGTT<br>AACTGA | |
| 35 | ATGCCTCCTCAGCTGCAAAACGGCCTGAACCTCTCGGCCAAAGTTGTCCAGGGAA<br>GCCTGGACAGCCTACCCCAGGCAGTGAGGGAGTTTCTCGAGAATAACGCTGAGCT<br>GTGTCAGCCTGATCACATCCACATCTGTGACGGCTCTGAGGAGGAGAATGGGCGG<br>CTTCTGGGCCAGATGGAGGAAGAGGGCATCCTCAGGCGGCTGAAGAAGTATGACA<br>ACTGCTGGTTGGCTCTCACTGACCCCAGGGATGTGGCCAGGATCGAAAGCAAGAC<br>GGTTATCGTCACCCAAGAGCAAAGAGACACAGTGCCCATCCCCAAAACAGGCCTC<br>AGCCAGCTCGGTCGCTGGATGTCAGAGGAGGATTTTGAGAAAGCGTTCAATGCCA<br>GGTTCCCAGGGTGCATGAAAGGTCGCACCATGTACGTCATCCCATTCAGCATGGG<br>GCCGCTGGGCTCGCCTCTGTCAAAGATCGGCATCGAGCTGACGGATTCACCCTAC<br>GTGGTGGCCAGCATGCGGATCATGACGCGGATGGGCACGCCCGTCCTGGAAGCAG<br>TGGGCGATGGGGAGTTTGTCAAATGCCTCCATTCTGTGGGGTGCCCTCTGCCTTT<br>ACAAAAGCCTTTGGTCAACAACTGGCCCTGCAACCCGGAGCTGACGCTCATCGCC<br>CACCTGCCTGACCGCAGAGAGATCATCTCCTTTGGCAGTGGGTACGGCGGGAACT<br>CGCTGCTCGGGAAGAAGTGCTTTGCTCTCAGGATGGCCAGCCGGCTGGCCAAGGA<br>GGAAGGGTGGCTGGCAGAGCACATGCTGATTCTGGGTATAACCAACCCTGAGGGT<br>GAGAAGAAGTACCTGGCGGCCGCATTTCCCAGCGCCTGCGGGAAGACCAACCTGG<br>CCATGATGAACCCCAGCCTCCCCGGGTGGAAGGTTGAGTGCGTCGGGGATGACAT<br>TGCCTGGATGAAGTTTGACGCACAAGGTCATTTAAGGGCCATCAACCCAGAAAAT<br>GGCTTTTTCGGTGTCGCTCCTGGGACTTCAGTGAAGACCAACCCCAATGCCATCA<br>AGACCATCCAGAAGAACACAATCTTTACCAATGTGGCCGAGACCAGCGACGGGGG<br>CGTTTACTGGGAAGGCATTGATGAGCCGCTAGCTTCAGGTGTCACCATCACGTCC<br>TGGAAGAATAAGGAGTGGAGCTCAGAGGATGGGGAACCTTGTGCCCACCCCAACT<br>CGAGGTTCTGCACCCCTGCCAGCCAGTGCCCCATCATTGATGCTGCCTGGGAGTC<br>TCCGGAAGGTGTTCCCATTGAAGGCATTATCTTTGGAGGCCGTAGACCTGCTGGT<br>GTCCCTCTAGTCTATGAAGCTCTCAGCTGGCAACATGGAGTCTTTGTGGGGGCGG<br>CCATGAGATCAGAGGCCACAGCGGCTGCAGAACATAAAGGCAAAATCATCATGCA<br>TGACCCCTTTGCCATGCGGCCCTTCTTTGGCTACAACTTCGGCAAATACCTGGCC<br>CACTGGCTTAGCATGGCCCAGCACCCAGCAGCCAAACTGCCCAAGATCTTCCATG<br>TCAACTGGTTCCGGAAGGACAAGGAAGGCAAATTCCTCTGGCCAGGCTTTGGAGA<br>GAACTCCAGGGTGCTGGAGTGGATGTTCAACCGGATCGATGGAAAAGCCAGCACC<br>AAGCTCACGCCCATAGGCTACATCCCCAAGGAGGATGCCCTGAACCTGAAAGGCC<br>TGGGGCACATCAACATGATGGAGCTTTTCAGCATCTCCAAGGAATTCTGGGAGAA<br>GGAGGTGGAAGACATCGAGAAGTATCTGGAGGATCAAGTCAATGCCGACCTCCCC<br>TGTGAAATCGAGAGAGAGATCCTTGCCTTGAAGCAAAGAATAAGCCAGATGTAA | PCK1<br>*Homo sapiens*<br>Coding sequence of<br>NCBI Reference<br>Sequence:<br>NM_002591.3 |
| 36 | ATGGATTTGTGGCCAGGGGCATGGATGCTGCTGCTGCTGCTCTTCCTGCTGCTGC<br>TCTTCCTGCTGCCCACCCTGTGGTTCTGCAGCCCCAGTGCCAAGTACTTCTTCAA<br>GATGGCCTTCTACAATGGCTGGATCCTCTTCCTGGCTGTGCTCGCCATCCCTGTG<br>TGTGCCGTGCGAGGACGCAACGTCGAGAACATGAAGATCTTGCGTCTAATGCTGC<br>TCCACATCAAATACCTGTACGGGATCCGAGTGGAGGTGCGAGGGGCTCACCACTT<br>CCCTCCCTCGCAGCCCTATGTTGTTGTCTCCAACCACCAGAGCTCTCTCGATCTG<br>CTTGGGATGATGGAGGTACTGCCAGGCCGCTGTGTGCCCATTGCCAAGCGCGAGC<br>TACTGTGGGCTGGCTCTGCCGGGCTGGCCTGCTGGCTGGCAGGAGTCATCTTCAT<br>CGACCGGAAGCGCACGGGGGATGCCATCAGTGTCATGTCTGAGGTCGCCCAGACC<br>CTGCTCACCCAGGACGTGAGGGTCTGGGTGTTTCCTGAGGGAACGAGAAACCACA<br>ATGGCTCCATGCTGCCCTTCAAACGTGGCGCCTTCCATCTTGCAGTGCAGGCCCA<br>GGTTCCCATTGTCCCCATAGTCATGTCCTCCTACCAAGACTTCTACTGCAAGAAG<br>GAGCGTCGCTTCACCTCGGGACAATGTCAGGTGCGGGTGCTGCCCCCAGTGCCCA<br>CGGAAGGGCTGACACCAGATGACGTCCCAGCTCTGGCTGACAGAGTCCGGCACTC | AGPAT1<br>*Homo sapiens*<br>Coding sequence of<br>NCBI Reference<br>Sequence:<br>NM_006411.3 |

-continued

SEQUENCES

| SEQ ID NO. | SEQUENCE | DESCRIPTION |
|---|---|---|
| | CATGCTCACTGTTTTCCGGGAAATCTCCACTGATGGCCGGGGTGGTGGTGACTAT<br>CTGAAGAAGCCTGGGGGCGGTGGGTGA | |
| 37 | ATGGAGCTGTGGCCGTGTCTGGCCGCGGCGCTGCTGTTGCTGCTGCTGCTGGTGC<br>AGCTGAGCCGCGCGGCCGAGTTCTACGCCAAGGTCGCCCTGTACTGCGCGCTGTG<br>CTTCACGGTGTCCGCCGTGGCCTCGCTCGTCTGCCTGCTGCGCCACGGCGGCCGG<br>ACGGTGGAGAACATGAGCATCATCGGCTGGTTCGTGCGAAGCTTCAAGTACTTTT<br>ACGGGCTCCGCTTCGAGGTGCGGGACCCGCGCAGGCTGCAGGAGGCCCGTCCCTG<br>TGTCATCGTCTCCAACCACCAGAGCATCCTGGACATGATGGGCCTCATGGAGGTC<br>CTTCCGGAGCGCTGCGTGCAGATCGCCAAGCGGGAGCTGCTCTTCCTGGGGCCCG<br>TGGGCCTCATCATGTACCTCGGGGGCGTCTTCTTCATCAACCGGCAGCGCTCTAG<br>CACTGCCATGACAGTGATGGCCGACCTGGGCGAGCGCATGGTCAGGGAGAACCTC<br>AAAGTGTGGATCTATCCCGAGGGTACTCGCAACGACAATGGGGACCTGCTGCCTT<br>TTAAGAAGGGCGCCTTCTACCTGGCAGTCCAGGCACAGGTGCCCATCGTCCCCGT<br>GGTGTACTCTTCCTTCTCCTCCTTCTACAACACCAAGAAGAAGTTCTTCACTTCA<br>GGAACAGTCACAGTGCAGGTGCTGGAAGCCATCCCCACCAGCGGCCTCACTGCGG<br>CGGACGTCCCTGCGCTCGTGGACACCTGCCACCGGGCCATGAGGACCACCTTCCT<br>CCACATCTCCAAGACCCCCCAGGAGAACGGGGCCACTGCGGGGTCTGGCGTGCAG<br>CCGGCCCAGTAG | AGPAT2 isoform α<br>precursor<br>*Homo sapiens*<br>Coding sequence of<br>NCBI Reference<br>Sequence:<br>NM_006412.3 |
| 38 | ATGGAGCTGTGGCCGTGTCTGGCCGCGGCGCTGCTGTTGCTGcTGcTGcTGGTGC<br>AGCTGAGCCGCGCGGCCGAGTTCTACGCCAAGGTCGCCCTGTACTGCGCGCTGTG<br>CTTCACGGTGTCCGCCGTGGCCTCGCTCGTCTGCCTGCTGCGCCACGGCGGCCGG<br>ACGGTGGAGAACATGAGCATCATCGGCTGGTTCGTGCGAAGCTTCAAGTACTTTT<br>ACGGGCTCCGCTTCGAGGTGCGGGACCCGCGCAGGCTGCAGGAGGCCCGTCCCTG<br>TGTCATCGTCTCCAACCACCAGAGCATCCTGGACATGATGGGCCTCATGGAGGTC<br>CTTCCGGAGCGCTGCGTGCAGATCGCCAAGCGGGAGCTGCTCTTCCTGGGGCCCG<br>TGGGCCTCATCATGTACCTCGGGGGCGTCTTCTTCATCAACCGGCAGCGCTCTAG<br>CACTGCCATGACAGTGATGGCCGACCTGGGCGAGCGCATGGTCAGGGAGAACGTG<br>CCCATCGTCCCCGTGGTGTACTCTTCCTTCTCCTCCTTCTACAACACCAAGAAGA<br>AGTTCTTCACTTCAGGAACAGTCACAGTGCAGGTGCTGGAAGCCATCCCCACCAG<br>CGGCCTCACTGCGGCGGACGTCCCTGCGCTCGTGGACACCTGCCACCGGGCCATG<br>AGGACCACCTTCCTCCACATCTCCAAGACCCCCCAGGAGAACGGGGCCACTGCGG<br>GGTCTGGCGTGCAGCCGGCCCAGTAG | AGPAT2 isoform β<br>precursor<br>*Homo sapiens*<br>Coding sequence of<br>NCBI Reference<br>Sequence:<br>NM_001012727.1 |
| 39 | ATGGGCCTGCTGGCCTTCCTGAAGACCCAGTTCGTGCTGCACCTGCTGGTCGGCT<br>TTGTCTTCGTGGTGAGTGGTCTGGTCATCAACTTCGTCCAGCTGTGCACGCTGGC<br>GCTCTGGCCGGTCAGCAAGCAGCTCTACCGCCGCCTCAACTGCCGCCTCGCCTAC<br>TCACTCTGGAGCCAACTGGTCATGCTGCTGGAGTGGTGGTCCTGCACGGAGTGTA<br>CACTGTTCACGGACCAGGCCACGGTAGAGCGCTTTGGGAAGGAGCACGCAGTCAT<br>CATCCTCAACCACAACTTCGAGATCGACTTCCTCTGTGGGTGGACCATGTGTGAG<br>CGCTTCGGAGTGCTGGGGAGCTCCAAGGTCCTCGCTAAGAAGGAGCTGCTCTACG<br>TGCCCCTCATCGGCTGGACGTGGTACTTTCTGGAGATTGTGTTCTGCAAGCGGAA<br>GTGGGAGGAGGACCGGGACACCGTGGTCGAAGGGCTGAGGCGCCTGTCGGACTAC<br>CCCGAGTACATGTGGTTTCTCCTGTACTGCGAGGGGACGCGCTTCACGGAGACCA<br>AGCACCGCGTTAGCATGGAGGTGGCGGCTGCTAAGGGGCTTCCTGTCCTCAAGTA<br>CCACCTGCTGCCGCGGACCAAGGGCTTCACCACCGCAGTCAAGTGCCTCCGGGGG<br>ACAGTCGCAGCTGTCTATGATGTAACCCTGAACTTCAGAGGAAACAAGAACCCGT<br>CCCTGCTGGGGATCCTCTACGGGAAGAAGTACGAGGCGGACATGTGCGTGAGGAG<br>ATTTCCTCTGGAAGACATCCCGCTGGATGAAAAGGAAGCAGCTCAGTGGCTTCAT<br>AAACTGTACCAGGAGAAGGACGCGCTCCAGGAGATATATAATCAGAAGGGCATGT<br>TTCCAGGGGAGCAGTTTAAGCCTGCCCGGAGGCCGTGGACCCTCCTGAACTTCCT<br>GTCCTGGGCCACCATTCTCCTGTCTCCCCTCTTCAGTTTTGTCTTGGGCGTCTTT<br>GCCAGCGGATCACCTCTCCTGATCCTGACTTTCTTGGGGTTTGTGGGAGCAGCTT<br>CCTTTGGAGTTCGCAGACTGATAGGAGTAACTGAGATAGAAAAAGGCTCCAGCTA<br>CGGAAACCAAGAGTTTAAGAAAAAGGAATAA | AGPAT3<br>*Homo sapiens*<br>Coding sequence of<br>NCBI Reference<br>Sequence:<br>NM_001037553.1<br>or NM_020132.4 |
| 40 | ATGTTCCTGTTGCTGCCTTTTGATAGCCTGATTGTCAACCTTCTGGGCATCTCCC<br>TGACTGTCCTCTTCACCCTCCTTCTCGTTTTCATCATAGTGCCAGCCATTTTTGG<br>AGTCTCCTTTGGTATCCGCAAACTCTACATGAAAAGTCTGTTAAAAATCTTTGCG<br>TGGGCTACCTTGAGAATGGAGCGAGGAGCCAAGGAGAAGAACCACCAGCTTTACA<br>AGCCCTACACCAACGGAATCATTGCAAAGGATCCCACTTCACTAGAAGAAGAGAT<br>CAAAGAGATTCGTCGAAGTGGTAGTAGTAAGGCTCTGGACAACACTCCAGAGTTC<br>GAGCTCTCTGACATTTTCTACTTTTGCCGGAAAGGAATGGAGACCATTATGGATG<br>ATGAGGTGACAAAGAGATTCTCAGCAGAAGAACTGGAGTCCTGGAACCTGCTGAG<br>CAGAACCAATTATAACTTCCAGTACATCAGCCTTCGGCTCACGGTCCTGTGGGGG<br>TTAGGAGTGCTGATTCGGTACTGCTTTCTGCTGCCGCTCAGGATAGCACTGGCTT<br>TCACAGGGATTAGCCTTCTGGTGGTGGGCACAACTGTGGTGGGATACTTGCCAAA<br>TGGGAGGTTTAAGGAGTTCATGAGTAAACATGTTCACTTAATGTGTTACCGGATC<br>TGCGTGCGAGCGCTGACAGCCATCATCACCTACCATGACAGGGAAAACAGACCAA<br>GAAATGGTGGCATCTGTGTGGCCAATCATACCTCACCGATCGATGTGATCATCTT<br>GGCCAGCGATGGCTATTATGCCATGGTGGGTCAAGTGCACGGGGGACTCATGGGT<br>GTGATTCAGAGAGCCATGGTGAAGGCCTGCCCACACGTCTGGTTTGAGCGCTCGG<br>AAGTGAAGGATCGCCACCTGGTGGCTAAGAGACTGACTGAACATGTGCAAGATAA | AGPAT6 (LPA-<br>MAG PA)<br>*Homo sapiens*<br>Coding sequence of<br>NCBI Reference<br>Sequence:<br>NM_178819.3 |

-continued

SEQUENCES

| SEQ ID NO. | SEQUENCE | DESCRIPTION |
|---|---|---|
| | AAGCAAGCTGCCTATCCTCATCTTCCCAGAAGGAACCTGCATCAATAATACATCG<br>GTGATGATGTTCAAAAAGGGAAGTTTTGAAATTGGAGCCACAGTTTACCCTGTTG<br>CTATCAAGTATGACCCTCAATTTGGCGATGCCTTCTGGAACAGCAGCAAATACGG<br>GATGGTGACGTACCTGCTGCGAATGATGACCAGCTGGGCCATTGTCTGCAGCGTG<br>TGGTACCTGCCTCCCATGACTAGAGAGGCAGATGAAGATGCTGTCCAGTTTGCGA<br>ATAGGGTGAAATCTGCCATTGCCAGGCAGGGAGGACTTGTGGACCTGCTGTGGGA<br>TGGGGGCCTGAAGAGGGAGAAGGTGAAGGACACGTTCAAGGAGGAGCAGCAGAAG<br>CTGTACAGCAAGATGATCGTGGGGAACCACAAGGACAGGAGCCGCTCCTGA | |
| 41 | ATGGCCACCATGTTGGAAGGCAGATGCCAAACTCAGCCAAGGAGCAGCCCCAGTG<br>GCCGAGAGGCTAGCCTGTGGTCGTCAGGCTTTGGGATGAAGCTGGAGGCTGTCAC<br>TCCATTCCTGGGGAAGTATCGCCCCTTTGTGGGTCGCTGTTGCCAGACCTGCACC<br>CCCAAGAGCTGGGAGTCCCTCTTCCACAGAAGCATAACGGACCTAGGCTTCTGCA<br>ATGTGATCCTGGTGAAGGAGGAGAACACAAGGTTTCGGGGCTGGCTGGTTCGGAG<br>GCTCTGCTATTTCCTGTGGTCCCTGGAGCAGCACATCCCCCCCTGCCAGGATGTC<br>CCACAGAAGATCATGGAAAGCACCGGGGTGCAGAACCTCCTCTCAGGGAGGGTCC<br>CAGGAGGCACTGGGGAAGGCCAGGTGCCTGACCTTGTGAAGAAGGAGGTACAGCG<br>CATCCTGGGTCACATCCAGGCCCCACCCCGTCCCTTCCTGGTCAGGCTGTTCAGC<br>TGGGCGCTGCTGAGGTTCCTGAACTGCCTGTTCCTGAATGTGCAGCTCCACAAGG<br>GTCAGATGAAGATGGTCCAGAAGGCCGCCCAGGCAGGCTTGCCGCTTGTCCTCCT<br>CTCTACTCACAAAACCCTCCTGGATGGGATCCTGCTGCCCTTTATGCTGCTCTCC<br>CAGGGCCTGGGTGTGCTTCGTGTGGCCTGGGACTCCCGCGCCTGCTCCCCTGCCC<br>TCAGAGCTCTGCTGAGGAAGCTTGGGGGGCTTTTCCTGCCCCCAGAGGCCAGCCT<br>CTCCCTGGACAGCTCTGAGGGGCTCCTTGCCAGGGCTGTGGTCCAGGCGGTCATA<br>GAGCAGCTGCTGGTTAGTGGGCAGCCCCTGCTCATCTTCCTGGAGGAACCTCCTG<br>GGGCTCTGGGGCCACGGCTGTCAGCCCTGGGCCAGGCTTGGGTGGGGTTTGTGGT<br>GCAGGCAGTCCAGGTGGGCATCGTCCCAGATGCTCTGCTGGTACCAGTGGCCGTC<br>ACCTATGACCTGGTTCCGGATGCACCGTGTGACATAGACCATGCCTCGGCCCCCC<br>TGGGGCTGTGGACAGGAGCTCTGGCTGTCCTACGTAGCTTGTGGAGCCGCTGGGG<br>CTGCAGCCACCGGATCTGCTCCCGGGTGCACCTAGCTCAGCCCTTTTCCCTGCAG<br>GAATACATCGTCAGTGCCAGAAGCTGCTGGGGCGGCAGACAGACCCTGGAGCAGC<br>TACTGCAGCCCATCGTGCTGGGCCAATGTACTGCTGTCCCAGACACTGAGAAGGA<br>GCAGGAGTGGACCCCCATAACTGGGCCTCTCCTGGCCCTCAAGGAAGAGGACCAG<br>CTCCTGGTCAGGAGACTGAGCTGTCATGTCCTGAGTGCCAGTGTAGGGAGCTCTG<br>CGGTGATGAGCACGGCCATTATGGCAACGCTGCTGCTCTTCAAGCATCAGAAGCT<br>CCTGGGGGAGTTCTCCTGGCTGACGGAGGAGATACTGTTGCGTGGCTTTGATGTA<br>GGCTTCTCTGGGCAGCTGCGGAGCCTGCTGCAGCACTCACTGAGCCTGCTGCGGG<br>CGCACGTGGCCCTGCTGCGCATCCGTCAGGGTGACTTGCTGGTGGTGCCGCAGCC<br>TGGCCCAGGCCTCACACACCTGGCACAACTGAGTGCTGAGCTGCTGCCCGTCTTC<br>CTGAGCGAGGCTGTGGGCGCCTGTGCAGTGCGGGGGCTGCTGGCAGGCAGAGTGC<br>CGCCCCAGGGGCCCTGGGAGCTGCAGGGCATATTGCTGCTGAGCCAGAATGAGCT<br>GTACCGCCAGATCCTGCTGCTGATGCACCTGCTGCCGCAAGACCTGCTGCTGCTA<br>AAGCCCTGCCAGTCTTCCTACTGCTACTGTCAGGAGGTGCTGGACCGGCTCATCC<br>AATGCGGGCTCCTGGTTGCTGAGGAGACCCCAGGCTCCCGGCCAGCCTGTGACAC<br>AGGGCGACAGCGATTGAGCAGAAAGCTGCTGTGGAAACCGAGTGGGGACTTTACT<br>GATAGTGACAGTGATGACTTCGGAGAGGCTGACGGCCGGTACTTCAGGCTCAGCC<br>AGCAGTCACACTGCCCAGATTTCTTTCTTTTCCTCTGCCGCCTGCTCAGCCCGCT<br>GCTCAAGGCCTTTGCACAGGCTGCCGCCTTCCTCCGCCAGGGCCAGCTGCCCGAT<br>ACTGAGTTGGGCTACACAGAGCAGCTGTTCCAGTTCCTGCAGGCCACCGCCCAGG<br>AAGAAGGGATCTTCGAGTGTGCGGACCCAAAGCTCGCCATCAGTGCTGTCTGGAC<br>CTTCAGAGACCTAGGGGTTCTGCAGCAGACGCCGAGCCCTGCAGGCCCCAGGCTC<br>CACCTGTCCCCTACTTTTGCCAGCCTGGACAATCAGGAAAAACTAGAACAGTTCA<br>TCCGGCAGTTCATTTGTAGCTAG | GPAT2<br>*Homo sapiens*<br>Coding sequence of NCBI Reference Sequence: NM_207328.2 |
| 42 | ATGGTAGAGTTCGCGCCCTTGTTTATGCCGTGGGAGCGCAGGCTGCAGACACTTG<br>CTGTCCTACAGTTTGTCTTCTCCTTCTTGGCACTGGCCGAGATCTGCACTGTGGG<br>CTTCATAGCCCTCCTGTTTACAAGATTCTGGCTCCTCACTGTCCTGTATGCGGCC<br>TGGTGGTATCTGGACCGAGACAAGCCACGGCAGGGGGGCCGGCACATCCAGGCCA<br>TCAGGTGCTGGACTATATGGAAGTACATGAAGGACTATTTCCCCATCTCGCTGGT<br>CAAGACTGCTGAGCTGGACCCCTCTCGGAACTACATTGCGGGCTTCCACCCCCAT<br>GGAGTCCTGGCAGTCGGAGCCTTTGCCAACCTGTGCACTGAGAGCACAGGCTTCT<br>CTTCGATCTTCCCCGGTATCCGCCCCCATCTGATGATGCTGACCTTGTGGTTCCG<br>GGCCCCCTTCTTCAGAGATTACATCATGTCTGCAGGGTTGGTCACATCAGAAAAG<br>GAGAGTGCTGCTCACATTCTGAACAGGAAGGGTGGCGGAAACTTGCTGGGCATCA<br>TTGTAGGGGGTGCCCAGGAGGCCCTGGATGCCAGGCCTGGATCCTTCACGCTGTT<br>ACTGCGGAACCGAAAGGGCTTCGTCAGGCTCGCCCTGACACACGGGGCACCCCTG<br>GTGCCAATCTTCTCCTTCGGGGAGAATGACCTATTTGACCAGATTCCCAACTCTT<br>CTGGCTCCTGGTTACGCTATATCCAGAATCGGTTGCAGAAGATCATGGGCATCTC<br>CCTCCCACTCTTTCATGGCCGTGGTGTCTTCCAGTACAGCTTTGGTTTAATACCC<br>TACCGCCGGCCCATCACCACTGTGGTGGGGAAGCCCATCGAGGTACAGAAGACGC<br>TGCATCCCTCGGAGGAGGAGGTGAACCAGCTGCACCAGCGTTATATCAAAGAGCT<br>GTGCAACCTCTTCGAGGCCCACAAACTTAAGTTCAACATCCCTGCTGACCAGCAC<br>TTGGAGTTCTGCTGA | MOGAT2<br>*Homo sapiens*<br>Coding sequence of NCBI Reference Sequence: NM_025098.2 |

-continued

SEQUENCES

| SEQ ID NO. | SEQUENCE | DESCRIPTION |
|---|---|---|
| 43 | ATGAAGACCCTCATAGCCGCCTACTCCGGGGTCCTGCGCGGCGAGCGTCAGGCCG<br>AGGCTGACCGGAGCCAGCGCTCTCACGGAGGACCTGCGCTGTCGCGCGAGGGGTC<br>TGGGAGATGGGGCACTGGATCCAGCATCCTCTCCGCCCTCCAGGACCTCTTCTCT<br>GTCACCTGGCTCAATAGGTCCAAGGTGGAAAAGCAGCTACAGGTCATCTCAGTGC<br>TCCAGTGGGTCCTGTCCTTCCTTGTACTGGGAGTGGCCTGCAGTGCCATCCTCAT<br>GTACATATTCTGCACTGATTGCTGGCTCATCGCTGTGCTCTACTTCACTTGGCTG<br>GTGTTTGACTGGAACACACCCAAGAAAGGTGGCAGGAGGTCACAGTGGGTCCGAA<br>ACTGGGCTGTGTGGCGCTACTTTCGAGACTACTTTCCCATCCAGCTGGTGAAGAC<br>ACACAACCTGCTGACCACCAGGAACTATATCTTTGGATACCACCCCCATGGTATC<br>ATGGGCCTGGGTGCCTTCTGCAACTTCAGCACAGAGGCCACAGAAGTGAGCAAGA<br>AGTTCCCAGGCATACGGCCTTACCTGGCTACACTGGCAGGCAACTTCCGAATGCC<br>TGTGTTGAGGGAGTACCTGATGTCTGGAGGTATCTGCCCTGTCAGCCGGGACACC<br>ATAGACTATTTGCTTTCAAAGAATGGGAGTGGCAATGCTATCATCATCGTGGTCG<br>GGGGTGCGGCTGAGTCTCTGAGCTCCATGCCTGGCAAGAATGCAGTCACCCTGCG<br>GAACCGCAAGGGCTTTGTGAAACTGGCCCTGCGTCATGGAGCTGACCTGGTTCCC<br>ATCTACTCCTTTGGAGAGAATGAAGTGTACAAGCAGGTGATCTTCGAGGAGGGCT<br>CCTGGGGCCGATGGGTCCAGAAGAAGTTCCAGAAATACATTGGTTTCGCCCCATG<br>CATCTTCCATGGTCGAGGCCTCTTCTCCTCCGACACCTGGGGGCTGGTGCCCTAC<br>TCCAAGCCCATCACCACTGTTGTGGGAGAGCCCATCACCATCCCCAAGCTGGAGC<br>ACCCAACCCAGCAAGACATCGACCTGTACCACACCATGTACATGGAGGCCCTGGT<br>GAAGCTCTTCGACAAGCACAAGACCAAGTTCGGCCTCCCGGAGACTGAGGTCCTG<br>GAGGTGAACTGA | DGAT2<br>*Homo sapiens*<br>Coding sequence of<br>NCBI Reference<br>Sequence:<br>NM_032564.4 |
| 44 | ATGCAGCCTGAGGGAGCAGAAAAGGGAAAAAGCTTCAAGCAGAGACTGGTCTTGA<br>AGAGCAGCTTAGCGAAAGAAACCCTCTCTGAGTTCTTGGGCACGTTCATCTTGAT<br>TGTCCTTGGATGTGGCTGTGTTGCCCAAGCTATTCTCAGTCGAGGACGTTTTGGA<br>GGGGTCATCACTATCAATGTTGGATTTTCAATGGCAGTTGCAATGGCCATTTATG<br>TGGCTGGCGGTGTCTCTGGTGGTCACATCAACCCAGCTGTGTCTTTAGCAATGTG<br>TCTCTTTGGACGGATGAAATGGTTCAAATTGCCATTTTATGTGGGAGCCCAGTTC<br>TTGGGAGCCTTTGTGGGGGCTGCAACCGTCTTTGGCATTTACTATGATGGACTTA<br>TGTCCTTTGCTGGTGGAAAACTGCTGATCGTGGGAGAAAATGCAACAGCACACAT<br>TTTTGCAACATACCCAGCTCCGTATCTATCTCTGGCGAACGCATTTGCAGATCAA<br>GTGGTGGCCACCATGATACTCCTCATAATCGTCTTTGCCATCTTTGACTCCAGAA<br>ACTTGGGAGCCCCCAGAGGCCTAGAGCCCATTGCCATCGGCCTCCTGATTATTGT<br>CATTGCTTCCTCCCTGGGACTGAACAGTGGCTGTGCCATGAACCCAGCTCGAGAC<br>CTGAGTCCCAGACTTTTCACTGCCTTGGCAGGCTGGGGGTTTGAAGTCTTCAGAG<br>CTGGAAACAACTTCTGGTGGATTCCTGTAGTGGGCCCTTTGGTTGGTGCTGTCAT<br>TGGAGGCCTCATCTATGTTCTTGTCATTGAAATCCACCATCCAGAGCCTGACTCA<br>GTCTTTAAGACAGAACAATCTGAGGACAAACCAGAGAAATATGAACTCAGTGTCA<br>TCATGTAG | AQP9<br>*Homo sapiens*<br>Coding sequence of<br>NCBI Reference<br>Sequence:<br>NM_020980.3 |
| 45 | ATGAATTACGTGGGGCAGTTAGCCGGCCAGGTGTTTGTCACCGTGAAGGAGCTCT<br>ACAAGGGGCTGAATCCCGCCACACTCTCAGGGTGCATTGACATCATTGTCATCCG<br>CCAGCCCAATGGAAACCTCCAATGCTCCCCTTTCCACGTCCGCTTTGGGAAGATG<br>GGGGTCCTGCGCTCCCGAGAGAAAGTGGTTGACATAGAAATCAATGGGGAATCTG<br>TGGATTTGCATATGAAATTGGGAGATAATGGAGAAGCATTTTTTGTTCAAGAAAC<br>AGATAATGATCAGGAAGTTATCCCTATGCACCTGGCCACCTCCCCCATCCTGTCA<br>GAAGGAGCTTCGAGAATGGAATGCCAGCTGAAAAGGGGCTCTGTGGACAGGATGA<br>GAGGCCTGGACCCCAGCACGCCAGCCCAAGTGATCGCTCCCAGCGAGACGCCGTC<br>AAGCAGCTCTGTAGTAAAGAAGAGAAGAAAAAGGAGGAGAAAGTCACAGCTGGAC<br>AGCCTGAAGAGAGATGACAACATGAACACATCTGAGGATGAGGACATGTTCCCCA<br>TCGAGATGAGCTCGGATGAGGCCATGGAGCTGCTGGAGAGCAGCAGAACTCTTCC<br>TAATGATATACCTCCATTCCAAGATGATATTCCTGAGGAAAACCTCTCCCTGGCT<br>GTGATTTACCCTCAGTCAGCCTCATACCCTAATTCGGATAGAGAGTGGTCACCCA<br>CTCCCAGTCCTTCCGGTTCCCGACCTTCAACACCTAAAAGTGATTCAGAATTGGT<br>CAGCAAGTCCACGGAAAGGACAGGGCAGAAGAACCCAGAAATGCTTTGGCTGTGG<br>GGAGAGCTGCCGCAGGCTGCTAAGTCTTCTTCTCCACACAAGATGAAAGAGTCCA<br>GCCCATTGAGCAGTAGAAAAATTTGTGATAAAAGTCACTTTCAGGCCATTCACAG<br>CGAATCTTCAGACACTTTTAGTGACCAATCGCCAACTCTGGTCGGTGGGGCACTT<br>TTGGACCAGAACAAGCCTCAGACAGAAATGCAGTTTGTGAATGAAGAAGACCTGG<br>AGACCTTAGGAGCAGCAGCGCCACTCTTGCCCATGATCGAGGAGCTCAAACCCCC<br>CTCTGCCAGTGTAGTCCAGACAGCAAACAAGACGGATTCTCCTTCCAGGAAAAGA<br>GATAAACGAAGCCGACATCTTGGTGCTGACGGCGTCTACTTGGATGACCTCACAG<br>ACATGGATCCTGAAGTGGCGGCCCTGTATTTTCCCAAAAACGGAGATCCTTCCGG<br>ACTCGCAAAACATGCAAGCGACAACGGAGCCCGGTCAGCCAACCAGTCCCCGCAG<br>TCGGTGGGCAGCTCGGGCGTGGACAGTGGCGTGGAGAGCACCTCGGACGGGCTGA<br>GGGACCTCCCTTCCATCGCCATCTCCCTCTGCGGGGGCCTCAGCGACCACCGGGA<br>GATCACGAAAGATGCATTCCTGGAGCAAGCTGTGTCATATCAACAGTTTGTGGAC<br>AACCCCGCTATTATCGATGACCCCAATCTCGTGGTAAAGATTGGGAGTAAATATT<br>ATAACTGGACAACAGCAGCACCCCTCCTCCTGGCAATGCAGGCCTTCCAGAAACC<br>TTTGCCAAAGGCCACTGTGGAATCTATCATGAGGGATAAAATGCCCAAAAAGGGA<br>GGAAGATGGTGGTTTTCATGGAGGGGAAGAAACACCACAATCAAGGAGGAAAGTA<br>AGCCAGAGCAGTGCTTGGCTGGCAAGGCCCATAGCACCGGAGAGCAACCGCCGCA<br>GCTCAGCTTGGCCACCAGGGTAAAGCATGAATCATCCTCCAGTGATGAGGAGCGC | LPIN1 (Lipin 1)<br>*Homo sapiens*<br>Coding sequence of<br>NCBI Reference<br>Sequence:<br>NM_145693.2 |

-continued

SEQUENCES

| SEQ ID NO. | SEQUENCE | DESCRIPTION |
|---|---|---|
| | GCAGCTGCCAAGCCATCAAACGCAGGCCACCTCCCTCTTCTGCCTAATGTCAGCT ACAAGAAGACTCTCCGGCTGACTTCCGAGCAGCTTAAAAGCTTGAAGTTGAAGAA TGGCCCCAACGACGTGGTTTTCAGTGTCACCACGCAGTACCAAGGCACGTGCCGC TGTGAGGGCACCATCTATCTGTGGAACTGGGATGATAAAGTCATCATTTCTGATA TTGATGGGACAATTACCAGATCAGATACTCTTGGCCACATTTTGCCCACCCTTGG GAAGGATTGGACCCATCAGGGCATCGCTAAGCTGTACCATAAAGTGAGCCAGAAT GGATATAAATTTCTCTACTGTTCTGCCCGTGCCATCGGGATGGCGGACATGACGC GGGGCTACCTGCACTGGGTCAACGAGAGGGGCACGGTGCTGCCCCAGGGGCCCCT GCTGCTGAGTCCCAGCAGCCTCTTCTCTGCCCTGCACAGAGAAGTGATTGAAAAG AAGCCAGAAAAGTTTAAAGTCCAGTGTTTGACAGACATCAAAAACCTGTTTTTCC CCAACACAGAACCCTTTTATGCTGCTTTTGGAAACCGACCAGCTGATGTGTATTC ATACAAGCAAGTAGGAGTGTCTTTGAATAGAATATTTACCGTCAACCCTAAAGGA GAGCTGGTACAGGAACATGCAAAGACCAACATCTCTTCGTATGTGAGACTCTGTG AAGTAGTCGACCACGTTTTCCCGTTGCTGAAAAGAAGCCATTCTTCAGACTTTCC CTGTTCGGATACCTTCAGTAACTTCACCTTTTGGAGAGAGCCACTGCCACCTTTT GAAAACCAGGACATTCATTCTGCCTCAGCGTAA | |
| 46 | ATGGCGGCGTCCGTGCGACAGGCACGCAGCCTACTAGGTGTGGCGGCGACCCTGG CCCCGGGTTCCCGTGGCTACCGGGCGCGGCCGCCCCCGCGCCGCAGGCCGGGACC CCGGTGGCCAGACCCCGAGGACCTCCTGACCCCGCGGTGGCAGCTGGGACCGCGC TACGCGGCTAAGCAGTTCGCGCGTTACGGCGCCGCCTCCGGGGTGGTCCCCGGTT CGTTATGGCCGTCGCCGGAGCAGCTGCGGGAGCTGGAGGCCGAAGAACGCGAATG GTACCCGAGCCTGGCGACCATGCAGGAGTCGCTGCGGGTGAAGCAGCTGGCCGAA GAGCAGAAGCGTCGGGAGAGGGAGCAGCACATCGCAGAGTGCATGGCCAAGATGC CACAGATGATTGTGAACTGGCAGCAGCAGCAGCGGGAGAACTGGGAGAAGGCCCA GGCTGACAAGGAGAGGAGGGCCCGACTGCAGGCTGAGGCCCAGGAGCTCCTGGGC TACCAGGTGGACCCAAGGAGTGCCCGCTTCCAGGAGCTGCTCCAGGACCTAGAGA AGAAGGAGCGCAAGCGCCTCAAGGAGGAAAAACAGAAACGGAAGAAGGAGGCGCG AGCTGCTGCATTGGCTGCAGCTGTGGCTCAAGACCCAGCAGCCTCTGGGGCACCC AGCTCCTGA | CRIF1 *Homo sapiens* Coding sequence of NCBI Reference Sequence: NM_052850.3 |
| 47 | ATGCAGATCCCACAGGCGCCCTGGCCAGTCGTCTGGGCGGTGCTACAACTGGGCT GGCGGCCAGGATGGTTCTTAGACTCCCCAGACAGGCCCTGGAACCCCCCCACCTT CTCCCCAGCCCTGCTCGTGGTGACCGAAGGGGACAACGCCACCTTCACCTGCAGC TTCTCCAACACATCGGAGAGCTTCGTGCTAAACTGGTACCGCATGAGCCCCAGCA ACCAGACGGACAAGCTGGCCGCCTTCCCCGAGGACCGCAGCCAGCCCGGCCAGGA CTGCCGCTTCCGTGTCACACAACTGCCCAACGGGCGTGACTTCCACATGAGCGTG GTCAGGGCCCGGCGCAATGACAGCGGCACCTACCTCTGTGGGGCCATCTCCCTGG CCCCCAAGGCGCAGATCAAAGAGAGCCTGCGGGCAGAGCTCAGGGTGACAGAGAG AAGGGCAGAAGTGCCCACAGCCCACCCCAGCCCCTCACCCAGGCCAGCCGGCCAG TTCCAAACCCTGGTGGTTGGTGTCGTGGGCGGCCTGCTGGGCAGCCTGGTGCTGC TAGTCTGGGTCCTGGCCGTCATCTGCTCCCGGGCCGCACGAGGGACAATAGGAGC CAGGCGCACCGGCCAGCCCCTGAAGGAGGACCCCTCAGCCGTGCCTGTGTTCTCT GTGGACTATGGGGAGCTGGATTTCCAGTGGCGAGAGAAGACCCCGGAGCCCCCCG TGCCCTGTGTCCCTGAGCAGACGGAGTATGCCACCATTGTCTTTCCTAGCGGAAT GGGCACCTCATCCCCCGCCCGCAGGGGCTCAGCTGACGGCCCTCGGAGTGCCCAG CCACTGAGGCCTGAGGATGGACACTGCTCTTGGCCCCTCTGA | PD1 *Homo sapiens* Coding sequence of GenBank: KJ865859.1 |
| 48 | ATGAGACCTCGCACCCACGGCGCCCCCCCGCGCAACATCATGTCCACCATCCCCA AGTGGTTCAAAGGGGCGCCCTTTGGGGTGCAGAGCCACAGGTTTGATGTCTCCGC TGTCTATCCCAACCAGAAGAAATTCAGCACCTTCACAGAGGCCCCATACTCCAGA CATCATTCGGTGGAACTGTCCCACATAGGACCTGGGACCTATAACTCCAAGGATA CCTGCTTCAGCAAGAAGTTCCTGGAACAGAAGTTGGGCTCAGGATGGTCCCAGGC CCACGAAGCCACTCGGCTGACCCAGCTACCCCACTTCCACTACCAGGCCATCAAG AAGGAAAAAGAGCAGCAGGTGCACAAGCGTGGCCCTGGCTCCTACAACATCAAAG ACTTCATAACTGAGCTGCAGAAGAAACCACAGAGCAAACGGGGGCTGCTCAGCTC TGGGGAGACACGTTTCCGAGGTTTTATTGGGAATTATTATCCTGGCCCTGGAAAT TATGGGGAGAAGGGGAACCCGTACACACAGCTGGAGGAGAAGGCCTGGAACCGCT CACATTCTGACGGCCTGATGTGTAGAGTGTCTAACAAGCCACCCTTGTTTCATCA GGGCAGTGGCCTGGGACCTGGTACCTACACCATCAAAAGCGATCTTGAGACCTTT GTGAAAAAGTCCACTGGTAATCGTGGCCCCTATGACATTTTCTCTGGTGAACGGA GCAGTCCTTTGCCCTATGGACATTACTCTGTGCAGAAAATGAAGCCCAAGGAACT GACAGATTACAAGAGCTTTCTGGACGAAATGAACTCACAACACAAGAAGAAACAA GGGGTTTTCTCGAAATATCCCCGAGATCCGAAACACCCCACAGAGAGAATTTTCT GGACAACCCTTAGTCAGTGCCCCAAAAATATGGATATAGCTGGCCCTGGTTCTTG GCTTCCTCATGAGACGGAACAGAAACATGTCAACCGGCCACCGTTCCTCCTGGCC TCCAAACGGTGCGGCCTAAAGGCCTACCAGATGATTTTGGGAACCTGGAACCCAG TTGGCGTAGGCCGCTATCTCAACACCACGCTGATGGAGTCCATAGACCGAAGGCA GCGATACCGTTCTCTGTACATGAGTGAGCCCAAGCGATACCTGCAAGACCTAACC CGAGACAGACTCATGCAGAAACGGATTACACCTATTACGAAGGGCAAGTGCCGTC CAACTGTGGACTACAATTCAGATCCTACTCCTTAA | Lymphocyte expansion molecule (LEM) *Mus musculus* Coding sequence of GenBank: KP939367.1 |

-continued

SEQUENCES

| SEQ ID NO. | SEQUENCE | DESCRIPTION |
|---|---|---|
| 49 | ESKYGPPCPPCP | spacer (IgG4hinge) (aa) *Homo sapiens* |
| 50 | GAATCTAAGTACGGACCGCCCTGCCCCCCTTGCCCT | spacer (IgG4hinge) (nt) *Homo sapiens* |
| 51 | ESKYGPPCPPCPGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQ KSLSLSLGK | Hinge-CH3 spacer *Homo sapiens* |
| 52 | ESKYGPPCPPCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQ KSLSLSLGK | Hinge-CH2-CH3 spacer *Homo sapiens* |
| 53 | RWPESPKAQASSVPTAQPQAEGSLAKATTAPATTRNTGRGGEEKKKEKEKEEQEE RETKTPECPSHTQPLGVYLLTPAVQDLWLRDKATFTCFVVGSDLKDAHLTWEVAG KVPTGGVEEGLLERHSNGSQSQHSRLTLPRSLWNAGTSVTCTLNHPSLPPQRLMA LREPAAQAPVKLSLNLLASSDPPEAASWLLCEVSGFSPPNILLMWLEDQREVNTS GFAPARPPPQPGSTTFWAWSVLRVPAPPSPQPATYTCVVSHEDSRTLLNASRSLE VSYVTDH | IgD-hinge-Fc *Homo sapiens* |
| 54 | LEGGGEGRGSLLTCGDVEENPGPR | T2A artificial |
| 55 | MLLLVTSLLLCELPHPAFLLIPRKVCNGIGIGEFKDSLSINATNIKHFKNCTSIS GDLHILPVAFRGDSFTHTPPLDPQELDILKTVKEITGFLLIQAWPENRTDLHAFE NLEIIRGRTKQHGQFSLAVVSLNITSLGLRSLKEISDGDVIISGNKNLCYANTIN WKKLFGTSGQKTKIISNRGENSCKATGQVCHALCSPEGCWGPEPRDCVSCRNVSR GRECVDKCNLLEGEPREFVENSECIQCHPECLPQAMNITCTGRGPDNCIQCAHYI DGPHCVKTCPAGVMGENNTLVWKYADAGHVCHLCHPNCTYGCTGPGLEGCPTNGP KIPSIATGMVGALLLLLVVALGIGLFM | tEGFR artificial |
| 56 | FWVLVVVGGVLACYSLLVTVAFIIFWV | CD28 (amino acids 153-179 of Accession No. P10747) *Homo sapiens* |
| 57 | IEVMYPPPYLDNEKSNGTIIHVKGKHLCPSPLFPGPSKPFWVLVVVGGVLACYSL LVTVAFIIFWV | CD28 (amino acids 114-179 of Accession No. P10747) *Homo sapiens* |
| 58 | RSKRSRLLHSDYMNMTPRRPGPTRKHYQPYAPPRDFAAYRS | CD28 (amino acids 180-220 of P10747) *Homo sapiens* |
| 59 | RSKRSRGGHSDYMNMTPRRPGPTRKHYQPYAPPRDFAAYRS | CD28 (LL to GG) *Homo sapiens* |
| 60 | KRGRKKLLYIFKQPFMRPVQTTQEEDGCSCRFPEEEEGGCEL | 4-1BB (amino acids 214-255 of Q07011.1) *Homo sapiens* |
| 61 | RVKFSRSADAPAYQQGQNQLYNELNLGRREEYDVLDKRRGRDPEMGGKPRRKNPQ EGLYNELQKDKMAEAYSEIGMKGERRRGKGHDGLYQGLSTATKDTYDALHMQALP PR | CD3 zeta *Homo sapiens* |
| 62 | RVKFSRSAEPPAYQQGQNQLYNELNLGRREEYDVLDKRRGRDPEMGGKPRRKNPQ EGLYNELQKDKMAEAYSEIGMKGERRRGKGHDGLYQGLSTATKDTYDALHMQALP PR | CD3 zeta *Homo sapiens* |
| 63 | RVKFSRSADAPAYKQGQNQLYNELNLGRREEYDVLDKRRGRDPEMGGKPRRKNPQ EGLYNELQKDKMAEAYSEIGMKGERRRGKGHDGLYQGLSTATKDTYDALHMQALP PR | CD3 zeta *Homo sapiens* |

-continued

| SEQ ID NO. | SEQUENCE | DESCRIPTION |
|---|---|---|
| 64 | EGRGSLLTCGDVEENPGP | T2A |
| 65 | GSGATNFSLLKQAGDVEENPGP | P2A |
| 66 | ATNFSLLKQAGDVEENPGP | P2A |
| 67 | QCTNYALLKLAGDVESNPGP | E2A |
| 68 | VKQTLNFDLLKLAGDVESNPGP | F2A |
| 69 | MRESQDAAGAHGWNRVGSTATKWFTGAPFGVQSHREDISAVYPNWKKFSTFTEAP YSTRYSTQVSHIGPGTYSSKETCFSKKKLMKEVDTGWAKAQEATRLTQLPHFQYQ AIMKEKRLKEQKLGPGSYNLKDFLEQLREKPCSTRGLLSSGEVRFRGLTGNYYPG PGNYGEKGNPYTKLEENAWNRSHSEGLMCRMSNKPHPRPHQGSGLGPGTYFEKSD LETYVARSVGTRGPYDTFSGDRSKPLPYGHYSMQKKKPRELMNEKSFVEELNSHH NKKHGVESKLPRNPKTPTERIYWANLSQCPRTLATSGPSEWLPQEKKCKPVNQPP FLLTSKGSGAKACQMIMGSWNPVGVGRYLNTWLMETKDRRQRYRSLELSGSKRYL SDLARDMLMQERITPFTKGKCPPTVDYNSDPTP | lymphocyte expansion molecule (LEM) isoform 2 *Homo sapiens* NCBI Reference Sequence: NP_001104003.1 |
| 70 | ATGAGGGAAAGCCAGGATGCCGCCGGAGCTCATGGCTGGAACCGCGTCGGCTCCA CGGCCACCAAGTGGTTCACCGGGGCGCCCTTCGGGGTGCAGAGCCACAGGTTTGA CATCTCTGCTGTTTATCCCAACTGGAAGAAGTTCAGCACCTTCACTGAGGCCCCA TACTCCACGCGTTATTCTACCCAAGTGTCCCACATAGGCCCTGGGACTTACAGCT CCAAAGAGACCTGCTTCAGCAAGAAGAAGCTGATGAAGGAGGTGGACACAGGCTG GGCCAAGGCCCAGGAAGCCACGCGGCTGACCCAGCTACCCCACTTCCAGTACCAG GCCATCATGAAAGAGAAGCGGCTGAAGGAGCAAAAGCTGGGCCCCGGCTCCTACA ACCTCAAAGACTTCTTAGAACAGCTGCGGGAGAAACCATGTAGCACCCGGGGGCT GCTCAGCTCTGGGGAGGTTCGCTTCCGAGGACTCACTGGGAACTACTATCCAGGC CCTGGAAATTATGGGGAGAAGGGTAACCCATACACCAAGCTGGAGGAGAATGCCT GGAACCGGTCTCATTCCGAGGGCCTCATGTGCAGGATGAGCAACAAGCCACACCC CCGGCCTCATCAGGGGAGTGGTCTGGGACCCGGCACCTACTTCTTCAAAAGCGAC CTTGAGACATATGTGGCACGATCCGTCGGCACCCCGCGGCCCCTATGACACTTTCT CTGGTGATCGGAGCAAGCCACTGCCTTATGGGCACTACTCCATGCAGAAAAAAAA GCCCAGGGAACTGATGAATTTCAAGAGCTTTGTAGAAGAACTTAACTCACATCAC AATAAGAAGCATGGGGTTTTTTCTAAACTTCCCCGAAACCCGAAAACCCCTACAG AGAGGATTTACTGGGCCAACCTCAGCCAGTGCCCCCGCACACTGGCCACATCTGG CCCCAGTTTCTGGCTTCCACAAGAGAAGAAATGCAAACCCGTCAACCAGCCCCCA TTCCTGTTGACCTCCAAGGGGTCAGGTGCAAAGGCCTGCCAGATGATTATGGGAA GCTGGAACCCAGTAGGTGTGGGCCGCTACCTCAACACCTGGCTGATGGAGACAAA GGACAGGCGGCAGCGATATCGATCCCTATTCCTGAGTGGATCCAAACGCTACCTC TCAGACCTGGCCCGGGACATGCTCATGCAGGAAAGGATCACACCATTTACTAAGG GAAAGTGCCCTCCAACTGTGGATTACAATTCAGATCCTACTCCT | lymphocyte expansion molecule (LEM) isoform 2 *Homo sapiens* NCBI Reference Sequence: NM_001110533.1 |
| 71 | CTCGAGGGCGGCGGAGAGGGCAGAGGAAGTCTTCTAACATGCGGTGACGTGGAGG AGAATCCCGGCCCTAGG | T2A (nt) |
| 72 | MLLLVTSLLLCELPHPAFLLIP | GMCSFR alpha chain signal sequence *Homo sapiens* UniProt No. P15509 |
| 73 | ATGCTTCTCCTGGTGACAAGCCTTCTGCTCTGTGAGTTACCACACCCAGCATTCC TCCTGATCCCA | GMCSFR alpha chain signal sequence DNA *Homo sapiens* |
| 74 | TGCCACCCTGAGTGTCAGCCCCAGAATGGCTCAGTGACCTGTTTTGGACCGGAGG CTGACCAGTGTGTGGCCTGTGCCCACTATAAGGACCCTCCCTTCTGCGTGGCCCG CTGCCCCAGCGGTGTGAAACCTGACCTCTCCTACATGCCCATCTGGAAGTTTCCA GATGAGGAGGGCGCATGCCAGCCTTGCCCCATCAACTGCACCCACTCCTGTGTGG ACCTGGATGACAAGGGCTGCCCCGCCGAGCAGAGAGCCAGCCCTCTGACGGGTGG AGGAAGCGGAGGTGGCAGCTCCATCATCTCTGCGGTGGTTGGCATTCTGCTGGTC GTGGTCTTGGGGGTGGTCTTTGGGATCCTCATC | Modified Her2t (nt) |
| 75 | CHPECQPQNGSVTCFGPEADQCVACAHYKDPPFCVARCPSGVKPDLSYMPIWKFP DEEGACQPCPINCTHSCVDLDDKGCPAEQRASPLTGGGSGGGSSIISAVVGILLV VVLGVVFGILI | Modified Her2t (aa) |
| 76 | ATGGGCGATCGCGGCAGCTCCCGGAGAAGGCGCACCGGCAGCCGGCCCTCTAGCC ACGGCGGCGGCGGCCCTGCTGCCGCCGAGGAGGAGGTGCGCGACGCCGCCGCCGG CCCTGATGTGGGAGCAGCAGGCGACGCACCAGCACCTGCCCCAAACAAGGACGGC | DAG O-acetyltransferase 1 (DGAT1) (nt) |

-continued

SEQUENCES

| SEQ ID NO. | SEQUENCE | DESCRIPTION |
|---|---|---|
| | GATGCAGGAGTGGGAAGCGGACACTGGGAGCTGAGATGCCACAGGCTGCAGGATT<br>CCCTGTTCTCCTCTGACAGCGGCTTTTCCAACTACAGAGGCATCCTGAATTGGTG<br>CGTGGTCATGCTGATCCTGTCCAACGCCAGGCTGTTCCTGGAGAATCTGATCAAG<br>TACGGCATCCTGGTGGATCCTATCCAGGTGGTGAGCCTGTTTCTGAAGGACCCAT<br>ATTCCTGGCCAGCACCTTGCCTGGTCATCGCAGCAAACGTGTTCGCAGTGGCAGC<br>CTTTCAGGTGGAGAAGCGGCTGGCCGTGGGCGCCCTGACCGAGCAGGCAGGCCTG<br>CTGCTGCACGTGGCCAATCTGGCCACAATCCTGTGCTTCCCAGCAGCAGTGGTGC<br>TGCTGGTGGAGTCTATCACCCCTGTGGGAAGCCTGCTGGCCCTGATGGCACACAC<br>AATCCTGTTCCTGAAGCTGTTTTCCTACAGAGACGTGAATTCTTGGTGTAGGAGA<br>GCAAGGGCAAAGGCAGCCTCTGCCGGCAAGAAGGCCAGCAGCGCCGCCGCCCCTC<br>ACACCGTGAGCTACCCAGATAACCTGACATATAGAGACCTGTACTATTTCCTGTT<br>TGCCCCCACCCTGTGCTATGAGCTGAATTTCCCAAGGTCCCCCAGGATCCGCAAG<br>CGGTTTCTGCTGAGGCGCATCCTGGAGATGCTGTTCTTTACCCAGCTGCAAGTGG<br>GCCTGATCCAGCAGTGGATGGTGCCAACAATCCAGAACTCCATGAAGCCCTTCAA<br>GGACATGGATTACTCTAGAATCATCGAGAGGCTGCTGAAGCTGGCCGTGCCCAAC<br>CACCTGATCTGGCTGATCTTCTTTTATTGGCTGTTTCACTCTTGCCTGAATGCCG<br>TGGCCGAGCTGATGCAGTTCGGCGATCGCGAGTTTTACCGGGACTGGTGGAATTC<br>CGAGTCTGTGACATATTTCTGGCAGAACTGGAATATCCCAGTGCACAAGTGGTGT<br>ATCCGCCACTTTTACAAGCCCATGCTGCGGAGAGGCTCTAGCAAGTGGATGGCCA<br>GAACCGGCGTGTTCCTGGCCTCTGCCTTCTTTCACGAGTATCTGGTGAGCGTGCC<br>TCTGCGCATGTTCCGGCTGTGGGCCTTTACAGGCATGATGGCCCAGATCCCACTG<br>GCCTGGTTTGTGGGCCGGTTCTTTCAGGGCAACTACGGCAATGCCGCCGTGTGGC<br>TGAGCCTGATCATCGGCCAGCCCATCGCCGTGCTGATGTACGTGCACGATTACTA<br>TGTGCTGAACTATGAGGCCCCTGCCGCCGAGGCC | |
| 77 | ATGGCAGCCAGCAAGAAGGCCGTGCTGGGCCCACTGGTGGGAGCAGTGGACCAGG<br>GCACCAGCTCCACAAGGTTCCTGGTGTTTAATAGCAAGACCGCAGAGCTGCTGTC<br>CCACCACCAGGTGGAGATCAAGCAGGAGTTTCCAAGGGAGGGATGGGTGGAGCAG<br>GACCCAAAGGAGATCCTGCACTCCGTGTACGAGTGCATCGAGAAGACCTGTGAGA<br>AGCTGGGCCAGCTGAATATCGACATCAGCAACATCAAGGCCATCGGCGTGTCCAA<br>TCAGCGGGAGACCACAGTGGTGTGGGACAAGATCACAGGCGAGCCCCTGTATAAC<br>GCCGTGGTGTGGCTGGATCTGAGGACCCAGAGCACAGTGGAGTCCCTGTCTAAGC<br>GCATCCCTGGCAACAATAACTTTGTGAAGTCCAAGACCGGCCTGCCACTGTCCAC<br>ATATTTCTCTGCCGTGAAGCTGAGGTGGCTGCTGGACAATGTGCGCAAGGTGCAG<br>AAGGCCGTGGAGGAGAAGAGGGCCCTGTTTGGCACCATCGATTCTTGGCTGATCT<br>GGAGCCTGACAGGAGGAGTGAACGGAGGCGTGCACTGCACCGACGTGACAAATGC<br>CTCTCGGACCATGCTGTTCAACATCCACAGCCTGGAGTGGGATAAGCAGCTGTGC<br>GAGTTCTTTGGCATCCCTATGGAGATCCTGCCAAACGTGAGATCTAGCTCCGAGA<br>TCTATGGCCTGATGAAGATCAGCCACTCCGTGAAGGCAGGCGCCCTGGAGGGAGT<br>GCCTATCTCTGGATGCCTGGGCGACCAGAGCGCCGCCCTGGTGGGACAGATGTGC<br>TTCCAGATCGGCCAGGCCAAGAATACCTACGGCACAGGCTGCTTTCTGCTGTGCA<br>ACACCGGCCACAAGTGCGTGTTCAGCGACCACGGCCTGCTGACCACAGTGGCCTA<br>TAAGCTGGGCAGGGATAAGCCCGTGTACTATGCACTGGAGGGATCTGTGGCAATC<br>GCAGGAGCCGTGATCAGGTGGCTGAGAGATAATCTGGGCATCATCAAGACCAGCG<br>AGGAGATCGAGAAGCTGGCCAAGGAAGTGGGCACATCCTACGGCTGTTATTTCGT<br>GCCTGCCTTTTCTGGCCTGTACGCACCATATTGGGAGCCAAGCGCCAGGGGAATC<br>ATCTGCGGCCTGACCCAGTTCACAAACAAGTGTCACATCGCCTTTGCCGCCCTGG<br>AGGCCGTGTGCTTCCAGACCCGGGAGATCCTGGACGCCATGAATAGAGATTGTGG<br>CATCCCTCTGTCCCACCTGCAGGTGGACGGAGGCATGACATCTAACAAGATCCTG<br>ATGCAGCTGCAGGCCGACATCCTGTATATCCCAGTGGTGAAGCCCTCCATGCCTG<br>AGACCACAGCCCTGGGAGCAGCAATGGCAGCAGGAGCAGCCGAGGGCGTGGGCGT<br>GTGGTCCCTGGAGCCAGAGGACCTGTCTGCCGTGACCATGGAGCGGTTTGAGCCT<br>CAGATCAATGCCGAGGAGTCCGAGATCAGATACTCTACATGGAAGAAGGCCGTGA<br>TGAAGTCCATGGGCTGGGTGACCACACAGTCTCCCGAGAGCGGCGATCCTAGCAT<br>CTTCTGCTCCCTGCCACTGGGCTTCTTTATCGTGTCTAGCATGGTCATGCTGATC<br>GGCGCCCGGTATATCTCTGGCATCCCC | Glycerol kinase (Gyk) (nt) |
| 78 | ATGGACGAGTCCGCCCTGACACTGGGCACCATCGACGTGAGCTACCTGCCACACA<br>GCTCCGAGTATTCTGTGGGCAGGTGCAAGCACACAAGCGAGGAGTGGGGAGAGTG<br>TGGCTTCCGGCCAACAATCTTTAGATCCGCCACCCTGAAGTGGAAGGAGAGCCTG<br>ATGTCCCGGAAGAGACCATTCGTGGGCCGGTGCTGTTACTCCTGCACCCCCCAGT<br>CTTGGGACAAGTTCTTTAACCCTTCTATCCCAAGCCTGGGCCTGAGAAACGTGAT<br>CTACATCAATGAGACCCACACAAGGCACAGGGGATGGCTGGCCCGGAGACTGAGC<br>TATGTGCTGTTCATCCAGGAGAGGGACGTGCACAAGGGCATGTTTGCCACAAATG<br>TGACCGAGAACGTGCTGAATTCTAGCCGCGTGCAGGAGGCAATCGCAGAGGTGGC<br>AGCAGAGCTGAACCCTGATGGAAGCGCCCAGCAGCAGTCCAAGGCAGTGAATAAG<br>GTGAAGAAGAAGGCCAAGCGGATCCTGCAGGAGATGGTGGCCACAGTGTCCCCAG<br>CCATGATCAGACTGACCGGCTGGGTGCTGCTGAAGCTGTTCAACTCTTTCTTTTG<br>GAATATCCAGATCCACAAGGGCCAGCTGGAGATGGTGAAGGCCGCCACCGAGACA<br>AACCTGCCACTGCTGTTTCTGCCCGTGCACCGCAGCCACATCGATTACCTGCTGC<br>TGACCTTCATCCTGTTTTGTCACAACATCAAGGCCCCTTATATCGCCAGCGGCAA<br>CAATCTGAATATCCCAATCTTCTCCACACTGATCCACAAGCTGGGCGGCTTCTTT<br>ATCAGGCGCCGGCTGGATGAGACCCCTGACGGCAGGAAGGATGTGCTGTACCGCG<br>CCCTGCTGCACGGACACATCGTGGAGCTGCTGAGGCAGCAGCAGTTCCTGGAGAT | Glycerol-3-phosphate acetyltransferase mitochondrial (GPAM) (nt) |

-continued

SEQUENCES

| SEQ ID NO. | SEQUENCE | DESCRIPTION |
|---|---|---|
| | CTTTCTGGAGGGCACACGGTCTAGAAGCGGCAAGACCTCCTGCGCAAGGGCAGGA CTGCTGTCCGTGGTGGTGGACACACTGTCTACCAACGTGATCCCCGACATCCTGA TCATCCCTGTGGGCATCTCTTACGACCGGATCATCGAGGGCCACTATAACGGCGA GCAGCTGGGCAAGCCCAAGAAGAATGAGTCCCTGTGGTCTGTGGCCAGGGGCGTG ATCCGGATGCTGAGAAAGAATTACGGATGCGTGCGGGTGGATTTCGCACAGCCTT TTTCCCTGAAGGAGTATCTGGAGTCCCAGTCTCAGAAGCCCGTGAGCGCCCTGCT GTCCCTGGAGCAGGCCCTGCTGCCTGCAATCCTGCCAAGCAGACCTTCCGATGCA GCAGACGAGGGAAGGGACACATCTATCAACGAGAGCAGAAATGCCACCGATGAGA GCCTGAGAAGGCGCCTGATCGCCAACCTGGCCGAGCACATCCTGTTCACAGCCAG CAAGTCCTGCGCCATCATGAGCACCCACATCGTGGCCTGTCTGCTGCTGTACCGG CACAGGCAGGGAATCGACCTGTCCACACTGGTGGAGGATTTCTTTGTGATGAAGG AGGAGGTGCTGGCCAGGGACTTCGATCTGGGCTTTTCTGGCAATAGCGAGGACGT GGTCATGCACGCCATCCAGCTGCTGGGCAACTGCGTGACCATCACACACACCTCC CGCAATGATGAGTTCTTTATCACCCCTTCTACCACAGTGCCAAGCGTGTTCGAGC TGAACTTTTACTCTAATGGCGTGCTGCACGTGTTTATCATGGAGGCCATCATCGC CTGCAGCCTGTATGCCGTGCTGAACAAGAGGGGACTGGGCGGCCCAACAAGCACC CCCCCTAATCTGATCTCCCAGGAGCAGCTGGTGAGAAAGGCCGCCTCCCTGTGCT ATCTGCTGTCTAACGAGGGCACAATCAGCCTGCCCTGCCAGACCTTCTACCAGGT GTGCCACGAGACAGTGGGCAAGTTTATCCAGTATGGCATCCTGACCGTGGCCGAG CACGACGATCAGGAGGACATCTCTCCTAGCCTGGCCGAGCAGCAGTGGGATAAGA AGCTGCCAGAGCCCCTGTCCTGGAGGTCTGACGAGGAGGACGAGGATAGCGACTT CGGCGAGGAGCAGCGCGATTGTTACCTGAAGGTGTCCCAGTCTAAGGAGCACCAG CAGTTCATCACCTTTCTGCAGCGGCTGCTGGGCCCACTGCTGGAGGCCTATTCCT CTGCCGCCATCTTCGTGCACAACTTTTCCGGCCCTGTGCCAGAGCCAGAGTACCT GCAGAAGCTGCACAAGTATCTGATCACAAGGACCGAGAGGAACGTGGCCGTGTAC GCAGAGAGCGCCACCTATTGCCTGGTGAAGAATGCCGTGAAGATGTTCAAGGACA TCGGCGTGTTTAAGGAGACAAAGCAGAAGCGGGTGTCTGTGCTGGAGCTGAGCTC CACCTTCCTGCCCCAGTGTAATAGACAGAAGCTGCTGGAGTACATCCTGAGCTTT GTGGTGCTG | |
| 79 | ATGGAGGGCGCCGGCGGCGCCAACGATAAGAAGAAGATCAGCTCCGAGCGGAGAA AGGAGAAGAGCAGGGACGCAGCACGCTCTAGGCGCAGCAAGGAGTCCGAGGTGTT CTACGAGCTGGCCCACCAGCTGCCACTGCCACACAACGTGTCTAGCCACCTGGAT AAGGCCAGCGTGATGCGGCTGACCATCTCCTATCTGCGGGTGAGAAAGCTGCTGG ACGCCGGCGATCTGGACATCGAGGACGATATGAAGGCCCAGATGAATTGCTTCTA CCTGAAGGCCCTGGACGGCTTTGTGATGGTGCTGACCGACGATGGCGACATGATC TACATCTCCGATAACGTGAATAAGTATATGGGCCTGACCCAGTTTGAGCTGACAG GCCACAGCGTGTTCGACTTTACCCACCCCTGCGATCACGAGGAGATGAGGGAGAT GCTGACACACCGCAACGGCCTGGTGAAGAAGGGCAAGGAGCAGAATACCCAGCGG TCTTTCTTTCTGAGAATGAAGTGTACCCTGACAAGCAGGGGCCGCACCATGAACA TCAAGTCCGCCACATGGAAGGTGCTGCACTGCACCGGCCACATCCACGTGTACGA TACCAACTCCAATCAGCCACAGTGTGGCTATAAGAAGCCCCCTATGACATGCCTG GTGCTGATCTGTGAGCCTATCCCACACCCCTCTAATATCGAGATCCCCCTGGACA GCAAGACCTTCCTGTCTCGGCACAGCCTGGACATGAAGTTTAGCTACTGCGATGA GAGAATCACAGAGCTGATGGGCTATGAGCCTGAGGAGCTGCTGGGCAGATCTATC TACGAGTACTATCACGCCCTGGATAGCGACCACCTGACCAAGACACACCACGACA TGTTCACCAAGGGCCAGGTGACCACAGGCCAGTACAGGATGCTGGCCAAGAGGGG AGGATACGTGTGGGTGGAGACCCAGGCCACAGTGATCTATAACACCAAGAATAGC CAGCCCCAGTGCATCGTGTGCGTGAACTACGTGGTGTCCGGCATCATCCAGCACG ATCTGATCTTTTCTCTGCAGCAGACCGAGTGCGTGCTGAAGCCTGTGGAGTCCTC TGACATGAAGATGACCCAGCTGTTCACAAAGGTGGAGTCCGAGGACACAAGCTCC CTGTTTGATAAGCTGAAGAAGGAGCCAGACGCACTGACCCTGCTGGCCCCAGCAG CAGGCGATACAATCATCTCTCTGGACTTCGGCAGCAATGATACCGAGACAGACGA TCAGCAGCTGGAGGAGGTGCCTCTGTATAACGATGTGATGCTGCCTTCTCCAAAT GAGAAGCTGCAGAACATCAATCTGGCAATGAGCCCACTGCCTACCGCAGAGACAC CAAAGCCACTGAGGTCTAGCGCCGACCCAGCCCTGAACCAGGAGGTGGCCCTGAA GCTGGAGCCTAATCCAGAGTCCCTGGAGCTGTCTTTTACAATGCCACAGATCCAG GACCAGACCCCATCCCCTTCTGATGGCAGCACACGCCAGTCCTCTCCAGAGCCCA ACAGCCCTTCCGAGTACTGCTTCTATGTGGATTCCGACATGGTGAATGAGTTCAA GCTGGAGCTGGTGGAGAAGCTGTTTGCCGAGGATACCGAGGCCAAGAACCCCTTC AGCACCCAGGATACAGACCTGGATCTGGAGATGCTGGCCCCCTATATCCCTATGG ACGATGACTTCCAGCTGCGGTCCTTTGACCAGCTGTCTCCTCTGGAGAGCTCCTC TGCCTCCCCTGAGTCTGCCAGCCCACAGTCTACCGTGACAGTGTTCCAGCAGACC CAGATCCAGGAGCCAACAGCCAATGCCACCACAACCACAGCCACCACAGATGAGC TGAAGACCGTGACAAAGGACCGGATGGAGGACATCAAGATCCTGATCGCCTCCCC TTCTCCAACCCACATCCACAAGGAGACCACATCCGCCACAAGCTCCCCTTACCGG GACACCCAGAGCAGAACAGCCTCCCCAAACAGAGCCGGCAAGGGCGTGATCGAGC AGACCGAGAAGTCTCACCCAAGGAGCCCCAATGTGCTGTCCGTGGCCCTGTCTCA GCGCACCACAGTGCCCGAGGAGGAGCTGAACCCTAAGATCCTGGCCCTGCAGAAT GCCCAGCGGAAGAGAAAGATGGAGCACGATGGAAGCCTGTTCCAGGCAGTGGGAA TCGGCACCCTGCTGCAGCAGCCAGATGACCACGCCGCCACCACAAGCCTGTCCTG GAAGAGGGTGAAGGGCTGTAAGTCTAGCGAGCAGAACGGCATGGAGCAGAAGACC ATCATCCTGATCCCATCCGACCTGGCATGCAGGCTGCTGGGCCAGAGCATGGATG | HIF1α (nt) |

-continued

SEQUENCES

| SEQ ID NO. | SEQUENCE | DESCRIPTION |
|---|---|---|
| | AGTCCGGCCTGCCCCAGCTGACAAGCTACGACTGTGAGGTGAACGCCCCTATCCA GGGCTCCCGGAATCTGCTGCAGGGCGAGGAGCTGCTGAGAGCCCTGGACCAGGTG AAT | |
| 80 | ATGAAGGTGGAGTTCGCCCCTCTGAACATCCAGCTGGCCCGGAGACTGCAGACCG TGGCCGTGCTGCAGTGGGTGCTGAAGTACCTGCTGCTGGGCCCAATGTCCATCGG CATCACAGTGATGCTGATCATCCACAATTACCTGTTCCTGTATATCCCCTATCTG ATGTGGCTGTATTTTGACTGGCACACCCCTGAGAGGGGCGGCAGGCGCAGCTCCT GGATCAAGAACTGGACACTGTGGAAGCACTTCAAGGATTACTTTCCAATCCACCT GATCAAGACCCAGGACCTGGATCCTTCTCACAATTATATCTTCGGCTTTCACCCA CACGGAATCATGGCAGTGGGAGCCTTCGGCAACTTTAGCGTGAATTACTCCGACT TCAAGGATCTGTTCCCCGGCTTTACCAGCTATCTGCACGTGCTGCCACTGTGGTT CTGGTGCCCCGTGTTTAGAGAGTACGTGATGTCCGTGGGCCTGGTGTCTGTGAGC AAGAAGTCCGTGTCTTATATGGTGTCCAAGGAGGGCGGCGGCAACATCTCTGTGA TCGTGCTGGGAGGAGCAAAGGAGTCTCTGGACGCCCACCCTGGCAAGTTCACCCT GTTTATCCGGCAGAGAAAGGGCTTTGTGAAGATCGCCCTGACACACGGAGCCTCT CTGGTGCCAGTGGTGAGCTTCGGCGAGAACGAGCTGTTTAAGCAGACCGATAATC CCGAGGGCAGCTGGATCAGGACAGTGCAGAACAAGCTGCAGAAGATCATGGGCTT CGCACTGCCACTGTTTCACGCAAGGGGCGTGTTCCAGTACAATTTTGGCCTGATG ACCTATAGAAAGGCCATCCACACAGTGGTGGGCAGGCCCATCCCTGTGCGCCAGA CCCTGAATCCCACACAGGAGCAGATCGAGGAGCTGCACCAGACCTACATGGAGGA GCTGCGCAAGCTGTTCGAGGAGCACAAGGGCAAGTATGGCATCCCTGAGCACGAG ACACTGGTGCTGAAG | MOGAT1 (nt) |
| 81 | ATGCCCCCTCAGCTGCAGAACGGCCTGAATCTGTCCGCCAAGGTGGTGCAGGGCT CCCTGGACTCTCTGCCTCAGGCCGTGAGGGAGTTTCTGGAGAACAATGCCGAGCT GTGCCAGCCAGACCACATCCACATCTGTGATGGCTCTGAGGAGGAGAACGGCCGC CTGCTGGGACAGATGGAGGAGGAGGGCATCCTGCGGAGACTGAAGAAGTACGATA ATTGCTGGCTGGCCCTGACCGACCCAAGGGATGTGGCACGCATCGAGAGCAAGAC CGTGATCGTGACACAGGAGCAGAGGGACACCGTGCCAATCCCCAAGACAGGCCTG TCTCAGCTGGGCCGCTGGATGAGCGAGGAGGATTTCGAGAAGGCCTTTAACGCCC GGTTCCCTGGCTGTATGAAGGGCAGAACCATGTACGTGATCCCCTTCAGCATGGG ACCTCTGGGAAGCCCACTGTCCAAGATCGGCATCGAGCTGACAGACTCCCCATAT GTGGTGGCCTCTATGCGGATCATGACCAGAATGGGAACACCCGTGCTGGAGGCAG TGGGCGATGGCGAGTTCGTGAAGTGCCTGCACTCCGTGGGCTGTCCTCTGCCACT GCAGAAGCCCCTGGTGAACAATTGGCCCTGCAACCCTGAGCTGACCCTGATCGCA CACCTGCCTGACAGGAGGGAGATCATCTCTTTTGGCAGCGGCTACGGCGGCAATA GCCTGCTGGGCAAGAAGTGTTTCGCACTGAGGATGGCCTCCCGCCTGGCCAAGGA GGAGGGATGGCTGGCCGAGCACATGCTGATCCTGGGCATCACCAATCCCGAGGGC GAGAAGAAGTATCTGGCTGCCGCCTTTCCTTCTGCCTGCGGCAAGACAAACCTGG CCATGATGAATCCAAGCCTGCCAGGATGGAAGGTGGAGTGCGTGGGCGACGACAT CGCCTGGATGAAGTTCGATGCACAGGGACACCTGAGGGCCATCAACCCAGAGAAT GGCTTCTTTGGCGTGGCCCCAGGCACCTCTGTGAAGACAAACCCCAATGCCATCA AGACCATCCAGAAGAACACCATCTTTACAAATGTGGCCGAGACAAGCGACGGAGG CGTGTACTGGGAGGGAATCGATGAGCCCCTGGCCAGCGGCGTGACCATCACATCC TGGAAGAACAAGGAGTGGAGCTCCGAGGACGGAGAGCCATGCGCACACCCTAATT CCAGATTCTGCACCCCCGCCTCTCAGTGTCCTATCATCGATGCAGCATGGGAGTC TCCAGAGGGAGTGCCAATCGAGGGCATCATCTTTGGCGGCCGGAGACCTGCAGGA GTGCCACTGGTGTATGAGGCCCTGTCCTGGCAGCACGGCGTGTTCGTGGGAGCAG CAATGCGGTCTGAGGCAACAGCTGCCGCCGAGCACAAGGGCAAGATCATCATGCA CGACCCATTTGCCATGAGACCCTTCTTTGGCTACAACTTCGGCAAGTATCTGGCA CACTGGCTGTCCATGGCACAGCACCCTGCAGCAAAGCTGCCAAAGATCTTTCACG TGAATTGGTTCAGGAAGGATAAGGAGGGCAAGTTTCTGTGGCCTGGCTTCGGCGA GAACAGCAGGGTGCTGGAGTGGATGTTCAATCGCATCGACGGCAAGGCCTCCACC AAGCTGACACCCATCGGCTACATCCCTAAGGAGGATGCCCTGAACCTGAAGGGCC TGGGCCACATCAATATGATGGAGCTGTTTTCTATCAGCAAGGAGTTCTGGGAGAA GGAGGTGGAGGACATCGAGAAGTATCTGGAGGACCAGGTGAACGCCGATCTGCCC TGTGAGATCGAGCGGGAGATCCTGGCCCTGAAGCAGAGAATCTCCCAGATG | PCK1 (nt) |
| 82 | GGGSGGGS | Linker |
| 83 | RKVCNGIGIGEFKDSLSINATNIKHFKNCTSISGDLHILPVAFRGDSFTHTPPLD PQELDILKTVKEITGFLLIQAWPENRTDLHAFENLEIIRGRTKQHGQFSLAVVSL NITSLGLRSLKEISDGDVIISGNKNLCYANTINWKKLFGTSGQKTKIISNRGENS CKATGQVCHALCSPEGCWGPEPRDCVSCRNVSRGRECVDKCNLLEGEPREFVENS ECIQCHPECLPQAMNITCTGRGPDNCTQCAHYIDGPHCVKTCPAGVMGENNTLVW KYADAGHVCHLCHPNCTYGCTGPGLEGCPTNGPKIPSIATGMVGALLLLLVVALG IGLFM | tEGFR artificial |
| 84 | ATGAGGGAAAGCCAGGATGCCGCCGGAGCTCATGGCTGGAACCGCGTCGGCTCCA CGGCCACCAAGTGGTTCACCGGGGCGCCCTTCGGGGTGCAGAGCCACAGGTTTGA CATCTCTGCTGTTTATCCCAACTGGAAGAAGTTCAGCACCTTCACTGAGGCCCCA TACTCCACGCGTTATTCTACCCAAGTGTCCCACATAGGCCCTGGGACTTACAGCT CCAAAGAGACCTGCTTCAGCAAGAAGAAGCTGATGAAGGAGGTGGACACAGGCTG | huLEM-T2A-Her2t (nt) |

-continued

SEQUENCES

| SEQ ID NO. | SEQUENCE | DESCRIPTION |
|---|---|---|
| | GGCCAAGGCCCAGGAAGCCACGCGGCTGACCCAGCTACCCCACTTCCAGTACCAG<br>GCCATCATGAAAGAGAAGCGGCTGAAGGAGCAAAAGCTGGGCCCCGGCTCCTACA<br>ACCTCAAAGACTTCTTAGAACAGCTGCGGGAGAAACCATGTAGCACCCGGGGGCT<br>GCTCAGCTCTGGGGAGGTTCGCTTCCGAGGACTCACTGGGAACTACTATCCAGGC<br>CCTGGAAATTATGGGGAGAAGGGTAACCCATACACCAAGCTGGAGGAGAATGCCT<br>GGAACCGGTCTCATTCCGAGGGCCTCATGTGCAGGATGAGCAACAAGCCACACCC<br>CCGGCCTCATCAGGGGAGTGGTCTGGGACCCGGCACCTACTTCTTCAAAAGCGAC<br>CTTGAGACATATGTGGCACGATCCGTCGGCACCCGCGGCCCCTATGACACTTTCT<br>CTGGTGATCGGAGCAAGCCACTGCCTTATGGGCACTACTCCATGCAGAAAAAAAA<br>GCCCAGGGAACTGATGAATTTCAAGAGCTTTGTAGAAGAACTTAACTCACATCAC<br>AATAAGAAGCATGGGGTTTTTTCTAAACTTCCCCGAAACCCGAAAACCCCTACAG<br>AGAGGATTTACTGGGCCAACCTCAGCCAGTGCCCCCGCACACTGGCCACATCTGG<br>CCCCAGTTTCTGGCTTCCACAAGAGAAGAAATGCAAACCCGTCAACCAGCCCCCA<br>TTCCTGTTGACCTCCAAGGGGTCAGGTGCAAAGGCCTGCCAGATGATTATGGGAA<br>GCTGGAACCCAGTAGGTGTGGGCCGCTACCTCAACACCTGGCTGATGGAGACAAA<br>GGACAGGCGGCAGCGATATCGATCCCTATTCCTGAGTGGATCCAAACGCTACCTC<br>TCAGACCTGGCCCGGGACATGCTCATGCAGGAAAGGATCACACCATTTACTAAGG<br>GAAAGTGCCCTCCAACTGTGGATTACAATTCAGATCCTACTCCTCTCGAGGGCGG<br>CGGAGAGGGCAGAGGAAGTCTTCTAACATGCGGTGACGTGGAGGAGAATCCCGGC<br>CCTAGGATGCTTCTCCTGGTGACAAGCCTTCTGCTCTGTGAGTTACCACACCCAG<br>CATTCCTCCTGATCCCATGCCACCCTGAGTGTCAGCCCCAGAATGGCTCAGTGAC<br>CTGTTTTGGACCGGAGGCTGACCAGTGTGTGGCCTGTGCCCACTATAAGGACCCT<br>CCCTTCTGCGTGGCCCGCTGCCCCAGCGGTGTGAAACCTGACCTCTCCTACATGC<br>CCATCTGGAAGTTTCCAGATGAGGAGGGCGCATGCCAGCCTTGCCCCATCAACTG<br>CACCCACTCCTGTGTGGACCTGGATGACAAGGGCTGCCCCGCCGAGCAGAGAGCC<br>AGCCCTCTGACGGGTGGAGGAAGCGGAGGTGGCAGCTCCATCATCTCTGCGGTGG<br>TTGGCATTCTGCTGGTCGTGGTCTTGGGGGTGGTCTTTGGGATCCTCATC | |
| 85 | MRESNAAGAHGWNRVGSTATKWFTGAPFGVQSHRFDISAVYPNWKKFSTFTEAP<br>YSTRYSTQVSHIGPGTYSSKETCFSKKKLMKEVDTGWAKAQEATRLTQLPHFQYQ<br>AIMKEKRLKEQKLGPGSYNLKDFLEQLREKPCSTRGLLSSGEVRFRGLTGNYYPG<br>PGNYGEKGNPYTKLEENAWNRSHSEGLMCRMSNKPHPRPHQGSGLGPGTYFFKSD<br>LETYVARSVGTRGPYDTFSGDRSKPLPYGHYSMQKKKPRELMNFKSFVEELNSHH<br>NKKHGVFSKLPRNPKTPTERIYWANLSQCPRTLATSGPSFWLPQEKKCKPVNQPP<br>FLLTSKGSGAKACQMIMGSWNPVGVGRYLNTWLMETKDRRQRYRSLFLSGSKRYL<br>SDLARDMLMQERITPFTKGKCPPTVDYNSDPTPLEGGGEGRGSLLTCGDVEENPG<br>PRMLLLVTSLLLCELPHPAFLLIPCHPECQPQNGSVTCFGPEADQCVACAHYKDP<br>PFCVARCPSGVKPDLSYMPIWKFPDEEGACQPCPINCTHSCVDLDDKGCPAEQRA<br>SPLTGGGSGGGSSIISAVVGILLVVVLGVVFGILI | huLEM-T2A-Her2t<br>(aa) |
| 86 | ATGGGCGATCGCGGCAGCTCCCGGAGAAGGCGCACCGGCAGCCGGCCCTCTAGCC<br>ACGGCGGCGGCGGCCCTGCTGCCGCCGAGGAGGAGGTGCGCGACGCCGCCGCCGG<br>CCCTGATGTGGGAGCAGCAGGCGACGCACCAGCACCTGCCCCAAACAAGGACGGC<br>GATGCAGGAGTGGGAAGCGGACACTGGGAGCTGAGATGCCACAGGCTGCAGGATT<br>CCCTGTTCTCCTCTGACAGCGGCTTTTCCAACTACAGAGGCATCCTGAATTGGTG<br>CGTGGTCATGCTGATCCTGTCCAACGCCAGGCTGTTCCTGGAGAATCTGATCAAG<br>TACGGCATCCTGGTGGATCCTATCCAGGTGGTGAGCCTGTTTCTGAAGGACCCAT<br>ATTCCTGGCCAGCACCTTGCCTGGTCATCGCAGCAAACGTGTTCGCAGTGGCAGC<br>CTTTCAGGTGGAGAAGCGGCTGGCCGTGGGCGCCCTGACCGAGCAGGCAGGCCTG<br>CTGCTGCACGTGGCCAATCTGGCCACAATCCTGTGCTTCCCAGCAGCAGTGGTGC<br>TGCTGGTGGAGTCTATCACCCCTGTGGGAAGCCTGCTGGCCCTGATGGCACACAC<br>AATCCTGTTCCTGAAGCTGTTTTCCTACAGAGACGTGAATTCTTGGTGTAGGAGA<br>GCAAGGGCAAAGGCAGCCTCTGCCGGCAAGAAGGCCAGCAGCGCCGCCGCCCCTC<br>ACACCGTGAGCTACCCAGATAACCTGACATATAGAGACCTGTACTATTTCCTGTT<br>TGCCCCCACCCTGTGCTATGAGCTGAATTTCCCAAGGTCCCCCAGGATCCGCAAG<br>CGGTTTCTGCTGAGGCGCATCCTGGAGATGCTGTTCTTTACCCAGCTGCAAGTGG<br>GCCTGATCCAGCAGTGGATGGTGCCAACAATCCAGAACTCCATGAAGCCCTTCAA<br>GGACATGGATTACTCTAGAATCATCGAGAGGCTGCTGAAGCTGGCCGTGCCCAAC<br>CACCTGATCTGGCTGATCTTCTTTTATTGGCTGTTTCACTCTTGCCTGAATGCCG<br>TGGCCGAGCTGATGCAGTTCGGCGATCGCGAGTTTTACCGGGACTGGTGGAATTC<br>CGAGTCTGTGACATATTTCTGGCAGAACTGGAATATCCCAGTGCACAAGTGGTGT<br>ATCCGCCACTTTTACAAGCCCATGCTGCGGAGAGGCTCTAGCAAGTGGATGGCCA<br>GAACCGGCGTGTTCCTGGCCTCTGCCTTCTTTCACGAGTATCTGGTGAGCGTGCC<br>TCTGCGCATGTTCCGGCTGTGGGCCTTTACAGGCATGATGGCCCAGATCCCACTG<br>GCCTGGTTTGTGGGCCGGTTCTTTCAGGGCAACTACGGCAATGCCGCCGTGTGGC<br>TGAGCCTGATCATCGGCCAGCCCATCGCCGTGCTGATGTACGTGCACGATTACTA<br>TGTGCTGAACTATGAGGCCCCTGCCGCCGAGGCCCTCGAGGGCGGCGGAGAGGGC<br>AGAGGAAGTCTTCTAACATGCGGTGACGTGGAGGAGAATCCCGGCCCTAGGATGC<br>TTCTCCTGGTGACAAGCCTTCTGCTCTGTGAGTTACCACACCCAGCATTCCTCCT<br>GATCCCATGCCACCCTGAGTGTCAGCCCCAGAATGGCTCAGTGACCTGTTTTGGA<br>CCGGAGGCTGACCAGTGTGTGGCCTGTGCCCACTATAAGGACCCTCCCTTCTGCG<br>TGGCCCGCTGCCCCAGCGGTGTGAAACCTGACCTCTCCTACATGCCCATCTGGAA<br>GTTTCCAGATGAGGAGGGCGCATGCCAGCCTTGCCCCATCAACTGCACCCACTCC<br>TGTGTGGACCTGGATGACAAGGGCTGCCCCGCCGAGCAGAGAGCCAGCCCTCTGA | DGAT1-T2A-Her2t<br>(nt) |

-continued

| SEQ ID NO. | SEQUENCE | DESCRIPTION |
|---|---|---|
| | CGGGTGGAGGAAGCGGAGGTGGCAGCTCCATCATCTCTGCGGTGGTTGGCATTCT<br>GCTGGTCGTGGTCTTGGGGGTGGTCTTTGGGATCCTCATC | |
| 87 | MGDRGSSRRRRTGSRPSSHGGGGPAAAEEEVRDAAAGPDVGAAGDAPAPAPNKDG<br>DAGVGSGHWELRCHRLQDSLFSSDSGFSNYRGILNWCVVMLILSNARLFLENLIK<br>YGILVDPIQVVSLFLKDPYSWPAPCLVIAANVFAVAAFQVEKRLAVGALTEQAGL<br>LLHVANLATILCFPAAVVLLVESITPVGSLLALMAHTILFLKLFSYRDVNSWCRR<br>ARAKAASAGKKASSAAAPHTVSYPDNLTYRDLYYFLFAPTLCYELNFPRSPRIRK<br>RFLLRRILEMLFFTQLQVGLIQQWMVPTIQNSMKPFKDMDYSRIIERLLKLAVPN<br>HLIWLIFFYWLFHSCLNAVAELMQFGDREFYRDWWNSESVTYFWQNWNIPVHKWC<br>IRHFYKPMLRRGSSKWMARTGVFLASAFFHEYLVSVPLRMFRLWAFTGMMAQIPL<br>AWFVGRFFQGNYGNAAVWLSLIIGQPIAVLMYVHDYYVLNYEAPAAEALEGGGEG<br>RGSLLTCGDVEENPGPRMLLLVTSLLLCELPHPAFLLIPCHPECQPQNGSVTCFG<br>PEADQCVACAHYKDPPFCVARCPSGVKPDLSYMPIWKFPDEEGACQPCPINCTHS<br>CVDLDDKGCPAEQRASPLTGGGSGGGSSIISAVVGILLVVVLGVVFGILI | DGAT1-T2A-Her2t (aa) |
| 88 | ATGGCAGCCAGCAAGAAGGCCGTGCTGGGCCCACTGGTGGGAGCAGTGGACCAGG<br>GCACCAGCTCCACAAGGTTCCTGGTGTTTAATAGCAAGACCGCAGAGCTGCTGTC<br>CCACCACCAGGTGGAGATCAAGCAGGAGTTTCCAAGGGAGGGATGGGTGGAGCAG<br>GACCCAAAGGAGATCCTGCACTCCGTGTACGAGTGCATCGAGAAGACCTGTGAGA<br>AGCTGGGCCAGCTGAATATCGACATCAGCAACATCAAGGCCATCGGCGTGTCCAA<br>TCAGCGGGAGACCACAGTGGTGTGGGACAAGATCACAGGCGAGCCCCTGTATAAC<br>GCCGTGGTGTGGCTGGATCTGAGGACCCAGAGCACAGTGGAGTCCCTGTCTAAGC<br>GCATCCCTGGCAACAATAACTTTGTGAAGTCCAAGACCGGCCTGCCACTGTCCAC<br>ATATTTCTCTGCCGTGAAGCTGAGGTGGCTGCTGGACAATGTGCGCAAGGTGCAG<br>AAGGCCGTGGAGGAGAAGAGGGCCCTGTTTGGCACCATCGATTCTTGGCTGATCT<br>GGAGCCTGACAGGAGGAGTGAACGGAGGCGTGCACTGCACCGACGTGACAAATGC<br>CTCTCGGACCATGCTGTTCAACATCCACAGCCTGGAGTGGGATAAGCAGCTGTGC<br>GAGTTCTTTGGCATCCCTATGGAGATCCTGCCAAACGTGAGATCTAGCTCCGAGA<br>TCTATGGCCTGATGAAGATCAGCCACTCCGTGAAGGCAGGCGCCCTGGAGGGAGT<br>GCCTATCTCTGGATGCCTGGGCGACCAGAGCGCCGCCCTGGTGGGACAGATGTGC<br>TTCCAGATCGGCCAGGCCAAGAATACCTACGGCACAGGCTGCTTTCTGCTGTGCA<br>ACACCGGCCACAAGTGCGTGTTCAGCGACCACGGCCTGCTGACCACAGTGGCCTA<br>TAAGCTGGGCAGGGATAAGCCCGTGTACTATGCACTGGAGGGATCTGTGGCAATC<br>GCAGGAGCCGTGATCAGGTGGCTGAGAGATAATCTGGGCATCATCAAGACCAGCG<br>AGGAGATCGAGAAGCTGGCCAAGGAAGTGGGCACATCCTACGGCTGTTATTTCGT<br>GCCTGCCTTTTCTGGCCTGTACGCACCATATTGGGAGCCAAGCGCCAGGGGAATC<br>ATCTGCGGCCTGACCCAGTTCACAAACAAGTGTCACATCGCCTTTGCCGCCCTGG<br>AGGCCGTGTGCTTCCAGACCCGGGAGATCCTGGACGCCATGAATAGAGATTGTGG<br>CATCCCTCTGTCCCACCTGCAGGTGGACGGAGGCATGACATCTAACAAGATCCTG<br>ATGCAGCTGCAGGCCGACATCCTGTATATCCCAGTGGTGAAGCCCTCCATGCCTG<br>AGACCACAGCCCTGGGAGCAGCAATGGCAGCAGGAGCAGCCGAGGGCGTGGGCGT<br>GTGGTCCCTGGAGCCAGAGGACCTGTCTGCCGTGACCATGGAGCGGTTTGAGCCT<br>CAGATCAATGCCGAGGAGTCCGAGATCAGATACTCTACATGGAAGAAGGCCGTGA<br>TGAAGTCCATGGGCTGGGTGACCACACAGTCTCCCGAGAGCGGCGATCCTAGCAT<br>CTTCTGCTCCCTGCCACTGGGCTTCTTTATCGTGTCTAGCATGGTCATGCTGATC<br>GGCGCCCGGTATATCTCTGGCATCCCCCTCGAGGGCGGCGGAGAGGGCAGAGGAA<br>GTCTTCTAACATGCGGTGACGTGGAGGAGAATCCCGGCCCTAGGATGCTTCTCCT<br>GGTGACAAGCCTTCTGCTCTGTGAGTTACCACACCCAGCATTCCTCCTGATCCCA<br>TGCCACCCTGAGTGTCAGCCCCAGAATGGCTCAGTGACCTGTTTTGGACCGGAGG<br>CTGACCAGTGTGTGGCCTGTGCCCACTATAAGGACCCTCCCTTCTGCGTGGCCCG<br>CTGCCCCAGCGGTGTGAAACCTGACCTCTCCTACATGCCCATCTGGAAGTTTCCA<br>GATGAGGAGGGCGCATGCCAGCCTTGCCCCATCAACTGCACCCACTCCTGTGTGG<br>ACCTGGATGACAAGGGCTGCCCCGCCGAGCAGAGAGCCAGCCCTCTGACGGGTGG<br>AGGAAGCGGAGGTGGCAGCTCCATCATCTCTGCGGTGGTTGGCATTCTGCTGGTC<br>GTGGTCTTGGGGGTGGTCTTTGGGATCCTCATC | GYK-T2A-Her2t (nt) |
| 89 | MAASKKAVLGPLVGAVDQGTSSTRFLVFNSKTAELLSHHQVEIKQEFPREGWVE4<br>DPKEILHSVYECIEKTCEKLGQLNIDISNIKAIGVSNQRETTVVWDKITGEPLYN<br>AVVWLDLRTQSTVESLSKRIPGNNNFVKSKTGLPLSTYFSAVKLRWLLDNVRKVQ<br>KAVEEKRALFGTIDSWLIWSLTGGVNGGVHCTDVTNASRTMLFNIHSLEWDKQLC<br>EFFGIPMEILPNVRSSSEIYGLMKISHSVKAGALEGVPISGCLGDQSAALVGQMC<br>FQIGQAKNTYGTGCFLLCNTGHKCVFSDHGLLTTVAYKLGRDKPVYYALEGSVAI<br>AGAVIRWLRDNLGIIKTSEEIEKLAKEVGTSYGCYFVPAFSGLYAPYWEPSARGI<br>ICGLTQFTNKCHIAFAALEAVCFQTREILDAMNRDCGIPLSHLQVDGGMTSNKIL<br>MQLQADILYIPVVKPSMPETTALGAAMAAGAAEGVGVWSLEPEDLSAVTMERFEP<br>QINAEESEIRYSTWKKAVMKSMGWVTTQSPESGDPSIFCSLPLGFFIVSSMVMLI<br>GARYISGIPLEGGGEGRGSLLTCGDVEENPGPRMLLLVTSLLLCELPHPAFLLIP<br>CHPECQPQNGSVTCFGPEADQCVACAHYKDPPFCVARCPSGVKPDLSYMPIWKFP<br>DEEGACQPCPINCTHSCVDLDDKGCPAEQRASPLTGGGSGGGSSIISAVVGILLV<br>VVLGVVFGILI | GYK-T2A-Her2t (aa) |

-continued

SEQUENCES

| SEQ ID NO. | SEQUENCE | DESCRIPTION |
|---|---|---|
| 90 | ATGGACGAGTCCGCCCTGACACTGGGCACCATCGACGTGAGCTACCTGCCACACA GCTCCGAGTATTCTGTGGGCAGGTGCAAGCACACAAGCGAGGAGTGGGGAGAGTG TGGCTTCCGGCCAACAATCTTTAGATCCGCCACCCTGAAGTGGAAGGAGAGCCTG ATGTCCCGGAAGAGACCATTCGTGGGCCGGTGCTGTTACTCCTGCACCCCCCAGT CTTGGGACAAGTTCTTTAACCCTTCTATCCCAAGCCTGGGCCTGAGAAACGTGAT CTACATCAATGAGACCCACACAAGGCACAGGGGATGGCTGGCCCGGAGACTGAGC TATGTGCTGTTCATCCAGGAGAGGGACGTGCACAAGGGCATGTTTGCCACAAATG TGACCGAGAACGTGCTGAATTCTAGCCGCGTGCAGGAGGCAATCGCAGAGGTGGC AGCAGAGCTGAACCCTGATGGAAGCGCCCAGCAGCAGTCCAAGGCAGTGAATAAG GTGAAGAAGAAGGCCAAGCGGATCCTGCAGGAGATGGTGGCCACAGTGTCCCCAG CCATGATCAGACTGACCGGCTGGGTGCTGCTGAAGCTGTTCAACTCTTTCTTTTG GAATATCCAGATCCACAAGGGCCAGCTGGAGATGGTGAAGGCCGCCACCGAGACA AACCTGCCACTGCTGTTTCTGCCCGTGCACCGCAGCCACATCGATTACCTGCTGC TGACCTTCATCCTGTTTTGTCACAACATCAAGGCCCCTTATATCGCCAGCGGCAA CAATCTGAATATCCCAATCTTCTCCACACTGATCCACAAGCTGGGCGGCTTCTTT ATCAGGCGCCGGCTGGATGAGACCCCTGACGGCAGGAAGGATGTGCTGTACCGCG CCCTGCTGCACGGACACATCGTGGAGCTGCTGAGGCAGCAGCAGTTCCTGGAGAT CTTTCTGGAGGGCACACGGTCTAGAAGCGGCAAGACCTCCTGCGCAAGGGCAGGA CTGCTGTCCGTGGTGGTGGACACACTGTCTACCAACGTGATCCCCGACATCCTGA TCATCCCTGTGGGCATCTCTTACGACCGGATCATCGAGGGCCACTATAACGGCGA GCAGCTGGGCAAGCCCAAGAAGAATGAGTCCCTGTGGTCTGTGGCCAGGGGCGTG ATCCGGATGCTGAGAAAGAATTACGGATGCGTGCGGGTGGATTTCGCACAGCCTT TTTCCCTGAAGGAGTATCTGGAGTCCCAGTCTCAGAAGCCCGTGAGCGCCCTGCT GTCCCTGGAGCAGGCCCTGCTGCCTGCAATCCTGCCAAGCAGACCTTCCGATGCA GCAGACGAGGGAAGGGACACATCTATCAACGAGAGCAGAAATGCCACCGATGAGA GCCTGAGAAGGCGCCTGATCGCCAACCTGGCCGAGCACATCCTGTTCACAGCCAG CAAGTCCTGCGCCATCATGAGCACCCACATCGTGGCCTGTCTGCTGCTGTACCGG CACAGGCAGGGAATCGACCTGTCCACACTGGTGGAGGATTTCTTTGTGATGAAGG AGGAGGTGCTGGCCAGGGACTTCGATCTGGGCTTTTCTGGCAATAGCGAGGACGT GGTCATGCACGCCATCCAGCTGCTGGGCAACTGCGTGACCATCACACACACCTCC CGCAATGATGAGTTCTTTATCACCCCTTCTACCACAGTGCCAAGCGTGTTCGAGC TGAACTTTTACTCTAATGGCGTGCTGCACGTGTTTATCATGGAGGCCATCATCGC CTGCAGCCTGTATGCCGTGCTGAACAAGAGGGGACTGGGCGGCCCAACAAGCACC CCCCCTAATCTGATCTCCCAGGAGCAGCTGGTGAGAAAGGCCGCCTCCCTGTGCT ATCTGCTGTCTAACGAGGGCACAATCAGCCTGCCCTGCCAGACCTTCTACCAGGT GTGCCACGAGACAGTGGGCAAGTTTATCCAGTATGGCATCCTGACCGTGGCCGAG CACGACGATCAGGAGGACATCTCTCCTAGCCTGGCCGAGCAGCAGTGGGATAAGA AGCTGCCAGAGCCCCTGTCCTGGAGGTCTGACGAGGAGGACGAGGATAGCGACTT CGGCGAGGAGCAGCGCGATTGTTACCTGAAGGTGTCCCAGTCTAAGGAGCACCAG CAGTTCATCACCTTTCTGCAGCGGCTGCTGGGCCCACTGCTGGAGGCCTATTCCT CTGCCGCCATCTTCGTGCACAACTTTTCCGGCCCTGTGCCAGAGCCAGAGTACCT GCAGAAGCTGCACAAGTATCTGATCACAAGGACCGAGAGGAACGTGGCCGTGTAC GCAGAGAGCGCCACCTATTGCCTGGTGAAGAATGCCGTGAAGATGTTCAAGGACA TCGGCGTGTTTAAGGAGACAAAGCAGAAGCGGGTGTCTGTGCTGGAGCTGAGCTC CACCTTCCTGCCCCAGTGTAATAGACAGAAGCTGCTGGAGTACATCCTGAGCTTT GTGGTGCTGCTCGAGGGCGGCGGAGAGGGCAGAGGAAGTCTTCTAACATGCGGTG ACGTGGAGGAGAATCCCGGCCCTAGGATGCTTCTCCTGGTGACAAGCCTTCTGCT CTGTGAGTTACCACACCCAGCATTCCTCCTGATCCCATGCCACCCTGAGTGTCAG CCCCAGAATGGCTCAGTGACCTGTTTTGGACCGGAGGCTGACCAGTGTGTGGCCT GTGCCCACTATAAGGACCCTCCCTTCTGCGTGGCCCGCTGCCCCAGCGGTGTGAA ACCTGACCTCTCCTACATGCCCATCTGGAAGTTTCCAGATGAGGAGGGCGCATGC CAGCCTTGCCCCATCAACTGCACCCACTCCTGTGTGGACCTGGATGACAAGGGCT GCCCCGCCGAGCAGAGAGCCAGCCCTCTGACGGGTGGAGGAAGCGGAGGTGGCAG CTCCATCATCTCTGCGGTGGTTGGCATTCTGCTGGTCGTGGTCTTGGGGGTGGTC TTTGGGATCCTCATC | GPAM-T2A-Her2t (nt) |
| 91 | MDESALTLGTIDVSYLPHSSEYSVGRCKHTSEEWGECGFRPTIFRSATLKWKESL MSRKRPFVGRCCYSCTPQSWDKFFNPSIPSLGLRNVIYINETHTRHRGWLARRLS YVLFIQERDVHKGMFATNVTENVLNSSRVQEAIAEVAAELNPDGSAQQQSKAVNK VKKKAKRILQEMVATVSPAMIRLTGWVLLKLFNSFFWNIQIHKGQLEMVKAATET NLPLLFLPVHRSHIDYLLLTFILFCHNIKAPYIASGNNLNIPIFSTLIHKLGGFF IRRRLDETPDGRKDVLYRALLHGHIVELLRQQQFLEIFLEGTRSRSGKTSCARAG LLSVVVDTLSTNVIPDILIIPVGISYDRIIEGHYNGEQLGKPKKNESLWSVARGV IRMLRKNYGCVRVDFAQPFSLKEYLESQSQKPVSALLSLEQALLPAILPSRPSDA ADEGRDTSINESRNATDESLRRRLIANLAEHILFTASKSCAIMSTHIVACLLLYR HRQGIDLSTLVEDFFVMKEEVLARDFDLGFSGNSEDVVMHAIQLLGNCVTITHTS RNDEFFITPSTTVPSVFELNFYSNGVLHVFIMEAIIACSLYAVLNKRGLGGPTST PPNLISQEQLVRKAASLCYLLSNEGTISLPCQTFYQVCHETVGKFIQYGILTVAE HDDQEDISPSLAEQQWDKKLPEPLSWRSDEEDEDSDFGEEQRDCYLKVSQSKEHQ QFITFLQRLLGPLLEAYSSAAIFVHNFSGPVPEPEYLQKLHKYLITRTERNVAVY AESATYCLVKNAVKMFKDIGVFKETKQKRVSVLELSSTFLPQCNRQKLLEYILSF VVLLEGGGEGRGSLLTCGDVEENPGPRMLLLVTSLLLCELPHPAFLLIPCHPECQ | GPAM-T2A-Her2t (aa) |

-continued

SEQUENCES

| SEQ ID NO. | SEQUENCE | DESCRIPTION |
|---|---|---|
| | PQNGSVTCFGPEADQCVACAHYKDPPFCVARCPSGVKPDLSYMPIWKFPDEEGAC<br>QPCPINCTHSCVDLDDKGCPAEQRASPLTGGGSGGGSSIISAVVGILLVVVLGVV<br>FGILI | |
| 92 | ATGGAGGGCGCCGGCGGCGCCAACGATAAGAAGAAGATCAGCTCCGAGCGGAGAA<br>AGGAGAAGAGCAGGGACGCAGCACGCTCTAGGCGCAGCAAGGAGTCCGAGGTGTT<br>CTACGAGCTGGCCCACCAGCTGCCACTGCCACACAACGTGTCTAGCCACCTGGAT<br>AAGGCCAGCGTGATGCGGCTGACCATCTCCTATCTGCGGGTGAGAAAGCTGCTGG<br>ACGCCGGCGATCTGGACATCGAGGACGATATGAAGGCCCAGATGAATTGCTTCTA<br>CCTGAAGGCCCTGGACGGCTTTGTGATGGTGCTGACCGACGATGGCGACATGATC<br>TACATCTCCGATAACGTGAATAAGTATATGGGCCTGACCCAGTTTGAGCTGACAG<br>GCCACAGCGTGTTCGACTTTACCCACCCCTGCGATCACGAGGAGATGAGGGAGAT<br>GCTGACACACCGCAACGGCCTGGTGAAGAAGGGCAAGGAGCAGAATACCCAGCGG<br>TCTTTCTTTCTGAGAATGAAGTGTACCCTGACAAGCAGGGGCCGCACCATGAACA<br>TCAAGTCCGCCACATGGAAGGTGCTGCACTGCACCGGCCACATCCACGTGTACGA<br>TACCAACTCCAATCAGCCACAGTGTGGCTATAAGAAGCCCCCTATGACATGCCTG<br>GTGCTGATCTGTGAGCCTATCCCACACCCCTCTAATATCGAGATCCCCCTGGACA<br>GCAAGACCTTCCTGTCTCGGCACAGCCTGGACATGAAGTTTAGCTACTGCGATGA<br>GAGAATCACAGAGCTGATGGGCTATGAGCCTGAGGAGCTGCTGGGCAGATCTATC<br>TACGAGTACTATCACGCCCTGGATAGCGACCACCTGACCAAGACACACCACGACA<br>TGTTCACCAAGGGCCAGGTGACCACAGGCCAGTACAGGATGCTGGCCAAGAGGGG<br>AGGATACGTGTGGGTGGAGACCCAGGCCACAGTGATCTATAACACCAAGAATAGC<br>CAGCCCCAGTGCATCGTGTGCGTGAACTACGTGGTGTCCGGCATCATCCAGCACG<br>ATCTGATCTTTTCTCTGCAGCAGACCGAGTGCGTGCTGAAGCCTGTGGAGTCCTC<br>TGACATGAAGATGACCCAGCTGTTCACAAAGGTGGAGTCCGAGGACACAAGCTCC<br>CTGTTTGATAAGCTGAAGAAGGAGCCAGACGCACTGACCCTGCTGGCCCCAGCAG<br>CAGGCGATACAATCATCTCTCTGGACTTCGGCAGCAATGATACCGAGACAGACGA<br>TCAGCAGCTGGAGGAGGTGCCTCTGTATAACGATGTGATGCTGCCTTCTCCAAAT<br>GAGAAGCTGCAGAACATCAATCTGGCAATGAGCCCACTGCCTACCGCAGAGACAC<br>CAAAGCCACTGAGGTCTAGCGCCGACCCAGCCCTGAACCAGGAGGTGGCCCTGAA<br>GCTGGAGCCTAATCCAGAGTCCCTGGAGCTGTCTTTTACAATGCCACAGATCCAG<br>GACCAGACCCCATCCCCTTCTGATGGCAGCACACGCCAGTCCTCTCCAGAGCCCA<br>ACAGCCCTTCCGAGTACTGCTTCTATGTGGATTCCGACATGGTGAATGAGTTCAA<br>GCTGGAGCTGGTGGAGAAGCTGTTTGCCGAGGATACCGAGGCCAAGAACCCCTTC<br>AGCACCCAGGATACAGACCTGGATCTGGAGATGCTGGCCCCCTATATCCCTATGG<br>ACGATGACTTCCAGCTGCGGTCCTTTGACCAGCTGTCTCCTCTGGAGAGCTCCTC<br>TGCCTCCCCTGAGTCTGCCAGCCCACAGTCTACCGTGACAGTGTTCCAGCAGACC<br>CAGATCCAGGAGCCAACAGCCAATGCCACCACAACCACAGCCACCACAGATGAGC<br>TGAAGACCGTGACAAAGGACCGGATGGAGGACATCAAGATCCTGATCGCCTCCCC<br>TTCTCCAACCCACATCCACAAGGAGACCACATCCGCCACAAGCTCCCCTTACCGG<br>GACACCCAGAGCAGAACAGCCTCCCCAAACAGAGCCGGCAAGGGCGTGATCGAGC<br>AGACCGAGAAGTCTCACCCAAGGAGCCCCAATGTGCTGTCCGTGGCCCTGTCTCA<br>GCGCACCACAGTGCCCGAGGAGGAGCTGAACCCTAAGATCCTGGCCCTGCAGAAT<br>GCCCAGCGGAAGAGAAAGATGGAGCACGATGGAAGCCTGTTCCAGGCAGTGGGAA<br>TCGGCACCCTGCTGCAGCAGCCAGATGACCACGCCGCCACCACAAGCCTGTCCTG<br>GAAGAGGGTGAAGGGCTGTAAGTCTAGCGAGCAGAACGGCATGGAGCAGAAGACC<br>ATCATCCTGATCCCATCCGACCTGGCATGCAGGCTGCTGGGCCAGAGCATGGATG<br>AGTCCGGCCTGCCCCAGCTGACAAGCTACGACTGTGAGGTGAACGCCCCTATCCA<br>GGGCTCCCGGAATCTGCTGCAGGGCGAGGAGCTGCTGAGAGCCCTGGACCAGGTG<br>AATCTCGAGGGCGGCGGAGAGGGCAGAGGAAGTCTTCTAACATGCGGTGACGTGG<br>AGGAGAATCCCGGCCCTAGGATGCTTCTCCTGGTGACAAGCCTTCTGCTCTGTGA<br>GTTACCACACCCAGCATTCCTCCTGATCCCATGCCACCCTGAGTGTCAGCCCCAG<br>AATGGCTCAGTGACCTGTTTTGGACCGGAGGCTGACCAGTGTGTGGCCTGTGCCC<br>ACTATAAGGACCCTCCCTTCTGCGTGGCCCGCTGCCCCAGCGGTGTGAAACCTGA<br>CCTCTCCTACATGCCCATCTGGAAGTTTCCAGATGAGGAGGGCGCATGCCAGCCT<br>TGCCCCATCAACTGCACCCACTCCTGTGTGGACCTGGATGACAAGGGCTGCCCCG<br>CCGAGCAGAGAGCCAGCCCTCTGACGGGTGGAGGAAGCGGAGGTGGCAGCTCCAT<br>CATCTCTGCGGTGGTTGGCATTCTGCTGGTCGTGGTCTTGGGGGTGGTCTTTGGG<br>ATCCTCATC | HIF1α-T2A-Her2t<br>(nt) |
| 93 | MEGAGGANDKKKISSERRKEKSRDAARSRRSKESEVFYELAHQLPLPHNVSSHLD<br>KASVMRLTISYLRVRKLLDAGDLDIEDDMKAQMNCFYLKALDGFVMVLTDDGDMI<br>YISDNVNKYMGLTQFELTGHSVFDFTHPCDHEEMREMLTHRNGLVKKGKEQNTQR<br>SFFLRMKCTLTSRGRTMNIKSATWKVLHCTGHIHVYDTNSNQPQCGYKKPPMTCL<br>VLICEPIPHPSNIEIPLDSKTFLSRHSLDMKFSYCDERITELMGYEPEELLGRSI<br>YEYYHALDSDHLTKTHHDMFTKGQVTTGQYRMLAKRGGYVWVETQATVIYNTKNS<br>QPQCIVCVNYVVSGIIQHDLIFSLQQTECVLKPVESSDMKMTQLFTKVESEDTSS<br>LFDKLKKEPDALTLLAPAAGDTIISLDFGSNDTETDDQQLEEVPLYNDVMLPSPN<br>EKLQNINLAMSPLPTAETPKPLRSSADPALNQEVALKLEPNPESLELSFTMPQIQ<br>DQTPSPSDGSTRQSSPEPNSPSEYCFYVDSDMVNEFKLELVEKLFAEDTEAKNPF<br>STQDTDLDLEMLAPYIPMDDDFQLRSFDQLSPLESSSASPESASPQSTVTVFQQT<br>QIQEPTANATTTTATTDELKTVTKDRMEDIKILIASPSPTHIHKETTSATSSPYR<br>DTQSRTASPNRAGKGVIEQTEKSHPRSPNVLSVALSQRTTVPEEELNPKILALQN<br>AQRKRKMEHDGSLFQAVGIGTLLQQPDDHAATTSLSWKRVKGCKSSEQNGMEQKT | HIF1α-T2A-Her2t<br>(aa) |

-continued

SEQUENCES

| SEQ ID NO. | SEQUENCE | DESCRIPTION |
| --- | --- | --- |
| | IILIPSDLACRLLGQSMDESGLPQLTSYDCEVNAPIQGSRNLLQGEELLRALDQV NLEGGGEGRGSLLTCGDVEENPGPRMLLLVTSLLLCELPHPAFLLIPCHPECQPQ NGSVTCFGPEADQCVACAHYKDPPFCVARCPSGVKPDLSYMPIWKFPDEEGACQP CPINCTHSCVDLDDKGCPAEQRASPLTGGGSGGGSSIISAVVGILLVVVLGVVFG ILI | |
| 94 | ATGAAGGTGGAGTTCGCCCCTCTGAACATCCAGCTGGCCCGGAGACTGCAGACCG TGGCCGTGCTGCAGTGGGTGCTGAAGTACCTGCTGCTGGGCCCAATGTCCATCGG CATCACAGTGATGCTGATCATCCACAATTACCTGTTCCTGTATATCCCCTATCTG ATGTGGCTGTATTTTGACTGGCACACCCCTGAGAGGGGCGGCAGGCGCAGCTCCT GGATCAAGAACTGGACACTGTGGAAGCACTTCAAGGATTACTTTCCAATCCACCT GATCAAGACCCAGGACCTGGATCCTTCTCACAATTATATCTTCGGCTTTCACCCA CACGGAATCATGGCAGTGGGAGCCTTCGGCAACTTTAGCGTGAATTACTCCGACT TCAAGGATCTGTTCCCCGGCTTTACCAGCTATCTGCACGTGCTGCCACTGTGGTT CTGGTGCCCCGTGTTTAGAGAGTACGTGATGTCCGTGGGCCTGGTGTCTGTGAGC AAGAAGTCCGTGTCTTATATGGTGTCCAAGGAGGGCGGCGGCAACATCTCTGTGA TCGTGCTGGGAGGAGCAAAGGAGTCTCTGGACGCCCACCCTGGCAAGTTCACCCT GTTTATCCGGCAGAGAAAGGGCTTTGTGAAGATCGCCCTGACACACGGAGCCTCT CTGGTGCCAGTGGTGAGCTTCGGCGAGAACGAGCTGTTTAAGCAGACCGATAATC CCGAGGGCAGCTGGATCAGGACAGTGCAGAACAAGCTGCAGAAGATCATGGGCTT CGCACTGCCACTGTTTCACGCAAGGGGCGTGTTCCAGTACAATTTTGGCCTGATG ACCTATAGAAAGGCCATCCACACAGTGGTGGGCAGGCCCATCCCTGTGCGCCAGA CCCTGAATCCCACACAGGAGCAGATCGAGGAGCTGCACCAGACCTACATGGAGGA GCTGCGCAAGCTGTTCGAGGAGCACAAGGGCAAGTATGGCATCCCTGAGCACGAG ACACTGGTGCTGAAGCTCGAGGGCGGCGGAGAGGGCAGAGGAAGTCTTCTAACAT GCGGTGACGTGGAGGAGAATCCCGGCCCTAGGATGCTTCTCCTGGTGACAAGCCT TCTGCTCTGTGAGTTACCACACCCAGCATTCCTCCTGATCCCATGCCACCCTGAG TGTCAGCCCCAGAATGGCTCAGTGACCTGTTTTGGACCGGAGGCTGACCAGTGTG TGGCCTGTGCCCACTATAAGGACCCTCCCTTCTGCGTGGCCCGCTGCCCCAGCGG TGTGAAACCTGACCTCTCCTACATGCCCATCTGGAAGTTTCCAGATGAGGAGGGC GCATGCCAGCCTTGCCCCATCAACTGCACCCACTCCTGTGTGGACCTGGATGACA AGGGCTGCCCCGCCGAGCAGAGAGCCAGCCCTCTGACGGGTGGAGGAAGCGGAGG TGGCAGCTCCATCATCTCTGCGGTGGTTGGCATTCTGCTGGTCGTGGTCTTGGGG GTGGTCTTTGGGATCCTCATC | MOGAT1-T2A-Her2t (nt) |
| 95 | MKVEFAPLNIQLARRLQTVAVLQWVLKYLLLGPMSIGITVMLIIHNYLFLYIPYL MWLYFDWHTPERGGRRSSWIKNWTLWKHFKDYFPIHLIKTQDLDPSHNYIFGFHP HGIMAVGAFGNFSVNYSDFKDLFPGFTSYLHVLPLWFWCPVFREYVMSVGLVSVS KKSVSYMVSKEGGGNISVIVLGGAKESLDAHPGKFTLFIRQRKGFVKIALTHGAS LVPVVSFGENELFKQTDNPEGSWIRTVQNKLQKIMGFALPLFHARGVFQYNFGLM TYRKAIHTVVGRPIPVRQTLNPTQEQIEELHQTYMEELRKLFEEHKGKYGIPEHE TLVLKLEGGGEGRGSLLTCGDVEENPGPRMLLLVTSLLLCELPHPAFLLIPCHPE CQPQNGSVTCFGPEADQCVACAHYKDPPFCVARCPSGVKPDLSYMPIWKFPDEEG ACQPCPINCTHSCVDLDDKGCPAEQRASPLTGGGSGGGSSIISAVVGILLVVVLG VVFGILI | MOGAT1-T2A-Her2t (aa) |
| 96 | ATGCCCCCTCAGCTGCAGAACGGCCTGAATCTGTCCGCCAAGGTGGTGCAGGGCT CCCTGGACTCTCTGCCTCAGGCCGTGAGGGAGTTTCTGGAGAACAATGCCGAGCT GTGCCAGCCAGACCACATCCACATCTGTGATGGCTCTGAGGAGGAGAACGGCCGC CTGCTGGGACAGATGGAGGAGGAGGGCATCCTGCGGAGACTGAAGAAGTACGATA ATTGCTGGCTGGCCCTGACCGACCCAAGGGATGTGGCACGCATCGAGAGCAAGAC CGTGATCGTGACACAGGAGCAGAGGGACACCGTGCCAATCCCCAAGACAGGCCTG TCTCAGCTGGGCCGCTGGATGAGCGAGGAGGATTTCGAGAAGGCCTTTAACGCCC GGTTCCCTGGCTGTATGAAGGGCAGAACCATGTACGTGATCCCCTTCAGCATGGG ACCTCTGGGAAGCCCACTGTCCAAGATCGGCATCGAGCTGACAGACTCCCCATAT GTGGTGGCCTCTATGCGGATCATGACCAGAATGGGAACACCCGTGCTGGAGGCAG TGGGCGATGGCGAGTTCGTGAAGTGCCTGCACTCCGTGGGCTGTCCTCTGCCACT GCAGAAGCCCCTGGTGAACAATTGGCCCTGCAACCCTGAGCTGACCCTGATCGCA CACCTGCCTGACAGGAGGGAGATCATCTCTTTTGGCAGCGGCTACGGCGGCAATA GCCTGCTGGGCAAGAAGTGTTTCGCACTGAGGATGGCCTCCCGCCTGGCCAAGGA GGAGGGATGGCTGGCCGAGCACATGCTGATCCTGGGCATCACCAATCCCGAGGGC GAGAAGAAGTATCTGGCTGCCGCCTTTCCTTCTGCCTGCGGCAAGACAAACCTGG CCATGATGAATCCAAGCCTGCCAGGATGGAAGGTGGAGTGCGTGGGCGACGACAT CGCCTGGATGAAGTTCGATGCACAGGGACACCTGAGGGCCATCAACCCAGAGAAT GGCTTCTTTGGCGTGGCCCCAGGCACCTCTGTGAAGACAAACCCCAATGCCATCA AGACCATCCAGAAGAACACCATCTTTACAAATGTGGCCGAGACAAGCGACGGAGG CGTGTACTGGGAGGGAATCGATGAGCCCCTGGCCAGCGGCGTGACCATCACATCC TGGAAGAACAAGGAGTGGAGCTCCGAGGACGGAGAGCCATGCGCACACCCTAATT CCAGATTCTGCACCCCCGCCTCTCAGTGTCCTATCATCGATGCAGCATGGGAGTC TCCAGAGGGAGTGCCAATCGAGGGCATCATCTTTGGCGGCCGGAGACCTGCAGGA GTGCCACTGGTGTATGAGGCCCTGTCCTGGCAGCACGGCGTGTTCGTGGGAGCAG CAATGCGGTCTGAGGCAACAGCTGCCGCCGAGCACAAGGGCAAGATCATCATGCA CGACCCATTTGCCATGAGACCCTTCTTTGGCTACAACTTCGGCAAGTATCTGGCA CACTGGCTGTCCATGGCACAGCACCCTGCAGCAAAGCTGCCAAAGATCTTTCACG | PCK1-T2A-Her2t (nt) |

-continued

SEQUENCES

| SEQ ID NO. | SEQUENCE | DESCRIPTION |
|---|---|---|
| | TGAATTGGTTCAGGAAGGATAAGGAGGGCAAGTTTCTGTGGCCTGGCTTCGGCGA<br>GAACAGCAGGGTGCTGGAGTGGATGTTCAATCGCATCGACGGCAAGGCCTCCACC<br>AAGCTGACACCCATCGGCTACATCCCTAAGGAGGATGCCCTGAACCTGAAGGGCC<br>erein the cells are CD4+ or CD8+ cells. 113. The<br>sition of<br>TGTGAGATCGAGCGGGAGATCCTGGCCCTGAAGCAGAGAATCTCCCAGATGCTCG<br>AGGGCGGCGGAGAGGGCAGAGGAAGTCTTCTAACATGCGGTGACGTGGAGGAGAA<br>TCCCGGCCCTAGGATGCTTCTCCTGGTGACAAGCCTTCTGCTCTGTGAGTTACCA<br>CACCCAGCATTCCTCCTGATCCCATGCCACCCTGAGTGTCAGCCCCAGAATGGCT<br>CAGTGACCTGTTTTGGACCGGAGGCTGACCAGTGTGTGGCCTGTGCCCACTATAA<br>GGACCCTCCCTTCTGCGTGGCCCGCTGCCCCAGCGGTGTGAAACCTGACCTCTCC<br>TACATGCCCATCTGGAAGTTTCCAGATGAGGAGGGCGCATGCCAGCCTTGCCCCA<br>TCAACTGCACCCACTCCTGTGTGGACCTGGATGACAAGGGCTGCCCCGCCGAGCA<br>GAGAGCCAGCCCTCTGACGGGTGGAGGAAGCGGAGGTGGCAGCTCCATCATCTCT<br>GCGGTGGTTGGCATTCTGCTGGTCGTGGTCTTGGGGGTGGTCTTTGGGATCCTCA<br>TC | |
| 97 | MPPQLQNGLNLSAKVVQGSLDSLPQAVREFLENNAELCQPDHIHICDGSEEENGR<br>LLGQMEEEGILRRLKKYDNCWLALTDPRDVARIESKTVIVTQEQRDTVPIPKTGL<br>SQLGRWMSEEDFEKAFNARFPGCMKGRTMYVIPFSMGPLGSPLSKIGIELTDSPY<br>VVASMRIMTRMGTPVLEAVGDGEFVKCLHSVGCPLPLQKPLVNNWPCNPELTLIA<br>HLPDRREIISFGSGYGGNSLLGKKCFALRMASRLAKEEGWLAEHMLILGITNPEG<br>EKKYLAAAFPSACGKTNLAMMNPSLPGWKVECVGDDIAWMKFDAQGHLRAINPEN<br>GFFGVAPGTSVKTNPNAIKTIQKNTIFTNVAETSDGGVYWEGIDEPLASGVTITS<br>WKNKEWSSEDGEPCAHPNSRFCTPASQCPIIDAAWESPEGVPIEGIIFGGRRPAG<br>VPLVYEALSWQHGVFVGAAMRSEATAAAEHKGKIIMHDPFAMRPFFGYNFGKYLA<br>HWLSMAQHPAAKLPKIFHVNWFRKDKEGKFLWPGFGENSRVLEWMFNRIDGKAST<br>KLTPIGYIPKEDALNLKGLGHINMMELFSISKEFWEKEVEDIEKYLEDQVNADLP<br>CEIEREILALKQRISQMLEGGGEGRGSLLTCGDVEENPGPRMLLLVTSLLLCELP<br>HPAFLLIPCHPECQPQNGSVTCFGPEADQCVACAHYKDPPFCVARCPSGVKPDLS<br>YMPIWKFPDEEGACQPCPINCTHSCVDLDDKGCPAEQRASPLTGGGSGGGSSIIS<br>AVVGILLVVVLGVVFGILI | PCK1-T2A-Her2t<br>(aa) |

The invention claimed is:

1. An engineered immune cell, comprising:

(a) a genetically engineered receptor that specifically binds to a ligand; and (b) a recombinant molecule or a functional and/or catalytically-active portion or variant thereof, wherein the recombinant molecule is involved in or capable of modulating a metabolic pathway and is under the control of a constitutive promoter, enhancer, or transactivator.

2. The engineered immune cell of claim 1, wherein the metabolic pathway is or comprises triacylglyceride (TAG) synthesis, TAG storage, glycerol phosphate pathway, glycerophospholipid synthesis and/or glycerol uptake.

3. The engineered immune cell of claim 1, wherein the recombinant molecule is or comprises a Glycerol kinase (GYK), a Glycerol-3-phosphate acetyltransferase (GPAT), a Monoacylglycerol O-acetyltransferase (MOGAT), a DAG O-acetyltransferase (DGAT), an acylglycerolphosphate acyltransferase (AGPAT), or a Lipin.

4. The engineered immune cell of claim 3, wherein the molecule is or comprises a GYK, a GPAT1, a MOGAT1, or a DGAT1.

5. The engineered immune cell of claim 1, wherein the recombinant molecule is or comprises an aquaporin-9 (AQP9).

6. The engineered immune cell of claim 1, wherein the recombinant molecule is or comprises a palmitoyltransferase.

7. The engineered immune cell of claim 1, wherein the metabolic pathway comprises oxidative phosphorylation (OXPHOS), generation or accumulation of reactive oxygen species (ROS), cellular respiration, spare respiratory capacity (SPC) and/or mitochondrial respiratory capacity.

8. The engineered immune cell of claim 1, wherein the recombinant molecule does not promote or enhance glycolysis.

9. The engineered immune cell of claim 1, wherein the recombinant molecule is capable of interacting with or associating with, directly or indirectly, a CR6 interacting factor (CRIF), a lymphocyte expansion molecule (LEM) or a 39S subunit.

10. The engineered immune cell of claim 1, wherein the recombinant molecule is or comprises a lymphocyte expansion molecule (LEM).

11. The engineered immune cell of claim 1, wherein the recombinant molecule is a molecule that is upregulated or activated in response to antigen-receptor signaling, IL-17-mediated signaling, IL-15-mediated signaling, TRAF-mediated signaling, TRAF6-mediated signaling, IL-7-mediated signaling, IL-21-mediated signaling, low-oxygen conditions, succinate, release of reactive oxygen species (ROS), mTOR-induced signaling, or a functional variant thereof.

12. The engineered immune cell of claim 1, wherein the recombinant molecule comprises a hypoxia-induced factor (HIF).

13. The engineered immune cell of claim 12, wherein the recombinant molecule comprises a HIF1-alpha.

14. The engineered immune cell of claim 1, wherein the recombinant molecule is capable of promoting generation of a glycolysis metabolite.

15. The engineered immune cell of claim 1, wherein the recombinant molecule comprises a phosphoenolpyruvate carboxykinase 1 (PCK1).

16. The engineered immune cell of claim 1, wherein the recombinant molecule is or interacts with GLUT4 or SGK-1.

17. The engineered immune cell of claim 1, wherein the recombinant molecule is capable of promoting said metabolic pathway; and/or wherein an outcome of the metabolic pathway is enhanced in the engineered immune cell compared to a reference cell substantially identical to the engineered immune cell, but not expressing the recombinant molecule.

18. The engineered immune cell of claim 1, wherein the recombinant molecule is a nucleic acid or a protein capable of interfering with expression, activity, or stability of a negative regulator of the metabolic pathway, or a molecule that stabilizes the expression or longevity of a molecule that promotes said pathway.

19. The engineered immune cell of claim 17, wherein the recombinant molecule is a nucleic acid and the nucleic acid is an RNAi, siRNA, or shRNA molecule.

20. The engineered immune cell of claim 1, further comprising a disruption in expression or function of an immune checkpoint molecule, wherein the disruption in expression thereby promotes activation, proliferation, expansion, or reduced exhaustion, of the engineered immune cell and/or is capable of reducing generation of or longevity of memory T cells or central memory T cells ($T_{CM}$).

21. The engineered immune cell of claim 20, wherein the immune checkpoint molecule comprises a PD-1, PD-L1, TIM3, CTLA4 or an adenosine receptor.

22. The engineered immune cell of claim 1, wherein persistence of the engineered immune cell and/or of reprograming in favor of memory T cell, central memory T cell ($T_{CM}$), T memory stem cells ($T_{SCM}$), and/or undifferentiated phenotype cells, and/or reduction in exhaustion phenotype, and/or reduction in regulatory T cells, is enhanced or increased in the engineered immune cell as compared to a cell substantially the same as the engineered immune cell not comprising the recombinant molecule, under the same conditions.

23. The engineered immune cell of claim 22, wherein the conditions comprise activation via an antigen receptor, a TCR, an ITAM-containing signaling molecule, cytokine signaling, TNFR signaling, and/or adoptive transfer to a subject containing cells expressing the ligand.

24. The engineered immune cell of claim 1, wherein the cell is a T cell, a natural killer (NK) cell or an iPS-derived cell.

25. The engineered immune cell of claim 24, wherein the cell is a T cell and the T cell is a CD8+ T cell or a CD4+ T cell.

26. The engineered immune cell of claim 1, wherein the genetically engineered receptor that specifically binds to a ligand is a chimeric antigen receptor (CAR).

27. The engineered immune cell of claim 1, wherein the genetically engineered receptor that specifically binds to a ligand is a transgenic T cell receptor (TCR).

28. The engineered immune cell of claim 1, wherein the recombinant molecule is ectopically expressed in the cell.

29. A nucleic acid molecule(s), comprising:

a nucleotide sequence encoding a genetically engineered receptor that specifically binds to a ligand; and a nucleotide sequence encoding a recombinant molecule that is involved in or capable of modulating a metabolic pathway, or a functional and/or catalytically-active portion or variant thereof.

30. The nucleic acid molecule(s) of claim 29, wherein the genetically engineered receptor that specifically binds to a ligand is a chimeric antigen receptor (CAR).

31. The nucleic acid molecule(s) of claim 29, wherein the genetically engineered receptor that specifically binds to a ligand is a transgenic T cell receptor (TCR).

32. A vector, comprising the nucleic acid molecule(s) of claim 29.

33. An engineered immune cell, comprising the nucleic acid molecules(s) of claim 29.

34. A composition comprising the engineered immune cell of claim 1.

35. A composition comprising the engineered immune cell of claim 33.

36. A method of treatment, comprising administering the engineered immune cell of claim 1 to a subject having a disease or condition.

37. The method of claim 36, wherein the disease or condition is a cancer, a tumor, an autoimmune disease or disorder, or an infectious disease.

38. A method of treatment, comprising administering the engineered immune cell of claim 33 to a subject having a disease or condition.

39. The method of claim 38, wherein the disease or condition is a cancer, a tumor, an autoimmune disease or disorder, or an infectious disease.

40. The engineered immune cell of claim 1, wherein the recombinant molecule does not promote or enhance glycolysis in T cells.

41. The engineered immune cell of claim 1, wherein the recombinant molecule does not promote or enhance glycolysis under conditions under which the recombinant molecule promotes or enhances FAS, FAO, OXPHOS, ROS accumulation or generation, cellular respiration, or respiratory capacity.

42. The engineered immune cell of claim 1, wherein the recombinant molecule is a molecule that is differentially expressed or activated under nutrient-rich versus nutrient-poor conditions, or under hypoxic vs. normoxic conditions, or in effector or vs naive or central memory T cells and/or in exhausted vs non-exhausted T cells, and/or in terminally differentiated T cells vs. non-terminally differentiated T cells.

43. The engineered immune cell of claim 14, wherein the engineered immune cells exhibit increased generation of said glycolysis metabolite compared to reference cells substantially identical to the engineered immune cells but not expressing the recombinant molecule, under the same conditions.

44. The engineered immune cell of claim 1, wherein the recombinant molecule is capable of inhibiting said metabolic pathway; and/or wherein an outcome of the metabolic pathway is inhibited or reduced in the engineered immune cell compared to a reference cell substantially identical to the engineered immune cell, but not expressing the recombinant molecule.

45. The engineered immune cell of claim 10, wherein the cell is a T cell.

46. The engineered immune cell of claim 10, wherein the genetically engineered receptor that specifically binds to a ligand is a CAR.

47. The engineered immune cell of claim 46, wherein the cell is a T cell.

48. The engineered immune cell of claim 10, wherein the genetically engineered receptor that specifically binds to a ligand is a TCR.

49. The engineered immune cell of claim 48, wherein the cell is a T cell.

* * * * *